US008772323B2

(12) United States Patent
Grauert et al.

(10) Patent No.: US 8,772,323 B2
(45) Date of Patent: Jul. 8, 2014

(54) BENZOXAZOLE- AND TETRAHYDROBENZOXAZOLE-SUBSTITUTED PYRIDAZINONES AS GPR119 AGONISTS

(75) Inventors: Matthias Grauert, Biberach an der Riss (DE); Remko Bakker, Biberach an der Riss (DE); Steffen Breitfelder, Attenweiler (DE); Frank Buettner, Attenweiler (DE); Peter Eickelmann, Mittelbiberach (DE); Thomas Fox, Biberach an der Riss (DE); Marc Grundl, Biberach an der Riss (DE); Thorsten Lehmann-Lintz, Ochsenhausen (DE); Wolfgang Rist, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/696,094

(22) PCT Filed: May 6, 2011

(86) PCT No.: PCT/EP2011/057285

§ 371 (c)(1), (2), (4) Date: Dec. 12, 2012

(87) PCT Pub. No.: WO2011/138427

PCT Pub. Date: Nov. 10, 2011

(65) Prior Publication Data

US 2013/0172323 A1 Jul. 4, 2013

(30) Foreign Application Priority Data

May 7, 2010 (EP) .................................... 10162364

(51) Int. Cl.

*A61K 31/423* (2006.01)
*C07D 263/54* (2006.01)

(52) U.S. Cl.

USPC ............. 514/375; 540/598; 544/60; 544/114; 544/238; 544/333; 544/359; 546/210; 546/268.1; 548/131; 548/136; 548/143; 548/217; 548/235; 548/335.1; 548/560; 548/579; 549/59; 549/356; 549/429; 549/505

(58) Field of Classification Search

USPC ............. 514/375; 540/598; 544/60, 114, 238, 544/333, 359; 546/210, 268.1; 548/131, 548/136, 143, 217, 235, 335.1, 560, 579; 549/59, 356, 429, 505

See application file for complete search history.

(56) References Cited

FOREIGN PATENT DOCUMENTS

| | | | |
|---|---|---|---|
| CA | 1257588 | A1 | 7/1989 |
| EP | 0196005 | A1 | 10/1986 |
| WO | 2007003961 | A2 | 1/2007 |
| WO | 2009062576 | A2 | 5/2009 |
| WO | WO 2011/138427 | * | 11/2011 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report PCT/EP2011/057285 and written opinion, mailed Jan. 19, 2012.
Jones, R.M., et al., "GPR119 Agonists for the treatment of type 2 diabetes", Expert Opinion on Therapeutic Patents 2009, Informa Healthcare, vol. 19, No. 10, p. 1339-1359.

* cited by examiner

*Primary Examiner* — Douglas M Willis
(74) *Attorney, Agent, or Firm* — Michael P. Morris; Timothy X. Witkowski

(57) ABSTRACT

The present invention relates to pyridazinone derivatives of general formula I, wherein the groups A, G and $R^1$ are as defined in the application, the tautomers thereof, stereoisomers thereof, the mixtures thereof and the salts thereof, which have valuable pharmacological properties, and in particular bind to the GPR119 receptor and modulate its activity.

(I)

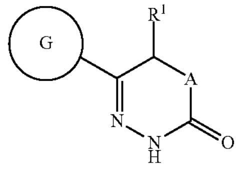

11 Claims, No Drawings

BENZOXAZOLE- AND TETRAHYDROBENZOXAZOLE-SUBSTITUTED PYRIDAZINONES AS GPR119 AGONISTS

CROSS-REFERENCE TO RELATED APPLICATIONS

This application is a 35 U.S.C. §371 National Stage filing of International Application No. PCT/EP2011/057285, filed May 6, 2011, which claims priority to European Patent Application No. 10162364.3, filed May 7, 2010, the contents of which are each hereby incorporated by reference in their entirety.

BACKGROUND OF THE INVENTION

The present invention relates to pyridazinone derivatives of general formula I

I

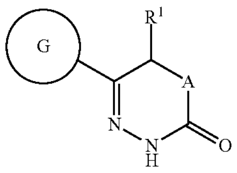

wherein the groups A, G and $R^1$ are defined as hereinafter, including the tautomers thereof, stereoisomers (e.g. diastereomers and enantiomers), the mixtures thereof and the salts thereof, particularly the pharmaceutically acceptable salts thereof, which have valuable pharmacological properties, in particular they bind to the G-protein-coupled receptor GPR119 (also known as GPCR2, RUP3, SNORF25 or GDIR) and modulate its activity.

These compounds according to the invention may be used in the pharmaceutical industry for preparing pharmaceutical compositions for human and/or veterinary medicine.

The invention further relates to pharmaceutical compositions containing one or more compounds according to the invention as well as the use of the compounds according to the invention as medicaments, particularly for preparing pharmaceutical compositions for the therapeutic treatment of metabolic disorders, particularly obesity and diabetes, especially type 2 diabetes, and the complications thereof and/or associated diseases. In addition, the invention relates to processes for preparing the compounds and pharmaceutical compositions according to the invention.

Diabetes mellitus is a serious metabolic disease which affects more than 100 million people worldwide. In the USA there are more than 12 million diabetics with 600,000 new cases diagnosed every year. The prevalence of diabetes mellitus is on the increase, which means in particular a high frequency of complications as well, leading to a substantial impairment of quality of life and life expectancy. Because of diabetes-associated microvascular complications, in the industrialised countries type 2 diabetes is currently the most common cause of adult-onset loss of vision, renal insufficiency and amputations. In addition, type 2 diabetes is associated with a two- to five-fold increase in the risk of cardiovascular disease.

The UKPDS study (United Kingdom Prospective Diabetes Study) showed that intensive treatment with common therapeutic agents, e.g. metformin, sulphonylureas or insulin, results in only a limited improvement in glycaemic control (difference in the HbA1c value ~0.9%). Moreover, glycaemic control deteriorated considerably over time even in patients in the intensive treatment group, and this was put down to a deterioration in beta cell function. Diabetes is also a major cause of damage to the retina at the back of the eye and increases the risk of cataract and glaucoma. Finally, diabetes is associated with nerve damage, particularly in the legs and feet, which affects the patient's ability to feel pain and contributes to serious infections. All in all, complications of diabetes are one of the major causes of death worldwide.

Adiposity (obesity) is the result of an imbalance between calorie intake and energy consumption. It correlates to a high degree with insulin resistance and diabetes. However, the molecular mechanisms that are involved in obesity/diabetes syndromes are not yet clear. At an early stage of the development of obesity, an increased insulin secretion balances out the insulin resistance and protects the patient from hyperglycaemia. However, after a time, the beta cell function worsens and non-insulin-dependent diabetes develops in about 20% of the obese population. Obesity has thus become a critical risk factor for diabetes, but the factors that predispose one group of patients to a pathological change in insulin secretion as a response to the accumulation of fat are currently unknown.

Obesity also significantly increases the risk of the development of cardiovascular disease. Diabetes is also implicated in the formation of kidney complaints, eye complaints and problems of the nervous system. Kidney disease, also known as nephropathy, sets in when the filtering mechanism of the kidneys is disrupted and proteins escape into the urine in excessive amounts and finally the kidney fails. Therefore there is a medical need for medicaments for preventing and/or treating metabolic disorders (particularly diabetes, predominantly type 2 diabetes) and the complications thereof. In particular there is a need for medicaments with good activity in terms of glycaemic control, disease-modifying properties and reducing cardiovascular morbidity and mortality, and which also have a better safety profile.

GPR119 is a Gs-protein coupled receptor which is expressed overwhelmingly in the beta cells of the pancreas and in the L cells of the bowel. Activation of the receptor stimulates the cAMP signal pathway, in the way that GLP-1R agonists do. Therefore, a GPR119 agonist can be expected to bring about an improvement in the beta cell function and the beta cell mass. In fact, activation of GPR119 stimulates insulin secretion in-vitro and in-vivo (in rodents) in a glucose-dependent manner. It has recently been shown that GPR agonists effectively lower the blood glucose level in diabetic rodents without the risk of hypoglycaemia. In addition, GPR119 expression has been observed in the gastrointestinal tract and in the brain of rodents, but not in the human brain. It was shown that the activation of GPR119 in neuroendocrine cells of the bowel stimulates the release of GLP-1, therefore the activation of GPR119 combines a direct effect on the beta cells with an indirect glucoregulatory effect through an intestinal increase in the release of GLP-1. Therefore the GPR119 agonists may be expected to have a therapeutic benefit in metabolic diseases. Examples of such diseases include type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction and bone-related diseases (such as osteoporosis, rheumatoid arthritis or osteoarthritis).

The publication EP 0196005 describes certain pyridazinone derivatives and their medical use based on a cardiotonic and/or hypotensive and antithrombotic activity.

SUMMARY OF THE INVENTION

It has now been found that the compounds according to the invention described in more detail hereinafter have surprising and particularly advantageous properties, and in particular may be used as GPR119 agonists.

In a first aspect the invention thus relates to compounds of formula I

I

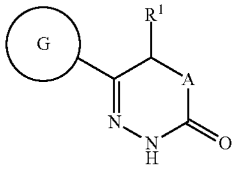

wherein $R^1$ denotes hydrogen, 1-4C-alkyl, 3-7C-cycloalkyl, 3-7C-cycloalkyl-1-4C-alkyl, 1-4C-alkenyl, 1-4C-alkynyl, 1-4C-alkoxy, 1-4C-alkoxy-1-4C-alkyl, wholly or partially fluorine substituted 1-4C-alkyl, or wholly or partially fluorine substituted 1-4C-alkoxy, A denotes $CR^2R^3$, O, S, or $NR^2$, wherein $R^2$ denotes a group selected from among hydrogen, 1-4C-alkyl, 3-7C-cycloalkyl, 3-7C-cycloalkyl-1-4C-alkyl, 1-4C-alkenyl, 1-4C-alkynyl, 1-4C-alkoxy, 1-4C-alkoxy-1-4C-alkyl, wholly or partially fluorine substituted 1-4C-alkyl, or wholly or partially fluorine substituted 1-4C-alkoxy, or $R^1$ and $R^2$ together represent a bond, or a 1-7C-alkanediyl group wherein optionally one or two $—CH_2—$ groups may each be replaced by —O—, and $R^3$ denotes hydrogen or 1-4C-alkyl, G denotes a bicyclic system selected from among the following systems G1, G2 and G3:

G1

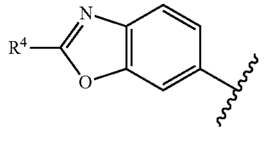

G2

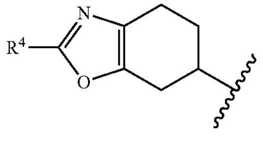

and

G3

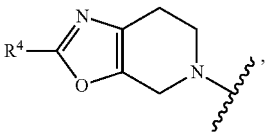

, wherein $R^4$ denotes a group optionally substituted by one to four $R^5$ and/or $R^6$, which may be identical or different, selected from among 1-4C-alkyl, 3-7C-cycloalkyl, 3-7C-cycloalkyl-1-4C-alkyl, 1-4C-alkenyl, 1-4C-alkynyl, aryl, heteroaryl, aryl-1-4C-alkyl, heteroaryl-1-4C-alkyl, heterocyclyl, and heterocyclyl-1-4C-alkyl, wherein each $R^5$ independently denotes hydrogen or a group optionally substituted by one to four $R^{10}$ and/or $R^{11}$ and/or $R^{12}$, which may be identical or different, selected from among:

1-4C-alkyl, 3-7C-cycloalkyl, 3-7C-cycloalkyl-1-4C-alkyl, 1-4C-alkenyl, 1-4C-alkynyl, aryl, heteroaryl, heterocyclyl, aryl-1-4C-alkyl, heteroaryl-1-4C-alkyl, and heterocyclyl-1-4C-alkyl, wherein each $R^6$ independently denotes hydrogen or a group selected from among:

halogen, trifluoromethyl, cyano, oxo, $—OR^7$, $—N(R^7)R^8$, $—SR^7$, $—C(O)OR^7$, $—C(O)N(R^7)R^8$, $—S(O)_2N(R^7)R^8$, $—C(O)R^9$, $—S(O)_2R^9$, $—S(O)R^9$, $—N(R^{81})C(O)OR^7$, $—N(R^{81})C(O)N(R^7)R^8$, $—N(R^{81})S(O)_2\,N(R^7)R^8$, $—N(R^{81})C(O)R^9$, $—N(R^{81})S(O)_2R^9$, and $—N(R^{81})S(O)R^9$, wherein each $R^7$ independently denotes hydrogen or a group optionally substituted by one to four $R^{10}$ and/or $R^{11}$ and/or $R^{12}$, which may be identical or different, selected from among:

1-4C-alkyl, 3-7C-cycloalkyl, 3-7C-cycloalkyl-1-4C-alkyl, 1-4C-alkenyl, 1-4C-alkynyl, aryl, heteroaryl, heterocyclyl, aryl-1-4C-alkyl, heteroaryl-1-4C-alkyl, and heterocyclyl-1-4C-alkyl, each $R^8$ independently denotes hydrogen or a group selected from among:

1-4C-alkyl and 3-7C-cycloalkyl, or $R^7$ and $R^8$ together represent a 1-9C-alkanediyl group wherein optionally one or two $—CH_2—$ groups may each be replaced by —O, $—NR^{81}$, —S, —SO or $—SO_2—$, each $R^{81}$ independently denotes hydrogen or 1-4C-alkyl, each $R^9$ independently denotes a group optionally substituted by one to four $R^{10}$ and/or $R^{11}$ and/or $R^{12}$, which may be identical or different, selected from among:

1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, wherein each $R^{10}$ independently denotes a group selected from among:

hydrogen, 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, each $R^{11}$ independently denotes hydrogen or a group selected from among:

halogen, trifluoromethyl, cyano, oxo, $—OR^{13}$, $—N(R^{13})R^{14}$ and $—SR^{13}$, each $R^{12}$ independently denotes hydrogen or a group selected from among:

$—C(O)OR^{13}$, $—C(O)N(R^{13})R^{14}$, $—S(O)_2N(R^{13})R^{14}$, $—C(O)R^{15}$, $—S(O)_2R^{15}$, $—S(O)R^{15}$, $—N(R^{141})C(O)OR^{13}$, $—N(R^{141})C(O)N(R^{13})R^{14}$, $—N(R^{141})S(O)_2N(R^{13})R^{14}$, $—N(R^{141})C(O)R^{15}$, $—N(R^{141})S(O)_2R^{15}$, and $—N(R^{141})S(O)R^{15}$, wherein each $R^{13}$ independently denotes a group selected from among:

hydrogen, 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, each $R^{14}$ independently denotes a group selected from among:

hydrogen, 1-4C-alkyl, and 3-7C-cycloalkyl, or $R^{13}$ and $R^{14}$ together represent a 1-9C-alkanediyl group wherein optionally one or two —$CH_2$— groups may each be replaced by —O, —$NR^{141}$, —S, —SO or —$SO_2$—, each $R^{141}$ independently denotes hydrogen or 1-4C-alkyl, each $R^{15}$ independently denotes a group selected from among:

1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, wherein aryl, on its own or as part of another group, denotes a carbocyclic aromatic monocyclic ring system containing 6 carbon atoms, which may optionally be annelated to a second 5- or 6-membered carbocyclic aromatic, saturated or unsaturated ring system, heteroaryl, on its own or as part of another group, denotes a 5- to 12-membered, aromatic, monocyclic or condensed-polycyclic ring system containing 1 to 4 identical or different heteroatoms independently selected from among N, O and $S(O)_r$, with r=0, 1 or 2, wherein at least one of the heteroatoms is part of the aromatic ring, and heterocyclyl, on its own or as part of another group, a 3- to 12-membered, saturated, unsaturated or aromatic, monocyclic or condensed, bridged or spiro-polycyclic ring system containing 1 to 4 identical or different heteroatoms independently selected from among N, O and $S(O)_r$, with r=0, 1 or 2, wherein none of the heteroatoms is part of the aromatic ring;

the tautomers, enantiomers, diastereomers, the mixtures thereof and the salts thereof.

One embodiment of the compounds according to the invention relates to compounds of formula I, wherein the groups A, G and $R^1$ are as described herein, with the proviso that the following compounds are excluded (cf. EP 0196005):

5-methyl-6-[2-(3-thienyl)-benzoxazol-6-yl]-4,5-dihydro-3(2H)-pyridazinone, 5-methyl-6-[2-(2-pyridyl)-benzoxazol-6-yl]-4,5-dihydro-3(2H)-pyridazinone, 5-methyl-6-[2-(2-furyl)-benzoxazol-6-yl]-4,5-dihydro-3(2H)-pyridazinone, 5-methyl-6-[2-(2-thienyl)-benzoxazol-6-yl]-4,5-dihydro-3(2H)-pyridazinone, 5-methyl-6-[2-(3-pyridyl)-benzoxazol-6-yl]-4,5-dihydro-3(2H)-pyridazinone, 5-methyl-6-[2-(2-pyrazinyl)-benzoxazol-6-yl]-4,5-dihydro-3(2H)-pyridazinone, 5-methyl-6-[2-(4-pyridyl)-benzoxazol-6-yl]-4,5-dihydro-3(2H)-pyridazinone, 5-methyl-6-[2-(1-acetyl-piperidino)-benzoxazol-6-yl]-4,5-dihydro-3(2H)-pyridazinone, 5-methyl-6-[2-(4-methyl-5-oxazolyl)-benzoxazol-6-yl]-4,5-dihydro-3(2H)-pyridazinone, 5-methyl-6-[2-(5-pyrimidinyl)-benzoxazol-6-yl]-4,5-dihydro-3(2H)-pyridazinone, 5-methyl-6-[2-(2-amino-5-pyridyl)-benzoxazol-6-yl]-4,5-dihydro-3(2H)-pyridazinone, 6-[2-(2-pyridyl)-benzoxazol-6-yl]-4,5-dihydro-3(2H)-pyridazinone, 6-[2-(2-furyl)-benzoxazol-6-yl]-4,5-dihydro-3(2H)-pyridazinone, 5-methyl-6-[2-(4-thiomorpholino)-benzoxazol-6-yl]-4,5-dihydro-3(2H)-pyridazinone, 5-methyl-6-[2-(1-piperidino)-benzoxazol-6-yl]-4,5-dihydro-3(2H)-pyridazinone, 5-methyl-6-[2-(1-oxido-4-thiomorpholino)-benzoxazol-6-yl]-4,5-dihydro-3(2H)-pyridazinone, 5-methyl-6-[2-(1.1-dioxido-4-thiomorpholino)-benzoxazol-6-yl]-4,5-dihydro-3(2H)-pyridazinone, 5-methyl-6-[2-(4-methyl-1-piperazinyl)-benzoxazol-6-yl]-4,5-dihydro-3(2H)-pyridazinone, 5-methyl-6-[2-(4-carbethoxy-1-piperazinyl)-benzoxazol-6-yl]-4,5-dihydro-3(2H)-pyridazinone, 5-methyl-6-[2-(1-pyrrolidinyl)-benzoxazol-6-yl]-4,5-dihydro-3(2H)-pyridazinone, 5-methyl-6-[2-(1-piperazinyl)-benzoxazol-6-yl]-4,5-dihydro-3(2H)-pyridazinone, 5-methyl-6-[2-(4-methyl-1-imidazolyl)-benzoxazol-6-yl]-4,5-dihydro-3(2H)-pyridazinone, 6-[2-(1-piperidino)-benzoxazol-6-yl]-4,5-dihydro-3(2H)-pyridazinone, 6-[2-(4-morpholino)-benzoxazol-6-yl]-4,5-dihydro-3(2H)-pyridazinone, 6-[2-(1-pyrrolidinyl)-benzoxazol-6-yl]-4,5-dihydro-3(2H)-pyridazinone, 6-[2-(4-methyl-1-imidazolyl)-benzoxazol-6-yl]-4,5-dihydro-3(2H)-pyridazinone, 6-[2-(4-carbethoxy-1-piperazinyl)-benzoxazol-6-yl]-4,5-dihydro-3(2H)-pyridazinone, 6-[2-(1-piperazinyl)-benzoxazol-6-yl]-4,5-dihydro-3(2H)-pyridazinone, 6-[2-(1-oxido-4-thiomorpholino)-benzoxazol-6-yl]-4,5-dihydro-3(2H)-pyridazinone, 6-[2-(1.1-dioxido-4-thiomorpholino)-benzoxazol-6-yl]-4,5-dihydro-3(2H)-pyridazinone, 6-[2-(4-methyl-1-piperazinyl)-benzoxazol-6-yl]-4,5-dihydro-3(2H)-pyridazinone, 6-[2-(4-thiomorpholino)-benzoxazol-6-yl]-4,5-dihydro-3(2H)-pyridazinone, 5-methyl-6-[2-(1-imidazolyl)-benzoxazol-6-yl]-4,5-dihydro-3(2H)-pyridazinone, 5-methyl-6-[2-(4-morpholino)-benzoxazol-6-yl]-4,5-dihydro-3(2H)-pyridazinone, 6-[2-(3-thienyl)-benzoxazol-6-yl]-4,5-dihydro-3(2H)-pyridazinone, 5-methyl-6-[2-(2-acetamido-5-pyridyl)-benzoxazol-6-yl]-4,5-dihydro-3(2H)-pyridazinone, 5-methyl-6-[2-(2,6-dichloro-3-pyridyl)-benzoxazol-6-yl]-4,5-dihydro-3(2H)-pyridazinone and 5-methyl-6-[2-(2-chloro-6-morpholino-3-pyridyl)-benzoxazol-6-yl]-4,5-dihydro-3(2H)-pyridazinone, the tautomers, enantiomers, diastereomers, the mixtures thereof and the salts thereof.

In another aspect the invention also relates to the regio- or stereoisomeric forms, e.g. tautomers, stereoisomers (e.g. enantiomers, diastereomers) of the compounds of formula I according to the invention, the mixtures and salts thereof, particularly the pharmaceutically acceptable salts.

In another aspect the invention relates to compounds of formula I as described herein, the tautomers, enantiomers, diastereomers, the mixtures thereof or the pharmaceutically acceptable salts thereof, for use as pharmaceutical compositions.

In another aspect the invention relates to a pharmaceutical composition containing as active substance at least one compound of formula I according to the invention, or a tautomer, enantiomer, diastereomer, mixture or pharmaceutically acceptable salt of such a compound, optionally in addition to one or more conventional carriers and/or diluents.

In another aspect the invention relates to the use of at least one compound of formula I according to the invention or a tautomer, enantiomer, diastereomer, mixture or pharmaceutically acceptable salt thereof, for preparing a pharmaceutical composition for the prevention and/or treatment of metabolic diseases, such as for example those mentioned herein.

In another aspect the invention relates to the use of at least one compound of formula I according to the invention or a tautomer, enantiomer, diastereomer, mixture or pharmaceutically acceptable salt of such a compound according to the invention, for preparing a pharmaceutical composition that is suitable for the prevention and/or treatment of diseases or conditions that can be influenced by binding to and modulating the activity of the G-protein coupled receptor GPR119.

In another aspect the invention relates to compounds of formula I according to the invention as disclosed herein, the tautomers, enantiomers, diastereomers thereof, the mixtures thereof or the pharmaceutically acceptable salts thereof, for use in the prevention and/or treatment of metabolic diseases (particularly obesity and diabetes, predominantly type 2 diabetes).

In another aspect the invention relates to compounds of formula I according to the invention, the tautomers, enantiomers, diastereomers thereof, the mixtures thereof or the pharmaceutically acceptable salts thereof, for use in preventing, delaying, slowing the progression of and/or treating metabolic diseases, particularly in improving the glycaemic control and/or beta cell function in the patient.

In another aspect the invention relates to compounds of formula I according to the invention, the tautomers, enantiomers, diastereomers thereof, the mixtures thereof or the pharmaceutically acceptable salts thereof, for use in preventing, delaying, slowing the progression of and/or treating type 2 diabetes, overweight, obesity, complications of diabetes and associated pathological conditions.

In another aspect the invention relates to compounds of formula I according to the invention as disclosed herein, the tautomers, enantiomers, diastereomers thereof, the mixtures thereof or the pharmaceutically acceptable salts thereof, for use in one or more of the following processes:

- for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);
- for improving glycaemic control and/or reducing fasting plasma glucose, postprandial plasma glucose and/or the glycosylated haemoglobin HbA1c;
- for preventing, delaying, slowing or reversing the progression of disrupted glucose tolerance, insulin resistance and/or metabolic syndrome to type 2 diabetes;
- for preventing, delaying, slowing the progression of or treating a condition or a disease selected from among the complications of diabetes, such as for example retinopathy, nephropathy or neuropathies, diabetic foot, ulcers or macroangiopathies;
- for reducing weight or preventing weight gain or assisting weight loss;
- for preventing or treating the degradation of pancreatic beta cells and/or improving and/or restoring the functionality of pancreatic beta cells and/or restoring the functionality of pancreatic insulin secretion;
- for maintaining and/or improving insulin sensitivity and/or preventing or treating hyperinsulinaemia and/or insulin resistance.

In another aspect the invention relates to a process for the prevention and/or treatment of metabolic diseases, such as for example those mentioned herein, this process comprising administering an effective amount of a compound of formula I according to the invention, or a tautomer, enantiomer, diastereomer, a mixture or a pharmaceutical acceptable salt thereof, to the patient (particularly a human patient).

In another aspect the invention relates to a compound of formula I according to the invention or a tautomer, enantiomer, diastereomer, mixture or pharmaceutically acceptable salt of such a compound according to the invention, for use in the prevention and/or treatment of metabolic diseases or conditions (as described herein, for example), which are affected by binding to and modulating the activity of the G-protein coupled receptor GPR119, particularly diabetes or obesity, preferably type 2 diabetes.

In another aspect the invention relates to a compound of formula I according to the invention or a tautomer, enantiomer, diastereomer, mixture or pharmaceutically acceptable salt of such a compound according to the invention, for binding to and modulating the activity of the G-protein coupled receptor GPR119, particularly for use as a GPR119 agonist, preferably for the treatment of diabetes or obesity, preferably type 2 diabetes.

In another aspect the invention relates to a process for preparing a pharmaceutical composition according to the invention, wherein a compound according to the invention is incorporated in one or more conventional carriers and/or diluents preferably by a non-chemical method.

In another aspect the invention relates to a process for preparing the compounds of formula I according to the invention, the tautomers, enantiomers, diastereomers, the mixtures thereof and the salts thereof.

Further aspects of the invention will become apparent from the foregoing and following embodiments of the description (comprising the Examples) as well as the claims.

Unless stated otherwise, the groups, residues and substituents, particularly G, A, $R^1$-$R^{15}$, $R^{81}$ and $R^{141}$, have the meanings given hereinbefore and hereinafter.

If residues, substituents, fragments or groups occur more than once in a compound, they are independent of one another and may have the same or different meanings.

Compounds according to the invention that are more worthy of mention are those compounds of formula I wherein $R^1$ denotes hydrogen, 1-4C-alkyl, 3-7C-cycloalkyl, 3-7C-cycloalkyl-1-4C-alkyl, 1-4C-alkenyl, 1-4C-alkynyl, 1-4C-alkoxy, 1-4C-alkoxy-1-4C-alkyl, wholly or partially fluorine substituted 1-4C-alkyl, or wholly or partially fluorine substituted 1-4C-alkoxy, A denotes $CR^2R^3$, O, S, or $NR^2$, wherein $R^2$ denotes a group selected from among hydrogen, 1-4C-alkyl and 1-4C-alkenyl, or $R^1$ and $R^2$ together represent a bond, or a 1-4C-alkanediyl group wherein optionally one or two $—CH_2—$ groups may each be replaced by —O—, and $R^3$ denotes hydrogen, G denotes a bicyclic system selected from among the following systems G1, G2 and G3:

G1

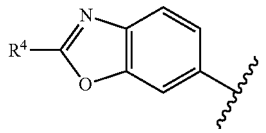

G2

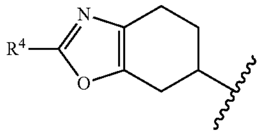

and

G3

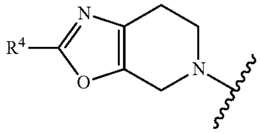

, wherein $R^4$ denotes a group optionally substituted by one, two or three $R^5$ and/or $R^6$, which may be identical or different, selected from among 3-7C-cycloalkyl, aryl and heteroaryl, wherein each $R^5$ independently denotes hydrogen or a group optionally substituted by one to four $R^{10}$ and/or $R^{11}$ and/or $R^{12}$, which may be identical or different, selected from among:

1-4C-alkyl, 1-4C-alkenyl, heterocyclyl, phenyl-1-4C-alkyl and heterocyclyl-1-4C-alkyl, wherein each $R^6$ independently denotes hydrogen or a group selected from among:

halogen, trifluoromethyl, cyano, oxo,

—$OR^7$, —$N(R^7)R^8$, —$SR^7$,

—$C(O)OR^7$, —$C(O)N(R^7)R^8$, —$S(O)_2N(R^7)R^8$,

—$C(O)R^9$, —$S(O)_2R^9$, —$S(O)R^9$,

—$N(R^{81})C(O)OR^7$, —$N(R^{81})C(O)N(R^7)R^8$, —$N(R^{81})S(O)_2N(R^7)R^8$,

—$N(R^{81})C(O)R^9$, —$N(R^{81})S(O)_2R^9$ and —$N(R^{81})S(O)R^9$, wherein each $R^7$ independently denotes hydrogen or a group optionally substituted by one to four $R^{10}$ and/or $R^{11}$ and/or $R^{12}$, which may be identical or different, selected from among:

1-4C-alkyl, 3-7C-cycloalkyl, 3-7C-cycloalkyl-1-4C-alkyl, 1-4C-alkenyl, aryl, heteroaryl, heterocyclyl, aryl-1-4C-alkyl, heteroaryl-1-4C-alkyl and heterocyclyl-1-4C-alkyl, each $R^8$ independently denotes hydrogen or a group selected from among:

1-4C-alkyl and 3-7C-cycloalkyl, or $R^7$ and $R^8$ together represent a 1-9C-alkanediyl group wherein optionally one or two —$CH_2$— groups may each be replaced by —O, —$NR^{81}$, —S, —SO or —$SO_2$—, each $R^{81}$ independently denotes hydrogen or 1-4C-alkyl, each $R^9$ independently denotes a group optionally substituted by one to four $R^{10}$ and/or $R^{11}$ and/or $R^{12}$, which may be identical or different, selected from among:

1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl and heterocyclyl-1-4C-alkyl, wherein each $R^{10}$ independently denotes a group selected from among:

hydrogen, 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl and heterocyclyl-1-4C-alkyl, each $R^{11}$ independently denotes hydrogen or a group selected from among:

halogen, trifluoromethyl, cyano, oxo,

—$OR^{13}$, —$N(R^{13})R^{14}$ and —$SR^{13}$, each $R^{12}$ independently denotes hydrogen or a group selected from among:

—$C(O)OR^{13}$, —$C(O)N(R^{13})R^{14}$, —$S(O)_2N(R^{13})R^{14}$,

—$C(O)R^{15}$, —$S(O)_2R^{15}$, —$S(O)R^{15}$,

—$N(R^{141})C(O)OR^{13}$, —$N(R^{141})C(O)N(R^{13})R^{14}$, —$N(R^{141})S(O)_2N(R^{13})R^{14}$,

—$N(R^{141})C(O)R^{15}$, —$N(R^{141})S(O)_2R^{15}$, and —$N(R^{141})S(O)R^{15}$, wherein each $R^{13}$ independently denotes a group selected from among:

hydrogen, 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl and heterocyclyl-1-4C-alkyl, each $R^{14}$ independently denotes a group selected from among:

hydrogen, 1-4C-alkyl and 3-7C-cycloalkyl, or $R^{13}$ and $R^{14}$ together represent a 1-9C-alkanediyl group wherein optionally one or two —$CH_2$— groups may each be replaced by —O, —$NR^{141}$, —S, —SO or —$SO_2$—, each $R^{141}$ independently denotes hydrogen or 1-4C-alkyl, each $R^{15}$ independently denotes a group selected from among:

1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl and heterocyclyl-1-4C-alkyl, wherein aryl, on its own or as part of another group, denotes a carbocyclic aromatic monocyclic ring system containing 6 carbon atoms, which may optionally be annelated to a second 5- or 6-membered carbocyclic aromatic, saturated or unsaturated ring system, heteroaryl, on its own or as part of another group, denotes a 5- to 12-membered, aromatic, monocyclic or condensed-polycyclic ring system containing 1 to 4 identical or different heteroatoms independently selected from among N, O and $S(O)_r$, with r=0, 1 or 2, wherein at least one of the heteroatoms is part of the aromatic ring, and heterocyclyl, on its own or as part of another group, denotes a 3- to 12-membered, saturated, unsaturated or aromatic, monocyclic or condensed, bridged or spiro-polycyclic ring system containing 1 to 4 identical or different heteroatoms independently selected from among N, O and $S(O)_r$, with r=0, 1 or 2, wherein none of the heteroatoms is part of the aromatic ring;

the tautomers, enantiomers, diastereomers, the mixtures thereof and the salts thereof.

Compounds according to the invention deserving special mention are those compounds of formula I, wherein $R^1$ denotes hydrogen, 1-4C-alkyl or 1-4C-alkoxy, A denotes $CR^2R^3$, O, S, or $NR^2$, wherein $R^2$ denotes a group selected from among hydrogen, 1-4C-alkyl and 1-4C-alkenyl, or $R^1$ and $R^2$ together represent a bond or a 1-4C-alkanediyl group, and $R^3$ denotes hydrogen, G denotes a bicyclic system selected from among the following systems G1, G2 and G3:

G1

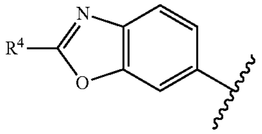

G2

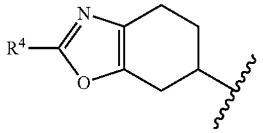

and

G3

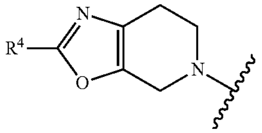

wherein $R^4$ denotes a phenyl group optionally substituted by one or two $R^5$ and/or $R^6$, which may be identical or different, wherein each $R^5$ independently denotes hydrogen or a group optionally substituted by one to four, preferably one or two, $R^{10}$ and/or $R^{11}$ and/or $R^{12}$ which may be identical or different, selected from among:

1-4C-alkyl, 1-4C-alkenyl, heterocyclyl, phenyl-1-4C-alkyl and heterocyclyl-1-4C-alkyl, wherein each $R^6$ independently denotes hydrogen or a group selected from among:

halogen, cyano, —$OR^7$ and —$N(R)R^8$, wherein each $R^7$ independently denotes hydrogen or a group optionally substituted by one to four, preferably one or two $R^{10}$ and/or $R^{11}$ and/or $R^{12}$, which may be identical or different, selected from among:

1-4C-alkyl, 1-4C-alkenyl, 1-4C-alkenyl, 3-7C-cycloalkyl, 3-7C-cycloalkyl-1-4C-alkyl, phenyl, heterocyclyl, phenyl-1-4C-alkyl, heteroaryl-1-4C-alkyl and heterocyclyl-1-4C-alkyl, each $R^8$ independently denotes hydrogen or 1-4C-alkyl, or $R^7$ and $R^8$ together represent a 1-7C-alkanediyl group wherein optionally one or two —$CH_2$— groups may each be replaced by —O, —$NR^{81}$, —S, —SO or —$SO_2$—, each $R^{81}$ independently denotes hydrogen or 1-4C-alkyl, wherein each $R^{10}$ independently denotes a group selected from among:

hydrogen, 1-4C-alkyl and heterocyclyl, each $R^{11}$ independently denotes hydrogen or a group selected from among:

halogen, cyano, oxo, —$OR^{13}$ and —$N(R^{13})R^{14}$, each $R^{12}$ independently denotes hydrogen or a group selected from among:

—$C(O)OR^{13}$, —$C(O)N(R^{13})R^{14}$, —$C(O)R^{15}$ and —$S(O)_2R^{15}$, wherein each $R^{13}$ independently denotes a group selected from among:

hydrogen and 1-4C-alkyl, each $R^{14}$ independently denotes a group selected from among:

hydrogen and 1-4C-alkyl, or $R^{13}$ and $R^{14}$ together represent a 1-7C-alkanediyl group wherein optionally one or two —$CH_2$— groups may each be replaced by —O, —$NR^{141}$, —S, —SO or —$SO_2$—, each $R^{141}$ independently denotes hydrogen or 1-4C-alkyl, each $R^{15}$ independently denotes a group selected from among:

1-4C-alkyl, wherein heteroaryl, on its own or as part of another group, denotes a 5- or 6-membered aromatic, monocyclic ring system containing 1 to 3 identical or different heteroatoms independently selected from among N, O and S, and heterocyclyl, on its own or as part of another group, denotes a 3- to 12-membered, saturated, monocyclic or bridged or spiro-bicyclic ring system containing 1 or 2 identical or different heteroatoms independently selected from among N, O and $S(O)_r$, with r=0, 1 or 2;

the tautomers, enantiomers, diastereomers, the mixtures thereof and the salts thereof.

In one embodiment, preferred compounds according to the invention are those compounds of formula I wherein $R^1$ denotes 1-4C-alkyl, particularly methyl or ethyl, A denotes $CR^2R^3$, O, S, or NH, wherein $R^2$ denotes a group selected from among hydrogen and 1-4C-alkyl, particularly hydrogen, methyl, ethyl or propyl, or $R^1$ and $R^2$ together represent a 1-2C-alkanediyl group, and $R^3$ denotes hydrogen, G denotes a bicyclic system selected from among the following systems G1, G2 and G3:

G1

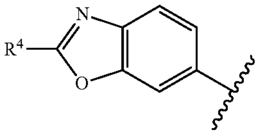

G2

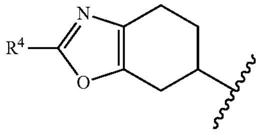

and

G3

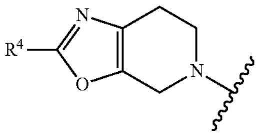

, wherein $R^4$ denotes a phenyl group optionally substituted by one or two $R^5$ and/or $R^6$, which may be identical or different, wherein each $R^5$ independently denotes hydrogen, 1-4C-alkyl or heterocyclyl, wherein each $R^6$ independently denotes hydrogen or a group selected from among:

halogen, cyano, —$OR^7$ and —$N(R^7)R^8$, wherein each $R^7$ independently denotes a group selected from among: hydrogen, 1-4C-alkyl, 3-7C-cycloalkyl, 3-7C-cycloalkyl-1-4C-alkyl, $H_2N$-2-4C-alkyl, mono- or di-(1-4C-alkylamino)-2-4C-alkyl, 1-4C-alkoxy-2-4C-alkyl, hydroxy-2-4C-alkyl, 1-4C-alkoxycarbonyl-1-4C-alkyl, phenyl, heterocyclyl, benzyl, 2-phenylethyl, heteroaryl-1-4C-alkyl and heterocyclyl-1-4C-alkyl, wherein 3-7C-cycloalkyl, on its own or as part of another group, may optionally be substituted by a hydroxy, mono- or di-1-4C-alkylamino, or heterocyclyl, each $R^8$ independently denotes hydrogen or 1-4C-alkyl, or $R^7$ and $R^8$ together represent a 1-7C-alkanediyl group wherein optionally one or two —$CH_2$— groups may each be replaced by —O, —$NR^{81}$, —S, —SO or —$SO_2$—, each $R^{81}$ independently denotes hydrogen or 1-4C-alkyl, wherein heteroaryl, on its own or as part of another group, denotes a 5- or 6-membered aromatic, monocyclic ring system containing 1 to 3 identical or different heteroatoms independently selected from among N, O and S, which may optionally be substituted by one or two, identical or different halogen and/or 1-4C-alkyl, and heterocyclyl, on its own or as part of another group, denotes a 3- to 12-membered, saturated, monocyclic or bridged or spiro-bicyclic ring system containing 1 or 2 identical or different heteroatoms independently selected from among N, O and $S(O)_r$ with r=0, 1 or 2, which may optionally be substituted by one to four, preferably one or two, identical or different halogen, cyano, 1-4C-alkoxycarbonyl and/or 1-4C-alkyl, the tautomers, enantiomers, diastereomers, the mixtures thereof and the salts thereof.

In another embodiment, preferred compounds according to the invention are compounds of formula I, wherein $R^1$ 1 denotes -4C-alkyl, particularly methyl or ethyl, A denotes $CR^2R^3$, O, S, or NH, wherein $R^2$ denotes a group selected from among 1-4C-alkyl, particularly methyl, ethyl, or propyl, or $R^1$ and $R^2$ together represent a 1-2C-alkanediyl group, and $R^3$ denotes hydrogen, G denotes a bicyclic system selected from among the following systems G1, G2 and G3:

G1

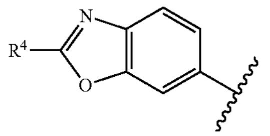

G2

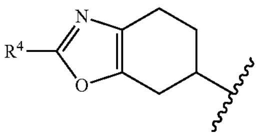

and

G3

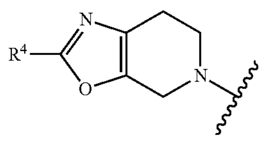

wherein $R^4$ denotes a group optionally substituted by one or two, identical or different $R^5$ and/or $R^6$ selected from among phenyl and heteroaryl, wherein each $R^5$ independently denotes hydrogen, 1-4C-alkyl or heterocyclyl, wherein each $R^6$ independently denotes hydrogen or a group selected from among: halogen, cyano, —$OR^7$ and —$N(R^7)R^8$, wherein each $R^7$ independently denotes a group selected from among: hydrogen, 1-4C-alkyl, 3-7C-cycloalkyl, 3-7C-cycloalkyl-1-4C-alkyl, $H_2N$-2-4C-alkyl, mono- or di-(1-4C-alkylamino)-2-4C-alkyl, 1-4C-alkoxy-2-4C-alkyl, hydroxy-2-4C-alkyl, 1-4C-alkoxycarbonyl-1-4C-alkyl, phenyl, heterocyclyl, benzyl, 2-phenylethyl, heteroaryl-1-4C-alkyl and heterocyclyl-1-4C-alkyl, wherein 3-7C-cycloalkyl, on its own or as part of another group, may optionally be substituted by a hydroxy, mono- or di-1-4C-alkylamino, or heterocyclyl, each $R^8$ independently denotes hydrogen or 1-4C-alkyl, or $R^7$ and $R^8$ together represent a 1-7C-alkanediyl group wherein optionally one or two —$CH_2$— groups may each be replaced by —O, —$NR^{81}$, —S, —SO or —$SO_2$—, each $R^{81}$ independently denotes hydrogen or 1-4C-alkyl, wherein heteroaryl, on its own or as part of another group, denotes a 5- or 6-membered aromatic, monocyclic ring system containing 1 to 3 identical or different heteroatoms independently selected from among N, O and S, which may optionally be substituted by one or two, identical or different halogen and/or 1-4C-alkyl, and heterocyclyl, on its own or as part of another group, denotes a 3- to 12-membered, saturated, monocyclic or bridged or spiro-bicyclic ring system containing 1 or 2 identical or different heteroatoms independently selected from among N, O and $S(O)_r$ with r=0, 1 or 2, which may optionally be substituted by one to four, preferably one or two, identical or different halogen, cyano, 1-4C-alkoxycarbonyl and/or 1-4C-alkyl, the tautomers, enantiomers, diastereomers, the mixtures thereof and the salts thereof.

Particularly preferred compounds according to the invention are compounds of formula I, wherein $R^1$ denotes 1-4C-alkyl, particularly methyl or ethyl, A denotes $CR^2R^3$, O, S, or NH, wherein $R^2$ denotes a group selected from among hydrogen and 1-4C-alkyl, particularly hydrogen, methyl, ethyl or propyl, or $R^1$ and $R^2$ together represent a 1-2C-alkanediyl group, and $R^3$ denotes hydrogen, G denotes a bicyclic system G1:

G1

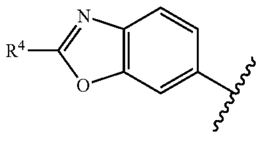

wherein $R^4$ denotes a phenyl group optionally substituted by $R^6$ and/or one or two, identical or different halogen and/or 1-2C-alkyl, wherein $R^6$ denotes —$OR^7$, wherein the phenyl group carries the substituent $R^6$ in the meta or para position, relative to the point of attachment of the phenyl group to the system G1, wherein each $R^7$ independently denotes a group selected from among: hydrogen, 1-4C-alkyl, 3-7C-cycloalkyl, 3-7C-cycloalkyl-1-4C-alkyl, di-(1-4C-alkylamino)-2-4C-alkyl, 1-4C-alkoxy-2-4C-alkyl, hydroxy-2-4C-alkyl, 1-4C-alkoxycarbonyl-1-4C-alkyl, phenyl, heterocyclyl, benzyl, 2-phenylethyl, heteroaryl-1-4C-alkyl and heterocyclyl-1-4C-alkyl, wherein 3-7C-cycloalkyl, on its own or as part of another group, may optionally be substituted by a hydroxy, di-1-4C-alkylamino, piperidin-1-yl, pyrrolidin-1-yl or morpholin-1-yl, wherein heteroaryl, on its own or as part of another group, denotes a 5- or 6-membered aromatic, monocyclic ring system containing 1 to 3 identical or different heteroatoms independently selected from among N, O and S, which may optionally be substituted by one or two identical or different halogen and/or 1-4C-alkyl, and heterocyclyl, on its own or as part of another group, denotes a 3- to 12-membered, saturated, monocyclic or bridged or spiro-bicyclic ring system containing 1 or 2 identical or different heteroatoms independently selected from among N, O and $S(O)_r$, with r=0, 1 or 2, which may optionally be substituted by one to four, preferably one or two identical or different halogen, cyano, 1-4C-alkoxycarbonyl and/or 1-4C-alkyl, the tautomers, enantiomers, diastereomers, the mixtures thereof and the salts thereof.

Some particular definitions of the groups and substituents of the compounds according to the invention are given below.

Particular embodiments of the present invention are characterised by the following definitions:

In one embodiment of the present invention $R^1$ is selected from the group a1 consisting of: hydrogen, 1-4C-alkyl, 3-7C-cycloalkyl and 1-4C-alkoxy.

In another embodiment of the present invention $R^1$ is selected from the group a2 consisting of: hydrogen, methyl, ethyl, propyl, isopropyl, cyclopropyl and methoxy.

In another embodiment of the present invention $R^1$ is selected from the group a3 consisting of: methyl and ethyl.

In one embodiment of the present invention

A is selected from the group b1 consisting of: $CR^2R^3$, wherein $R^2$ denotes hydrogen, 1-4C-alkyl or 1-4C-alkenyl, and $R^3$ denotes hydrogen.

In another embodiment of the present invention

A is selected from the group b2 consisting of: $CR^2R^3$, wherein $R^2$ denotes hydrogen, methyl, ethyl, propyl, butyl or allyl, and $R^3$ denotes hydrogen.

In another embodiment of the present invention

A is selected from the group b3 consisting of: $CR^2R^3$, wherein $R^2$ denotes methyl, ethyl or propyl, and $R^3$ denotes hydrogen.

In another embodiment of the present invention

A is selected from the group b4 consisting of: $CR^2R^3$, wherein $R^2$ denotes hydrogen, and $R^3$ denotes hydrogen.

In another embodiment of the present invention

A is selected from the group b5 consisting of: O, S and NH.

In another embodiment of the present invention

A is selected from the group b6 consisting of: O.

In another embodiment of the present invention

A is selected from the group b7 consisting of: S.

In another embodiment of the present invention

A is selected from the group b8 consisting of: NH.

In one embodiment of the present invention $R^1$ and A are selected from the group c1 consisting of the following combinations for $R^1$ and A:

$R^1$ is hydrogen, 1-4C-alkyl, 3-7C-cycloalkyl or 1-4C-alkoxy, preferably $R^1$ denotes hydrogen, methyl, ethyl, propyl, isopropyl or methoxy, more preferably $R^1$ denotes methyl or ethyl, and A is $CR^2R^3$, O, S or NH, wherein $R^2$ denotes hydrogen, 1-4C-alkyl or 1-4C-alkenyl, preferably $R^2$ denotes hydrogen, methyl, ethyl or propyl, and $R^3$ denotes hydrogen;

A is $CR^2R^3$, wherein $R^1$ and $R^2$ together represent a bond;

and $R^3$ denotes hydrogen;

and

A is $CR^2R^3$, wherein $R^1$ and $R^2$ together represent a 1-4C-alkanediyl group wherein optionally one or two $—CH_2—$ groups may each be replaced by —O—, preferably $R^1$ and $R^2$ together represent a $—CH_2$ or $—CH_2—CH_2—$ group, and $R^3$ denotes hydrogen.

In another embodiment of the present invention $R^1$ and A are selected from the group c2 consisting of the following combination for $R^1$ and A:

$R^1$ is hydrogen, methyl, ethyl, propyl, isopropyl or methoxy, preferably $R^1$ denotes methyl, and A is $CR^2R^3$, wherein $R^2$ denotes hydrogen or 1-4C-alkyl, preferably $R^2$ denotes hydrogen, methyl, ethyl or propyl, and $R^3$ denotes hydrogen.

In another embodiment of the present invention $R^1$ and A are selected from the group c3 consisting of the following combination for $R^1$ and A:

$R^1$ is hydrogen, methyl, ethyl, propyl, isopropyl or methoxy, preferably $R^1$ denotes ethyl, and A is $CR^2R^3$, wherein $R^2$ denotes hydrogen or 1-4C-alkyl, preferably $R^2$ denotes hydrogen, methyl, ethyl or propyl, and $R^3$ denotes hydrogen.

In another embodiment of the present invention $R^1$ and A are selected from the group c4 consisting of the following combination for $R^1$ and A:

$R^1$ is hydrogen, methyl, ethyl, propyl, isopropyl or methoxy, preferably $R^1$ denotes methyl or ethyl, and A is $CR^2R^3$, wherein $R^2$ denotes hydrogen, and $R^3$ denotes hydrogen.

In another embodiment of the present invention $R^1$ and A are selected from the group c5 consisting of the following combination for $R^1$ and A:

$R^1$ is hydrogen, methyl, ethyl, propyl, isopropyl or methoxy, preferably $R^1$ denotes methyl or ethyl, and A is $CR^2R^3$, wherein $R^2$ denotes methyl, and $R^3$ denotes hydrogen.

In another embodiment of the present invention $R^1$ and A are selected from the group c6 consisting of the following combination for $R^1$ and A:

$R^1$ is hydrogen, methyl, ethyl, propyl, isopropyl or methoxy, preferably $R^1$ denotes methyl or ethyl, and A is $CR^2R^3$, wherein $R^2$ denotes ethyl, and $R^3$ denotes hydrogen.

In another embodiment of the present invention $R^1$ and A are selected from the group c7 consisting of the following combination for $R^1$ and A:

$R^1$ is hydrogen, methyl, ethyl, propyl, isopropyl or methoxy, preferably $R^1$ denotes methyl or ethyl, and A is $CR^2R^3$, wherein $R^2$ denotes propyl, and $R^3$ denotes hydrogen.

In another embodiment of the present invention $R^1$ and A are selected from the group c8 consisting of the following combination for $R^1$ and A:

$R^1$ is hydrogen, methyl, ethyl, propyl, isopropyl or methoxy, preferably $R^1$ denotes methyl or ethyl, and A is O.

In another embodiment of the present invention $R^1$ and A are selected from the group c9 consisting of the following combination for $R^1$ and A:

$R^1$ is hydrogen, methyl, ethyl, propyl, isopropyl or methoxy, preferably $R^1$ denotes methyl or ethyl, and A is S.

In another embodiment of the present invention $R^1$ and A are selected from the group c10 consisting of the following combination for $R^1$ and A:

$R^1$ is hydrogen, methyl, ethyl, propyl, isopropyl or methoxy, preferably $R^1$ denotes methyl or ethyl, and A is NH.

In another embodiment of the present invention $R^1$ and A are selected from the group c11 consisting of the following combination for $R^1$ and A:

A is $CR^2R^3$, wherein $R^1$ and $R^2$ together represent a bond;

and $R^3$ denotes hydrogen.

In another embodiment of the present invention $R^1$ and A are selected from the group c12 consisting of the following combination for $R^1$ and A:

A is $CR^2R^3$, wherein $R^1$ and $R^2$ together represent a 1-4C-alkanediyl group, preferably $R^1$ and $R^2$ together represent a $—CH_2$ or $—CH_2—CH_2—$ group.

In one embodiment of the present invention

G is selected from the group d1 consisting of:

G1

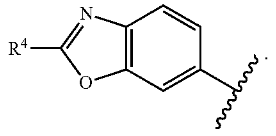

In another embodiment of the present invention

G is selected from the group d2 consisting of:

G2

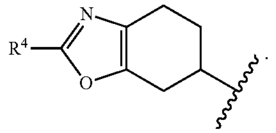

In another embodiment of the present invention

G is selected from the group d3 consisting of:

G3

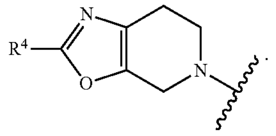

In one embodiment of the present invention $R^4$ is selected from the group e1 consisting of: a group optionally substituted by one, two or three identical or different $R^5$ and/or $R^6$ selected from among 3-7C-cycloalkyl (e.g. cyclopropyl), aryl (e.g. phenyl) and heteroaryl (e.g. thienyl, furanyl, pyrrolyl or pyridyl).

In another embodiment of the present invention $R^4$ is selected from the group e2 consisting of: a group optionally substituted by one or two identical or different $R^5$ and/or $R^6$ selected from among 5- or 6-membered monocyclic heteroaryl containing 1 to 3 identical or different heteroatoms independently selected from among N, O and S.

In another embodiment of the present invention $R^4$ is selected from the group e3 consisting of: a group optionally substituted by one or two identical or different $R^5$ and/or $R^6$ selected from among: phenyl.

In one embodiment of the present invention $R^5$ is selected from the group f1 consisting of: hydrogen, and a group optionally substituted by one to four, preferably one or two identical or different $R^{10}$ and/or $R^{11}$ and/or $R^{12}$ selected from among:

1-4C-alkyl, heterocyclyl, phenyl-1-4C-alkyl, and heterocyclyl-1-4C-alkyl.

In another embodiment of the present invention $R^5$ is selected from the group f2 consisting of: hydrogen, and a group optionally substituted by one to four, preferably one or two identical or different $R^{10}$ and/or $R^{11}$ and/or $R^{12}$ selected from among:

1-4C-alkyl, benzyl, 2-phenylethyl, heterocyclyl and heterocyclyl-1-2-alkyl, wherein heterocyclyl, on its own or as part of heterocyclyl-1-2-alkyl, denotes a 5- or 6-membered, saturated, monocyclic ring system containing 1 or 2 identical or different heteroatoms independently selected from among N, O and $S(O)_r$, with r=0, 1 or 2 (e.g. piperidinyl, pyrrolidinyl, piperazinyl, morpholinyl or thiomorpholinyl).

In another embodiment of the present invention $R^5$ is selected from the group f3 consisting of: hydrogen, 1-4C-alkyl, benzyl, 2-phenylethyl, $H_2N$-1-4C-alkyl, mono- or di-(1-4C-alkylamino)-1-4C-alkyl, 1-4C-alkoxy-1-4C-alkyl, heterocyclyl and heterocyclyl-1-2-alkyl, wherein heterocyclyl, on its own or as part of heterocyclyl-1-2-alkyl, denotes a group optionally substituted by one to four, preferably one or two identical or different halogen and/or 1-4C-alkyl selected from among piperidinyl (e.g. piperidin-1-yl), pyrrolidinyl (e.g. pyrrolidin-1-yl), piperazinyl (e.g. piperazin-1-yl) and morpholinyl (e.g. morpholin-4-yl).

In another embodiment of the present invention $R^5$ is selected from the group f4 consisting of: 1-3C-alkyl (e.g. methyl, ethyl or isopropyl).

In another embodiment of the present invention $R^5$ is selected from the group f5 consisting of: hydrogen.

In one embodiment of the present invention $R^6$ is selected from the group g1 consisting of: hydrogen, or a group selected from among: halogen, cyano, —$OR^7$ and —$N(R^7)R^8$.

In another embodiment of the present invention $R^6$ is selected from the group g2 consisting of: hydrogen.

In another embodiment of the present invention $R^6$ is selected from the group g3 consisting of: halogen.

In another embodiment of the present invention $R^6$ is selected from the group g4 consisting of: —$OR^7$.

In another embodiment of the present invention $R^6$ is selected from the group g5 consisting of: —$N(R^7)R^8$.

In another embodiment of the present invention $R^4$ has one of the following structures:

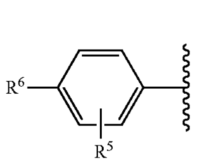 or 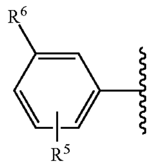, wherein in particular $R^5$ is hydrogen.

In another embodiment of the present invention $R^4$ has the following structure:

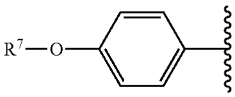, wherein $R^7$ is as herein defined.

In another embodiment of the present invention $R^4$ has the following structure:

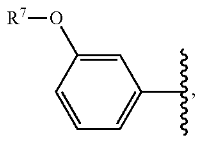, wherein $R^7$ is as herein defined.

In another embodiment of the present invention $R^4$ has the following unsubstituted structure:

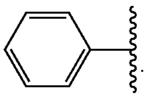.

In one embodiment of the present invention $R^7$ is selected from the group h1 consisting of: hydrogen, and a group optionally substituted by one to four, preferably one or two identical or different $R^{10}$ and/or $R^{11}$ and/or $R^{12}$ selected from among:

1-4C-alkyl, 3-7C-cycloalkyl, 3-7C-cycloalkyl-1-4C-alkyl, phenyl, heterocyclyl, phenyl-1-4C-alkyl, heteroaryl-1-4C-alkyl and heterocyclyl-1-4C-alkyl.

In another embodiment of the present invention $R^7$ is selected from the group h2 consisting of: hydrogen, and a group optionally substituted by one to four, preferably one or two identical or different $R^{10}$ and/or $R^{11}$ and/or $R^{12}$ selected from among:

1-4C-alkyl, 3-7C-cycloalkyl, 3-7C-cycloalkyl-1-2C-alkyl, phenyl, heterocyclyl, benzyl, 2-phenylethyl, heteroaryl-1-4C-alkyl and heterocyclyl-1-4C-alkyl, wherein heterocyclyl, on its own or as part of heterocyclyl-1-4C-alkyl, denotes a 3- to 12-membered, saturated, monocyclic or bridged or spiro-bicyclic ring system containing 1 or 2 identical or different heteroatoms independently selected from among N, O and $S(O)_r$ with r=0, 1 or 2 (e.g. piperidinyl, pyrrolidinyl, tetrahydrofuranyl, tetrahydropyranyl, homopiperidinyl, piperazinyl, morpholinyl, thiomorpholinyl, pyrrolidonyl, 2-azabicylo[2.2.1]heptyl or 3-aza-spiro[5.5]undecyl), and wherein heteroaryl, as part of heteroaryl-1-4C-alkyl, denotes a 5- or 6-membered, monocyclic aromatic ring system containing 1 to 3 identical or different heteroatoms independently selected from among N, O and S (e.g. pyridyl, pyrimidinyl, thienyl, pyrrolyl, furanyl, oxadiazolyl or oxazolyl).

In another embodiment of the present invention $R^7$ is selected from the group h3 consisting of: hydrogen, 1-4C-alkyl, 5-6C-cycloalkyl, 5-6C-cycloalkyl-1-2C-alkyl, $H_2N$-2-4C-alkyl, mono- or di-(1-4C-alkylamino)-2-4C-alkyl, 1-4C-alkoxy-2-4C-alkyl, hydroxy-2-4C-alkyl, 1-4C-alkoxycarbonyl-1-2C-alkyl, phenyl, heterocyclyl, benzyl, 2-phenylethyl, heteroaryl-1-4C-alkyl and heterocyclyl-1-4C-alkyl, wherein heterocyclyl, on its own or as part of heterocyclyl-1-4C-alkyl, denotes a group optionally substituted by one to four, preferably one or two identical or different halogen, cyano, 1-4C-alkoxycarbonyl and/or 1-4C-alkyl selected from among: 3- to 12-membered, saturated, monocyclic or bridged or spiro-bicyclic heterocyclyl containing 1 or 2 identical or different heteroatoms independently selected from among N, O and $S(O)_r$ with r=0, 1 or 2 (e.g. piperidinyl, pyrrolidinyl, tetrahydrofuranyl, tetrahydropyranyl, homopiperidinyl, piperazinyl, morpholinyl, thiomorpholinyl, 2-azabicylo[2.2.1]heptyl or 3-aza-spiro[5.5]undecyl), and wherein heteroaryl, as part of heteroaryl-1-4C-alkyl, denotes a group optionally substituted by one or two, identical or different halogen and/or 1-4C-alkyl selected from among 5- or 6-membered monocyclic heteroaryl containing 1 to 3 identical or different heteroatoms independently selected from among N, O and S (e.g. pyridyl, pyrimidinyl, thienyl, pyrrolyl, furanyl, oxadiazolyl or oxazolyl), and wherein 5-6C-cycloalkyl, on its own or as part of 5-6C-cycloalkyl-1-4C-alkyl, denotes a group optionally substituted by a hydroxy, mono- or di-1-4C-alkylamino, piperidino, pyrrolidino or morpholino selected from among: cyclohexyl and cyclopentyl.

In one embodiment of the present invention $R^8$ is selected from the group i1 consisting of: hydrogen and 1-4C-alkyl.

In another embodiment of the present invention $R^8$ is selected from the group i2 consisting of: hydrogen.

In another embodiment of the present invention $R^8$ is selected from the group i3 consisting of: 1-4C-alkyl.

In one embodiment of the present invention $R^9$ is selected from the group j1 consisting of: 1-4C-alkyl.

In one embodiment of the present invention $R^{10}$ is selected from the group k1 consisting of:

hydrogen, 1-4C-alkyl and heterocyclyl, wherein heterocyclyl denotes a 5- or 6-membered, saturated, monocyclic heterocyclyl containing 1 or 2 identical or different heteroatoms independently selected from among N, O and $S(O)_r$, with r=0, 1 or 2 (e.g. piperidinyl, pyrrolidinyl, morpholinyl or thiomorpholinyl).

In another embodiment of the present invention $R^{10}$ is selected from the group k2 consisting of: hydrogen.

In another embodiment of the present invention $R^{10}$ is selected from the group k3 consisting of: 1-4C-alkyl.

In one embodiment of the present invention $R^{11}$ is selected from the group l1 consisting of:

hydrogen, halogen, cyano, oxo, —$OR^{13}$ and —$N(R^{13})R^{14}$.

In another embodiment of the present invention $R^{11}$ is selected from the group l2 consisting of:

halogen, cyano, oxo, 1-4C-alkoxy, hydroxyl, —$NH_2$, and mono- or di-1-4C-alkylamino.

In another embodiment of the present invention $R^{11}$ is selected from the group l3 consisting of: hydrogen.

In one embodiment of the present invention $R^{12}$ is selected from the group m1 consisting of:

hydrogen, —$C(O)OR^{13}$, —$C(O)N(R^{13})R^{14}$, —$C(O)R^{15}$ and —$S(O)_2R^{15}$, In another embodiment of the present invention $R^{12}$ is selected from the group m2 consisting of:

—$C(O)OR^{13}$, —$C(O)N(R^{13})R^{14}$, —$C(O)R^{15}$, and —$S(O)_2R^{15}$, wherein each $R^{13}$, $R^{14}$ independently denotes hydrogen or 1-4C-alkyl, or $R^{13}$ and $R^{14}$ together represent a 1-7C-alkanediyl group wherein optionally one or two —$CH_2$— groups may each be replaced by —O, —$NR^{141}$, —S, —SO or —$SO_2$—, and $R^{141}$ denotes hydrogen or 1-4C-alkyl, and $R^{15}$ denotes 1-4C-alkyl.

In another embodiment of the present invention $R^{12}$ is selected from the group m3 consisting of: hydrogen.

In another embodiment of the present invention $R^{12}$ is selected from the group m3 consisting of:

—$C(O)OR^{13}$, —$C(O)N(R^{13})R^{14}$, —$C(O)R^{15}$, and —$S(O)_2R^{15}$, wherein each $R^{13}$, $R^{14}$ or $R^{15}$ independently denotes 1-4C-alkyl, or $R^{13}$ and $R^{14}$ together and with the inclusion of the nitrogen atom to which they are attached, represent a piperidine, piperazine, morpholine or thiomorpholine.

In another embodiment of the present invention $R^{12}$ is selected from the group m4 consisting of: hydrogen.

In one embodiment of the present invention $R^{13}$ is selected from the group n1 consisting of: hydrogen.

In another embodiment of the present invention $R^{13}$ is selected from the group n2 consisting of: 1-4C-alkyl.

In one embodiment of the present invention $R^{14}$ is selected from the group o1 consisting of: hydrogen.

In another embodiment of the present invention $R^{14}$ is selected from the group o2 consisting of: 1-4C-alkyl.

In another embodiment of the present invention $R^{15}$ is selected from the group p1 consisting of: 1-4C-alkyl.

Within the present invention the above mentioned sets of definitions or embodiments may be combined with one another.

Individual embodiments of the compounds of formula I (including the tautomers and stereoisomers thereof, the mixtures thereof and the salts thereof) are each characterised by a combination of the embodiments disclosed hereinbefore and hereinafter.

The present invention includes all the stereoisomeric forms of the compounds of formula I and the salts thereof. Asymmetric carbon atoms in compounds of formula I may each independently be in the S configuration or R configuration. The invention includes all possible stereoisomers, particularly enantiomers and diastereomers, and mixtures of two or more stereoisomers (for example mixtures of enantiomers and/or diastereomers), in all quantities and ratios.

Numbering:

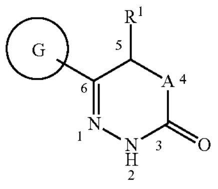

I

If $R^1$ is other than hydrogen and also $R^1$ and $R^2$ do not together denote a bond, the compounds of formula I according to the invention, the tautomers thereof and the salts thereof, have at least one stereogenic centre in position 5.

If A denotes $CR^2R^3$, wherein $R^2$ and $R^3$ are different and also $R^1$ and $R^2$ do not together denote a bond, the compounds of formula I according to the invention, the tautomers thereof and the salts thereof have at least one stereogenic centre in the 4 position.

If $R^1$ is other than hydrogen and A denotes $CR^2R^3$, wherein $R^2$ and $R^3$ are different, and also $R^1$ and $R^2$ do not together denote a bond, the compounds of formula I according to the invention, the tautomers thereof and the salts thereof, have at least two stereogenic centres, in the 4 position and 5 position.

Each of the stereogenic centres may assume the absolute configuration R or the absolute configuration S (according to the rules of Cahn, Ingold and Prelog). Accordingly, the possible stereoisomers (4R), (4S), (5R), (5S), (4R,5R), (4S,5S), (4R,5S) and (4S,5R), in which the numbers relates to the atoms designated in formula I below:

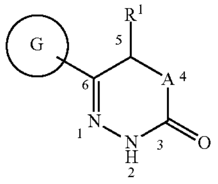

I the tautomers, mixtures and salts thereof, are regarded as part of the invention.

If G denotes a structure of formula G2, the compounds of formula I according to the invention, the tautomers thereof and the salts thereof, have at least one stereogenic centre in position 1' (i.e. the point of attachment of the pyridazinone structure to the fragment G2), and optionally—depending on the meanings of $R^1$ and A—further stereogenic centres in the 4 and/or 5 position:

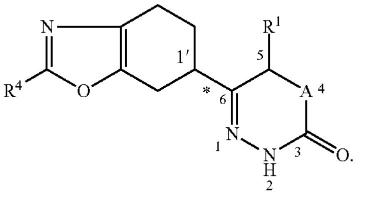

Each of the stereogenic centres may assume the absolute configuration R or the absolute configuration S (according to the rules of Cahn, Ingold and Prelog). Accordingly, the possible stereoisomers (1'R), (1'S), (1'R, 4R), (1'S, 4R), (1'R , 4S), (1'S, 4S), (1'R, 5R), (1'S, 5R), (1'R, 5S), (1'S, 5S), (1'R, 4R, 5R), (1'S, 4S, 5S), (1'S, 4R, 5R), (1'R, 4S, 5S), (1'R, 4S, 5R), (1'S, 4R, 5S), (1'R, 4R, 5S) and (1'S, 4S, 5R), in which the numbers relate to the atoms designated in the formula below:

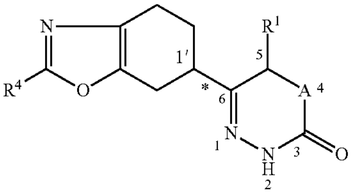

the tautomers, mixtures and salts thereof, are regarded as being part of the invention.

The compounds of formula I according to the invention, wherein the substituents have the meanings stated herein, with the proviso that neither is $R^1$ a hydrogen atom nor do $R^1$ and $R^2$ together denote a bond, are chiral compounds, with at least one chiral centre in position 5.

One embodiment of the compounds of formula I according to the invention relates to compounds of formula I*

I*

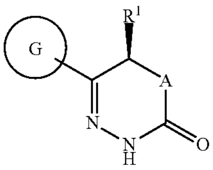

the tautomers and stereoisomers thereof, the mixtures thereof and the salts thereof.

A subsidiary embodiment relates to compounds of formula I*, wherein A denotes $CH_2$, the tautomers and stereoisomers thereof, the mixtures thereof and the salts thereof.

A subsidiary embodiment relates to compounds of formula I*, wherein A denotes O, the tautomers and stereoisomers thereof, the mixtures thereof and the salts thereof.

A subsidiary embodiment relates to compounds of formula I*, wherein A denotes S, the tautomers and stereoisomers thereof, the mixtures thereof and the salts thereof.

A subsidiary embodiment relates to compounds of formula I*, wherein A denotes $NR^2$ (particularly NH), the tautomers and stereoisomers thereof, the mixtures thereof and the salts thereof.

Another preferred embodiment of the compounds of formula I according to the invention relates to compounds of formula I**

I**

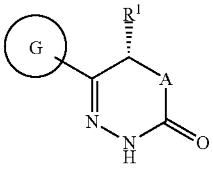

the tautomers and stereoisomers thereof, the mixtures thereof and the salts thereof.

A subsidiary embodiment relates to compounds of formula I**, wherein A denotes $CH_2$, the tautomers and stereoisomers thereof, the mixtures thereof and the salts thereof.

A subsidiary embodiment relates to compounds of formula I**, wherein A denotes O, the tautomers and stereoisomers thereof, the mixtures thereof and the salts thereof.

A subsidiary embodiment relates to compounds of formula I**, wherein A denotes S, the tautomers and stereoisomers thereof, the mixtures thereof and the salts thereof.

A subsidiary embodiment relates to compounds of formula I**, wherein A denotes $NR^2$ (particularly NH), the tautomers and stereoisomers thereof, the mixtures thereof and the salts thereof.

The compounds of formula I according to the invention, wherein A denotes $CR^2R^3$, i.e. compounds of formula Ia, wherein $R^2$ and $R^3$ are as herein defined, and the other substituents have the meanings stated herein, with the proviso that $R^1$ and $R^2$ do not together denote a bond, contains at least one chiral centre in position 5, if $R^1$ is not a hydrogen atom, and/or at least one chiral centre in the 4 position, if $R^2$ and $R^3$ are not identical.

Numbering:

Ia

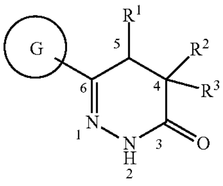

Compounds of formula Ia, wherein the substituents have the meanings stated herein, with the proviso that neither is $R^1$ a hydrogen atom nor do $R^1$ and $R^2$ together denote a bond, are chiral compounds with at least one chiral centre in position 5, and —if $R^2$ and $R^3$ are not identical—another chiral centre in the 4 position.

One embodiment of the compounds according to the invention relates to compounds of formula Ia'

Ia'

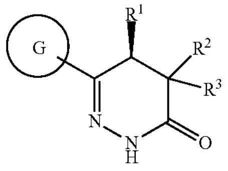

the tautomers and stereoisomers thereof, the mixtures thereof and the salts thereof.

A subsidiary embodiment relates to compounds of formula Ia', wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia', wherein $R^3$ denotes hydrogen and $R^2$ is different from hydrogen, the tautomers and stereoisomers thereof, the mixtures thereof and the salts thereof.

Another embodiment of the compounds according to the invention relates to compounds of formula Ia"

Ia"

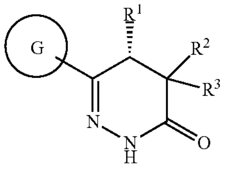

the tautomers and stereoisomers thereof, the mixtures thereof and the salts thereof.

A subsidiary embodiment relates to compounds of formula Ia", wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia", wherein $R^3$ denotes hydrogen and $R^2$ is different from hydrogen, the tautomers and stereoisomers thereof, the mixtures thereof and the salts thereof.

Compounds of formula Ia, wherein the substituents have the meanings stated herein, with the proviso that neither are $R^2$ and $R^3$ identical nor do $R^1$ and $R^2$ together denote a bond, are chiral compounds with at least one chiral centre in the 4 position, and —if $R^1$ is different from hydrogen—another chiral centre in position 5.

One embodiment of the compounds according to the invention relates to compounds of formula Ia"'

Ia"'

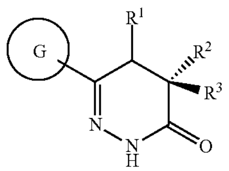

the tautomers and stereoisomers thereof, the mixtures thereof and the salts thereof.

A subsidiary embodiment relates to compounds of formula Ia"', wherein $R^1$ denotes hydrogen, the tautomers and stereoisomers thereof, the mixtures thereof and the salts thereof.

Another subsidiary embodiment relates to compounds of formula Ia"', wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia"', wherein $R^3$ denotes hydrogen and $R^2$ is different from hydrogen, the tautomers and stereoisomers thereof, the mixtures thereof and the salts thereof.

Another subsidiary embodiment relates to compounds of formula Ia"', wherein $R^1$ and $R^3$ both represent hydrogen and $R^2$ is different from hydrogen, the tautomers and stereoisomers thereof, the mixtures thereof and the salts thereof.

Another embodiment of the compounds according to the invention relates to compounds of formula Ia""

Ia""

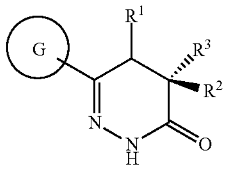

the tautomers and stereoisomers thereof, the mixtures thereof and the salts thereof.

A subsidiary embodiment relates to compounds of formula Ia"", wherein $R^1$ denotes hydrogen, the tautomers and stereoisomers thereof, the mixtures thereof and the salts thereof.

Another subsidiary embodiment relates to compounds of formula Ia"", wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia"", wherein $R^3$ denotes hydrogen and $R^2$ is different from hydrogen, the tautomers and stereoisomers thereof, the mixtures thereof and the salts thereof.

Another subsidiary embodiment relates to compounds of formula Ia"", wherein $R^1$ and $R^3$ both denote hydrogen and $R^2$ is different from hydrogen, the tautomers and stereoisomers thereof, the mixtures thereof and the salts thereof.

Compounds of formula Ia, wherein the substituents have the meanings stated herein, with the proviso that neither is $R^1$ a hydrogen atom, nor do $R^1$ and $R^2$ together denote a bond, nor are $R^2$ and $R^3$ identical, are chiral compounds with at least two chiral centres (one chiral centre in position 5 and another chiral centre in the 4 position).

One embodiment of the compounds according to the invention relates to compounds of formula Ia*

Ia*

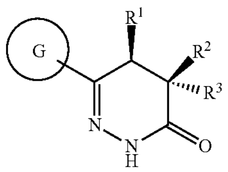

the tautomers and stereoisomers thereof, the mixtures thereof and the salts thereof.

A subsidiary embodiment relates to compounds of formula Ia*, wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia*, wherein $R^3$ denotes hydrogen and $R^2$ is different from hydrogen, the tautomers and stereoisomers thereof, the mixtures thereof and the salts thereof.

Another embodiment of the compounds according to the invention relates to compounds of formula Ia**

Ia**

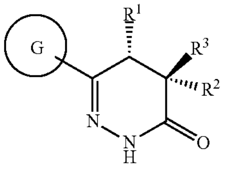

the tautomers and stereoisomers thereof, the mixtures thereof and the salts thereof.

A subsidiary embodiment relates to compounds of formula Ia**, wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia**, wherein $R^3$ denotes hydrogen and $R^2$ is different from hydrogen, the tautomers and stereoisomers thereof, the mixtures thereof and the salts thereof.

One embodiment of the compounds according to the invention relates to compounds of formula Ia***

Ia***

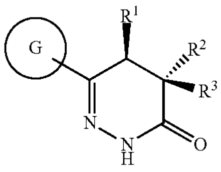

the tautomers and stereoisomers thereof, the mixtures thereof and the salts thereof.

A subsidiary embodiment relates to compounds of formula Ia***, wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia***, wherein $R^3$ denotes hydrogen and $R^2$ is different from hydrogen, the tautomers and stereoisomers thereof, the mixtures thereof and the salts thereof.

Another embodiment of the compounds according to the invention relates to compounds of formula Ia****

Ia****

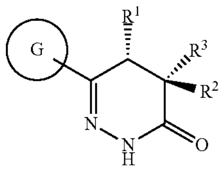

the tautomers and stereoisomers thereof, the mixtures thereof and the salts thereof.

A subsidiary embodiment relates to compounds of formula Ia****, wherein one of $R^2$ and $R^3$ denotes hydrogen and the other is different from hydrogen, the tautomers and stereoisomers thereof, the mixtures thereof and the salts thereof.

Another subsidiary embodiment relates to compounds of formula Ia****, wherein $R^3$ denotes hydrogen and $R^2$ is different from hydrogen, the tautomers and stereoisomers thereof, the mixtures thereof and the salts thereof.

The compounds of formula I according to the invention, wherein A has the meaning $CR^2H$, i.e. compounds of formula Ib, wherein $R^2$ asherein defined is different from hydrogen, and the other substituents have the meanings stated herein, with the proviso that neither is $R^1$ a hydrogen atom nor do $R^1$ and $R^2$ together denote a bond, are chiral compounds, with at least two chiral centres in the 5 position and in the 4 position.

Numbering:

Ib

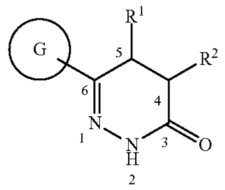

The substituents $R^1$ and $R^2$ of the compounds of formula Ib according to the invention are arranged either cis or trans relative to one another. Particularly preferred in the compounds according to the invention is the trans configuration of the substituents $R^1$ and $R^2$.

A preferred embodiment of the compounds of formula I according to the invention relates to compounds of formula Ib*

Ib*

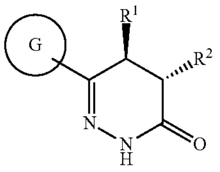

the tautomers and stereoisomers thereof, the mixtures thereof and the salts thereof.

A particularly preferred embodiment of the compounds of formula I according to the invention relates to compounds of formula Ib**

Ib**

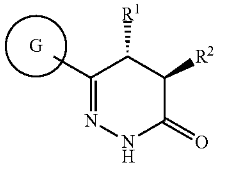

the tautomers and stereoisomers thereof, the mixtures thereof and the salts thereof.

The present invention further includes all the mixtures of the stereoisomers mentioned herein, independently of their proportions, including the racemates.

DETAILED DESCRIPTION OF THE INVENTION

Terms that are used hereinbefore and hereinafter to describe the compounds according to the invention are explained more fully below.

The term halogen relates to an atom selected from among F, Cl, Br and I, particularly F, Cl and Br.

The term 1-nC-alkyl, wherein n may have a value as defined hereinbefore or hereinafter, relates to a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term 2-nC-alkenyl, wherein n has a value as defined hereinbefore or hereinafter relates to a branched or unbranched hydrocarbon group with 2 to n C atoms and a C═C-double bond. Examples of such groups include ethenyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl, etc.

The term 2-nC-alkynyl, wherein n has a value as defined hereinbefore or hereinafter, relates to a branched or unbranched hydrocarbon group with 2 to n C atoms and a C≡C-triple bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl, etc.

The term 1-nC-alkoxy or 1-nC-alkyloxy relates to a 1-nC-alkyl-O— group, wherein 1-nC-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term 3-nC-cycloalkyl, wherein n has a value as defined hereinbefore or hereinafter, relates to a saturated mono- or polycarbocyclic (e.g. bi or tricarbocyclic) group which may comprise condensed, bridged and/or spirocyclic groups, with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, spiro[5.5]undecyl, norpinyl, norbornyl, norcaryl, adamantyl, etc. In one embodiment the term 3-nC-cycloalkyl includes saturated monocyclic groups, such as for example cyclopropyl, cyclobutyl, cyclopentyl, cyclohexyl or cycloheptyl.

The term 3-nC-cycloalkyl-1-nC-alkyl relates to a 1-nC-alkyl group, as hereinbefore defined, which is independently substituted by a 3-nC-cycloalkyl group, as hereinbefore defined. Examples of such groups include 3-nC-cycloalkyl-methyl, 2-(3-nC-cycloalkyl)-ethyl, etc.

The term 1-nC-alkoxy-1-nC-alkyl relates to a 1-nC-alkyl group, as hereinbefore defined, which is independently substituted by a 1-nC-alkoxy group, as hereinbefore defined. Examples of such groups include 1-nC-alkoxy-methyl, 2-(1-nC-alkoxy)-ethyl, 3-(1-nC-alkoxy)-propyl, etc.

The term mono- or di-1-nC-alkylamino relates to a 1-nC-alkyl-NH or $(1\text{-nC-alkyl})_2$-NH group, wherein in each case 1-nC-alkyl independently is as hereinbefore defined.

Examples of a mono-1-nC-alkylamino group include N-methylamino, N-ethylamino, N-propylamino, N-isopropylamino, etc.

Examples of a di-1-nC-alkylamino group include N,N-dimethylamino, N,N-diethylamino, N,N-dipropylamino, N,N-diisopropylamino, N,N-diisobutylamino, N-ethyl-N-methylamino, N-isopropyl-N-methylamino, N-ethyl-N-isopropylamino, N-isopropyl-N-propylamino, etc.

$H_2N$-1-nC-alkyl relates to a 1-nC-alkyl group, as hereinbefore defined, which is substituted by an amino group. Examples of such a group include aminomethyl, 2-aminoethyl, 3-aminopropyl, etc.

Hydroxy-1-nC-alkyl relates to a 1-nC-alkyl group, as hereinbefore defined, which is substituted by a hydroxyl group. Examples of such a group include hydroxymethyl, 2-hydroxyethyl, 3-hydroxypropyl, etc.

Mono- or di-1-nC-alkylamino-1-nC-alkyl relates to a 1-nC-alkyl group, as hereinbefore defined, which is independently substituted by a mono- or di-1-nC-alkylamino group, as hereinbefore defined. Examples of such a group include mono- or di-1-nC-alkylamino-methyl, 2-(mono- or di-1-nC-alkylamino)-ethyl, 3-(mono- or di-1-nC-alkylamino)-propyl, etc.

1-nC-alkoxycarbonyl relates to a 1-nC-alkyl-O—C(═O)— group, wherein 1-nC-alkyl is as hereinbefore defined. Examples of such groups include methoxycarbonyl, ethoxycarbonyl, tert-butoxycarbonyl, etc.

1-nC-alkoxycarbonyl-1-nC-alkyl relates to a 1-nC-alkyl group, as hereinbefore defined, which is independently substituted by a 1-nC-alkoxycarbonyl group, as hereinbefore defined. Examples of such groups include methoxycarbonyl-methyl, 2-methoxycarbonyl-ethyl, tert-butoxycarbonyl-methyl, 2-tert-butoxycarbonyl-ethyl, etc.

The term 1-nC-alkanediyl, wherein n may have a value as defined hereinbefore or hereinafter, relates to a divalent group which is derived from a branched or unbranched 1-nC-alkyl group as hereinbefore defined by the removal of a hydrogen atom. Examples of such groups include methylene ($—CH_2—$), dimethylene ($—CH_2—CH_2—$), trimethylene ($—CH_2—CH_2—CH_2—$), tetramethylene ($—CH_2—CH_2—CH_2—CH_2—$), pentamethylene ($—CH_2—CH_2—CH_2—CH_2—CH_2—$), hexamethylene ($—CH_2—CH_2—CH_2—CH_2—CH_2—CH_2—$), heptamethylene ($—CH_2—CH_2—CH_2—CH_2—CH_2—CH_2—CH_2—$), etc.

Examples of wholly or partially fluorine substituted 1-nC-alkyls include for example the 2,2,3,3,3-pentafluoropropyl, the 1,1,1,3,3,3-hexafluoroisopropyl, the pentafluoroethyl, the 1,2,2-trifluoroethyl, the 1,1-difluoro-1-ethyl, the 1,1,2,2-tetrafluoroethyl, the 2,2,2-trifluoroethyl, the 2,2-difluoroethyl, the difluoromethyl or the trifluoromethyl group. Partly fluorine-substituted 1-nC-alkyl in one embodiment relates predominantly to fluorine-substituted 1-nC-alkyl. "Predominantly" in this context means that more than half the hydrogen atoms of the 1-nC-alkyl group are replaced by fluorine atoms.

Examples of wholly or partially fluorine-substituted 1-nC-alkoxy include the 2,2,3,3,3-pentafluoropropoxy, the 1,1,1,3,3,3-hexafluoroisopropoxy, the pentafluoroethoxy, the 1,2,2-trifluoroethoxy, the 1,1-difluoro-1-ethoxy, the 1,1,2,2-tetrafluoroethoxy, the 2,2,2-trifluoroethoxy, the 2,2-difluoroethoxy, the difluoromethoxy or the trifluoromethoxy group. Partly fluorine-substituted 1-nC-alkoxy in one embodiment relates predominantly to fluorine-substituted 1-nC-alkoxy. "Predominantly" in this context means that more than half the hydrogen atoms of the 1-nC-alkoxy group are replaced by fluorine atoms.

The term aryl, on its own or as part of another group, relates to a carbocyclic aromatic monocyclic ring system containing 6 carbon atoms, which may optionally be annelated to a second 5- or 6-membered carbocyclic aromatic, saturated or unsaturated ring system. Examples of such aryl groups include phenyl and naphthyl, preferably phenyl.

The term heteroaryl, on its own or as part of another group, relates to a 5- to 12-membered, (wholly or partly) aromatic, monocyclic or condensed-polycyclic (e.g. bi- or tricyclic) ring system containing 1 to 4 (preferably 1, 2 or 3) identical or different heteroatoms independently selected from among N, O and $S(O)_r$ with r=0, 1 or 2, wherein at least one of the heteroatoms is part of the aromatic ring. One particular embodiment of heteroaryl relates to 5- or 6-membered monocyclic heteroaromatic rings containing 1 to 4 (preferably 1 to 3) identical or different heteroatoms independently selected from among N, O and S.

Examples of such 5- or 6-membered monocyclic heteroaryl groups include pyridyl, pyridazinyl, pyrimidinyl, pyridazinyl, thienyl, furanyl, pyrrolyl, thiazolyl, oxazolyl, imidazolyl, pyrazolyl, isoxazolyl, isothiazolyl, triazolyl, tetrazolyl, thiadiazolyl and oxadiazolyl.

Heteroaryl for the purposes of the present invention may also include mono- or polysubstituted oxo-substituted (e.g. mono- or di-oxo-substituted) derivatives of the heteroaryl ring systems mentioned herein, such as e.g. N-oxy-pyridine or systems in which one or more CH groups are replaced by C═O, such as e.g. pyridone, pyrimidone, pyrazinone, pyridazinone or pyrazolone.

The term heterocyclyl, on its own or as part of another group, relates to a 3- to 12-membered, saturated, unsaturated or (partly) aromatic, monocyclic or condensed, bridged or spiro-polycyclic (e.g. bi- or tricyclic) ring system containing 1 to 4 (preferably 1 or 2) identical or different heteroatoms independently selected from among N, O and $S(O)_r$ with r=0, 1 or 2, wherein none of the heteroatoms is part of the aromatic ring. In one embodiment heterocyclyl relates to heterocycloalkyl. In another embodiment the term heterocyclyl encompasses 3- to 7-membered saturated monocyclic rings.

Examples of such heterocyclyl groups include pyrrolidinyl, piperidinyl, piperazinyl, morpholinyl, thiomorpholinyl, tetrahydropyranyl, tetrahydrofuranyl, homopiperidinyl (azepanyl), homopiperazinyl, homomorpholinyl, homothiomorpholinyl, 5-azabicyclo[2.1.1]hexyl, 2-azabicyclo[2.1.1]hexyl, 7-azabicyclo[2.2.1]heptyl, 2-azabicyclo[2.2.1]heptyl, 2,5-diazabicyclo[2.2.1]heptyl, 2-oxa-5-azabicyclo[2.2.1]heptyl, 2-azabicyclo[2.2.2]octyl, 2,5-diazabicyclo[2.2.2]octyl, 3,8-diazabicyclo[3.2.1]octyl, 3-oxa-8-azabicyclo[3.2.1]octyl, 3-aza-spiro[5.5]undecyl, benzo[1.3]dioxolyl, chromanyl, chromenyl, 2,3-dihydro-benzo[1.4]dioxinyl, 2,3-dihydroindolyl, 2,3-dihydroisoindolyl, 1,2,3,4-tetrahydroquinolinyl, 1,2,3,4-tetrahydroisoquinolinyl, 3,4-dihydrobenzo[1.4]oxazinyl and 1,2,3,4-tetrahydroquinazolinyl.

Heterocyclyl for the purposes of the present invention may also encompass mono- or polysubstituted oxo-substituted (e.g. mono- or di-oxo-substituted) derivatives of the heterocyclyl ring systems mentioned herein, such as e.g. systems in which one or more $CH_2$ groups are replaced by C═O, such as e.g. pyrrolidinone or piperidinone.

The oxo substituent for the purposes of the invention denotes a mono- or polysubstituted bound oxygen (e.g. ═O) which is bound to a carbon atom or a heteroatom (e.g. N or S), in order to form for example a carbonyl group (C═O), an N-oxide, an S-oxide or an S,S-dioxide.

The heteroaryl or heterocyclyl groups specified, unless stated otherwise, encompass all the possible isomeric forms (e.g. tautomers, positional isomers, etc.). For example a pyridyl group may be present as a pyridin-2-yl, pyridin-3-yl or pyridin-4-yl, a thienyl group may be present as a thiophen-2-yl or thiophen-3-yl, a piperidinyl group may be present as a piperidin-1-yl (piperidino), piperidin-2-yl, piperidin-3-yl or piperidin-4-yl.

The term aryl-1-nC-alkyl relates to a 1-nC-alkyl group, as hereinbefore defined, which is substituted by an aryl group, as hereinbefore defined. Examples of such groups include benzyl, phenylethyl (e.g. 2-phenylethyl), etc.

The term heteroaryl-1-nC-alkyl relates to a 1-nC-alkyl group, as hereinbefore defined, which is substituted by a heteroaryl group, as hereinbefore defined.

The term heterocyclyl-1-nC-alkyl relates to a 1-nC-alkyl group, as hereinbefore defined, which is substituted by a heterocyclyl group, as hereinbefore defined.

Generally speaking, for groups that have two or more subgroups, the last-mentioned subgroup is the point of attachment of the group, for example the substituent aryl-1-nC-alkyl denotes an aryl group which is bound to an 1-nC-alkyl group, while the latter is bound to the nucleus or to the group to which the substituent is attached.

Unless stated otherwise, the substituents, groups, residues or fragments mentioned herein may be linked or bound via any possible position.

For example, unless stated otherwise, the aryl, heteroaryl or heterocyclyl groups specified herein may be attached to their neighbouring group(s) via any suitable cyclic carbon or cyclic nitrogen atom.

Moreover, unless stated otherwise, the heteroaryl or heterocyclyl groups mentioned herein that have one or more substituents may carry their substituents at any desired possible position, i.e. any suitable cyclic carbon or cyclic nitrogen atom.

Moreover, unless stated otherwise, the phenyl groups mentioned herein that have one or more substituents may carry their substituents in each case in the ortho, meta or para position relative to the point of attachment at which the phenyl group is attached to its neighbouring group.

Possible salts for compounds of formula I—depending on the substitution or the presence of one or more acidic or basic groups—may be acid addition salts or salts with bases, particularly all the pharmaceutically acceptable acid addition salts or salts with bases. Particular mention should be made of the physiologically acceptable salts with inorganic and organic acids and bases conventionally used in pharmaceuticals. The salts include water-insoluble and, more particularly, water-soluble salts.

Inorganic acids that are suitable for forming pharmaceutically acceptable acid addition salts include for example hydrochloric acid, hydrobromic acid, phosphoric acid, sulphuric acid, etc. Organic acids that are suitable for forming pharmaceutically acceptable acid addition salts include for example citric acid, maleic acid, fumaric acid, succinic acid, lactic acid, tartaric acid, methanesulphonic acid, etc.

Pharmaceutically acceptable acid addition salts with inorganic or organic acids thus include for example hydrochlorides, hydrobromides, phosphates, sulphates, citrates, maleates, fumarates, succinates, lactates, tartrates, methanesulphonates (mesylates), etc.

Salts that are unsuitable for pharmaceutical use but which may optionally be used for example for isolating or purifying the free compounds of formula I or the pharmaceutically acceptable salts thereof are also included.

Salts that are not pharmaceutically acceptable, which may be obtained for example as process products during the preparation of the compounds according to the invention, are converted into pharmaceutically acceptable salts using methods familiar to the skilled man.

All the isomeric forms, particularly all the regio- and stereoisomeric forms, e.g. all the chiral, enantiomeric, diastereomeric, racemic forms, tautomeric (e.g. keto/enol tautomeric), positional isomeric and all the geometric isomeric (e.g. cis/trans isomeric) forms, of a compound of formula I, or of a salt thereof, are considered within the scope of the present invention, if the specific isomeric form is not individually stated. Naturally, the preferred isomer is the one that is most effective and most free from side effects.

If for example the compounds according to the invention, independently of the substituents, have at least one asymmetrically substituted carbon atom, they may be isolated in optically active (e.g. as dextro- or laevo-rotatory antipodes) or in racemic form, e.g. as pure enantiomers in the R or S configuration in each case or as mixtures thereof in any mixing ratio (including in racemic form), and if they have at least two asymmetrically substituted carbon atoms, they may be isolated as pure diastereomers or as diastereoisomeric mixtures in optically active or racemic form.

The present invention encompasses all the possible region- and stereoisomers, particularly the diastereomers and enantiomers mentioned herein, e.g. in substantially pure form, in concentrated form (e.g. substantially free from one or all other unwanted diastereomers and/or enantiomers) and/or in any mixing ratio, including the racemic forms, and the salts thereof.

The following compounds are mentioned as examples of compounds according to the invention:

| Example | IUPAC Name |
|---|---|
| 1 | (5S)-5-methyl-6-(2-phenyl-1,3-benzoxazol-6-yl)-2,3,4,5-tetrahydropyridazin-3-one, |
| 2 | (4S)-4-methyl-6-(2-phenyl-1,3-benzoxazol-6-yl)-2,3,4,5-tetrahydropyridazin-3-one, |
| 3 | (5R)-5-methyl-6-(2-phenyl-1,3-benzoxazol-6-yl)-2,3,4,5-tetrahydropyridazin-3-one, |
| 4 | (4R)-4-methyl-6-(2-phenyl-1,3-benzoxazol-6-yl)-2,3,4,5-tetrahydropyridazin-3-one, |
| 5 | 5-(2-phenyl-1,3-benzoxazol-6-yl)-3,4-diazabicyclo[4.1.0]hept-4-en-2-one, |
| 6 | 5-(7-methyl-2-phenyl-1,3-benzoxazol-6-yl)-3,4-diazabicyclo[4.1.0]hept-4-en-2-one, |
| 7 | 6-(2-phenyl-1,3-benzoxazol-6-yl)-4-(prop-2-en-1-yl)-2,3,4,5-tetrahydropyridazin-3-one, |
| 8 | 6-(2-phenyl-1,3-benzoxazol-6-yl)-5-propyl-2,3,4,5-tetrahydropyridazin-3-one, |
| 9 | 6-(2-phenyl-1,3-benzoxazol-6-yl)-4-propyl-2,3,4,5-tetrahydropyridazin-3-one, |
| 10 | 5-(2-phenyl-1,3-benzoxazol-6-yl)-3,4-diazabicyclo[4.2.0]oct-4-en-2-one, |
| 11 | 5-(4-methyl-2-phenyl-1,3-benzoxazol-6-yl)-3,4-diazabicyclo[4.1.0]hept-4-en-2-one, |
| 12 | 5-[2-(3-methylphenyl)-1,3-benzoxazol-6-yl]-3,4-diazabicyclo[4.1.0]hept-4-en-2-one, |
| 13 | 5-[2-(4-methylphenyl)-1,3-benzoxazol-6-yl]-3,4-diazabicyclo[4.1.0]hept-4-en-2-one, |
| 14 | 5-[2-(3,4-dimethylphenyl)-1,3-benzoxazol-6-yl]-3,4-diazabicyclo[4.1.0]hept-4-en-2-one, |
| 15 | 5-{2-[4-(piperidin-1-ylmethyl)phenyl]-1,3-benzoxazol-6-yl}-3,4-diazabicyclo[4.1.0]hept-4-en-2-one, |
| 16 | 6-(2-phenyl-1,3-benzoxazol-6-yl)-2,3,4,5-tetrahydropyridazin-3-one, |
| 17 | 5-[2-(3-fluorophenyl)-1,3-benzoxazol-6-yl]-3,4-diazabicyclo[4.1.0]hept-4-en-2-one, |
| 18 | 5-[2-(4-fluorophenyl)-1,3-benzoxazol-6-yl]-3,4-diazabicyclo[4.1.0]hept-4-en-2-one, |
| 19 | 5-[2-(4-fluorophenyl)-1,3-benzoxazol-6-yl]-3,4-diazabicyclo[4.2.0]oct-4-en-2-one, |
| 20 | 5-[2-(2-fluorophenyl)-1,3-benzoxazol-6-yl]-3,4-diazabicyclo[4.1.0]hept-4-en-2-one, |
| 21 | 4.4-dimethyl-6-(2-phenyl-1,3-benzoxazol-6-yl)-2,3,4,5-tetrahydropyridazin-3-one, |
| 22 | 5-{2-[4-(morpholin-4-ylmethyl)phenyl]-1,3-benzoxazol-6-yl}-3,4-diazabicyclo[4.1.0]hept-4-en-2-one, |
| 23 | tert-butyl 4-{[4-(6-{5-oxo-3,4-diazabicyclo[4.1.0]hept-2-en-2-yl}-1,3-benzoxazol-2-yl)phenyl]methyl}piperazine-1-carboxylate, |
| 24 | (4S,5R)-4,5-dimethyl-6-[2-(5-methylthiophen-2-yl)-1,3-benzoxazol-6-yl]-2,3,4,5-tetrahydropyridazin-3-one, |
| 25 | (4R,5S)-4,5-dimethyl-6-(2-phenyl-1,3-benzoxazol-6-yl)-2,3,4,5-tetrahydropyridazin-3-one, |
| 26 | (4S,5S)-4,5-dimethyl-6-(2-phenyl-1,3-benzoxazol-6-yl)-2,3,4,5-tetrahydropyridazin-3-one, |
| 27 | (5R)-5-methoxy-6-(2-phenyl-1,3-benzoxazol-6-yl)-2,3,4,5-tetrahydropyridazin-3-one, |
| 28 | (5S)-5-methoxy-6-(2-phenyl-1,3-benzoxazol-6-yl)-2,3,4,5-tetrahydropyridazin-3-one, |
| 29 | 5-ethyl-6-(2-phenyl-1,3-benzoxazol-6-yl)-2,3,4,5-tetrahydropyridazin-3-one, |
| 30 | (5S)-5-ethyl-6-(2-phenyl-1,3-benzoxazol-6-yl)-2,3,4,5-tetrahydropyridazin-3-one, |
| 31 | (5R)-5-ethyl-6-(2-phenyl-1,3-benzoxazol-6-yl)-2,3,4,5-tetrahydropyridazin-3-one, |
| 32 | 6-(2-phenyl-1,3-benzoxazol-6-yl)-5-(propan-2-yl)-2,3,4,5-tetrahydropyridazin-3-one, |
| 33 | 6-{2-[4-(benzyloxy)phenyl]-1,3-benzoxazol-6-yl}-5-ethyl-2,3,4,5-tetrahydropyridazin-3-one, |

-continued

| Example | IUPAC Name |
|---|---|
| 34 | 6-{2-[3-(benzyloxy)phenyl]-1,3-benzoxazol-6-yl}-5-methyl-2,3,4,5-tetrahydropyridazin-3-one, |
| 35 | 6-{2-[3-(benzyloxy)phenyl]-1,3-benzoxazol-6-yl}-5-ethyl-2,3,4,5-tetrahydropyridazin-3-one, |
| 36 | 6-{2-[4-(benzyloxy)phenyl]-1,3-benzoxazol-6-yl}-5-methyl-2,3,4,5-tetrahydropyridazin-3-one, |
| 37 | 5-ethyl-6-[2-(4-hydroxyphenyl)-1,3-benzoxazol-6-yl]-2,3,4,5-tetrahydropyridazin-3-one, |
| 38 | 6-[2-(3-hydroxyphenyl)-1,3-benzoxazol-6-yl]-5-methyl-2,3,4,5-tetrahydropyridazin-3-one, |
| 39 | 5-ethyl-6-[2-(3-hydroxyphenyl)-1,3-benzoxazol-6-yl]-2,3,4,5-tetrahydropyridazin-3-one, |
| 40 | 5-ethyl-6-{2-[4-(pyrimidin-2-ylmethoxy)phenyl]-1,3-benzoxazol-6-yl}-2,3,4,5-tetrahydropyridazin-3-one, |
| 41 | 2-{4-[6-(4-ethyl-6-oxo-1,4,5,6-tetrahydropyridazin-3-yl)-1,3-benzoxazol-2-yl]phenoxy}-N,N-dimethylacetamide, |
| 42 | 5-ethyl-6-(2-{4-[(1-methyl-1H-imidazol-5-yl)methoxy]phenyl}-1,3-benzoxazol-6-yl)-2,3,4,5-tetrahydropyridazin-3-one, |
| 43 | 2-{4-[6-(4-ethyl-6-oxo-1,4,5,6-tetrahydropyridazin-3-yl)-1,3-benzoxazol-2-yl]phenoxy}-N-methylacetamide, |
| 44 | 5-ethyl-6-(2-{4-[2-(4-methylpiperazin-1-yl)ethoxy]phenyl}-1,3-benzoxazol-6-yl)-2,3,4,5-tetrahydropyridazin-3-one, |
| 45 | 5-ethyl-6-{2-[3-(pyridin-3-ylmethoxy)phenyl]-1,3-benzoxazol-6-yl}-2,3,4,5-tetrahydropyridazin-3-one, |
| 46 | 5-ethyl-6-{2-[4-(pyridin-4-ylmethoxy)phenyl]-1,3-benzoxazol-6-yl}-2,3,4,5-tetrahydropyridazin-3-one, |
| 47 | 5-ethyl-6-{2-[4-(pyridin-2-ylmethoxy)phenyl]-1,3-benzoxazol-6-yl}-2,3,4,5-tetrahydropyridazin-3-one, |
| 48 | 5-ethyl-6-{2-[4-(thiophen-3-ylmethoxy)phenyl]-1,3-benzoxazol-6-yl}-2,3,4,5-tetrahydropyridazin-3-one, |
| 49 | 5-ethyl-6-(2-{4-[2-(piperidin-1-yl)ethoxy]phenyl}-1,3-benzoxazol-6-yl)-2,3,4,5-tetrahydropyridazin-3-one, |
| 50 | 5-ethyl-6-[2-(4-{[3-(propan-2-yl)-1,2,4-oxadiazol-5-yl]methoxy}phenyl)-1,3-benzoxazol-6-yl]-2,3,4,5-tetrahydropyridazin-3-one, |
| 51 | 5-ethyl-6-{2-[4-(thiophen-2-ylmethoxy)phenyl]-1,3-benzoxazol-6-yl}-2,3,4,5-tetrahydropyridazin-3-one, |
| 52 | 5-ethyl-6-[2-(4-propoxyphenyl)-1,3-benzoxazol-6-yl]-2,3,4,5-tetrahydropyridazin-3-one, |
| 53 | 6-(2-{4-[2-(azepan-1-yl)ethoxy]phenyl}-1,3-benzoxazol-6-yl)-5-ethyl-2,3,4,5-tetrahydropyridazin-3-one, |
| 54 | 6-{2-[4-(cyclohexylmethoxy)phenyl]-1,3-benzoxazol-6-yl}-5-ethyl-2,3,4,5-tetrahydropyridazin-3-one, |
| 55 | 6-(2-{4-[2-(dimethylamino)ethoxy]phenyl}-1,3-benzoxazol-6-yl)-5-ethyl-2,3,4,5-tetrahydropyridazin-3-one, |
| 56 | 6-{2-[4-(2-cyclohexylethoxy)phenyl]-1,3-benzoxazol-6-yl}-5-ethyl-2,3,4,5-tetrahydropyridazin-3-one, |
| 57 | 6-[2-(4-{2-[bis(propan-2-yl)amino]ethoxy}phenyl)-1,3-benzoxazol-6-yl]-5-ethyl-2,3,4,5-tetrahydropyridazin-3-one, |
| 58 | 5-ethyl-6-(2-{4-[2-(2,2,6,6-tetramethylpiperidin-1-yl)ethoxy]phenyl}-1,3-benzoxazol-6-yl)-2,3,4,5-tetrahydropyridazin-3-one, |
| 59 | 5-ethyl-6-{2-[4-(pyrimidin-5-ylmethoxy)phenyl]-1,3-benzoxazol-6-yl}-2,3,4,5-tetrahydropyridazin-3-one, |
| 60 | 5-ethyl-6-{2-[4-(pyridin-3-ylmethoxy)phenyl]-1,3-benzoxazol-6-yl}-2,3,4,5-tetrahydropyridazin-3-one, |
| 61 | 5-ethyl-6-(2-{4-[2-oxo-2-(piperidin-1-yl)ethoxy]phenyl}-1,3-benzoxazol-6-yl)-2,3,4,5-tetrahydropyridazin-3-one, |
| 62 | 6-(2-{4-[3-(dimethylamino)propoxy]phenyl}-1,3-benzoxazol-6-yl)-5-ethyl-2,3,4,5-tetrahydropyridazin-3-one, |
| 63 | 5-ethyl-6-{2-[4-(1,3-oxazol-5-ylmethoxy)phenyl]-1,3-benzoxazol-6-yl}-2,3,4,5-tetrahydropyridazin-3-one, |
| 64 | 5-ethyl-6-(2-{4-[2-(morpholin-4-yl)ethoxy]phenyl}-1,3-benzoxazol-6-yl)-2,3,4,5-tetrahydropyridazin-3-one, |
| 65 | 5-ethyl-6-{2-[3-(pyridin-2-ylmethoxy)phenyl]-1,3-benzoxazol-6-yl}-2,3,4,5-tetrahydropyridazin-3-one, |
| 66 | tert-butyl 2-{4-[6-(4-ethyl-6-oxo-1,4,5,6-tetrahydropyridazin-3-yl)-1,3-benzoxazol-2-yl]phenoxy}acetate, |
| 67 | tert-butyl 4-{4-[6-(4-ethyl-6-oxo-1,4,5,6-tetrahydropyridazin-3-yl)-1,3-benzoxazol-2-yl]phenoxymethyl}piperidine-1-carboxylate, |
| 68 | tert-butyl 4-{4-[6-(4-ethyl-6-oxo-1,4,5,6-tetrahydropyridazin-3-yl)-1,3-benzoxazol-2-yl]phenoxy}piperidine-1-carboxylate, |
| 69 | tert-butyl 4-{3-[6-(4-methyl-6-oxo-1,4,5,6-tetrahydropyridazin-3-yl)-1,3-benzoxazol-2-yl]phenoxymethyl}piperidine-1-carboxylate, |
| 70 | 2-{4-[6-(4-ethyl-6-oxo-1,4,5,6-tetrahydropyridazin-3-yl)-1,3-benzoxazol-2-yl]phenoxy}acetic acid, |
| 71 | 5-ethyl-6-{2-[4-(piperidin-4-ylmethoxy)phenyl]-1,3-benzoxazol-6-yl}-2,3,4,5-tetrahydropyridazin-3-one, |

-continued

| Example | IUPAC Name |
| --- | --- |
| 72 | 5-ethyl-6-{2-[4-(piperidin-4-yloxy)phenyl]-1,3-benzoxazol-6-yl}-2,3,4,5-tetrahydropyridazin-3-one, |
| 73 | 5-methyl-6-{2-[3-(piperidin-4-ylmethoxy)phenyl]-1,3-benzoxazol-6-yl}-2,3,4,5-tetrahydropyridazin-3-one, |
| 74 | 5-ethyl-6-(2-{4-[(1-methanesulphonylpiperidin-4-yl)methoxy]phenyl}-1,3-benzoxazol-6-yl)-2,3,4,5-tetrahydropyridazin-3-one, |
| 75 | 5-ethyl-6-(2-{4-[(E)-2-phenylethenyl]phenyl}-1,3-benzoxazol-6-yl)-2,3,4,5-tetrahydropyridazin-3-one, |
| 76 | 5-ethyl-6-{2-[4-(2-phenylethyl)phenyl]-1,3-benzoxazol-6-yl}-2,3,4,5-tetrahydropyridazin-3-one, |
| 77 | 6-ethyl-5-(2-phenyl-1,3-benzoxazol-6-yl)-3,6-dihydro-2H-1,3,4-thiadiazin-2-one, |
| 78 | 6-ethyl-5-(2-phenyl-1,3-benzoxazol-6-yl)-3,6-dihydro-2H-1,3,4-oxadiazin-2-one, |
| 79 | (6R)-6-ethyl-5-(2-phenyl-1,3-benzoxazol-6-yl)-3,6-dihydro-2H-1,3,4-oxadiazin-2-one, |
| 80 | (6S)-6-ethyl-5-(2-phenyl-1,3-benzoxazol-6-yl)-3,6-dihydro-2H-1,3,4-oxadiazin-2-one, |
| 81 | 6-methyl-5-(2-phenyl-1,3-benzoxazol-6-yl)-3,6-dihydro-2H-1,3,4-oxadiazin-2-one, |
| 82 | 5-methyl-6-(2-phenyl-1,3-benzoxazol-6-yl)-2,3,4,5-tetrahydropyridazin-3-one, |
| 83 | 6-[2-(4-methoxyphenyl)-1,3-benzoxazol-6-yl]-5-methyl-2,3,4,5-tetrahydropyridazin-3-one, |
| 84 | 6-[2-(4-chlorophenyl)-1,3-benzoxazol-6-yl]-5-methyl-2,3,4,5-tetrahydropyridazin-3-one, |
| 85 | 6-[2-(3-methoxyphenyl)-1,3-benzoxazol-6-yl)-5-methyl-2,3,4,5-tetrahydropyridazin-3-one, |
| 86 | 6-[2-(2-methoxyphenyl)-1,3-benzoxazol-6-yl]-5-methyl-2,3,4,5-tetrahydropyridazin-3-one, |
| 87 | 5-methyl-6-[2-(5-methylthiophen-2-yl)-1,3-benzoxazol-6-yl]-2,3,4,5-tetrahydropyridazin-3-one, |
| 88 | 6-[2-(3-chlorophenyl)-1,3-benzoxazol-6-yl]-5-methyl-2,3,4,5-tetrahydropyridazin-3-one, |
| 89 | 6-[2-(2-chlorophenyl)-1,3-benzoxazol-6-yl]-5-methyl-2,3,4,5-tetrahydropyridazin-3-one, |
| 90 | methyl 4-[6-(4-methyl-6-oxo-1,4,5,6-tetrahydropyridazin-3-yl)-1,3-benzoxazol-2-yl]benzoate, |
| 91 | 5-ethyl-6-[2-(2-fluoro-4-methoxyphenyl)-1,3-benzoxazol-6-yl]-2,3,4,5-tetrahydropyridazin-3-one, |
| 92 | 6-[2-(3,4-dimethoxyphenyl)-1,3-benzoxazol-6-yl]-5-ethyl-2,3,4,5-tetrahydropyridazin-3-one, |
| 93 | 5-ethyl-6-[2-(4-fluoro-3-methoxyphenyl)-1,3-benzoxazol-6-yl]-2,3,4,5-tetrahydropyridazin-3-one, |
| 94 | 6-[2-(4-ethoxyphenyl)-1,3-benzoxazol-6-yl]-5-ethyl-2,3,4,5-tetrahydropyridazin-3-one, |
| 95 | 5-ethyl-6-[2-(4-phenoxyphenyl)-1,3-benzoxazol-6-yl]-2,3,4,5-tetrahydropyridazin-3-one, |
| 96 | 6-{2-[4-(dimethylamino)phenyl]-1,3-benzoxazol-6-yl}-5-ethyl-2,3,4,5-tetrahydropyridazin-3-one |
| 97 | 5-ethyl-6-[2-(4-methylthiophen-2-yl)-1,3-benzoxazol-6-yl]-2,3,4,5-tetrahydropyridazin-3-one, |
| 98 | 5-ethyl-6-[2-(3-fluoro-4-methoxyphenyl)-1,3-benzoxazol-6-yl]-2,3,4,5-tetrahydropyridazin-3-one, |
| 99 | 5-ethyl-6-{2-[4-(propan-2-yloxy)phenyl]-1,3-benzoxazol-6-yl}-2,3,4,5-tetrahydropyridazin-3-one, |
| 100 | 5-ethyl-6-{2-[3-(propan-2-yloxy)phenyl]-1,3-benzoxazol-6-yl}-2,3,4,5-tetrahydropyridazin-3-one, |
| 101 | 5-ethyl-6-[2-(5-methylthiophen-2-yl)-1,3-benzoxazol-6-yl]-2,3,4,5-tetrahydropyridazin-3-one, |
| 102 | 5-ethyl-6-[2-(3-methoxyphenyl)-1,3-benzoxazol-6-yl]-2,3,4,5-tetrahydropyridazin-3-one, |
| 103 | 5-ethyl-6-{2-[4-(trifluoromethoxy)phenyl]-1,3-benzoxazol-6-yl}-2,3,4,5-tetrahydropyridazin-3-one, |
| 104 | 5-ethyl-6-[2-(4-methoxyphenyl)-1,3-benzoxazol-6-yl]-2,3,4,5-tetrahydropyridazin-3-one, |
| 105 | 5-ethyl-6-{2-[4-(oxan-4-yloxy)phenyl]-1,3-benzoxazol-6-yl}-2,3,4,5-tetrahydropyridazin-3-one, |
| 106 | 5-methyl-6-[2-(thiophen-2-yl)-1,3-benzoxazol-6-yl]-2,3,4,5-tetrahydropyridazin-3-one, |
| 107 | 5-methyl-6-[2-(thiophen-3-yl)-1,3-benzoxazol-6-yl]-2,3,4,5-tetrahydropyridazin-3-one, |
| 108 | 6-[2-(furan-2-yl)-1,3-benzoxazol-6-yl]-5-methyl-2,3,4,5-tetrahydropyridazin-3-one, |
| 109 | 6-[2-(6-aminopyridin-3-yl)-1,3-benzoxazol-6-yl]-5-methyl-2,3,4,5-tetrahydropyridazin-3-one, |

-continued

| Example | IUPAC Name |
|---|---|
| 110 | 5-methyl-6-[2-(pyridin-3-yl)-1,3-benzoxazol-6-yl]-2,3,4,5-tetrahydropyridazin-3-one, |
| 111 | 6-[2-(thiophen-2-yl)-1,3-benzoxazol-6-yl]-2,3,4,5-tetrahydropyridazin-3-one, |
| 112 | 6-[2-(furan-2-yl)-1,3-benzoxazol-6-yl]-2,3,4,5-tetrahydropyridazin-3-one, |
| 113 | 5-methyl-6-[2-(thiomorpholin-4-yl)-1,3-benzoxazol-6-yl]-2,3,4,5-tetrahydropyridazin-3-one, |
| 114 | ethyl 4-[6-(4-methyl-6-oxo-1,4,5,6-tetrahydropyridazin-3-yl)-1,3-benzoxazol-2-yl]piperazine-1-carboxylate, |
| 115 | 5-methyl-6-[2-(piperidin-1-yl)-1,3-benzoxazol-6-yl]-2,3,4,5-tetrahydropyridazin-3-one, |
| 116 | 5-methyl-6-[2-(morpholin-4-yl)-1,3-benzoxazol-6-yl]-2,3,4,5-tetrahydropyridazin-3-one, |
| 117 | 5-methyl-6-[2-(piperazin-1-yl)-1,3-benzoxazol-6-yl]-2,3,4,5-tetrahydropyridazin-3-one, |
| 118 | 6-[2-(piperidin-1-yl)-1,3-benzoxazol-6-yl]-2,3,4,5-tetrahydropyridazin-3-one, |
| 119 | 6-[2-(thiomorpholin-4-yl)-1,3-benzoxazol-6-yl]-2,3,4,5-tetrahydropyridazin-3-one, |
| 120 | 6-[2-(2,6-dichloropyridin-3-yl)-1,3-benzoxazol-6-yl]-5-methyl-2,3,4,5-tetrahydropyridazin-3-one, |
| 121 | 6-{2-[2-chloro-6-(morpholin-4-yl)pyridin-3-yl]-1,3-benzoxazol-6-yl}-5-methyl-2,3,4,5-tetrahydropyridazin-3-one, |
| 122 | 4-[6-(4-methyl-6-oxo-1,4,5,6-tetrahydropyridazin-3-yl)-1,3-benzoxazol-2-yl]benzonitrile, |
| 123 | 3-[6-(4-methyl-6-oxo-1,4,5,6-tetrahydropyridazin-3-yl)-1,3-benzoxazol-2-yl]benzonitrile, |
| 124 | 6-{2-[4-(aminomethyl)phenyl]-1,3-benzoxazol-6-yl}-5-methyl-2,3,4,5-tetrahydropyridazin-3-one, |
| 125 | 6-{2-[3-(aminomethyl)phenyl]1,3-benzoxazol-6-yl}-5-methyl-2,3,4,5-tetrahydropyridazin-3-one, |
| 126 | (4S,5S)-4-ethyl-5-methyl-6-(2-phenyl-1,3-benzoxazol-6-yl)-2,3,4,5-tetrahydropyridazin-3-one, |
| 127 | (4R,5S)-4-ethyl-5-methyl-6-(2-phenyl-1,3-benzoxazol-6-yl)-2,3,4,5-tetrahydropyridazin-3-one, |
| 128 | (4S,5S)-5-methyl-6-(2-phenyl-1,3-benzoxazol-6-yl)-4-propyl-2,3,4,5-tetrahydropyridazin-3-one, |
| 129 | (4R,5S)-5-methyl-6-(2-phenyl-1,3-benzoxazol-6-yl)-4-propyl-2,3,4,5-tetrahydropyridazin-3-one, |
| 130 | 5-(2-phenyl-4,5,6,7-tetrahydro-1,3-benzoxazol-6-yl)-3,4-diazabicyclo[4.1.0]hept-4-en-2-one, |
| 131 | (1R,6S)-5-[(6S)-2-phenyl-4,5,6,7-tetrahydro-1,3-benzoxazol-6-yl]-3,4-diazabicyclo[4.1.0]hept-4-en-2-one, |
| 132 | (1R,6S)-5-[(6R)-2-phenyl-4,5,6,7-tetrahydro-1,3-benzoxazol-6-yl]-3,4-diazabicyclo[4.1.0]hept-4-en-2-one, |
| 133 | (1S,6R)-5-[(6S)-2-phenyl-4,5,6,7-tetrahydro-1,3-benzoxazol-6-yl]-3,4-diazabicyclo[4.1.0]hept-4-en-2-one, |
| 134 | (1S,6R)-5-[(6R)-2-phenyl-4,5,6,7-tetrahydro-1,3-benzoxazol-6-yl]-3,4-diazabicyclo[4.1.0]hept-4-en-2-one, |
| 135 | 5-{2-phenyl-4H,5H,6H,7H-pyrido[4.3-d][1.3]oxazol-5-yl}-3,4-diazabicyclo[4.1.0]hept-4-en-2-one, |
| 136 | 5-(2-benzyl-1,3-benzoxazol-6-yl)-3,4-diazabicyclo[4.1.0]hept-4-en-2-one, |
| 137 | 5-(2-{4-[2-(morpholin-4-yl)ethoxy]phenyl}-1,3-benzoxazol-6-yl)-3,4-diazabicyclo[4.1.0]hept-4-en-2-one, |
| 138 | 4-ethyl-6-{2-phenyl-4H,5H,6H,7H-pyrido[4.3-d][1.3]oxazol-5-yl}-2,3,4,5-tetrahydropyridazin-3-one, |
| 139 | 4-methyl-6-[2-(thiophen-2-yl)-1,3-benzoxazol-6-yl]-2,3,4,5-tetrahydropyridazin-3-one, |
| 140 | 4-butyl-6-[2-(thiophen-2-yl)-1,3-benzoxazol-6-yl]-2,3,4,5-tetrahydropyridazin-3-one, |
| 141 | 4-ethyl-6-[2-(thiophen-2-yl)-1,3-benzoxazol-6-yl]-2,3,4,5-tetrahydropyridazin-3-one, |
| 142 | 5-methyl-6-(2-phenyl-1,3-benzoxazol-6-yl)-2,3,4,5-tetrahydro-1,2,4-triazin-3-one, |
| 143 | 6-(2-phenyl-1,3-benzoxazol-6-yl)-2,3,4,5-tetrahydro-1,2,4-triazin-3-one, |
| 144 | 5-ethyl-6-(2-phenyl-1,3-benzoxazol-6-yl)-2,3,4,5-tetrahydro-1,2,4-triazin-3-one, |
| 145 | (4S,5S)-5-ethyl-4-methyl-6-(2-phenyl-1,3-benzoxazol-6-yl)-2,3,4,5-tetrahydropyridazin-3-one, |
| 146 | (4S,5R)-5-ethyl-4-methyl-6-(2-phenyl-1,3-benzoxazol-6-yl)-2,3,4,5-tetrahydropyridazin-3-one, |
| 147 | (4R,5R)-5-ethyl-4-methyl-6-(2-phenyl-1,3-benzoxazol-6-yl)-2,3,4,5-tetrahydropyridazin-3-one, |
| 148 | 5-ethyl-6-(2-{3-[2-(piperidin-1-yl)ethoxy]phenyl}-1,3-benzoxazol-6-yl)-2,3,4,5-tetrahydropyridazin-3-one, |
| 149 | 6-(2-{3-[2-(azepan-1-yl)ethoxy]phenyl}-1,3-benzoxazol-6-yl)-5-ethyl-2,3,4,5-tetrahydropyridazin-3-one, |

-continued

| Example | IUPAC Name |
|---|---|
| 150 | 5-ethyl-6-{2-[3-(pyridin-4-ylmethoxy)phenyl]-1,3-benzoxazol-6-yl}-2,3,4,5-tetrahydropyridazin-3-one, |
| 151 | 5-ethyl-6-(2-{3-[2-(2,2,6,6-tetramethylpiperidin-1-yl)ethoxy]phenyl}-1,3-benzoxazol-6-yl)-2,3,4,5-tetrahydropyridazin-3-one, |
| 152 | 5-ethyl-6-(2-{3-[3-(piperidin-1-yl)propoxy]phenyl}-1,3-benzoxazol-6-yl)-2,3,4,5-tetrahydropyridazin-3-one, |
| 153 | 1-(2-{3-[6-(4-ethyl-6-oxo-1,4,5,6-tetrahydropyridazin-3-yl)-1,3-benzoxazol-2-yl]phenoxy}ethyl)piperidine-4-carbonitrile, |
| 154 | 6-[2-(3-{2-[bis(propan-2-yl)amino]ethoxy}phenyl)-1,3-benzoxazol-6-yl]-5-ethyl-2,3,4,5-tetrahydropyridazin-3-one, |
| 155 | tert-butyl 4-(2-{3-[6-(4-ethyl-6-oxo-1,4,5,6-tetrahydropyridazin-3-yl)-1,3-benzoxazol-2-yl]phenoxy}ethyl)piperazine-1-carboxylate, |
| 156 | 6-[2-(3-{2-[bis(2-methylpropyl)amino]ethoxy}phenyl)-1,3-benzoxazol-6-yl]-5-ethyl-2,3,4,5-tetrahydropyridazin-3-one, |
| 157 | 6-[2-(3-{2-[4-(butan-2-yl)piperazin-1-yl]ethoxy}phenyl)-1,3-benzoxazol-6-yl]-5-ethyl-2,3,4,5-tetrahydropyridazin-3-one, |
| 158 | 5-ethyl-6-(2-{4-[(4-methanesulphonylphenyl)methoxy]phenyl}-1,3-benzoxazol-6-yl)-2,3,4,5-tetrahydropyridazin-3-one, |
| 159 | 5-ethyl-6-(2-{4-[2-(pyrrolidin-1-yl)ethoxy]phenyl}-1,3-benzoxazol-6-yl)-2,3,4,5-tetrahydropyridazin-3-one, |
| 160 | 6-[2-(4-{2-[bis(2-methylpropyl)amino]ethoxy}phenyl)-1,3-benzoxazol-6-yl]-5-ethyl-2,3,4,5-tetrahydropyridazin-3-one, |
| 161 | 5-ethyl-6-(2-{4-[3-(piperidin-1-yl)propoxy]phenyl}-1,3-benzoxazol-6-yl)-2,3,4,5-tetrahydropyridazin-3-one, |
| 162 | 6-(2-{4-[2-(4-acetylpiperazin-1-yl)ethoxy]phenyl}-1,3-benzoxazol-6-yl)-5-ethyl-2,3,4,5-tetrahydropyridazin-3-one, |
| 163 | 1-(2-{4-[6-(4-ethyl-6-oxo-1,4,5,6-tetrahydropyridazin-3-yl)-1,3-benzoxazol-2-yl]phenoxy}ethyl)piperidine-4-carbonitrile, |
| 164 | 6-[2-(4-{2-[(1R,4S)-2-azabicyclo[2.2.1]heptan-2-yl]ethoxy}phenyl)-1,3-benzoxazol-6-yl]-5-ethyl-2,3,4,5-tetrahydropyridazin-3-one, |
| 165 | tert-butyl 4-(2-{4-[6-(4-ethyl-6-oxo-1,4,5,6-tetrahydropyridazin-3-yl)-1,3-benzoxazol-2-yl]phenoxy}ethyl)piperazine-1-carboxylate, |
| 166 | 6-[2-(4-{2-[4-(butan-2-yl)piperazin-1-yl]ethoxy}phenyl)-1,3-benzoxazol-6-yl]-5-ethyl-2,3,4,5-tetrahydropyridazin-3-one, |
| 167 | 5-ethyl-6-(2-{4-[2-(2-oxopyrrolidin-1-yl)ethoxy]phenyl}-1,3-benzoxazol-6-yl)-2,3,4,5-tetrahydropyridazin-3-one, |
| 168 | 5-ethyl-6-[2-(4-{2-[4-(propan-2-yl)piperazin-1-yl]ethoxy}phenyl)-1,3-benzoxazol-6-yl]-2,3,4,5-tetrahydropyridazin-3-one, |
| 169 | (4R,5S)-6-[2-(4-{2-[bis(propan-2-yl)amino]ethoxy}phenyl)-1,3-benzoxazol-6-yl]-5-methyl-4-propyl-2,3,4,5-tetrahydropyridazin-3-one, |
| 170 | (4S,5S)-6-[2-(4-{2-[bis(propan-2-yl)amino]ethoxy}phenyl)-1,3-benzoxazol-6-yl]-5-methyl-4-propyl-2,3,4,5-tetrahydropyridazin-3-one, |
| 171 | (4S,5S)-5-methyl-6-{2-[4-(propan-2-yloxy)phenyl]-1,3-benzoxazol-6-yl}-4-propyl-2,3,4,5-tetrahydropyridazin-3-one, |
| 172 | (4S,5S)-5-methyl-6-(2-{4-[3-(piperidin-1-yl)propoxy]phenyl}-1,3-benzoxazol-6-yl)-4-propyl-2,3,4,5-tetrahydropyridazin-3-one, |
| 173 | (4R,5R)-5-methyl-6-(2-{4-[2-(piperidin-1-yl)ethoxy]phenyl}-1,3-benzoxazol-6-yl)-4-propyl-2,3,4,5-tetrahydropyridazin-3-one, |
| 174 | (4R,5R)-6-[2-(4-methoxyphenyl)-1,3-benzoxazol-6-yl]-5-methyl-4-propyl-2,3,4,5-tetrahydropyridazin-3-one, |
| 175 | 5-ethyl-6-{2-[4-(propan-2-yl)phenyl]-1,3-benzoxazol-6-yl}-2,3,4,5-tetrahydropyridazin-3-one, |
| 176 | 6-{2-[4-(cyclopentyloxy)phenyl]-1,3-benzoxazol-6-yl}-5-ethyl-2,3,4,5-tetrahydropyridazin-3-one, |
| 177 | 5-ethyl-6-{2-[4-morpholin-4-yl)phenyl]-1,3-benzoxazol-6-yl}-2,3,4,5-tetrahydropyridazin-3-one, |
| 178 | (4R,5R)-5-ethyl-4-methyl-6-{2-[4-(propan-2-yloxy)phenyl]-1,3-benzoxazol-6-yl}-2,3,4,5-tetrahydropyridazin-3-one, |
| 179 | (4R,5S)-5-ethyl-4-methyl-6-{2-[4-(propan-2-yloxy)phenyl]-1,3-benzoxazol-6-yl}-2,3,4,5-tetrahydropyridazin-3-one, |
| 180 | 5-ethyl-6-{2-[4-(1-methoxyethyl)phenyl]-1,3-benzoxazol-6-yl}-2,3,4,5-tetrahydropyridazin-3-one, |
| 181 | 5-ethyl-6-{2-[4-(oxolan-3-yloxy)phenyl]-1,3-benzoxazol-6-yl}-2,3,4,5-tetrahydropyridazin-3-one, |
| 182 | (4R,5R)-6-[2-(4-fluorophenyl)-1,3-benzoxazol-6-yl]-5-methyl-4-propyl-2,3,4,5-tetrahydropyridazin-3-one, |
| 183 | (4R,5R)-5-methyl-4-propyl-6-[2-(thiophen-2-yl)-1,3-benzoxazol-6-yl]-2,3,4,5-tetrahydropyridazin-3-one, |
| 184 | (4R,5R)-5-methyl-6-[2-(5-methylthiophen-2-yl)-1,3-benzoxazol-6-yl]-4-propyl-2,3,4,5-tetrahydropyridazin-3-one, |
| 185 | (4R,5R)-6-[2-(4-chlorophenyl)-1,3-benzoxazol-6-yl]-5-methyl-4-propyl-2,3,4,5-tetrahydropyridazin-3-one, |
| 186 | (4R,5R)-5-methyl-6-[2-(4-methylthiophen-2-yl)-1,3-benzoxazol-6-yl]-4-propyl-2,3,4,5-tetrahydropyridazin-3-one, |
| 187 | (4R,5R)-5-methyl-4-propyl-6-[2-(thiophen-3-yl)-1,3-benzoxazol-6-yl]-2,3,4,5-tetrahydropyridazin-3-one, |

-continued

| Example | IUPAC Name |
|---|---|
| 188 | (4R,5R)-6-[2-(furan-2-yl)-1,3-benzoxazol-6-yl]-5-methyl-4-propyl-2,3,4,5-tetrahydropyridazin-3-one, |
| 189 | (4R,5R)-6-[2-(2,5-dimethylfuran-3-yl)-1,3-benzoxazol-6-yl]-5-methyl-4-propyl-2,3,4,5-tetrahydropyridazin-3-one, |
| 190 | (5R)-5-ethyl-6-[2-(4-methoxyphenyl)-1,3-benzoxazol-6-yl]-2,3,4,5-tetrahydropyridazin-3-one, |
| 191 | (5R)-6-{2-[4-(dimethylamino)phenyl]-1,3-benzoxazol-6-yl}-5-ethyl-2,3,4,5-tetrahydropyridazin-3-one, |
| 192 | (5S)-5-ethyl-6-{2-[4-(propan-2-yloxy)phenyl]-1,3-benzoxazol-6-yl}-2,3,4,5-tetrahydropyridazin-3-one, |
| 193 | (5R)-5-ethyl-6-{2-[4-(propan-2-yloxy)phenyl]-1,3-benzoxazol-6-yl}-2,3,4,5-tetrahydropyridazin-3-one, |
| 194 | (5S)-5-ethyl-6-{2-[4-(oxan-4-yloxy)phenyl]-1,3-benzoxazol-6-yl}-2,3,4,5-tetrahydropyridazin-3-one, |
| 195 | (5R)-5-ethyl-6-{2-[4-(oxan-4-yloxy)phenyl]-1,3-benzoxazol-6-yl}-2,3,4,5-tetrahydropyridazin-3-one, |
| 196 | (4R,5R)-5-methyl-6-(2-phenyl-1,3-benzoxazol-6-yl)-4-propyl-2,3,4,5-tetrahydropyridazin-3-one, |
| 197 | (4S,5S)-4-butyl-5-methyl-6-(2-phenyl-1,3-benzoxazol-6-yl)-2,3,4,5-tetrahydropyridazin-3-one, |
| 198 | (4R,5S)-5-methyl-6-(2-phenyl-1,3-benzoxazol-6-yl)-4-(prop-2-en-1-yl)-2,3,4,5-tetrahydropyridazin-3-one, |
| 199 | (4R,5S)-6-{2-[4-(benzyloxy)phenyl]-1,3-benzoxazol-6-yl}-5-methyl-4-propyl-2,3,4,5-tetrahydropyridazin-3-one, |
| 200 | (4S,5S)-6-{2-[4-(benzyloxy)phenyl]-1,3-benzoxazol-6-yl}-5-methyl-4-propyl-2,3,4,5-tetrahydropyridazin-3-one, |
| 201 | 5-ethyl-6-(2-{3-[2-(pyrrolidin-1-yl)ethoxy]phenyl}-1,3-benzoxazol-6-yl)-2,3,4,5-tetrahydropyridazin-3-one, |
| 202 | (5R)-5-ethyl-6-{2-phenyl-4H,5H,6H,7H-pyrido[4.3-d][1.3]oxazol-5-yl}-2,3,4,5-tetrahydropyridazin-3-one, |
| 203 | (4S,5S)-6-[2-(4-hydroxyphenyl)-1,3-benzoxazol-6-yl]-5-methyl-4-propyl-2,3,4,5-tetrahydropyridazin-3-one, |
| 204 | 6-(2-phenyl-1,3-benzoxazol-6-yl)-2,3-dihydropyridazin-3-one, |
| 205 | 6-ethyl-5-{2-phenyl-4H,5H,6H,7H-pyrido[4.3-d][1.3]oxazol-5-yl}-3,6-dihydro-2H-1,3,4-oxadiazin-2-one, |
| 206 | (6R)-6-ethyl-5-{2-phenyl-4H,5H,6H,7H-pyrido[4.3-d][1.3]oxazol-5-yl}-3,6-dihydro-2H-1,3,4-oxadiazin-2-one, |
| 207 | (6S)-6-ethyl-5-{2-phenyl-4H,5H,6H,7H-pyrido[4.3-d][1.3]oxazol-5-yl}-3,6-dihydro-2H-1,3,4-oxadiazin-2-one, |
| 208 | (4R,5R)-5-ethyl-4-methyl-6-{2-[4-(propan-2-yloxy)phenyl]-1,3-benzoxazol-6-yl}-2,3,4,5-tetrahydropyridazin-3-one, |
| 209 | 5-ethyl-6-(2-{4-[2-(pyrrolidin-1-yl)propoxy]phenyl}-1,3-benzoxazol-6-yl)-2,3,4,5-tetrahydropyridazin-3-one, |
| 210 | 5-ethyl-6-[2-(4-{[1-(pyrrolidin-1-yl)propan-2-yl]oxy}phenyl)-1,3-benzoxazol-6-yl]-2,3,4,5-tetrahydropyridazin-3-one, |
| 211 | 5-ethyl-6-{2-[4-(2-hydroxypropoxy)phenyl]-1,3-benzoxazol-6-yl}-2,3,4,5-tetrahydropyridazin-3-one, |
| 212 | 5-ethyl-6-(2-{4-[(2-hydroxycyclohexyl)oxy]phenyl}-1,3-benzoxazol-6-yl)-2,3,4,5-tetrahydropyridazin-3-one, |
| 213 | 5-ethyl-6-{2-[4-(prop-2-en-1-yloxy)phenyl]-1,3-benzoxazol-6-yl}-2,3,4,5-tetrahydropyridazin-3-one, |
| 214 | 5-ethyl-6-{2-[4-(2-methoxyethoxy)phenyl]-1,3-benzoxazol-6-yl}-2,3,4,5-tetrahydropyridazin-3-one, |
| 215 | 5-ethyl-6-[2-(4-{2-[ethyl(propan-2-yl)amino]ethoxy}phenyl)-1,3-benzoxazol-6-yl]-2,3,4,5-tetrahydropyridazin-3-one, |
| 216 | 6-(2-{3-[2-(2,6-dimethylmorpholin-4-yl)ethoxy]phenyl}-1,3-benzoxazol-6-yl)-5-ethyl-2,3,4,5-tetrahydropyridazin-3-one, |
| 217 | 5-ethyl-6-[2-(3-{2-[methyl(propan-2-yl)amino]ethoxy}phenyl)-1,3-benzoxazol-6-yl]-2,3,4,5-tetrahydropyridazin-3-one, |
| 218 | 5-ethyl-6-[2-(3-{2-[ethyl(propan-2-yl)amino]ethoxy}phenyl)-1,3-benzoxazol-6-yl]-2,3,4,5-tetrahydropyridazin-3-one, |
| 219 | 5-ethyl-6-[2-(4-{2-[methyl(propan-2-yl)amino]ethoxy}phenyl)-1,3-benzoxazol-6-yl]-2,3,4,5-tetrahydropyridazin-3-one, |
| 220 | 6-(2-{4-[2-(2,6-dimethylmorpholin-4-yl)ethoxy]phenyl}-1,3-benzoxazol-6-yl)-5-ethyl-2,3,4,5-tetrahydropyridazin-3-one, |
| 221 | 5-ethyl-6-[2-(4-{[1-(morpholin-4-yl)propan-2-yl]oxy}phenyl)-1,3-benzoxazol-6-yl]-2,3,4,5-tetrahydropyridazin-3-one, |
| 222 | 6-(2-{4-[2-(diethylamino)ethoxy]phenyl}-1,3-benzoxazol-6-yl)-5-ethyl-2,3,4,5-tetrahydropyridazin-3-one, |
| 223 | (4S,5S)-6-[2-(4-{2-[(2R,6S)-2,6-dimethylmorpholin-4-yl]ethoxy}phenyl)-1,3-benzoxazol-6-yl]-5-methyl-4-propyl-2,3,4,5-tetrahydropyridazin-3-one, |
| 224 | 6-[2-(4-{[(1R,2R)-2-(diethylamino)cyclohexyl]oxy}phenyl)-1,3-benzoxazol-6-yl]-5-ethyl-2,3,4,5-tetrahydropyridazin-3-one, |
| 225 | 5-ethyl-6-[2-(4-{[(1R,2R)-2-(piperidin-1-yl)cyclopentyl]oxy}phenyl)-1,3-benzoxazol-6-yl]-2,3,4,5-tetrahydropyridazin-3-one, |
| 226 | tert-butyl (2S)-2-{4-[6-(4-ethyl-6-oxo-1,4,5,6-tetrahydropyridazin-3-yl)-1,3-benzoxazol-2-yl]phenoxymethyl}pyrrolidine-1-carboxylate, |

-continued

| Example | IUPAC Name |
|---|---|
| 227 | tert-butyl (2R)-2-{4-[6-(4-ethyl-6-oxo-1,4,5,6-tetrahydropyridazin-3-yl)-1,3-benzoxazol-2-yl]phenoxymethyl}pyrrolidine-1-carboxylate, |
| 228 | 5-ethyl-6-[2-(4-{[2-methyl-1-(pyrrolidin-1-yl)propan-2-yl]oxy}phenyl)-1,3-benzoxazol-6-yl]-2,3,4,5-tetrahydropyridazin-3-one, |
| 229 | 5-ethyl-6-(2-{4-[2-methyl-2-(pyrrolidin-1-yl)propoxy]phenyl}-1,3-benzoxazol-6-yl)-2,3,4,5-tetrahydropyridazin-3-one, |
| 230 | 5-ethyl-6-[2-(3-{[1-(piperidin-1-yl)propan-2-yl]oxy}phenyl)-1,3-benzoxazol-6-yl]-2,3,4,5-tetrahydropyridazin-3-one, |
| 231 | 5-ethyl-6-[2-(4-{[2-methyl-1-(morpholin-4-yl)propan-2-yl]oxy}phenyl)-1,3-benzoxazol-6-yl]-2,3,4,5-tetrahydropyridazin-3-one, |
| 232 | 5-ethyl-6-(2-{4-[2-methyl-2-(morpholin-4-yl)propoxy]phenyl}-1,3-benzoxazol-6-yl)-2,3,4,5-tetrahydropyridazin-3-one, |
| 233 | 5-ethyl-6-(2-{4-[(1-methylpiperidin-2-yl)methoxy]phenyl}-1,3-benzoxazol-6-yl)-2,3,4,5-tetrahydropyridazin-3-one, |
| 234 | 5-ethyl-6-(2-{4-[(1-methylazepan-2-yl)oxy]phenyl}-1,3-benzoxazol-6-yl)-2,3,4,5-tetrahydropyridazin-3-one, |
| 235 | (5R)-5-ethyl-6-[2-(4-{[1-(piperidin-1-yl)propan-2-yl]oxy}phenyl)-1,3-benzoxazol-6-yl]-2,3,4,5-tetrahydropyridazin-3-one, |
| 236 | (5S)-5-ethyl-6-(2-{4-[2-(piperidin-1-yl)propoxy]phenyl}-1,3-benzoxazol-6-yl)-2,3,4,5-tetrahydropyridazin-3-one, |
| 237 | (5R)-5-ethyl-6-(2-{4-[2-(piperidin-1-yl)propoxy]phenyl}-1,3-benzoxazol-6-yl)-2,3,4,5-tetrahydropyridazin-3-one, |
| 238 | 5-ethyl-6-(2-{4-[(2S)-pyrrolidin-2-ylmethoxy]phenyl}-1,3-benzoxazol-6-yl)-2,3,4,5-tetrahydropyridazin-3-one, |
| 239 | 5-ethyl-6-(2-{4-[(2R)-pyrrolidin-2-ylmethoxy]phenyl}-1,3-benzoxazol-6-yl)-2,3,4,5-tetrahydropyridazin-3-one, |
| 240 | 5-ethyl-6-[2-(4-{[(2S)-1-(propan-2-yl)pyrrolidin-2-yl]methoxy}phenyl)-1,3-benzoxazol-6-yl]-2,3,4,5-tetrahydropyridazin-3-one, |
| 241 | 5-ethyl-6-[2-(4-{[(2R)-1-(propan-2-yl)pyrrolidin-2-yl]methoxy}phenyl)-1,3-benzoxazol-6-yl]-2,3,4,5-tetrahydropyridazin-3-one, |
| 242 | 5-ethyl-6-[2-(4-{[(2S)-1-methylpyrrolidin-2-yl]methoxy}phenyl)-1,3-benzoxazol-6-yl]-2,3,4,5-tetrahydropyridazin-3-one, |
| 243 | 5-ethyl-6-(2-{4-[2-(4-methylpiperidin-1-yl)ethoxy]phenyl}-1,3-benzoxazol-6-yl)-2,3,4,5-tetrahydropyridazin-3-one, |
| 244 | 5-ethyl-6-(2-{4-[2-(4-propylpiperidin-1-yl)ethoxy]phenyl}-1,3-benzoxazol-6-yl)-2,3,4,5-tetrahydropyridazin-3-one, |
| 245 | 6-{2-[4-(2-{3-azaspiro[5.5]undecan-3-yl}ethoxy)phenyl]-1,3-benzoxazol-6-yl}-5-ethyl-2,3,4,5-tetrahydropyridazin-3-one, |
| 246 | 6-[2-(4-{2-[(2R,6S)-2,6-dimethylmorpholin-4-yl]ethoxy}phenyl)-1,3-benzoxazol-6-yl]-5-ethyl-2,3,4,5-tetrahydropyridazin-3-one, |
| 247 | 5-ethyl-6-(2-{4-[2-(thiomorpholin-4-yl)ethoxy]phenyl}-1,3-benzoxazol-6-yl)-2,3,4,5-tetrahydropyridazin-3-one, |
| 248 | 5-ethyl-6-(2-{4-[2-(4-fluoropiperidin-1-yl)ethoxy]phenyl}-1,3-benzoxazol-6-yl)-2,3,4,5-tetrahydropyridazin-3-one, |
| 249 | 5-ethyl-6-[2-(4-{2-[propan-2-yl(propyl)amino]ethoxy}phenyl)-1,3-benzoxazol-6-yl]-2,3,4,5-tetrahydropyridazin-3-one, |
| 250 | 6-[2-(4-{2-[(2R,5R)-2,5-dimethylpyrrolidin-1-yl]ethoxy}phenyl)-1,3-benzoxazol-6-yl]-5-ethyl-2,3,4,5-tetrahydropyridazin-3-one, |
| 251 | 5-ethyl-6-(2-{4-[(1-hydroxypropan-2-yl)oxy]phenyl}-1,3-benzoxazol-6-yl)-2,3,4,5-tetrahydropyridazin-3-one, |
| 252 | (4R,5R)-5-methyl-6-[2-(1-methyl-1H-pyrrol-2-yl)-1,3-benzoxazol-6-yl]-4-propyl-2,3,4,5-tetrahydropyridazin-3-one, |
| 253 | (4R,5R)-6-(2-cyclopropyl-1,3-benzoxazol-6-yl)-5-methyl-4-propyl-2,3,4,5-tetrahydropyridazin-3-one, |
| 254 | methyl 3-[6-(4-methyl-6-oxo-1,6-dihydropyridazin-3-yl)-1,3-benzoxazol-2-yl]benzoate, |
| 255 | 4-[6-(4-methyl-6-oxo-1,6-dihydropyridazin-3-yl)-1,3-benzoxazol-2-yl]benzoic acid, |
| 256 | 5-methyl-6-[2-(thiophen-2-yl)-1,3-benzoxazol-6-yl]-2,3-dihydropyridazin-3-one, |
| 257 | 6-[2-(thiophen-2-yl)-1,3-benzoxazol-6-yl]-2,3-dihydropyridazin-3-one, |
| 258 | (5S)-6-[2-(4-{2-[bis(propan-2-yl)amino]ethoxy}phenyl)-1,3-benzoxazol-6-yl]-5-ethyl-2,3,4,5-tetrahydropyridazin-3-one, |
| 259 | (5R)-6-[2-(4-{2-[bis(propan-2-yl)amino]ethoxy}phenyl)-1,3-benzoxazol-6-yl]-5-ethyl-2,3,4,5-tetrahydropyridazin-3-one, |
| 260 | (4R,5R)-5-methyl-6-{2-[4-(propan-2-yloxy)phenyl]-1,3-benzoxazol-6-yl}-4-propyl-2,3,4,5-tetrahydropyridazin-3-one, |

the tautomers and stereoisomers thereof, the mixtures thereof and the salts thereof.

The compounds of formula I according to the invention are GPR119 agonists. The effect of the compounds on the activation of GPR119 and on the stimulation of intracellular cAMP concentration is determined using the AlphaScreen cAMP Assay Kit (Cat. No. #6760625R) made by PerkinElmer.

MIN6 cells [Miyazaki J et al. Endocrinology. 1990 July; 127(1):126-32] were stably transfected with an expression vector for human GPR119 cDNA (Acc. No. NP_848566). Min-6/hGPR119 cells are cultured in DMEM, 10% FBS, 50 μM β-mercaptoethanol, 0.3 mg/mL Geniticin, 2 mM GlutaMAX at 37° C. 5% CO2. For the assay, the cells are placed in Optiplates (white, 384-well, 160W-barcoded, TC, sterile with lid, Cat. No. #6007688 (Perkin Elmer); 10000 cells/well; 50 μl). The plates covered with lids are then incubated for 24 hours at 37° C./5% CO2.

After the medium has been sucked out of the wells completely, 10 μl of the test compound are added, the compounds are diluted beforehand with stimulating buffer (140 mM NaCl, 3.6 mM KCl, 0.5 mM NaH2PO4, 0.5 mM MgSO4, 1.5 mM CaCl2, 10 mM Hepes, 5 mM NaHCO3; pH 7.4. 0.5 mM IBMX and 0.1% BSA, the final DMSO concentration is 1%). After 45 minutes' incubation at RT, the cAMP concentrations are determined using the AlphaScreen cAMP Assay Kit (Cat. No. #6760625R from PerkinElmer). 10 μl of Biotin-cAMP (final concentration 1 U/well in lysing buffer (5 mM Hepes (pH 7.4), 0.1% BSA, 0.5% Tween) and 10 μL Bead solution (final concentration 1 U/well in lysing buffer) are added. The plates are incubated for a further 2 hours at 24° C. The cAMP concentrations are calculated using a cAMP standard curve from the Alpha Screen Counts. The data analysis is carried out by calculating the EC50 value and the maximum value based on a positive control, using suitable software (Prism). The compounds according to the invention increase the intracellular cAMP level by roughly a factor of 5.

The compounds according to the invention typically have $EC_{50}$ values in the range from about 20 nM to about 10 μM, preferably from 20 nM to 2 μM, preferably less than 1 μM, particularly preferably less than 500 nM, most particularly preferably less than 100 nM.

$EC_{50}$ values for representative compounds according to the invention are shown in the following Table (the number of the compound corresponds to the number of the Example in the experimental section):

| Example No. | EC50 (cAMP assay) |
|---|---|
| 1 | 660 |
| 2 | 787 |
| 3 | 82 |
| 4 | 596 |
| 5 | 243 |
| 6 | 1702 |
| 7 | 892 |
| 8 | 874 |
| 9 | 834 |
| 10 | 365 |
| 11 | >10000 |
| 12 | 246 |
| 13 | 153 |
| 14 | 264 |
| 15 | 701 |
| 16 | 314 |
| 17 | 223 |
| 18 | 153 |
| 19 | 469 |

-continued

| Example No. | EC50 (cAMP assay) |
|---|---|
| 20 | 157 |
| 21 | >10000 |
| 22 | 1750 |
| 23 | 1346 |
| 24 | 5100 |
| 25 | 2370 |
| 26 | 166 |
| 27 | 444 |
| 28 | 213 |
| 29 | 181 |
| 30 | >10000 |
| 31 | 66 |
| 32 | 869 |
| 33 | 70 |
| 34 | 193 |
| 35 | 148 |
| 36 | 58 |
| 37 | 636 |
| 38 | 890 |
| 39 | 329 |
| 40 | 275 |
| 41 | 1523 |
| 42 | 4176 |
| 43 | 1075 |
| 44 | 1093 |
| 45 | 807 |
| 46 | 345 |
| 47 | 226 |
| 48 | 348 |
| 49 | 114 |
| 50 | 223 |
| 51 | 158 |
| 52 | 189 |
| 53 | 205 |
| 54 | 145 |
| 55 | 486 |
| 56 | 170 |
| 57 | 37 |
| 58 | 76 |
| 59 | 1588 |
| 60 | 639 |
| 61 | 342 |
| 62 | 552 |
| 63 | 324 |
| 64 | 237 |
| 65 | 426 |
| 66 | 112 |
| 67 | 51 |
| 68 | 60 |
| 69 | 143 |
| 70 | 3911 |
| 71 | >10000 |
| 72 | 1814 |
| 73 | 6773 |
| 74 | 240 |
| 75 | 384 |
| 76 | 245 |
| 77 | 141 |
| 78 | 61 |
| 79 | 41 |
| 80 | 615 |
| 81 | 31 |
| 82 | 189 |
| 83 | 94 |
| 84 | 132 |
| 85 | 334 |
| 86 | 1146 |
| 87 | 100 |
| 88 | 260 |
| 89 | 415 |
| 90 | 763 |
| 91 | 142 |
| 92 | 460 |
| 93 | 397 |
| 94 | 114 |
| 95 | 67 |

-continued

| Example No. | EC50 (cAMP assay) |
|---|---|
| 96 | 42 |
| 97 | 225 |
| 98 | 294 |
| 99 | 59 |
| 100 | 442 |
| 101 | 194 |
| 102 | 316 |
| 103 | 1208 |
| 104 | 120 |
| 105 | 80 |
| 106 | 120 |
| 107 | 267 |
| 108 | 346 |
| 109 | 1412 |
| 110 | 4544 |
| 111 | 967 |
| 112 | 1324 |
| 113 | 1899 |
| 114 | 2288 |
| 115 | 1130 |
| 116 | 3446 |
| 117 | 9388 |
| 118 | 3741 |
| 119 | 3464 |
| 120 | 1342 |
| 121 | 379 |
| 122 | 3997 |
| 123 | 902 |
| 124 | 8716 |
| 125 | 1600 |
| 126 | 306 |
| 127 | 2590 |
| 128 | 56 |
| 129 | 6721 |
| 130 | 814 |
| 131 | 7705 |
| 132 | 4158 |
| 133 | 300 |
| 134 | 1627 |
| 135 | 391 |
| 136 | 2016 |
| 137 | 497 |
| 138 | 1306 |
| 139 | 1557 |
| 140 | >10000 |
| 141 | 7333 |
| 142 | 539 |
| 143 | 397 |
| 144 | 987 |
| 145 | 209 |
| 146 | 8851 |
| 147 | 79 |
| 148 | 1559 |
| 149 | 567 |
| 150 | 1263 |
| 151 | 116 |
| 152 | 1075 |
| 153 | 735 |
| 154 | 424 |
| 155 | 7748 |
| 156 | 248 |
| 157 | 2031 |
| 158 | 1963 |
| 159 | 623 |
| 160 | 124 |
| 161 | 293 |
| 162 | 9119 |
| 163 | 97 |
| 164 | 552 |
| 165 | 118 |
| 166 | 621 |
| 167 | 1032 |
| 168 | 3011 |
| 169 | 1035 |
| 170 | 53 |
| 171 | 37 |

-continued

| Example No. | EC50 (cAMP assay) |
|---|---|
| 172 | 755 |
| 173 | 218 |
| 174 | 92 |
| 175 | 462 |
| 176 | 82 |
| 177 | 134 |
| 178 | 108 |
| 179 | 3841 |
| 180 | 290 |
| 181 | 156 |
| 182 | 116 |
| 183 | 134 |
| 184 | 53 |
| 185 | 142 |
| 186 | 88 |
| 187 | 173 |
| 188 | 83 |
| 189 | 127 |
| 190 | 79 |
| 191 | 41 |
| 192 | 6057 |
| 193 | 30 |
| 194 | 333 |
| 195 | 51 |
| 196 | 39 |
| 197 | 1114 |
| 198 | 896 |
| 199 | 832 |
| 200 | 52 |
| 201 | 3033 |
| 202 | 133 |
| 203 | 962 |
| 204 | 414 |
| 205 | 50 |
| 206 | 27 |
| 207 | 578 |
| 208 | 88 |
| 209 | 311 |
| 210 | 590 |
| 211 | 395 |
| 212 | 108 |
| 213 | 241 |
| 214 | 122 |
| 215 | 106 |
| 216 | 639 |
| 217 | 2414 |
| 218 | 840 |
| 219 | 438 |
| 220 | 84 |
| 221 | 204 |
| 222 | 299 |
| 223 | 46 |
| 224 | 319 |
| 225 | 231 |
| 226 | 47 |
| 227 | 52 |
| 228 | 549 |
| 229 | 398 |
| 230 | 1187 |
| 231 | 120 |
| 232 | 69 |
| 233 | 848 |
| 234 | 306 |
| 235 | 104 |
| 236 | 1097 |
| 237 | 73 |
| 238 | 2953 |
| 239 | 1649 |
| 240 | 186 |
| 241 | 191 |
| 242 | 296 |
| 243 | 197 |
| 244 | 181 |
| 245 | 434 |
| 246 | 54 |
| 247 | 62 |

-continued

| Example No. | EC50 (cAMP assay) |
|---|---|
| 248 | 159 |
| 249 | 58 |
| 250 | 235 |
| 251 | 296 |
| 252 | 110 |
| 253 | 299 |
| 254 | 8952 |
| 255 | 7238 |
| 256 | 9384 |
| 257 | 456 |
| 258 | 605 |
| 259 | 22 |
| 260 | 24 |

The compounds of formula I and the physiologically acceptable salts thereof according to the invention have valuable pharmacological properties which make them commercially useful. Thus, for example, these compounds may act as GPR119 agonists.

In view of their ability to act as GPR119 agonists, the compounds of formula I according to the invention and the corresponding pharmaceutically acceptable salts thereof are theoretically suitable for treating and/or preventatively treating all those conditions or diseases that can be influenced by binding to the G-protein coupled receptor GPR119 and by modulation of its activity. Therefore the compounds according to the invention are suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells.

In addition the compounds according to the invention are suitable for use in one or more of the following therapeutic processes:

- for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);
- for improving glycaemic control and/or reducing fasting plasma glucose, postprandial plasma glucose and/or the glycosylated haemoglobin HbA1c;
- for preventing, delaying, slowing or reversing the progression of disrupted glucose tolerance, insulin resistance and/or metabolic syndrome to type 2 diabetes;
- for preventing, delaying, slowing the progression of or treating a condition or a disease selected from among the complications of diabetes, such as for example retinopathy, nephropathy or neuropathies, diabetic foot, ulcers or macroangiopathies;
- for reducing weight or preventing weight gain or assisting weight loss;
- for preventing or treating the degradation of pancreatic beta cells and/or improving and/or restoring the functionality of pancreatic beta cells and/or restoring the functionality of pancreatic insulin secretion;
- for maintaining and/or improving insulin sensitivity and/or preventing or treating hyperinsulinaemia and/or insulin resistance.

In particular, the compounds according to the invention, including the physiologically acceptable salts thereof, are suitable for the prevention and/or treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention, including the physiologically acceptable salts thereof, are most particularly suitable for treating type 2 diabetes mellitus.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 0.1 to 100 mg, preferably 0.5 to 50 mg, by intravenous route, and 1 to 1000 mg, preferably 1 to 100 mg, by oral route, in each case administered 1 to 4 times a day. For this purpose, the compounds according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may be administered by oral, transdermal, inhalative, parenteral or sublingual route. Of the possible methods of administration, oral or intravenous administration is preferred. The compounds according to the invention are present as active ingredients in the formulations conventionally used for this purpose, such as those mentioned above, for example. Oral formulations, particularly solid forms such as e.g. tablets or capsules are preferred.

The pharmaceutical preparations or formulations according to the invention contain at least one compound according to the invention (=active substance) for example in an amount of 0.1 to 99.9 percent by weight, or 5 to 95 percent by weight, or 20 to 80 percent by weight, optionally together with pharmaceutically acceptable excipients (comprising for example diluents, carriers, binders, disintegrants and/or other excipients).

The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

In addition to being used in monotherapy, the compounds according to the invention may also be used in conjunction with one or more other active substances, particularly for the treatment and/or prevention of the diseases and conditions mentioned above. Other active substances which are suitable for such combinations include in particular those which for example potentiate the therapeutic effect of one or more active substances with respect to one of the indications mentioned and/or which allow the dosage of one or more active substances to be reduced.

Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-(alpha, gamma or alpha/gamma) agonists or modulators (e.g. aleglitazar, indeglitazar), alpha-glucosidase inhibitors (e.g. miglitol, acarbose, voglibose), DPPIV inhibitors (e.g. sitagliptin, vildagliptin, saxagliptin, alogliptin, linagliptin), SGLT2-inhibitors (e.g. dapagliflozin, sergliflozin), insulin and insulin analogues, GLP-1 and GLP-1 analogues (e.g. exenatide, liraglutide, taspoglutide) or amylin and amylin analogues, cycloset, 11-β-HSD inhibitors or GPR119 agonists. Other suitable combination partners are inhibitors of protein tyrosinephosphatase 1 (e.g. trodusquemine), substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors (e.g. simvastatin, atorvastatin), fibrates (e.g. bezafibrate, fenofibrate), nicotinic acid and the derivatives thereof (e.g. niacin), PPAR-(alpha, gamma or alpha/gamma) agonists or modulators, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, MTP inhibitors, or HDL-raising compounds such as CETP inhibitors (e.g. dalcetrapib, anacetrapib) or ABC1 regulators.

Other suitable combination partners are one or more active substances for the treatment of obesity, such as for example sibutramine or tetrahydrolipstatin, alizyme, antagonists of the cannabinoid) receptor, MCH-1 receptor antagonists, MC4 receptor agonists, NPY5 or NPY2 antagonists (e.g. velneperit), β3-agonists, leptin or leptin mimetics, agonists of the 5HT2c receptor (e.g. lorcaserin), tesofensine, or the combinations of bupropione/naltrexone, bupropione/zonisamide, topiramate/phentermine or pramlintide/meterleptin.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are telmisartan, candesartan, valsartan, losartan, eprosartan, irbesartan, olmesartan, tasosartan, azilsartan, etc. Angiotensin II receptor antagonists are preferably used for the treatment or prevention of high blood pressure and complications of diabetes, often combined with a diuretic such as hydrochlorothiazide.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a medicament which is suitable for the treatment or prevention of diseases or conditions which can be affected by binding to the G-protein coupled receptor GPR 119 and by modulating its activity. This is preferably a metabolic disease, particularly one of the diseases or conditions listed above, most particularly diabetes or complications of diabetes.

The use of the compound according to the invention, or a physiologically acceptable salt thereof, in combination with one or more other active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times the two active substances are given to the patient within a period of less than or equal to 12 hours, but particularly less than or equal to 6 hours.

Consequently, in another aspect, this invention relates to a medicament which comprises a compound according to the invention or a physiologically acceptable salt of such a compound and at least one of the active substances described above as combination partners, optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The compounds according to the invention may be obtained using methods of synthesis that are known in principle. The compounds may be obtained using the preparation methods according to the invention that are explained in more detail hereinafter. Preferably, the compounds according to the invention are obtained as illustrated by way of example in the Examples.

Some methods of preparing the compounds of formula I according to the invention and their precursors are shown in the following synthesis schemes and also in the Examples, by way of illustration.

In some cases the sequence adopted in carrying out the reaction schemes may be varied.

The compounds according to the invention and their intermediates may be prepared according to the schemes shown and specific Examples or corresponding modifications thereof. Variants of these reactions that are known to the skilled man but are not described in detail here may also be used. The general processes for preparing the compounds according to the invention will become apparent to the skilled man on studying the schemes that follow.

Starting compounds are commercially available or may be prepared by methods that are described in the literature or herein, or may be prepared in an analogous or similar manner.

Before the reaction is carried out any corresponding functional groups in the compounds may be protected using conventional protecting groups. These protecting groups may be cleaved again at a suitable stage within the reaction sequence using methods familiar to the skilled man.

Compounds of formula I, wherein G denotes a system of formula G1, A denotes $CR^2R^3$, wherein $R^2$ and $R^3$ are as herein defined, and the other substituents have the meanings stated herein (i.e. compounds of formula 1a), may be prepared by process a) illustrated in Scheme 1 according to the invention, starting from a compound of formula 1c.

Scheme 1: Method a)

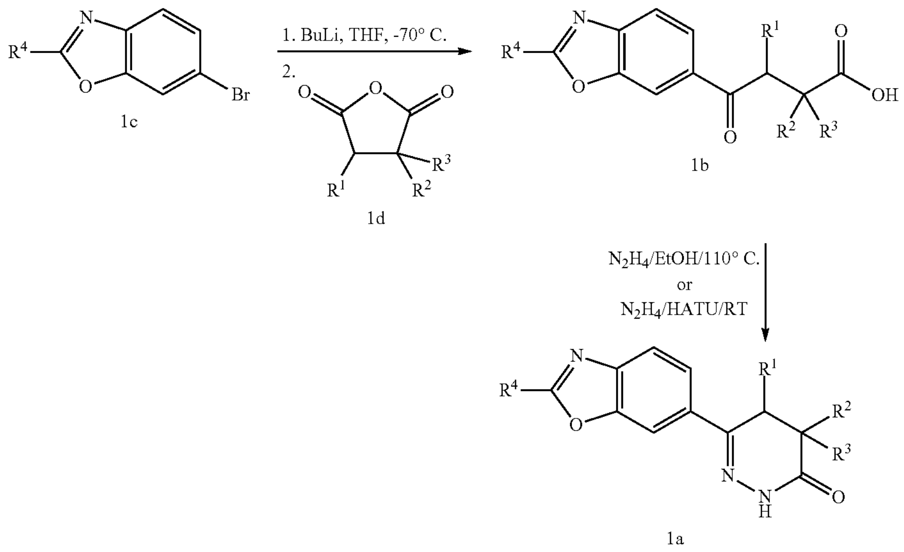

An aromatic halogen compound of formula 1c, wherein $R^4$ is as herein defined, is converted, by a halogen-metal exchange using a suitable lithium alkyl reagent, preferably butyl lithium, in a suitable solvent, such as e.g. tetrahydrofuran, at a suitable reaction temperature, e.g. at −70° C., into the corresponding lithium aryl compound, which is reacted with a cyclic anhydride of formula 1d, wherein $R^1$-$R^3$ are as herein defined, in a suitable solvent, such as e.g. tetrahydrofuran, at a suitable reaction temperature, e.g. at −70° C., to form the compound of formula 1b.

The compound of formula Ib is cyclocondensed with hydrazine to produce the corresponding compound of formula I (i.e. compound of formula 1a). The cyclisation may be carried out with hydrazine at an elevated temperature, e.g. in the range from 60° C. to 120° C., in a suitable solvent, such as e.g. ethanol or acetic acid, particularly for example using hydrazine hydrate in ethanol or hydrazine hydrate in glacial acetic acid at reflux temperature. Alternatively the cyclisation may also be carried out with hydrazine at ambient temperature using a common coupling reagent, e.g. a uranium coupling reagent such as e.g. HATU, in the presence of a suitable inorganic or, preferably, organic base, such as e.g. triethylamine or Hünig base, in a suitable solvent, such as e.g. DMF.

Alternatively compounds of formula I, wherein G denotes a system of formula G1, A has the meaning $CR^2R^3$ (particularly $CR^2H$), wherein $R^2$ and $R^3$ areas herein defined, and the other substituents have the meanings stated herein (i.e. compounds of formula 1a), with the proviso that $R^1$ and $R^2$ do not together denote a bond or a 1-4C-alkanediyl group as herein defined, may be prepared according to method b) according to the invention shown in Scheme 2, starting from a compound of formula 1c.

Scheme 2: Method b)

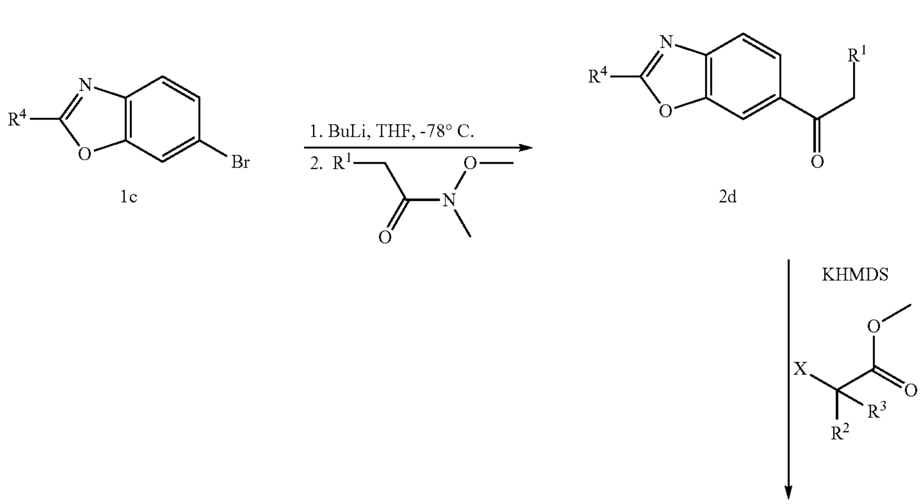

-continued

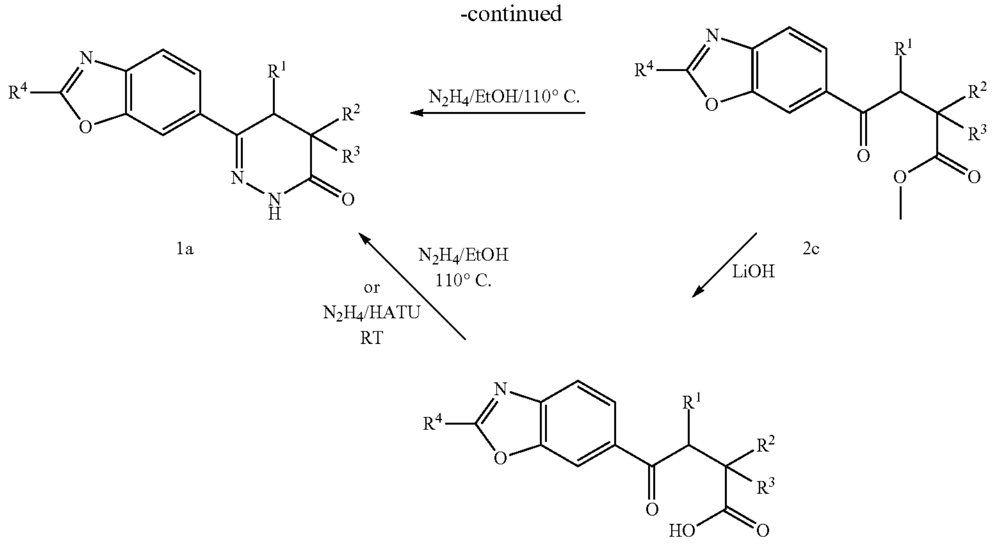

1a

2c

1b

X = Br, I, OTos

An aromatic halogen compound of formula 1c, wherein $R^4$ is as herein defined, is converted, by a halogen-metal exchange using a suitable lithium alkyl reagent, preferably butyl lithium, in a suitable solvent, such as e.g. tetrahydrofuran, at a suitable reaction temperature, e.g. at −70° C., into the corresponding lithium aryl compound, which is reacted with a compound of formula $R^1$—$(CH_2)$—$CON(CH_3)OCH_3$, wherein $R^1$ is as herein defined, in a suitable solvent, such as e.g. tetrahydrofuran, at a suitable reaction temperature, e.g. at −70° C., to form the compound of formula 2d.

The compound of formula 2d is deprotonated with a suitable inorganic or, preferably, organic base, such as e.g. potassium bis(trimethylsilyl)amide, in a suitable solvent, such as e.g. THF, at a suitable reaction temperature, e.g. at −70° C., in the alpha position to the carbonyl group and reacted with a compound of formula $R^2$—$CR^3X$—COOR, wherein $R^2$ and $R^3$ are as herein defined, R denotes a lower alkyl group, preferably methyl, and X denotes a suitable leaving group, such as e.g. bromine, iodine or a sulphonyloxy group (such as e.g. methylsulphonyloxy, tosylsulphonyloxy or trifluoromethylsulphonyloxy), in a suitable solvent, such as e.g. tetrahydrofuran, at a suitable reaction temperature, e.g. at −70° C., to form the compound of formula 2c.

The ester of formula 2c is cleaved to form the corresponding free acid 1b, e.g. by saponification with a suitable base, preferably an alkali metal hydroxide such as e.g. LiOH (preferably to saponify the methyl ester), in a suitable solvent, such as e.g. aqueous dioxane.

The free acid of formula Ib may be cyclised with hydrazine according to a process as hereinbefore described to form the corresponding compound of formula I (i.e compound of formula 1a). Alternatively the ester of formula 2c may also be cyclised with hydrazine at an elevated temperature, e.g. in the range from 60° C. to 120° C., in a suitable solvent, such as e.g. ethanol or acetic acid, particularly for example using hydrazine hydrate in ethanol or glacial acetic acid at reflux temperature, to obtain the corresponding compound of formula I (i.e compound of formula 1a).

Alternatively the compounds of formula I, wherein G denotes a system of formula G1, A has the meaning $CR^2H$, wherein $R^2$ is as herein defined, and the other substituents have the meanings stated herein (i.e compounds of formula 3a), with the proviso that $R^1$ and $R^2$ do not together denote a bond or a 1-4C-alkanediyl group as herein defined, may be prepared according to method c) according to the invention shown in Scheme 3, starting from a compound of formula 2d.

Scheme 3: Method c)

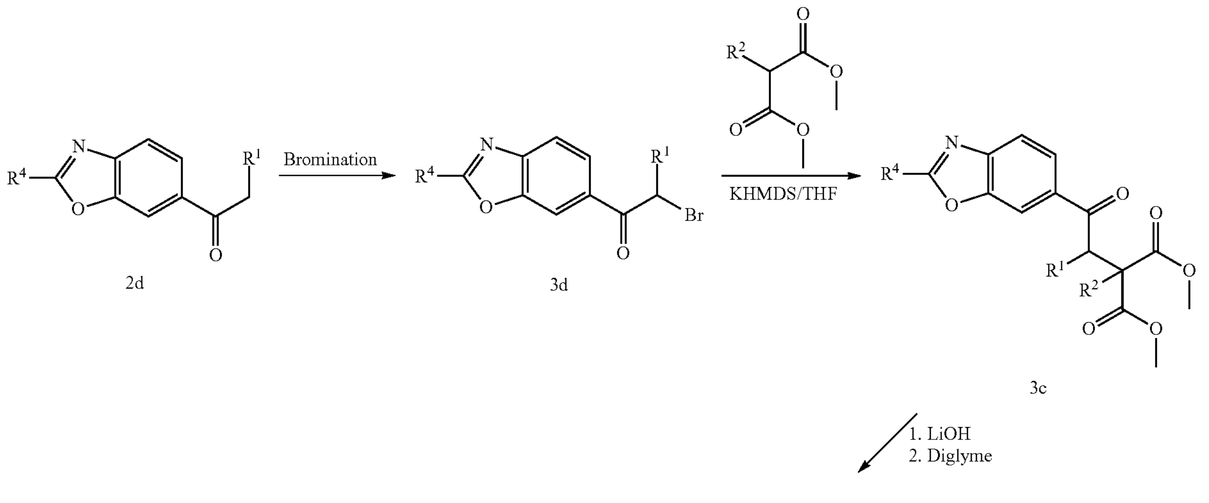

2d

3d

3c

-continued

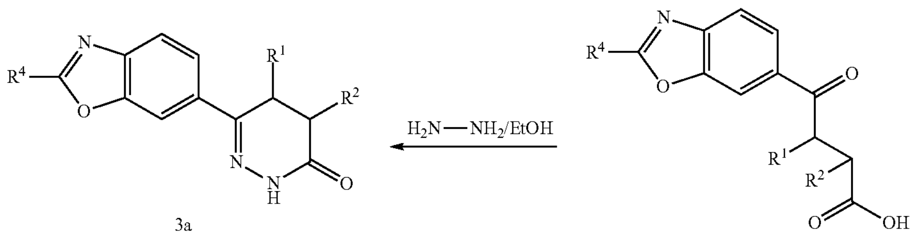

3a 3b

A compound of formula 2d, wherein $R^1$ and $R^4$ are as herein defined, is halogenated, preferably brominated, in the alpha position to the carbonyl group, for example using a suitable brominating agent, such as e.g. N-bromosuccinimide, elemental bromine or, preferably, pyridinium tribromide, preferably in the presence of a suitable acid, such as e.g. hydrogen bromide, in a suitable solvent, such as e.g. glacial acetic acid, and at a suitable reaction temperature, preferably ambient temperature, so as to obtain the compound of formula 3d.

The compound of formula 3d is subjected to malonic ester synthesis with a malonic ester of formula $RO_2C$—$CHR^2$—$CO_2R$, wherein $R^2$ is as herein defined and R denotes a lower alkyl group, preferably methyl. For this, the malonic ester of formula $RO_2C$—$CHR^2$—$CO_2R$ is deprotonated in a suitable solvent, such as e.g. THF, in each case at a suitable reaction temperature, with a suitable inorganic or, preferably, organic base, such as e.g. potassium bis(trimethylsilyl)amide and the deprotonated malonic acid ester is further reacted with the bromine compound of formula 3d to obtain the compound of formula 3c.

The malonic acid ester of formula 3c is cleaved to form the acid, e.g. by saponification with a suitable base, e.g. an alkali metal hydroxide such as LiOH, and decarboxylated to form the compound of formula 3b, e.g. by heating in a suitable solvent, such as e.g. diglyme.

The free acid of formula 3b may be cyclised with hydrazine using a process as hereinbefore described to form the corresponding compound of formula I (i.e. compound of formula 3a). Alternatively compounds of formula I, wherein G denotes a system of formula G1, A has the meaning $CR^2H$, wherein $R^2$ is as herein defined, and the remaining substituents have the meanings stated herein (i.e. compounds of formula 3a), with the proviso that $R^1$ and $R^2$ do not together denote a bond or a 1-4C-alkanediyl group as herein defined, may be prepared by method d) according to the invention shown in Scheme 4 starting from 2-benzoxazolinone.

Scheme 4: Method d)

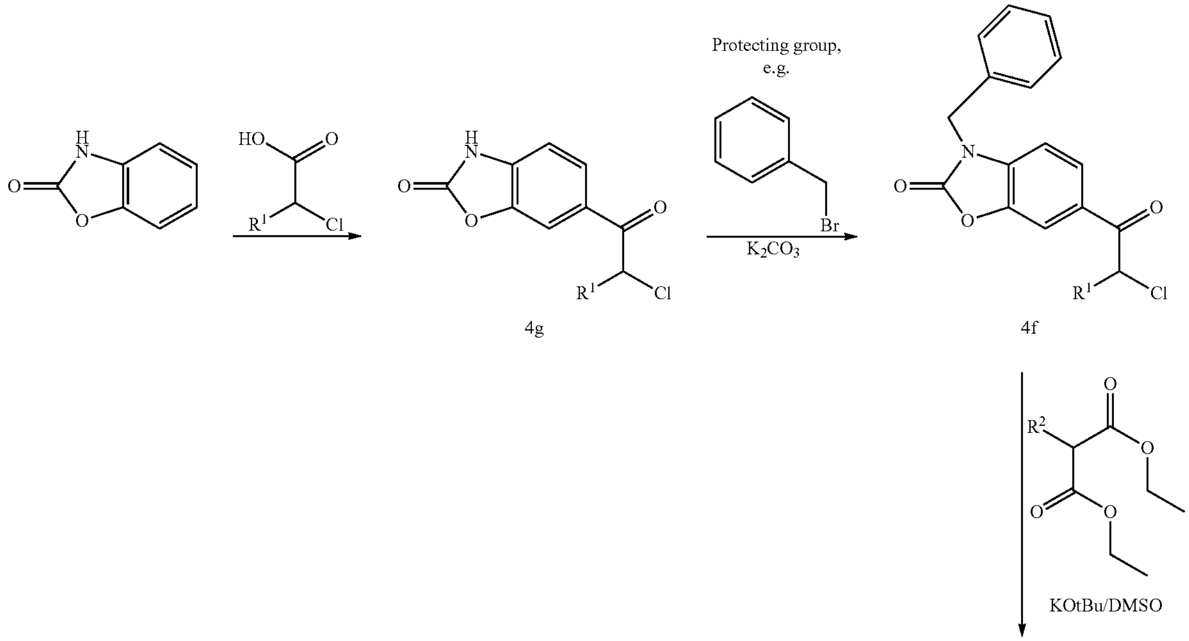

4g 4f

-continued

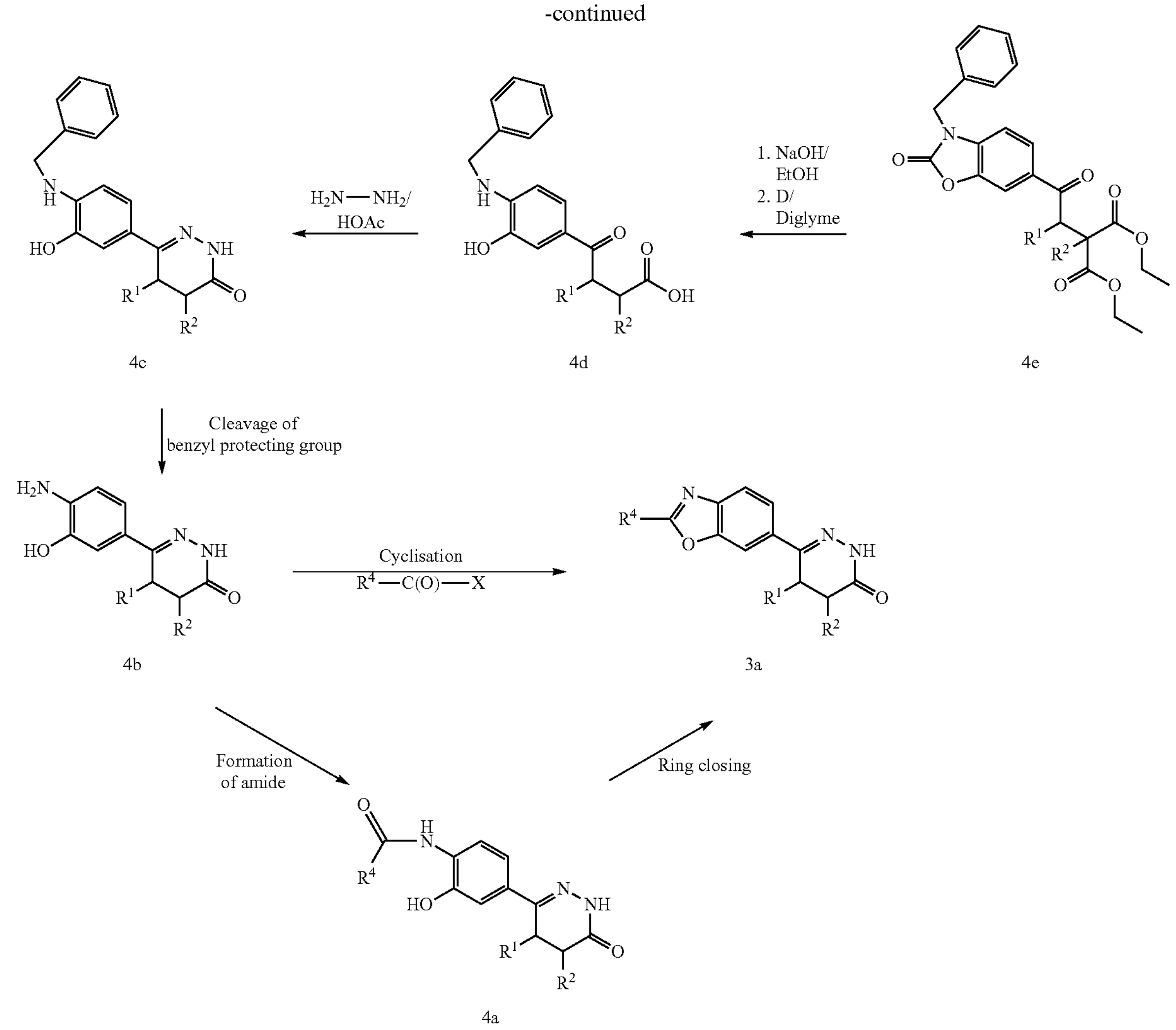

with X = OH, OAlkyl or Halogen,
or X = H and subsequent
oxident

2-Benzoxazolinone is acylated with an alpha halo-carboxylic acid, preferably alpha chloro-carboxylic acid of formula $R^1$—CHCl—COOH, wherein $R^1$ is as herein defined, for example in the presence of a suitable, preferably inorganic, acid, such as e.g. polyphosphoric acid, in a suitable solvent, preferably in an excess of the polyphosphoric acid used, at a suitable, preferably elevated, reaction temperature, e.g. 100° C.-130° C., and in this way a compound of formula 4g is obtained.

In a subsequent reaction step the NH group of the compound of formula 4g is protected with a suitable protecting group, such as e.g. a benzyl protecting group. The addition of the benzyl protecting group is carried out using a suitable benzylating agent, such as e.g. benzylbromide, in the presence of a suitable, preferably inorganic base, such as e.g. potassium carbonate, in a suitable solvent, such as e.g. acetone, and yields the protected compound of formula 4f.

The compound of formula 4f is subjected to a malonic acid ester synthesis with a malonic acid ester of formula $RO_2C$—$CHR^2$—$CO_2R$, wherein $R^2$ is as herein defined and R denotes a lower alkyl group, preferably ethyl. For this, the malonic acid ester of formula $RO_2C$—$CHR^2$—$CO_2R$ is deprotonated in a suitable solvent, such as e.g. DMSO, and in each case at a suitable reaction temperature, with a suitable inorganic or, preferably, organic base, such as e.g. potassium tert.-butoxide, and the deprotonated malonic acid ester is further reacted with the chlorine compound of formula 4f to obtain the compound of formula 4e.

The malonic acid ester of formula 4e obtained is cleaved to form the acid, e.g. by saponification with a suitable base, preferably alkali metal hydroxide such as e.g. NaOH, in a suitable solvent, such as e.g. aqueous ethanol, and decarboxylated to obtain the compound of formula 4d, e.g. by heating in a suitable solvent, such as e.g. diglyme.

The free acid of formula 4d may be cyclised with hydrazine using a process as hereinbefore described to form the corresponding compound of formula 4c.

The protected amino group of the compound of formula 4c is deprotected by cleaving the protecting group (e.g. using the benzyl protecting group, by hydrogenolytic debenzylation) and the aniline of formula 4b is obtained.

The compound of formula 4b is cyclocondensed with a carboxylic acid or carboxylic acid derivative of formula $R^4$—COX, wherein X denotes halogen, preferably chlorine, or OR, wherein R denotes hydrogen or lower alkyl, e.g. methyl or ethyl, to obtain the corresponding compound of formula I (i.e. compound of formula 3a).

This cyclisation may be carried out with a carboxylic acid of formula $R^4$—COOH in the presence of a suitable inorganic or organic acid, such as e.g. boric acid, p-toluenesulphonic acid or polyphosphoric acid, in a suitable solvent, such as e.g. xylene, acetic acid or in an excess of the acid used, preferably at elevated reaction temperatures, such as e.g. reflux temperature or 100° C.-130° C.

This cyclisation may also be carried out over two steps, where in the first step amide coupling of the carboxylic acid $R^4$—COOH or of an activated derivative thereof, such as e.g. the carboxylic acid chloride of formula $R^4$—COCl, with the aniline of formula 4b to obtain the amide of formula 4a. The amide coupling of the free carboxylic acids is carried out in the presence of a suitable activating reagent or coupling reagent, e.g. using 1,1-carbonyldiimidazole via the carboxylic acid imidazolide in a suitable solvent, such as e.g. DMF, and at a suitable, optionally elevated, reaction temperature. The amide coupling of the carboxylic acid chloride is carried out in the presence of a suitable inorganic or organic base, such as e.g. potassium carbonate or pyridine, in a suitable solvent, such as e.g. DMF or in an excess of pyridine.

The amide of formula 4a obtained intermediately may be isolated before the succeeding reaction of cyclisation or may be further cyclocondensed without being isolated, e.g. in a one-pot process or in situ, to obtain the corresponding compound of formula I (i.e. compound of formula 3a).

In the second step, the amide 4a obtained in the first step is cyclised to obtain the corresponding compound of formula I (i.e. compound of formula 3a). This cyclisation may be carried out as hereinbefore described, for example in the presence of a suitable inorganic or organic acid, such as e.g. p-toluenesulphonic acid or polyphosphoric acid, in a suitable solvent, such as e.g. xylene, acetic acid or in an excess of the polyphosphoric acid used, preferably at elevated reaction temperatures, such as e.g. reflux temperature or 100° C.-130° C.

By reacting a compound of formula 4b with a carboxylic acid chloride of formula $R^4$—COCl in the presence of a suitable base, such as e.g. pyridine, a suitable acid, such as e.g. p-toluenesulphonic acid, in a suitable solvent, such as e.g. xylene, and at a suitable, preferably elevated, reaction temperature, such as e.g. reflux temperature, the corresponding compound of formula I (i.e. compound of formula 3a) may be obtained directly in one step.

Alternatively the cyclisation of a compound of formula 4b with a carboxylic acid of formula $R^4$—COOH to obtain the corresponding compound of formula I (i.e. compound of formula 3a) may also be carried out directly using triphenylphosphine (preferably polymer-bound) and trichloroacetonitrile in a suitable solvent such as acetonitrile, at a suitable, preferably elevated, reaction temperature, such as e.g. 100° C.-130° C., optionally under microwave irradiation, preferably via the carboxylic acid chloride formed intermediately in situ.

The compound of formula 4b may also be cyclocondensed with an aldehyde of formula $R^4$—CHO and the resulting condensation product may be further reacted by oxidation to obtain the corresponding compound of formula I.

Alternatively compounds of formula I, wherein G denotes a system of formula G1, $R^1$ denotes hydrogen and A has the meaning $CR^2H$, wherein $R^2$ is as herein defined, and the remaining substituents have the meanings stated herein (i.e. compounds of formula 5a), may be prepared by the method e) according to the invention shown in Scheme 5 starting from a compound of formula 5g.

Scheme 5: Method e)

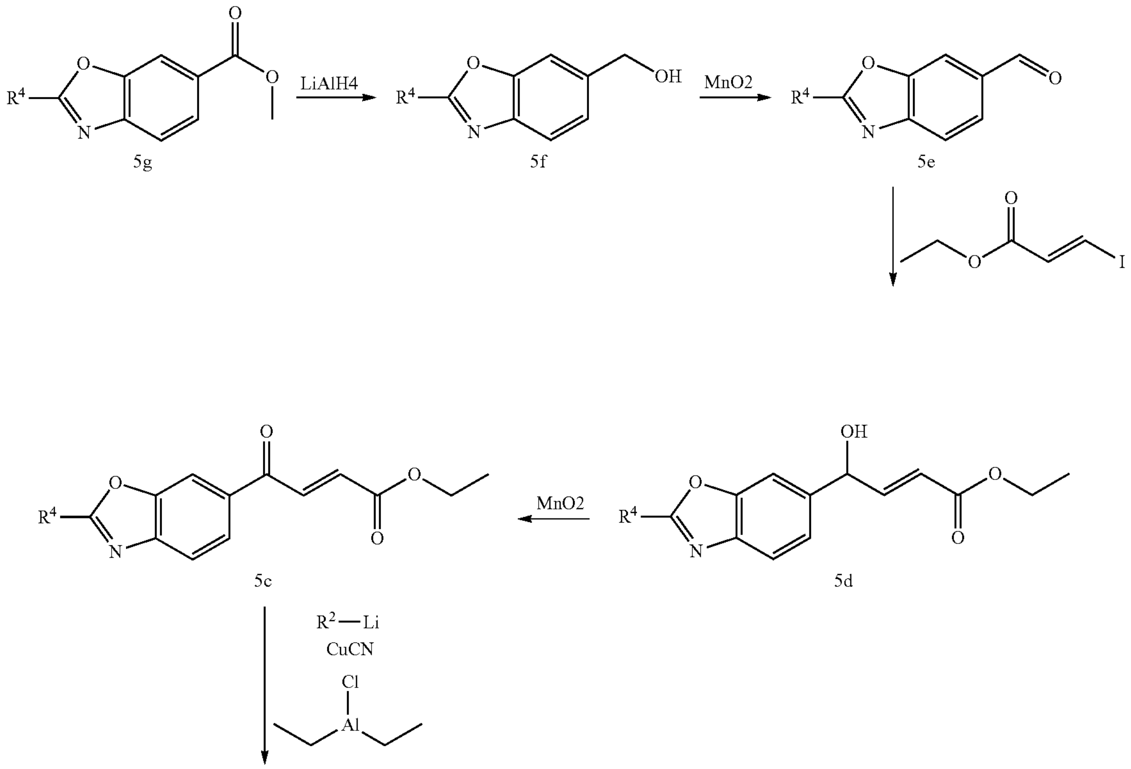

5g 5f 5e 5c 5d

-continued

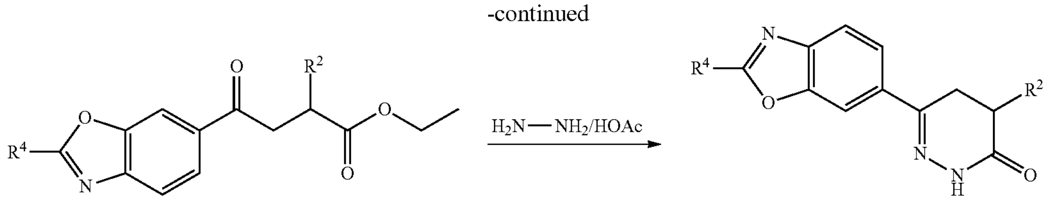

5b 5a

In this reaction an ester of formula 5g is reduced with a suitable reducing agent, such as e.g. lithium aluminium hydride, in a suitable solvent, such as e.g. THF, to obtain the alcohol of formula 5f. The alcohol of formula 5f is oxidised with a suitable oxidising agent, such as e.g. manganese dioxide, in a suitable solvent, such as e.g. dichloromethane, to form the aldehyde of formula 5e. Optionally the reduction of the ester to form the aldehyde may also be carried out directly in one step using a suitable selective reducing agent.

The aldehyde of formula 5e is reacted with a 3-halo-acrylic acid ester, preferably ethyl (E)-3-iodoacrylate, in a Nozaki-Hiyama-Kishi reaction to obtain the compound of formula 5d. This reaction is carried out in the presence of chromium (II), such as e.g. $CrCl_2$, and optionally catalysed by nickel(II), such as e.g. $NiCl_2$, in a suitable solvent, such as e.g. DMSO.

The compound of formula 5d is oxidised with a suitable oxidising agent, such as e.g. manganese dioxide, in a suitable solvent, such as e.g. dichloromethane, to form the compound of formula 5c.

The compound of formula 5c is reacted with a metal organyl of formula $R^2$-M, wherein $R^2$ is as herein defined and M denotes a suitable metal, such as e.g. lithium or copper, or a corresponding metal-containing group, in a Michael addition to form the compound of formula 5b. Preferably in this reaction a lithium organyl of formula $R^2$—Li is reacted in the presence of a copper(I) salt, such as e.g. CuCN, and, optionally, a suitable Lewis acid, such as e.g. diethyl aluminium chloride, and the Gilman and/or cyano-cuprate typically formed in situ is added to the compound of formula 5c. The reaction is carried out in a suitable solvent, such as e.g. THF, and at a suitable reaction temperature, such as e.g. −70° C.

The ester of formula 5b may be cyclised with hydrazine using a process as hereinbefore described to obtain the corresponding compound of formula I (i.e. compound of formula 5a).

Alternatively compounds of formula I, wherein G denotes a system of formula G1, A has the meaning $CR^2H$, wherein $R^2$ is as herein defined, and the remaining substituents have the meanings stated herein (i.e. compounds of formula 3a), may be prepared according to method f1) according to the invention shown in Scheme 6, right-hand branch, starting from a compound of formula 6f.

Scheme 6: Method f1) and f2)
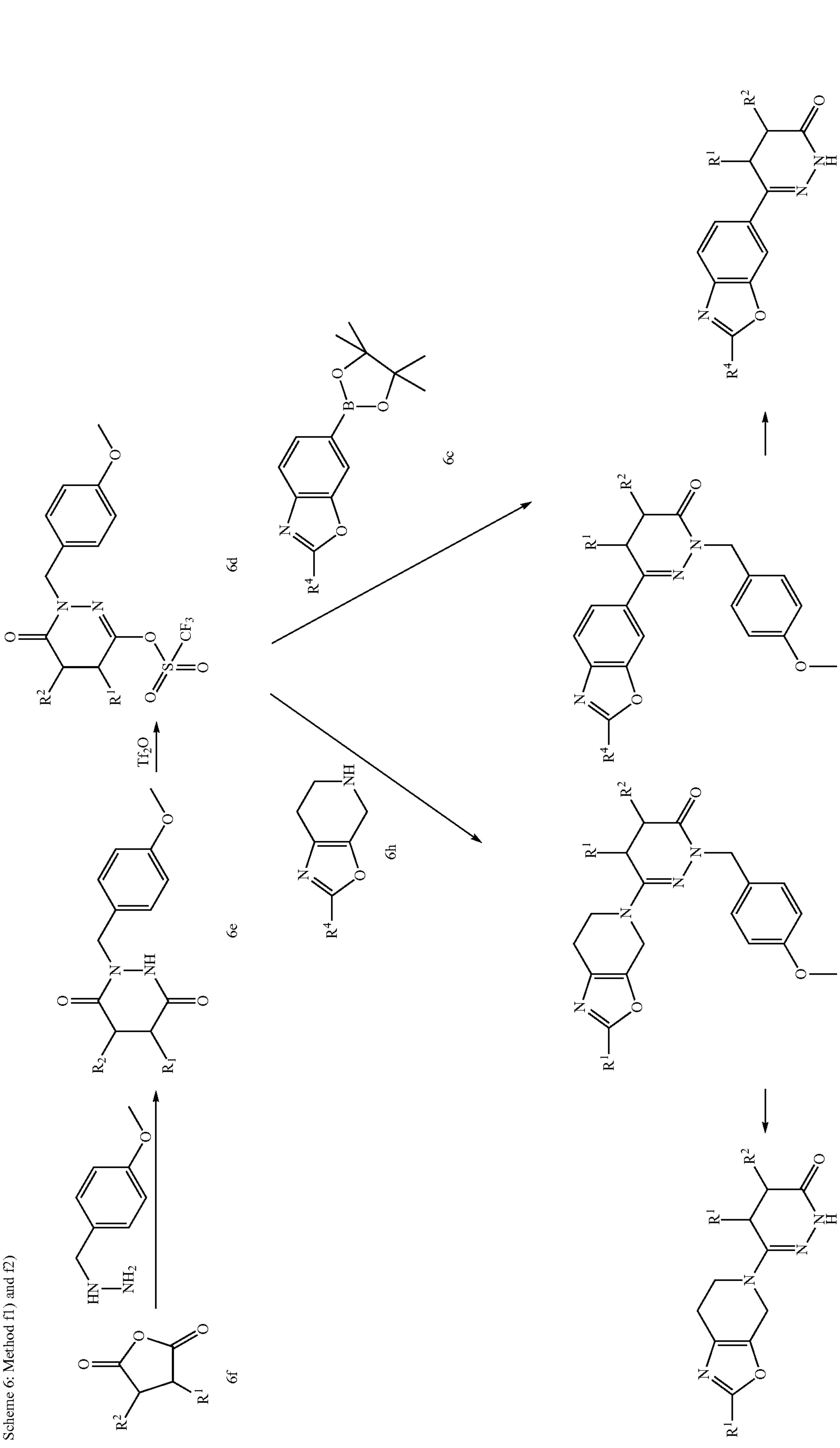
6f 6e 6d 6c 6h 6b 6g 3a 6a

A cyclic anhydride of formula 6f, wherein $R^1$ and $R^2$ are as herein defined, is converted with a suitably protected hydrazine, preferably e.g. 4-methoxybenzyl-hydrazine in a suitable solvent, such as e.g. acetonitrile, at a suitable reaction temperature, such as e.g. reflux temperature, in a compound of formula 6e.

The lactam of formula 6e is converted by O-sulphonylation, e.g. O-mesylation, O-tosylation or, preferably, O-triflation, with a suitable sulphonylating agent, such as for example sulphonic acid anhydride, sulphonic acid chloride or sulphonylimide, in suitable solvent, such as e.g. dichloromethane, at temperatures between −78° C. and 40° C., in the presence of a suitable base, such as e.g. triethylamine, into the methanesulphonic acid lactime ester, p-toluenesulphonic acid lactime ester or, preferably, trifluoromethanesulphonic acid lactime ester of formula 6d.

The triflate of formula 6d is reacted in a CC-linking reaction, e.g. Suzuki reaction, with a boric acid or boric acid ester of formula 6c, wherein $R^4$ is as herein defined, in a suitable solvent, such as e.g. dioxane, in the presence of a suitable base, such as e.g. aqueous sodium carbonate, and in the presence of a suitable (preferably palladium-containing) catalyst, such as e.g. tetrakistriphenylphosphine palladium, at a suitable reaction temperature, such as e.g. in the range from ambient temperature to 120° C., optionally with microwave irradiation, to obtain the compound of formula 6b.

After the methoxybenzyl protecting group has been cleaved from the compound of formula 6b under suitable conditions, preferably in trifluoroacetic acid, optionally in the presence of veratrol, optionally with microwave irradiation or with heating e.g. in a pressurised vessel, the corresponding compound of formula I (i.e. compound of formula 3a) is obtained.

Compounds of formula I wherein G denotes a system of formula G3, A has the meaning $CR^2H$, wherein $R^2$ is as herein defined, and the remaining substituents have the meanings stated herein (i.e. compounds of formula 6a), may be prepared by method f2) according to the invention as shown in Scheme 6, left-hand branch, again starting from a compound of formula 6f.

The triflate of formula 6d is reacted in a nucleophilic substitution reaction with a compound of formula 6h, wherein $R^4$ is as herein defined, in a suitable solvent, such as e.g. DMSO, optionally in the presence of a suitable base at a suitable reaction temperature, such as e.g. in the range from ambient temperature to 80° C., in order to obtain the compound of formula 6g.

After the methoxybenzyl protecting group has been cleaved from the compound of formula 6g under suitable conditions, preferably in trifluoroacetic acid, optionally in the presence of veratrol, optionally with microwave irradiation or with heating e.g. in a pressurised vessel, the corresponding compound of formula I (i.e. compound of formula 6a) is obtained.

Alternatively compounds of formula I, wherein G denotes a system of formula G3, A has the meaning $CR^2R^3$ (particularly $CR^2H$), wherein $R^2$ and $R^3$ are as herein defined, and the remaining substituents have the meanings stated herein (i.e. compounds of formula 7a), may be prepared using method g) according to the invention as shown in Scheme 7 starting from a compound of formula 6h or 7e.

Scheme 7: Method g)

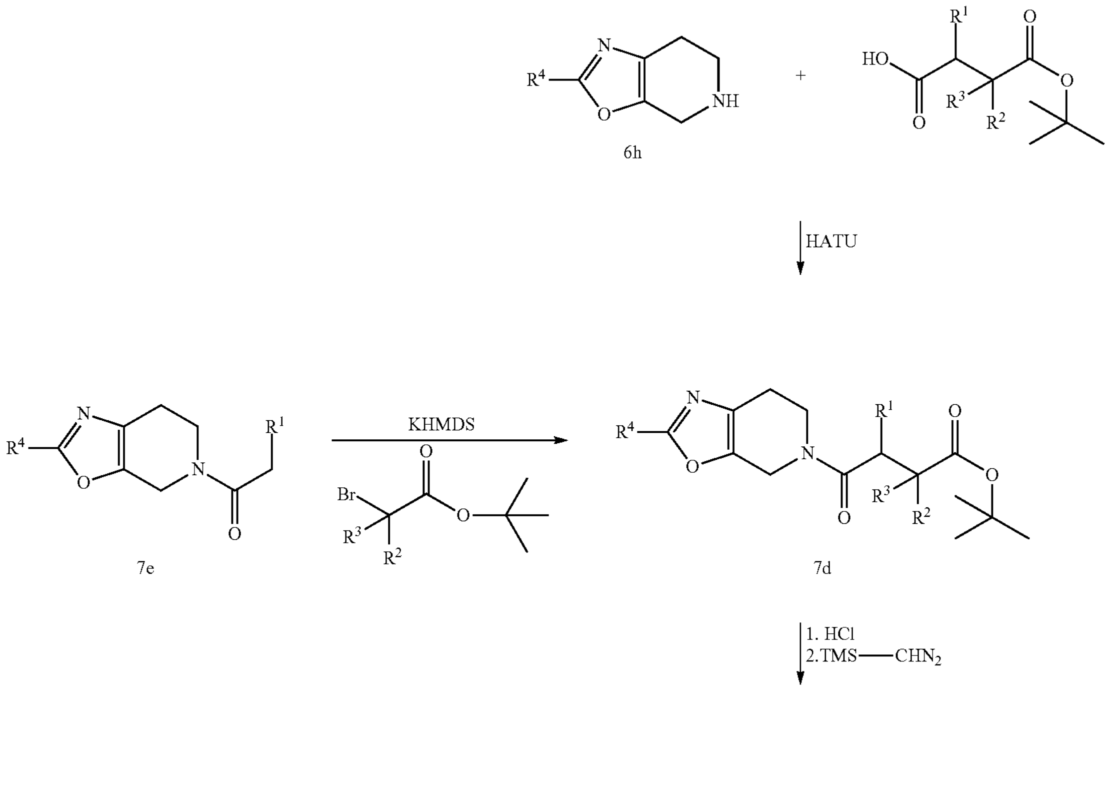

-continued

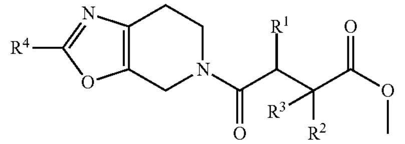

7c

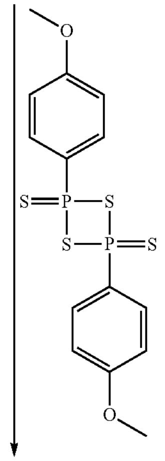

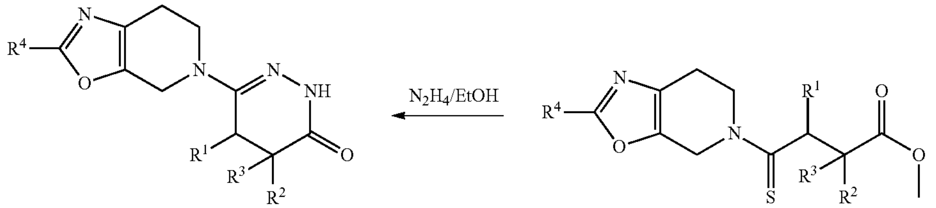

7a 7b

In this reaction a compound of formula 6h, wherein $R^4$ is as herein defined, is reacted with a suitably protected succinic acid monoester, e.g. with a succinic acid-mono-tert.-butyl ester of formula HO(O)C—C(H)$R^1$C($R^2$)$R^3$—C(O)COR, wherein $R^1$-$R^3$ are as herein defined and R denotes a suitable alkyl group, such as e.g. methyl or, preferably, tert.-butyl, in an amide coupling reaction to obtain the corresponding amide of formula 7d. The amide coupling is carried out by a method familiar to the skilled man or as herein described, e.g. by using a suitable coupling reagent, such as e.g. HATU.

Optionally in a following step the tert.-butyl-protecting group is cleaved from the compound of formula 7d obtained and the free acid obtained is reprotected, preferably using diazomethane, to form the methyl ester of formula 7c.

Alternatively the ester of formula 7d may also be obtained starting from the compound of formula 7e, wherein $R^1$ and $R^4$ are as herein defined, by deprotonation with a suitable base (e.g. KHMDS) and subsequent reaction with the compound of formula BrC($R^2$)$R^3$C(O)OR, wherein $R^2$ and $R^3$ are as herein defined and R denotes a suitable alkyl group, such as e.g. methyl or, preferably, tert.-butyl.

The amide of formula 7c is converted into the thioamide of formula 7b, e.g. using Lawsson's reagent.

The thioamide 7b may be cyclised with hydrazine using a process as hereinbefore described to obtain the corresponding compound of formula I (i.e. compound of formula 7a).

Compounds of formula I, wherein G denotes a system of formula G2, A has the meaning $CR^2H$, wherein $R^2$ is as herein defined, and the remaining substituents have the meanings stated herein (i.e. compounds of formula 8a), may be prepared using method h) according to the invention as shown in Scheme 8 starting from a cyclohexan-4-onecarboxylic acid ester.

Scheme 8: Method h)

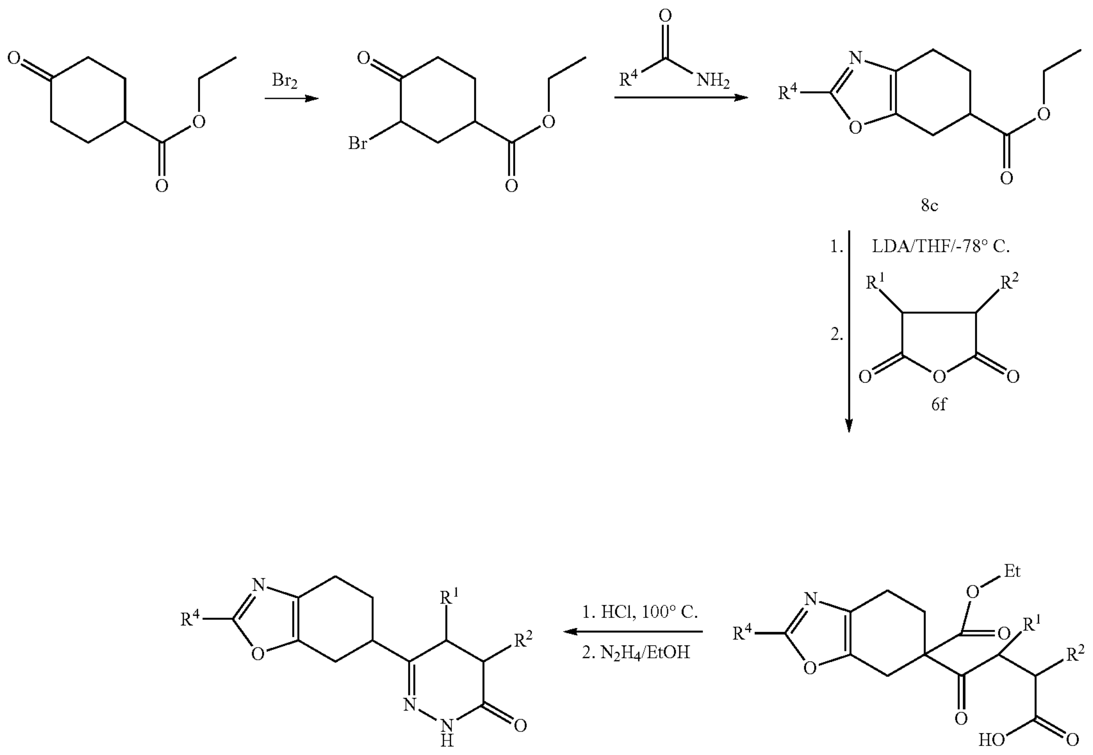

8c

6f

8a

8b

In this reaction a cyclohexan-4-onecarboxylic acid ester (e.g. alkyl cyclohexan-4-onecarboxylate), preferably ethyl cyclohexan-4-one-carboxylate, may be halogenated, preferably brominated, in the alpha position to the carbonyl group, e.g. using a method as described herein, preferably using elemental bromine in a suitable solvent, such as e.g. diethyl ether, in order to obtain ethyl 3-bromo-4-oxo-cyclohexanecarboxylate.

The ethyl 3-bromo-4-oxo-cyclohexanecarboxylate is cyclocondensed with an amide of formula $R^4$—$CONH_2$, wherein $R^4$ is as herein defined, to form the compound of formula 8c. This cyclisation is carried out in a suitable solvent, such as e.g. dichloroethane, at a suitable, preferably elevated reaction temperature, such as e.g. at 100-130° C., optionally with heating e.g. in a pressurised vessel, and optionally in the presence of a suitable base.

The compound of formula 8c is reacted with a cyclic anhydride of formula 6f, wherein $R^1$ and $R^2$ are as herein defined, in a Claisen reaction, using a suitable base, such as e.g. LDA, in a suitable solvent, such as e.g. THF, at a suitable reaction temperature, such as e.g. −70° C., to obtain the beta-keto ester of formula 8b.

The beta-keto ester of formula 8b obtained is subjected to ketone cleaving, e.g. decarboxylated by heating in the presence of a suitable dilute acid or base in a suitable solvent, such as e.g. aqueous dilute hydrochloric acid at reflux temperature. Then the ketone obtained may be cyclised with hydrazine using a process as hereinbefore described to obtain the corresponding compound of formula I (i.e. compound of formula 8a).

Compounds of formula I, wherein G denotes a system of formula G1, A has the meaning S or O and the remaining substituents have the meanings stated herein (i.e. compounds of formula 9a or formula 10a), may be prepared using method i) or j) according to the invention as shown in Scheme 9 or 10, respectively, from a compound of formula 2d.

Scheme 9: Method i)

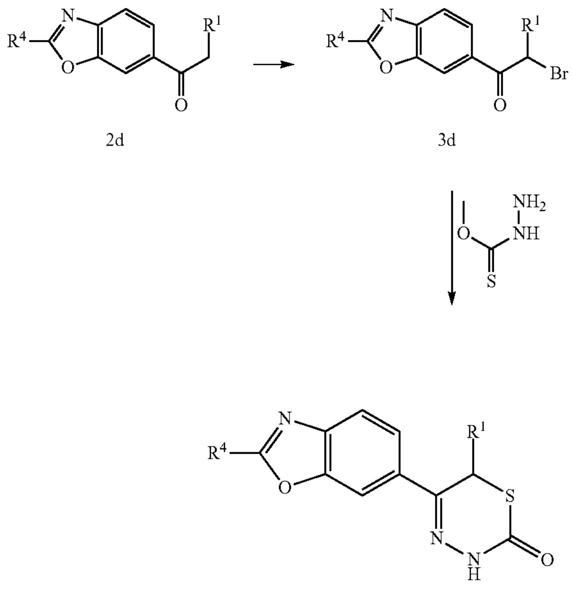

2d

3d

9a

Scheme 10: Method j)

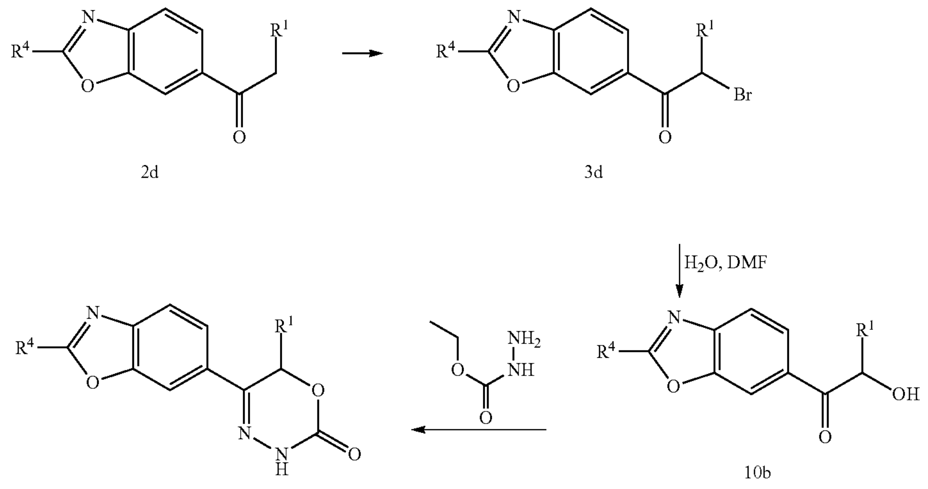

2d 3d 10b 10a

In both methods the compound of formula 2d is halogenated, preferably brominated, in the alpha position to the carbonyl group, e.g. using a method as described herein.

In the method according to Scheme 9 the bromine compound of formula 3d obtained is reacted with a suitable hydrazinethiocarbamic acid O-ester, such as e.g. O-methyl hydrazinethiocarbamate or O-phenyl hydrazinethiocarbamate, in the presence of a suitable base, such as e.g. triethylamine, in a suitable solvent, such as e.g. aqueous acetonitrile, at a suitable reaction temperature, such as e.g. 60-90° C., and the intermediate product obtained is cyclocondensed in the presence of a suitable acid, such as e.g. p-toluenesulphonic acid, in a suitable solvent, such as e.g. aqueous acetonitrile, at a suitable reaction temperature, such as e.g. 80-120° C., optionally with microwave irradiation, to obtain the corresponding compound of formula I (i.e. compound of formula 9a).

In the method according to Scheme 10 the bromine compound of formula 3d is hydrolysed to form the compound of formula 10b and the hydroxy compound obtained is reacted with a suitable hydrazinoformic acid ester, such as e.g. ethyl hydrazinoformate, in the presence of a suitable acid, such as e.g. dilute hydrochloric acid, in a suitable solvent, such as e.g. ethanol, at a suitable reaction temperature, such as e.g. reflux temperature, and the intermediate product obtained is cyclocondensed in the presence of a suitable base, e.g. an alkoxide such as e.g. sodium ethoxide, in a suitable solvent, such as e.g. ethanol, at a suitable reaction temperature to obtain the corresponding compound of formula I (i.e. compound of formula 10a).

Compounds of formula I, wherein G denotes a system of formula G1, A has the meaning $NR^2$, wherein $R^2$ is as herein defined, and the remaining substituents have the meanings stated herein (i.e. compounds of formula 11a), with the proviso that $R^1$ and $R^2$ do not together denote a bond, may be prepared using method k) according to the invention as shown in Scheme 11 starting from a compound of formula 1c.

Scheme 11: Method k)

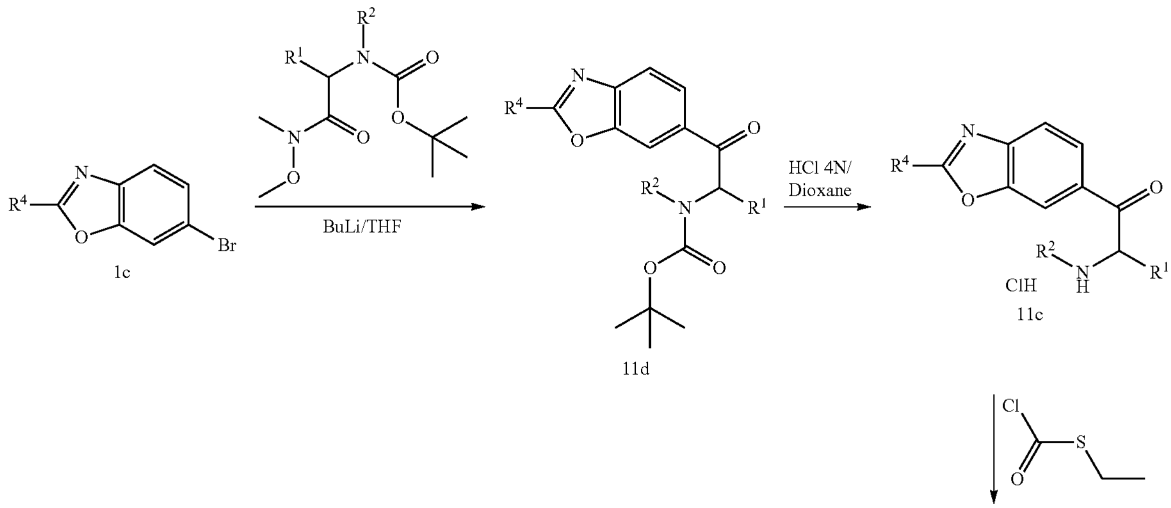

1c 11d 11c

-continued

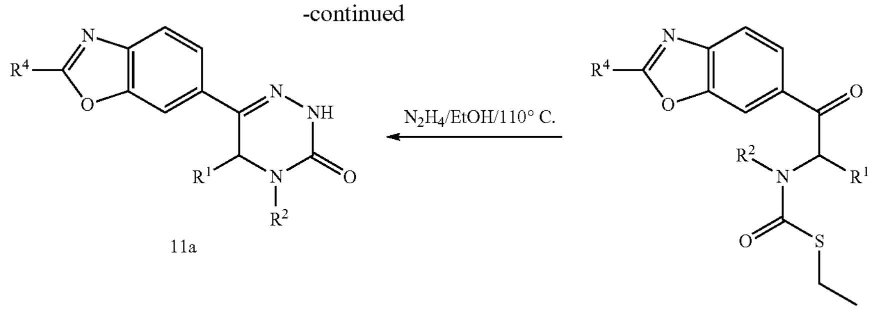

11a

11b

In this reaction an aromatic halogen compound of formula 1c, wherein $R^4$ is as herein defined, is converted, by a halogen-metal exchange using a suitable lithium alkyl reagent, preferably butyl lithium, in a suitable solvent, such as e.g. tetrahydrofuran, at a suitable reaction temperature, e.g. at −70° C., into the corresponding lithium aryl compound, which is further reacted with a compound of formula PG-N($R^3$)—$CHR^1$—$CON(CH_3)OCH_3$, wherein $R^1$ and $R^2$ are as herein defined and PG denotes a suitable protecting group, such as e.g. tert.-butyloxy, in a suitable solvent, such as e.g. tetrahydrofuran, at a suitable reaction temperature, e.g. at −70° C., to form the compound of formula 11d.

In the compound of formula 11d the N-protecting group is cleaved and the amino function of the compound of formula 11c obtained is reacted with a suitable alkylchlorothioformate, preferably with ethyl chlorothioformate, in the presence of a suitable base, such as e.g. triethylamine, in a suitable solvent, such as for example THF, to form the compound of formula 11b.

The compound of formula 11b may be cyclised with hydrazine using a process as hereinbefore described to obtain the corresponding compound of formula I (i.e. compound of formula 11a).

Besides the reactions described hereinbefore, other reactions of functional groups that are familiar to the skilled man may be carried out at any desired stages of the synthesis, provided that these reactions are compatible with other functional groups and provided that the functional groups thus introduced are stable during other reactions in the synthesis.

For example, hydroxyl, primary or secondary amino, or thiol groups may be converted by alkylation into optionally substituted alkoxy, mono- or dialkylamino, or alkylsulphanyl groups. This transformation is carried out by reaction with a suitable alkylating agent, such as e.g. an alkyl halide, alkyl methanesulphonate, alkyl p-toluenesulphonate or alkyl trifluoromethanesulphonate in the presence of a suitable base, such as e.g. sodium hydride, potassium carbonate, potassium hexamethyldisilazide, in a suitable solvent, such as e.g. diethyl ether, 1,4-dioxane, tetrahydrofuran, N,N-dimethylformamide, toluene or acetonitrile, at a suitable reaction temperature, such as e.g. in the range from −50° C. to 80° C., preferably −20° C. to 50° C.

Accordingly, haloalkyl groups, particularly chloroalkyl or bromoalkyl groups, may be converted analogously or in similar fashion by a reaction of nucleophilic substitution with O, N or S nucleophils, such as e.g. alcohols, primary or secondary amines, imines or mercaptans, into the correspondingly functionalised derivatives.

Aromatic chloroalkyl or, preferably, bromoalkyl groups may be obtained by radical chlorination or bromination of corresponding alkylaromatic groups. For example alkylaromatic groups may be converted by reaction with N-bromosuccinimide and a suitable radical starter, such as e.g. dibenzylperoxide, in a suitable solvent, such as e.g. carbon tetrachloride, into the corresponding bromoalkylaromatic groups.

Hydroxyl, primary or secondary amino, or thiol groups may also be converted by (hetero)arylation into optionally substituted (hetero)aryloxy, (hetero)arylamino, or (hetero)arylsulphanyl groups. This transformation is carried out by reaction with a suitable (hetero)arylating agent, such as e.g. a (hetero)aryl halide (preferably chloride, bromide or iodide), (hetero)arylmesylate, (hetero)aryltosylate or (hetero)aryltriflate in the presence of a suitable base and optionally a suitable (preferably Cu- or Pd-containing) catalyst (e.g. by an Ullmann or Buchwald-Hartwig reaction) or, as in a Chan-Lam reaction, a (hetero)arylboric acid in the presence of a Cu-containing catalyst, in a suitable solvent.

Accordingly, in analogous or similar fashion, (hetero)aromatic halogen atoms (preferably chlorine, bromine or iodine) or (hetero)aromatic sulphonyloxy groups, such as e.g. methylsulphonyloxy, tosylsulphonyloxy or trifluoromethylsulphonyloxy, may be converted by a reaction of nucleophilic substitution with O, N or S nucleophiles, such as e.g. alcohols, primary or secondary amines, imines or mercaptans, into the correspondingly functionalised derivatives.

(Hetero)aromatic sulphanyl, sulphinyl or sulphonyl groups may also be converted by a reaction of nucleophilic substitution of these groups with O, N or S nucleophiles, such as e.g. alcohols, primary or secondary amines, imines or mercaptans, in the presence of a suitable base, into the correspondingly O-, N- or S-functionalised derivatives.

Hydroxyl or primary or secondary amino groups may be converted by acylation or sulphonylation into corresponding carbonyloxy or sulphonyloxy or carbonylamino or sulphonylamino groups. The transformations are carried out by reacting corresponding hydroxyl or amino compounds with suitable acylating agents, such as for example carboxylic acid anhydrides, carboxylic acid halides (particularly carboxyl chlorides), activated carboxylic acid esters, carboxylic acid imidazolides or free carboxylic acids in the presence of suitable activating reagents (e.g. suitable coupling reagents such as e.g. diimides such as e.g. DCC, EDC, etc. or uronium reagents such as e.g. TOTU, HBTU, HATU, etc. or phosphonium reagents such as e.g. PyBOP, etc.) or with suitable sulphonylating agents, such as for example sulphonic acid anhydrides, sulphonic acid chlorides or sulphonylimides, in suitable solvents, such as e.g. dichloromethane, diethyl ether, 1,4-dioxane, tetrahydrofuran, toluene or acetonitrile, at temperatures between −78° C. and 40° C., in the presence of a suitable base, such as e.g. triethylamine, N,N-diisopropyl-N- ethylamine, pyridine or 2,6-lutidine, optionally in the presence of an acylation catalyst, such as e.g. 4-dimethylaminopyridine.

Accordingly, in analogous or similar fashion, free carboxyl or sulpho groups may be converted into the corresponding functionalised derivatives by activation (e.g. by conversion into chlorocarbonyl or chlorosulphonyl groups or by the use of suitable activation reagents) and by reaction with O or N nucleophiles, such as e.g. alcohols, primary or secondary amines or imines.

Also, (hetero)aromatic hydroxyl groups may be converted into (hetero)aromatic sulphonyloxy groups, such as e.g. methylsulphonyloxy, tosylsulphonyloxy or trifluoromethylsulphonyloxy. These (hetero)aromatic sulphonyloxy groups may be converted by CC-linking reaction (e.g. by Suzuki, Negishi or Heck reaction) into optionally substituted (cyclo)alkyl, (cyclo)alkenyl, (hetero)aryl or heterocyclyl groups. For this, the compounds are reacted with (hetero)aromatic sulphonyloxy groups, in the case of the Suzuki reaction, with corresponding potassium (cyclo)alkenyl, (hetero)aryl or heterocyclyl trifluoroborates, (cyclo)alkenyl-, (hetero)aryl- or heterocyclyl-boric acids or (cyclo)alkenyl-, (hetero)aryl- or heterocyclyl-boric acid pinacol esters or, in the case of the Heck reaction, with corresponding olefins, in a suitable solvent, such as e.g. toluene, DMF, isopropanol, acetonitrile, 1,4-dioxane or THF or mixtures, in the presence of a suitable base, such as e.g. aqueous sodium carbonate, caesium fluoride, triethylamine, Hünig base, etc., and in the presence of a suitable (preferably palladium-containing) catalyst, such as e.g. tetrakistriphenylphosphine palladium, etc. or a suitable palladium source, such as e.g. $Pd(OAc)_2$, in the presence of a suitable ligand, such as e.g. triphenylphosphine, tri-o-tolylphosphine, etc., at a suitable reaction temperature, such as e.g. in the range from 0° C. to 180° C., preferably from ambient temperature to 120° C.

An optionally substituted C═C double bond may be converted into the corresponding single bond by hydrogenation (e.g. catalytic hydrogenation with hydrogen). Optionally substituted cyclo(alkenyl) or unsaturated heterocyclyl groups, which may be obtained as hereinbefore described, may be converted into the corresponding (cyclo)alkyl or saturated heterocyclyl groups by hydrogenation, e.g. with hydrogen and in the presence of a suitable catalyst (such as e.g. Pd) in a suitable solvent (such as e.g. methanol, etc.), optionally under elevated pressure.

An optionally substituted C═C double bond may also be converted into the corresponding cyclopropyl group by cyclopropanation, e.g. by Simmons-Smith reaction in the presence of bromo-iodo-methane or diiodomethane and diethylzinc, optionally in the presence of trifluoroacetic acid.

Alkoxycarbonyl groups may be converted into hydroxymethyl groups by reduction with a suitable reducing agent (such as e.g. lithium aluminium hydride).

Cyano groups may be converted into aminomethyl groups by reduction with a suitable reducing agent (such as e.g. Raney nickel).

Ketones or aldehydes may be converted into the corresponding aminated compounds by reductive amination with primary or secondary amines or ammonia by Schiff's base formation and reduction using a suitable reducing agent.

In the reactions described hereinbefore, any reactive groups present such as carboxy, hydroxy, amino or alkylamino groups may be protected during the reaction by conventional protecting groups which are cleaved again after the reaction.

For example, a protecting group for a carboxy group may be a methyl, ethyl, tert. butyl or benzyl group.

For example, a protecting group for a hydroxy group may be an acetyl, benzyl or tetrahydropyranyl group.

For example, a protecting group for an amino or alkylamino group may be for example a formyl, acetyl, trifluoroacetyl, ethoxycarbonyl, tert.-butoxycarbonyl, benzyloxycarbonyl, benzyl, methoxybenzyl or 2,4-dimethoxybenzyl group.

A carboxymethyl or carboxyethyl unit may be cleaved hydrolytically, for example, in an aqueous solvent, e.g. in water, methanol/water, isopropanol/water, acetic acid/water, tetrahydrofuran/water or dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. in the presence of iodotrimethylsilane, at temperatures between 0 and 120° C., preferably at temperatures between 10 and 100° C.

A benzyl, methoxybenzyl or benzyloxycarbonyl group is advantageously cleaved hydrogenolytically, e.g. with hydrogen in the presence of a catalyst such as palladium on charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and under a hydrogen pressure of 1 to 7 bar, preferably 1 to 3 bar. The 4-methoxybenzyl group may also be cleaved hydrolytically in the presence of an acid (such as e.g. trifluoroacetic acid), or oxidatively in the presence of an oxidising agent such as e.g. 2,3-dichloro-5,6-dicyanobenzoquinone (DDQ). Preferably the 4-methoxybenzyl group is cleaved in trifluoroacetic acid in the presence of Veratrol. The cleaving of a 2,4-dimethoxybenzyl group is preferably carried out in trifluoroacetic acid in the presence of anisole.

A tert.-butyl or tert.-butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

Moreover the compounds of general formula I obtained, or intermediate products from the synthesis of compounds of general formula I, as already mentioned hereinbefore, may be resolved into their enantiomers and/or diastereomers. Thus, for example, cis/trans mixtures may be resolved into their cis and trans isomers, and compounds with at least one stereocentre may be resolved into their enantiomers.

Thus, for example, the cis/trans mixtures obtained may be resolved by chromatography into their cis and trans isomers, the compounds of general formula I obtained, or intermediate products from the synthesis of compounds of general formula I, which occur as racemates may be separated by methods known per se (cf. N. L. Allinger and E. L. Eliel in "Topics in Stereochemistry", Vol. 6, Wiley Interscience, 1971) into their optical antipodes, and compounds of general formula I, or intermediate products from the synthesis of compounds of general formula I, with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatography on chiral phases or by recrystallisation from an optically active solvent or by reacting with an optically active substance which forms salts or derivatives such as e.g. esters or amides with the racemic compound, particularly acids and the activated derivatives, amines or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+)- or (−)-menthol and an optically active acyl group in amides, for example, may be a (+)- or (−)-menthyloxycarbonyl.

Furthermore, the compounds of general formula I obtained, or intermediate products from the synthesis of compounds of general formula I, may be converted into the salts thereof, for pharmaceutical use in particular into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds of general formula I obtained, or intermediate products from the synthesis of compounds of general formula I, if they contain one or more acid groups (e.g. a carboxyl group), may, if desired, be converted into the salts thereof with inorganic or organic bases, for pharmaceutical use particularly into the physiologically acceptable salts thereof.

Suitable bases for this purpose include for example sodium hydroxide, potassium hydroxide, arginine, cyclohexylamine, ethanolamine, diethanolamine and triethanolamine.

The corresponding salts may be obtained by conventional methods that are known in principle to those skilled in the art, for example by reaction with an organic or inorganic acid or base in a suitable solvent or dispersant, or by anion or cation exchange with other salts.

The following Examples are mentioned in order to render the invention comprehensible. The Examples are intended to assist with illustrating the invention and should not restrict it in any way.

EXAMPLES

The following Examples are intended to describe the invention more fully without restricting its scope.

Melting points and/or IR, UV, $^1$H-NMR and/or mass spectra are generally available for the compounds obtained. Unless stated otherwise, $R_f$ values were determined using ready-made silica gel 60 $F_{254}$ TLC plates (E. Merck, Darmstadt, Article No. 1.05714) without chamber saturation. The $R_f$ values obtained under the heading Alox were determined using ready-made aluminium oxide 60 $F_{254}$ TLC plates (E. Merck, Darmstadt, Article no. 1.05713) without chamber saturation. The $R_f$ values obtained under the heading Reversed-phase-8 (RP-8) were determined using ready-made RP-8 $F_{254s}$ TLC plates (E. Merck, Darmstadt, Article no. 1.15684) without chamber saturation. The ratios specified for the eluants refer to units by volume of the respective solvent. For chromatographic purification, silica gel made by the company Merck KGaA (silica gel 60™, 40-63 μm) was used. If no more detailed information is given as to configuration, it remains unclear whether the substance is a pure stereoisomer or a mixture of enantiomers/diastereomers.

The following abbreviations are used in the test descriptions.

| | |
|---|---|
| DBAD | di-tert-butyl azodicarboxylate |
| DCM | dichloromethane |
| DIPEA | N-ethyl-diisopropylamine |
| DMF | N,N-dimethylformamide |
| DMSO | dimethylsulphoxide |
| EtOH | ethanol |
| EA | ethyl acetate |
| sat. | saturated |
| h | hour(s) |
| HATU | 2-(7-aza-1H-benzotriazol-1-yl)-1,1,3,3-tetramethyluronium hexafluorophosphate |
| H2O | water |
| i.V. | in vacuo |
| conc. | concentrated |
| solv. | solvent |
| min | minute(s) |
| org. | organic |
| $R_f$ | retention factor |
| $R_t$ | retention time |
| RT | ambient temperature |
| TBTU | O-(benzotriazol-1-yl)-N,N,N',N'-tetramethyluronium tetrafluoroborate |
| TFA | trifluoroacetic acid |
| THF | tetrahydrofuran |

Methods of Analysis

Method A

HPLC-MS: Waters ZMD, Alliance 2690/2695 HPLC, Waters 996/2996 diode array detector Wavelength range 210-400 nm.

Stationary phase: Merck Chromolith™ Flash RP-18e, 3 mm×100 mm (column temperature: constant at 25° C.).

Mobile phase: A: water with 0.10% TFA; B: acetonitrile with 0.10% TFA

| time in min | % A | % B | flow rate in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

Method B

HPLC-MS: Waters ZQ2000; Waters 1515 pump; Waters PDA 996 detector; Waters 2747 injector DAD 210-420 nm Stationary phase: X-terra™ MS C18, 4.6×30 mm, 2.5 μm Mobile phase: A: $H_2O$ 0.1% formic acid; B: acetonitrile 0.1% formic acid

| time in min | % A | % B | flow rate in ml/min |
|---|---|---|---|
| 0.00 | 95 | 5 | 1.0 |
| 0.10 | 95 | 5 | 1.0 |
| 3.10 | 2 | 98 | 1.0 |
| 4.50 | 2 | 98 | 1.0 |
| 5.00 | 95 | 5 | 1.0 |

Method C

HPLC-MS: Waters ZQ, Alliance 2690/2695 HPLC, Waters 996/2996 diode array detector Wavelength range 210-400 nm.

Stationary phase: Xbridge C18, 4.6 mm×20 mm, 3.5 μm (column temperature: constant at 40° C.).

Mobile phase: A: water with 0.10% TFA; B: acetonitrile with 0.10% TFA

| time in min | % A | % B | flow rate in ml/min |
|---|---|---|---|
| 0.00 | 95 | 5 | 4.00 |
| 0.20 | 95 | 5 | 4.00 |
| 1.60 | 0 | 100 | 4.00 |
| 2.10 | 0 | 100 | 4.00 |

Chiral Methods

Method D:

System: MultiGram II preparative SFC apparatus, UV detector measured in the wavelength range constant at 210 nm.

Stationary phase: Daicel Chiralpak, 2 cm×25 cm (column temperature: constant at 40° C.).

Mobile phase: A: 65% CO2; B: 35% MeOH+0.2% diethylamine (DEA)

Flow constant at 70 ml/min.

Method E:

System: MiniGram semi-preparative SFC-apparatus, UV detector measured in the wavelength range constant at 220 nm.

Stationary phase: 2× Daicel Chiralcel OJH in series, 1 cm×25 cm in each case (column temperature: constant at 40° C.).

Mobile phase: A: 65% CO2; B: 35% isopropanol+0.2% diethylamine

Flow constant at 9.5 ml/min.

Method F:

System: MiniGram semi-preparative SFC-apparatus, UV-detector measured in the wavelength range constant at 220 nm.

Stationary phase: 2× Daicel Chiralcel OJH in series, 1 cm×25 cm in each case (column temperature: constant at 40° C.).

Mobile phase: A: 65% CO2; B: 35% isopropanol+0.2% diethylamine

Flow constant at 9.5 ml/min.

Method G:

Preparative system: MiniGram semi-preparative SFC-apparatus,

UV detector measured in the wavelength range constant at 220 nm.

Stationary phase: Daicel IB, 250 mm×10 mm, 5 μm (column temperature: constant at 40° C.).

Mobile phase: see before the Example.

Flow constant at 10 ml/min.

Analytical system: Berger “Analytix”,

UV detector measured in the wavelength range constant at 220 nm.

Stationary phase: Daicel IB, 250 mm×4.6 mm, 5 μm (column temperature: constant at 40° C.).

Mobile phase: see before the Example.

Flow constant at 4 ml/min.

Method H:

Preparative system: MiniGram semi-preparative SFC-apparatus,

UV detector measured in the wavelength range constant at 220 nm.

Stationary phase: Daicel ODH, 250 mm×10 mm, 5 μm (column temperature: constant at 40° C.).

Mobile phase: see before the Example.

Flow constant at 10 ml/min.

Analytical system: Berger “Analytix”,

UV detector measured in the wavelength range constant at 220 nm.

Stationary phase: Daicel ODH, 250 mm×4.6 mm, 5 μm (column temperature: constant at 40° C.).

Mobile phase: see before the Example.

Flow constant at 4 ml/min.

Method I:

Preparative system: MiniGram semi-preparative SFC-apparatus,

UV detector measured in the wavelength range constant at 220 nm.

Stationary phase: Daicel OJH, 250 mm×10 mm, 5 μm (column temperature: constant at 40° C.).

Mobile phase: see before the Example.

Flow constant at 10 ml/min.

Analytical system: Berger “Analytix”,

UV detector measured in the wavelength range constant at 220 nm.

Stationary phase: Daicel OJH, 250 mm×4.6 mm, 5 μm (column temperature: constant at 40° C.).

Mobile phase: see before the Example.

Flow constant at 4 ml/min.

Method J:

Preparative system: MiniGram semi-preparative SFC-apparatus,

UV detector measured in the wavelength range constant at 220 nm.

Stationary phase: Daicel IA, 250 mm×10 mm, 5 μm (column temperature: constant at 40° C.).

Mobile phase: see before the Example.

Flow constant at 10 ml/min.

Analytical system: Berger “Analytix”,

UV detector measured in the wavelength range constant at 220 nm.

Stationary phase: Daicel IA, 250 mm×4.6 mm, 5 μm (column temperature: constant at 40° C.).

Mobile phase: see before the Example.

Flow constant at 4 ml/min.

Synthesis of the Intermediates

(a) 6-bromo-2-phenyl-benzoxazole 38.65 g (205.56 mmol) 4-bromo-2-hydroxy-aniline are boiled together with 25.10 g (205.56 mmol) benzoic acid and 12.75 g (205.56 mmol) boric acid in 500 ml of xylene for 6 days using the water separator. The solv. is eliminated in vacuo and the residue is taken up in DCM. The mixture is extracted 1× each with 1N sodium hydroxide solution, water, 2N hydrochloric acid and again with water. The org. phase is concentrated i. V. by rotary evaporation and the residue is separated through silica gel (eluant cyclohexane/EA).

Yield: 24.23 g (43%)

$R_t$-time: 1.89 min (method A)

$C_{13}H_8BrNO$ (274.11)

Mass spectrum: $(M+H)^+$=274/276

(b) 6-bromo-7-methyl-2-phenyl-benzoxazole

(b-1) 7-methyl-2-phenyl-benzoxazole

Preparation is carried out analogously to 4.1.a from 2-amino-6-methylphenol.

Yield: (51.4%)

$R_t$-time: 1.81 min (method A)

$C_{14}H_{11}NO$ (209.24)

Mass spectrum: $(M+H)^+$=209

(b-2) 6-bromo-7-methyl-2-phenyl-benzoxazole 1.55 g (7.41 mmol) 7-methyl-2-phenyl-benzoxazole are dissolved in 5 ml glacial acetic acid, then 0.74 g (9.02 mmol)

sodium acetate and 1.25 g (7.82 mmol) bromine are added. The mixture is stirred overnight at RT, then the solv. is eliminated by rotary evaporation in vacuo, the residue is dissolved with petroleum ether and extracted with water. The org. phase is dried on magnesium sulphate and evaporated down to ¼. The precipitated solid is suction filtered cold.

Yield: 1.47 g (68.9%)

$R_t$-time: 1.99 min (method A)

$C_{14}H_{10}BrNO$ (288.14)

Mass spectrum: $(M+H)^+$=288/290

(c) 6-bromo-4-methyl-2-phenyl-benzoxazole

Preparation is carried out analogously to 4.1.b from 2-amino-3-methylphenol

Yield: (77.9%)

$R_t$-time: 2.03 min (method A)

$C_{14}H_{10}BrNO$ (288.14)

Mass spectrum: $(M+H)^+$=288/290

(d) 6-bromo-2-m-tolyl-benzoxazole

Preparation is carried out analogously to 4.1.a from 4-bromo-2-hydroxy-aniline and 3-methyl-benzoic acid.

Yield: (32%)

$R_t$-time: 1.97 min (method A)

$C_{14}H_{10}BrNO$ (288.14)

Mass spectrum: $(M+H)^+$=288/290

(e) 6-bromo-2-p-tolyl-benzoxazole

Preparation is carried out analogously to 4.1.a from 4-bromo-2-hydroxy-aniline and 4-methyl-benzoic acid.

Yield: (29.8%)

$R_t$-time: 1.98 min (method A)

$C_{15}H_{10}BrNO$ (288.14)

Mass spectrum: $(M+H)^+$=288/290

(f) 6-bromo-2-(3,4-dimethyl-phenyl)-benzoxazole

Preparation is carried out analogously to 4.1.a from 4-bromo-2-hydroxy-aniline and 3,4-dimethyl-benzoic acid.

Yield: (33.6%)

$R_t$-time: 1.98 min (method A)

$C_{15}H_{12}BrNO$ (302.17)

Mass spectrum: $(M+H)^+$=302

(g) 6-bromo-2-(4-piperidin-1-ylmethyl-phenyl)-benzoxazole (g-1) 6-bromo-2-(4-bromomethyl-phenyl)-benzoxazole 3.00 g (10.41 mmol) 6-bromo-2-p-tolyl-benzoxazole are stirred together with 1.90 g (10.68 mmol) N-bromosuccinimide, 10.00 mg (0.04 mmol) dibenzoylperoxide and 60 ml carbon tetrachloride for 2 h at 90°. The reaction mixture is filtered through kieselguhr, then the solv. is eliminated by rotary evaporation in vacuo and the residue is recrystallised from petroleum ether.

Yield: 2.16 g (55.7%)

$R_t$-time: 1.94 min (method A)

$C_{14}H_9Br_2NO$ (367.04)

Mass spectrum: $(M+H)^+$=366/368/370

(g-2) 6-bromo-2-(4-piperidin-1-ylmethyl-phenyl) benzoxazole 200 mg (545 μmol) 6-bromo-2-(4-bromomethyl-phenyl)-benzoxazole and 100 mg (1174 μmol) piperidine are stirred for 20 min in 4 ml THF at RT, the solv. is eliminated by rotary evaporation in vacuo. The residue is dissolved in ether and extracted with water, the org. phase is dried on magnesium sulphate and the solv. is eliminated completely in vacuo.

Yield: 200 mg (98.9%)

$R_t$-time: 1.42 min (method A)

$C_{19}H_{19}BrN_2O$ (371.27)

Mass spectrum: $(M+H)^+$=371/373

(h) 6-bromo-2-(3-fluoro-phenyl)-benzoxazole

Preparation is carried out analogously to 4.1.a from 4-bromo-2-hydroxy-aniline and 3-fluorobenzoic acid.

Yield: (26.7%)

$R_t$-time: 1.90 min (method A)

$C_{13}H_7BrFNO$ (292.10)

Mass spectrum: $(M+H)^+$=292/294

(i) 6-bromo-2-(4-fluoro-phenyl)-benzoxazole

Preparation is carried out analogously to 4.1.a from 4-bromo-2-hydroxy-aniline and 4-fluorobenzoic acid.

Yield: (59.8%)

$R_t$-time: 1.88 min (method A)

$C_{13}H_7BrFNO$ (292.10)

Mass spectrum: $(M+H)^+$=292/294

(j) 6-bromo-2-(2-fluoro-phenyl)-benzoxazole

Preparation is carried out analogously to 4.1.a from 4-bromo-2-hydroxy-aniline and 2-fluorobenzoic acid.

Yield: (28.1%)

$R_t$-time: 1.83 min (method A)

$C_{13}H_7BrFNO$ (292.10)

Mass spectrum: $(M+H)^+$=292/294

(k) 6-bromo-2-(4-morpholine-1-ylmethyl-phenyl)-benzoxazole

Preparation is carried out analogously to 4.1.g-2 from 6-bromo-2-(4-bromomethyl-phenyl)-benzoxazole and morpholine Yield: (93.4%)

$R_t$-time: 1.35 min (method A)

$C_{18}H_{17}BrFN_2O_2$ (373.24)

Mass spectrum: $(M+H)^+$=373/375

(l) tert-butyl 4-[4-(6-bromo-benzoxazol-2-yl)-benzyl]-piperazine-1-carboxylate

Preparation is carried out analogously to 4.1.g-2 from 6-bromo-2-(4-bromomethyl-phenyl)-benzoxazole and tert.-butyl piperazine-1-carboxylate.

Yield: (63.7%)

$R_t$-time: 1.50 min (method A)

$C_{23}H_{26}BrN_3O_3$ (472.38)

Mass spectrum: $(M+H)^+$=472

(m) (R)-3-methoxy-dihydro-furan-2,5-dione 260 mg (1.76 mmol) (R)-methoxy-succinic acid are stirred together with 5 ml acetyl chloride for 2 days at RT, then the acetyl chloride is eliminated by rotary evaporation in vacuo.

Yield: 200 mg (87.6%)

$C_5H_6O_4$ (130.01)

Mass spectrum: $(M-H)^-$=129

(n) (S)-3-methoxy-dihydro-furan-2,5-dione

Preparation is carried out analogously to 4.1.m from (S)-methoxy-succinic acid.

Yield: (95.2%)

$C_5H_6O_4$ (130.01)

Mass spectrum: $(M-H)^-$=129

(o) 6-bromo-2-(5-methyl-thiophen-2-yl)-benzoxazole

Preparation is carried out analogously to 4.1.a from 5-methylthiophene-2-carboxylic acid and 4-bromo-2-hydroxy-aniline.

Yield: (25.1%)

$R_t$-time: 1.93 min (method A)

$C_{12}H_8BrNOS$ (294.17)

Mass spectrum: $(M+H)^+$=294

(p) methyl 2-thiophen-2-yl-benzoxazole-6-carboxylate

Preparation is carried out analogously to 4.1.a from thiophene-2-carboxylic acid and methyl 4-amino-3-hydroxy-benzoate.

Yield: (38.2%)

$R_t$-time: 1.67 min (method A)

$C_{13}H_6NO_3S$ (259.28)

Mass spectrum: $(M+H)^+$=260

(q) 2-(4-benzyloxy-phenyl)-6-bromo-benzoxazole

Preparation is carried out analogously to 4.1.a from 4-bromo-2-hydroxy-aniline and 4-benzyloxybenzoic acid.

Yield (47.6%)

$R_t$-time: 1.73 min (method C)

$C_{20}H_{14}BrNO_2$ (380.24)

Mass spectrum: $(M+H)^+$=380

(r) 4-(6-bromo-benzoxazol-2-yl)-phenol

Preparation is carried out analogously to 4.1.a from 4-bromo-2-hydroxy-aniline and 4-hydroxybenzoic acid Yield (12.4%)

$R_t$-time: 1.69 min (method C)

$C_{13}H_8BrNO_2$ (290.11)

Mass spectrum: $(M+H)^+$=290

(s) 6-(4-amino-3-hydroxy-phenyl)-5-ethyl-4-methyl-4,5-dihydro-2H-pyridazin-3-one (s-1) 6-(2-chloro-butyryl)-3H-benzoxazol-2-one 81.70 g (604.65 mmol) 2-benzoxazolinone are stirred together with 720.00 g polyphosphoric acid at 80° C. 63 mL (607.64 mmol) 2-chlorobutyric acid are added and the mixture is stirred for 3 h at 125° C. The reaction mixture is then poured onto ice water and extracted with DCM. The org. phase is concentrated by rotary evaporation i. V. and the residue is separated on silica gel (eluant cyclohexane/EA). The suitable fractions are concentrated by rotary evaporation i. V. and the residue is crystallised with diethyl ether.

Yield: 62.50 g (43.1%)

$R_t$-time: (method A)

$C_{11}H_{10}ClNO_3$ (239.65)

Mass spectrum: $(M+H)^+$=240

(s-2) 3-benzyl-6-(2-chloro-butyryl)-3H-benzoxazol-2-one 62.50 g (260.79 mmol) 6-(2-chloro-butyryl)-3H-benzoxazol-2-one, 31 mL (261.00 mmol) benzylbromide, 160.00 g (1157.74 mmol) potassium carbonate and 3000 mL acetone are stirred for 24 h at RT. The reaction mixture is concentrated by rotary evaporation i. V. and the residue is separated on silica gel (eluant cyclohexane/EA). The suitable fractions are concentrated by rotary evaporation i. V. and the residue is crystallised with EtOH.

Yield: 64.00 g (74.4%)

$R_t$-time: (method A)

$C_{18}H_{16}ClNO_3$ (329.78)

Mass spectrum: $(M+H)^+$=330

(s-3) diethyl 2-[1-(3-benzyl-2-oxo-2,3-dihydro-benzoxazole-6-carbonyl)-propyl]-2-methyl-malonate 23.00 g (204.96 mmol) potassium-tert.-butoxide are placed in 1200 mL DMSO and 36.00 g (206.67 mmol) diethyl 2-methyl-malonate are added. 64.00 g (194.07 mmol) 3-benzyl-6-(2-chloro-butyryl)-3H-benzoxazol-2-one are added batchwise while being cooled at 40° C. Then the mixture is stirred for 1 h, the reaction mixture is diluted with ice water and neutralised with 15 mL glacial acetic acid. The reaction mixture is extracted with DCM, the org. phase is concentrated by rotary evaporation i. V. and the residue is separated on silica gel (eluant cyclohexane/EA).

Yield: 29.35 g (32.3%)

$R_t$-time: (method A)

$C_{26}H_{29}NO_7$ (467.51)

Mass spectrum: $(M+H)^+$=468

(s-4) 2-[1-(3-benzylamino-3-hydroxy-benzoyl)-propyl]-2-methyl-malonic acid 29.35 g (62.78 mmol) diethyl 2-[1-(3-benzyl-2-oxo-2,3-dihydro-benzoxazole-6-carbonyl)-propyl]-2-methyl-malonate are placed in 250 mL EtOH and 300 mL (600.00 mmol) 2N sodium hydroxide solution are added. Then the mixture is stirred for 4 h at reflux temperature, the reaction mixture is concentrated down to half by rotary evaporation i. V. and adjusted to pH=2-3 with hydrochloric acid. The reaction mixture is extracted with DCM and the org. phase is concentrated by rotary evaporation i. V. The residue is used in the next step without purification.

Yield: 18.73 g (77.4%)

$R_t$-time: (method A)

$C_{21}H_{23}NO_6$ (385.41)

Mass spectrum: $(M+H)^+$=386

(s-5) 3-(4-benzylamino-3-hydroxy-benzoyl)-2-methyl-pentanoic acid 18.73 g (48.59 mmol) 2-[1-(3-benzylamino-3-hydroxy-benzoyl)-propyl]-2-methyl-malonic acid are stirred in 110 mL diglyme for 3 h at 140° C. Diglyme is concentrated by rotary evaporation i. V., the residue is made basic with 2N sodium hydroxide solution and extracted with diethyl ether. The aqueous phase is acidified with 2N hydrochloric acid and extracted with DCM. The org. phase is concentrated by rotary evaporation i. V. and the residue is separated on silica gel (eluant cyclohexane/EA/AcOH).

Yield: 3.00 g (18.1%)

$R_t$-time: (method A)
$C_{20}H_{23}NO_4$ (341.40)
Mass spectrum: $(M+H)^+$=342

(s-6) 6-(4-benzylamino-3-hydroxy-phenyl)-5-ethyl-4-methyl-4,5-dihydro-2H-pyridazin-3-one 3.00 g (8.79 mmol) 3-(4-benzylamino-3-hydroxy-benzoyl)-2-methyl-pentanoic acid, 6.31 mL (126.00 mmol) hydrazine hydrate and 25 mL glacial acetic acid are stirred for 3 h at 110° C. The reaction mixture is concentrated by rotary evaporation i. V. and the residue is separated through RP (xBridge, MeOH/$H_2O$/TFA).
Yield: 2.20 g (74.2%)
$R_t$-time: (method A)
$C_{20}H_{23}N_3O_2$ (337.42)
Mass spectrum: $(M+H)^+$=338

(s-7) 6-(4-amino-3-hydroxy-phenyl)-5-ethyl-4-methyl-4,5-dihydro-2H-pyridazin-3-on 2.20 g (6.52 mmol) 6-(4-benzylamino-3-hydroxy-phenyl)-5-ethyl-4-methyl-4,5-dihydro-2H-pyridazin-3-one, 120 mg 10% Pd/C and 20 mL MeOH are hydrogenated for 2 h at 3 bar H2. The reaction mixture is concentrated by rotary evaporation i. V. and the residue is crystallised with acetonitrile/diethyl ether.
Yield: 1.50 g (93.0%)
$R_t$-time: 0.70 and 0.77 min (method C)
$C_{13}H_{17}N_3O_2$ (247.29)
Mass spectrum: $(M+H)^+$=248

(t) cis-6-(4-amino-3-hydroxy-phenyl)-5-ethyl-4-methyl-4,5-dihydro-2H-pyridazin-3-one 1.10 g (4.45 mmol) 6-(4-amino-3-hydroxy-phenyl)-5-ethyl-4-methyl-4,5-dihydro-2H-pyridazin-3-one are separated by RP (xBridge, MeOH/$H_2O$/TFA).
Yield: 230.00 mg (14.3%)
$R_t$-time: 0.75 min (method C)
$C_{13}H_{17}N_3O_2$ (247.29)
Mass spectrum: $(M+H)^+$=248

(u) trans-6-(4-amino-3-hydroxy-phenyl)-5-ethyl-4-methyl-4,5-dihydro-2H-pyridazin-3-one Preparation is carried out analogously to t.
Yield: 500.00 mg (31.1%)
$R_t$-time: 0.69 min (method C)
$C_{13}H_{17}N_3O_2$ (247.29)
Mass spectrum: $(M+H)^+$=248

(v) 6-(4-amino-3-hydroxy-phenyl)-5-methyl-4-propyl-4,5-dihydro-2H-pyridazin-3-one (v-1) 6-propionyl-3H-benzoxazol-2-one 1000 g polyphosphoric acid are taken at 50° C., 100 g (740 mmol) 2-benzoxazolinone and 80 mL (1.07 mol) propionic acid are added and then the mixture is stirred for 2 h at 90° C. The reaction mixture is cooled to 50° C. and while being cooled it is combined with 1500 mL cold H2O. H2O phase is decanted off and the whole process is repeated twice more with 1500 mL H2O. Then the solid is suction filtered, triturated with diethyl ether/EtOH, suction filtered and washed with diethyl ether.
Yield: 70.20 g (49.6%)
$R_t$-time: 1.01 min (method C)
$C_{10}H_9NO_3$ (191.18)
Mass spectrum: $(M+H)^+$=192

(v-2) 3-benzyl-6-propionyl-3H-benzoxazol-2-one 94 g (492 mmol) 6-propionyl-3H-benzoxazol-2-one is placed in 1000 mL acetone and 160 g (1.157 mol) potassium carbonate and then 65 ml (546 mol) benzylbromide are added and the mixture is stirred for 4 h at 50° C. The reaction mixture is suction filtered hot and then the filtrate is slowly cooled. The solid is suction filtered and washed with acetone/diethyl ether.
Yield: 65.00 g (47.0%)
$R_t$-time: 1.36 min (method C)
$C_{17}H_{15}NO_3$ (281.31)
Mass spectrum: $(M+H)^+$=282

(v-3) methyl 2-[2-(3-benzyl-2-oxo-2,3-dihydro-benzoxazol-6-yl)-1-methyl-2-oxo-ethyl]-pentanoate 200 mL (0.5 mol/l in toluene, 100 mmol) bis-(trimethylsilyl)-potassium amide in 1.50 L THF are placed under protective gas and cooled to −60° C. with dry ice/EtOH. 20 g (71 mmol) of 3-benzyl-6-propionyl-3H-benzoxazol-2-one dissolved in 500 mL THF are slowly added dropwise. The reaction mixture is stirred for 30 min at −2° C. and then cooled to −60° C. again. 20 g (83 mmol) methyl 2-iodo-pentanoate are added and the mixture is stirred for 45 min at −60° C. Then the reaction mixture is combined with 500 mL of 2M HCl and extracted at RT with diethyl ether. The organic phase is washed with saline solution, suction filtered through cellulose and the solv. is eliminated i.V. The residue is purified through silica gel (DCM/MeOH)
Yield: 16.00 g (56.9%)
$R_t$-time: min (method C)
$C_{23}H_{25}NO_5$ (395.45)
Mass spectrum: $(M+H)^+$=396

(v-4) 242-(4-benzylamino-3-hydroxy-phenyl)-1-methyl-2-oxo-ethyl)-pentanoic acid 31.20 g (79 mmol) methyl 2-[2-(3-benzyl-2-oxo-2,3-dihydro-benzoxazol-6-yl)-1-methyl-2-oxo-ethyl]-pentanoate are dissolved in 600 mL THF, mixed with a solution of 15.00 g (626 mmol) lithium hydroxide in H2O and stirred overnight at RT. Then lithium hydroxide is added again and the mixture is stirred for 6 h at 90° C. and then overnight at 40° C. The reaction mixture is combined with 500 mL H2O and extracted with diethyl ether. The H2O phase is acidified with 4N HCl and extracted with diethyl ether. The diethyl ether phase is extracted with common salt, suction filtered through cellulose and the solv. is eliminated i.V.
Yield: 23.00 g (82.0%)
$R_t$-time: min (method C)
$C_{21}H_{25}NO_4$ (355.43)
Mass spectrum: $(M+H)^+$=356

(v-5) 6-(4-benzylamino-3-hydroxy-phenyl)-5-methyl-4-propyl-4,5-dihydro-2H-pyridazin-3-one Preparation is carried out analogously to s-6
Yield: (20.7%)
$R_t$-time: 1.39/1.45 min (method C)
$C_{21}H_{25}N_3O_2$ (351.44)
Mass spectrum: $(M+H)^+$=352

(v-6) 6-(4-amino-3-hydroxy-phenyl)-5-methyl-4-propyl-4,5-dihydro-2H-pyridazin-3-one Preparation is carried out analogously to s-7
Yield: (91.6%)
$R_t$-time: 0.86/0.96 min (method C)
$C_{14}H_{19}N_3O_2$ (261.32)
Mass spectrum: $(M+H)^+$=262

Synthesis of the Target Compounds

Example 1

(S)-5-methyl-6-(2-phenyl-benzoxazol-6-yl)-4,5-dihydro-2H-pyridazin-3-one

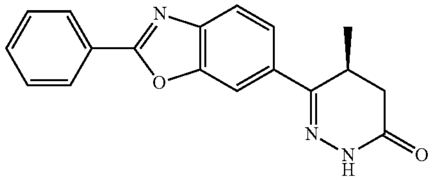 [SMILES: C[C@H]1CC(=O)NN=C1c1ccc2nc(-c3ccccc3)oc2c1]

(a) (S)-3-methyl-4-oxo-4-(2-phenyl-benzoxazol-6-yl)-butyric acid

The preparation is carried out under anhydrous conditions and under a protective gas atmosphere (argon).

400 mg (1.46 mmol) 6-bromo-2-phenyl-benzoxazole are dissolved in 15 ml THF and cooled to −70° C., and 1.22 ml (1.92 mmol) n-butyl lithium 1.6M in hexane are added dropwise. This solution chilled to −70° C. is added dropwise to an equally cold −70° C. solution of 220 mg (1.93 mmol) (S)-3-methyl-dihydro-furan-2,5-dione and 15 ml THF. After 15 min stirring the mixture is poured onto semisaturated, acetic acid-containing saline solution and extracted with EA. The org. phase is concentrated by rotary evaporation i. V. and the residue is separated through silica gel (eluant DCM/EA/glacial acetic acid).

Yield: 177 mg (39.2%)
$R_t$-time: 1.55 min (method A)
$C_{18}H_{15}NO_4$ (309.32)
Mass spectrum: $(M+H)^+$=310

(b) (S)-5-methyl-6-(2-phenyl-benzoxazol-6-yl)-4,5-dihydro-2H-pyridazin-3-one 177 mg (572 μmol) (S)-3-methyl-4-oxo-4-(2-phenyl-benzoxazol-6-yl)-butyric acid are combined with 10 ml of ethanol and 350 μl (7050 μmol) hydrazine hydrate. The reaction mixture is refluxed for 3 h. The solvent is eliminated by rotary evaporation in vacuo and the residue is separated through silica gel (eluant cyclohexane/EA).

Yield: 24 mg (13.7%)
$R_t$-time: 1.52 min (method A)
$C_{18}H_{15}N_3O_2$ (305.33)
Mass spectrum: $(M+H)^+$=306

The following compounds may be prepared analogously:

| Ex. | Structural formula | Yield | Mass peak(s) | HPLC |
|---|---|---|---|---|
| 2 | 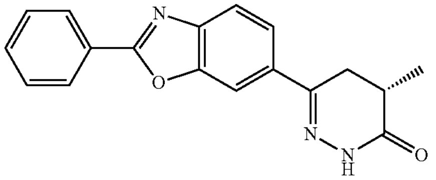 [SMILES: C[C@H]1CC(c2ccc3nc(-c4ccccc4)oc3c2)=NNC1=O] (S)-4-methyl-6-(2-phenyl-benzoxazol-6-yl)-4,5-dihydro-2H-pyridazin-3-one; | 29.2% | $(M + H)^+$ = 306 | 1.56 min (method A) |
| 3 | 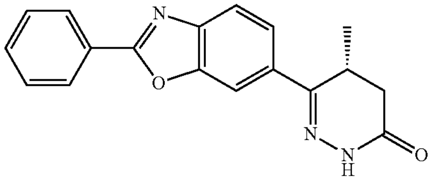 (R)-5-methyl-6-(2-phenyl-benzoxazol-6-yl)-4,5-dihydro-2H-pyridazin-3-one; | 8.4% | $(M + H)^+$ = 306 | 1.52 min (method A) |
| 4 | 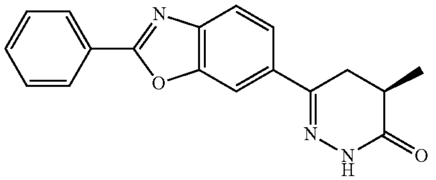 [SMILES: C[C@@H]1CC(c2ccc3nc(-c4ccccc4)oc3c2)=NNC1=O] (R)-4-methyl-6-(2-phenyl-benzoxazol-6-yl)-4,5-dihydro-2H-pyridazin-3-one; | 22.9% | $(M + H)^+$ = 306 | 1.55 min (method A) |

-continued

| Ex. | Structural formula | Yield | Mass peak(s) | HPLC |
|---|---|---|---|---|
| 5 | 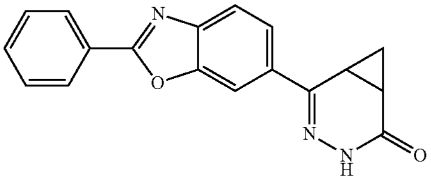 [SMILES: O=C1NN=C(c2ccc3nc(-c4ccccc4)oc3c2)C2CC12]<br>5-(2-phenyl-benzoxazol-6-yl)-3,4-diaza-bicyclo[4.1.0]hept-4-en-2-one; | 36.2% | $(M + H)^+ = 304$ | 1.49 min (method A) |
| 6 | 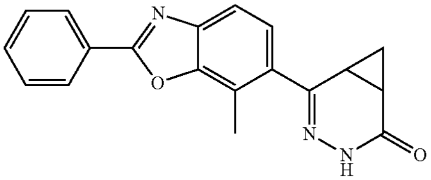 [SMILES: Cc1c(C2=NNC(=O)C3CC23)ccc2nc(-c3ccccc3)oc12]<br>5-(7-methyl-2-phenyl-benzoxazol-6-yl)-3,4-diaza-bicyclo[4.1.0]hept-4-en-2-one; | 22.3% | $(M + H)^+ = 318$ | 1.50 min (method A) |
| 7 | 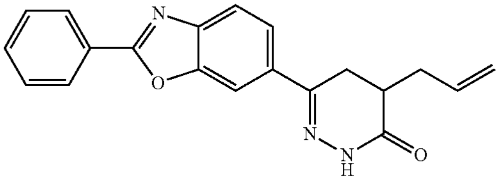 [SMILES: C=CCC1CC(c2ccc3nc(-c4ccccc4)oc3c2)=NNC1=O]<br>4-allyl-6-(2-phenyl-benzoxazol-6-yl)-4,5-dihydro-2H-pyridazin-3-one; | 2.7% | $(M + H)^+ = 332$ | 1.65 min (method A) |
| 8 | 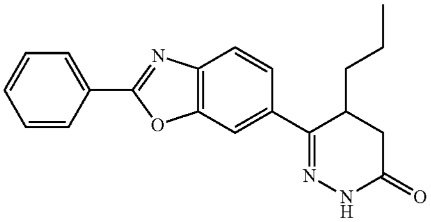 [SMILES: CCCC1CC(=O)NN=C1c1ccc2nc(-c3ccccc3)oc2c1]<br>6-(2-phenyl-benzoxazol-6-yl)-5-propyl-4,5-dihydro-2H-pyridazin-3-one; | 2.7% | $(M + H)^+ = 334$ | 1.65 min (method A) |
| 9 | 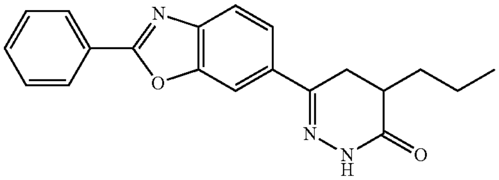 [SMILES: CCCC1CC(c2ccc3nc(-c4ccccc4)oc3c2)=NNC1=O]<br>6-(2-phenyl-benzoxazol-6-yl)-4-propyl-4,5-dihydro-2H-pyridazin-3-one; | 8.7% | $(M + H)^+ = 334$ | 1.68 min (method A) |
| 10 | 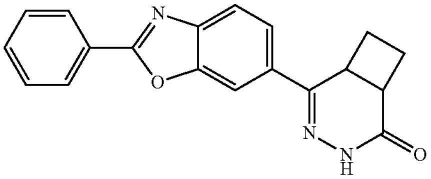 [SMILES: O=C1NN=C(c2ccc3nc(-c4ccccc4)oc3c2)C2CCC12]<br>5-(2-phenyl-benzoxazol-6-yl)-3,4-diaza-bicyclo[4.2.0]oct-4-en-2-one; | 39.1% | $(M + H)^+ = 318$ | 1.55 min (method A) |

-continued

| Ex. | Structural formula | Yield | Mass peak(s) | HPLC |
|---|---|---|---|---|
| 11 | 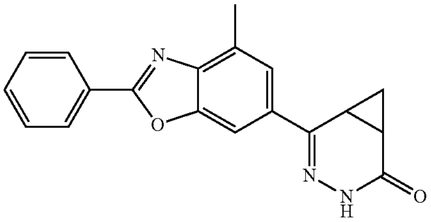 [SMILES: Cc1cc(C2=NNC(=O)C3CC23)cc2oc(-c3ccccc3)nc12]<br>5-(4-methyl-2-phenyl-benzoxazol-6-yl)-3,4-diaza-bicyclo[4.1.0]hept-4-en-2-one; | 1.4% | $(M+H)^+ = 318$ | 1.57 min (method A) |
| 12 | 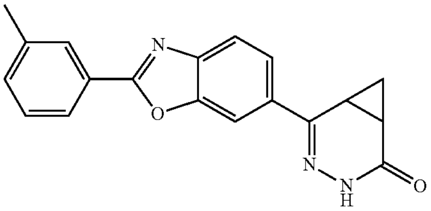 [SMILES: Cc1cccc(-c2nc3ccc(C4=NNC(=O)C5CC45)cc3o2)c1]<br>5-(2-m-tolyl-benzoxazol-6-yl)-3,4-diaza-bicyclo[4.1.0]hept-4-en-2-one; | 20.8% | $(M+H)^+ = 318$ | 1.58 min (method A) |
| 13 | 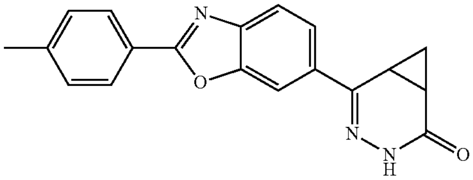 [SMILES: Cc1ccc(-c2nc3ccc(C4=NNC(=O)C5CC45)cc3o2)cc1]<br>5-(2-p-tolyl-benzoxazol-6-yl)-3,4-diaza-bicyclo[4.1.0]hept-4-en-2-one; | 23.8% | $(M+H)^+ = 318$ | 1.55 min (method A) |
| 14 | 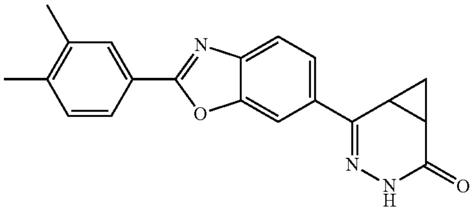 [SMILES: Cc1ccc(-c2nc3ccc(C4=NNC(=O)C5CC45)cc3o2)cc1C]<br>5-[2-(3,4-dimethyl-phenyl)-benzoxazol-6-yl]-3,4-diaza-bicyclo[4.1.0]hept-4-en-2-one; | 20.9% | $(M+H)^+ = 332$ | 1.62 min (method A) |
| 15 | 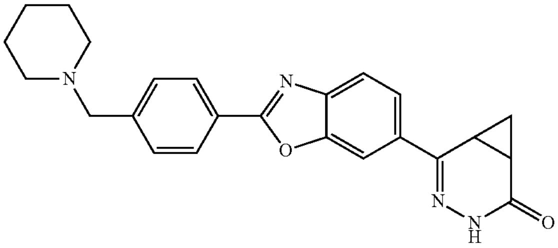 [SMILES: O=C1NN=C(c2ccc3nc(-c4ccc(CN5CCCCC5)cc4)oc3c2)C2CC12]<br>5-[2-(4-piperidin-1-ylmethyl-phenyl)-benoxazol-6-yl]-3,4-diaza-bicyclo[4.1.0]hept-4-en-2-one; | 11.6% | $(M+H)^+ = 401$ | 1.21 min (method A) |
| 16 | 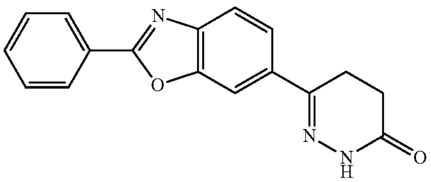 [SMILES: O=C1CCC(c2ccc3nc(-c4ccccc4)oc3c2)=NN1]<br>6-(2-phenyl-benzoxazol-6-yl)-4,5-dihydro-2H-pyridazin-3-one; | 25.3% | $(M+H)^+ = 292$ | 1.48 min (method A) |

-continued

| Ex. | Structural formula | Yield | Mass peak(s) | HPLC |
|---|---|---|---|---|
| 17 | 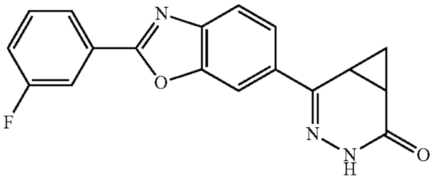 [SMILES: O=C1NN=C(c2ccc3nc(-c4cccc(F)c4)oc3c2)C2CC12] | 71.8% | $(M + H)^+ = 322$ | 1.52 min (method A) |
| | 5-[2-(3-fluoro-phenyl)-benzoxazol-6-yl]-3,4-diaza-bicyclo[4.1.0]hept-4-en-2-one; | | | |
| 18 | 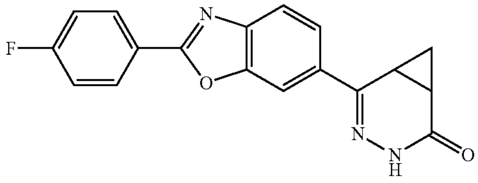 [SMILES: O=C1NN=C(c2ccc3nc(-c4ccc(F)cc4)oc3c2)C2CC12] | 4.2% | $(M + H)^+ = 322$ | 1.51 min (method A) |
| | 5-[2-(4-fluoro-phenyl)-benzoxazol-6-yl]-3,4-diaza-bicyclo[4.1.0]hept-4-en-2-one; | | | |
| 19 | 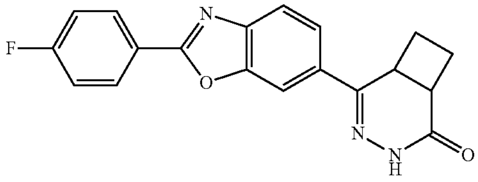 [SMILES: O=C1NN=C(c2ccc3nc(-c4ccc(F)cc4)oc3c2)C2CCC12] | 50.9% | $(M + H)^+ = 336$ | 1.57 min (method A) |
| | 5-[2-(4-fluoro-phenyl)-benzoxazol-6-yl]-3,4-diaza-bicyclo[4.2.0]oct-4-en-2-one; | | | |
| 20 | 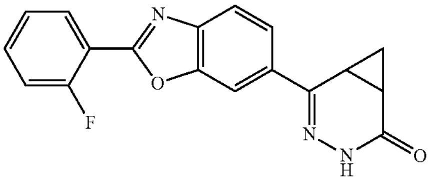 [SMILES: O=C1NN=C(c2ccc3nc(-c4ccccc4F)oc3c2)C2CC12] | 15.2% | $(M + H)^+ = 322$ | 1.45 min (method A) |
| | 5-[2-(2-fluoro-phenyl)-benzoxazol-6-yl]-3,4-diaza-bicyclo[4.1.0]hept-4-en-2-one; | | | |
| 21 | 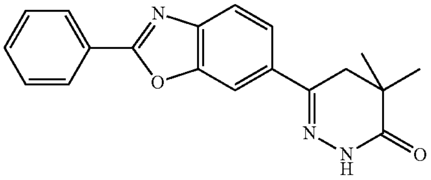 [SMILES: CC1(C)CC(c2ccc3nc(-c4ccccc4)oc3c2)=NNC1=O] | 56.7% | $(M + H)^+ = 320$ | 1.58 min (method A) |
| | 4,4-dimethyl-6-(2-phenyl-benzoxazol-6-yl)-4,5-dihydro-2H-pyridazin-3-one; | | | |
| 22 | 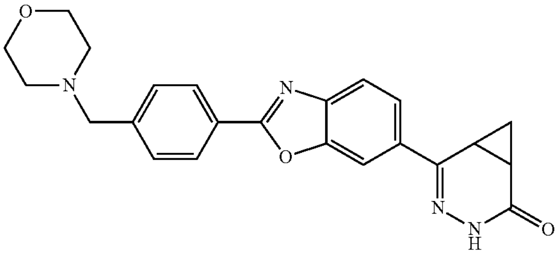 [SMILES: O=C1NN=C(c2ccc3nc(-c4ccc(CN5CCOCC5)cc4)oc3c2)C2CC12] | 6.3% | $(M + H)^+ = 403$ | 1.17 min (method A) |
| | 5-[2-(4-morpholin-4-ylmethyl-phenyl)-benzoxazol-6-yl]-3,4-diaza-bicyclo[4.1.0]hept-4-en-2-one; | | | |

-continued

| Ex. | Structural formula | Yield | Mass peak(s) | HPLC |
|---|---|---|---|---|
| 23 | 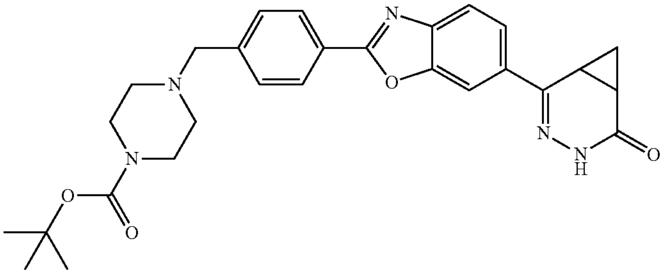 [SMILES: CC(C)(C)OC(=O)N1CCN(Cc2ccc(-c3nc4ccc(C5=NNC(=O)C6CC56)cc4o3)cc2)CC1]<br>tert.butyl 4-{4-[6-(5-oxo-3,4-diaza-bicyclo[4.1.0]hept-2-en-2-yl)-benzoxazol-2-yl]-benzyl}-piperazine-1-carboxylate; | 13.4% | $(M + H)^+ = 502$ | 1.30 min (method A) |
| 24 | 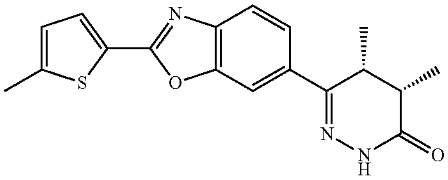<br>(4S,5R)-4,5-dimethyl-6-[2-(5-methyl-thiophen-2-yl)-benzoxazol-6-yl]-4,5-dihydro-2H-pyridazin-3-one; | 62.3% | $(M + H)^+ = 340$ | 1.64 min (method A) |
| 25 | 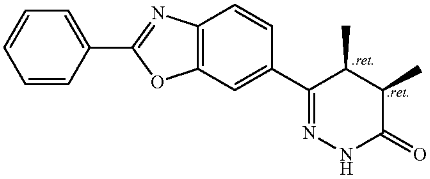 [SMILES: C[C@@H]1C(c2ccc3nc(-c4ccccc4)oc3c2)=NNC(=O)[C@@H]1C]<br>(4R,5S)-4,5-dimethyl-6-(2-phenyl-benzoxazol-6-yl)-4,5-dihydro-2H-pyridazin-3-one; | 32.3% | $(M + H)^+ = 320$ | 1.60 min (method A) |
| 26 | 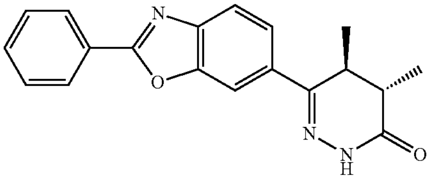 [SMILES: C[C@@H]1C(=O)NN=C(c2ccc3nc(-c4ccccc4)oc3c2)[C@H]1C]<br>(4S,5S)-4,5-dimethyl-6-(2-phenyl-benzoxazol-6-yl)-4,5-dihydro-2H-pyridazin-3-one; | 10.0% | $(M + H)^+ = 320$ | 1.56 min (method A) |

Example 27

(R)-5-methoxy-6-(2-phenyl-benzoxazol-6-yl)-4,5-dihydro-2H-pyridazin-3-one

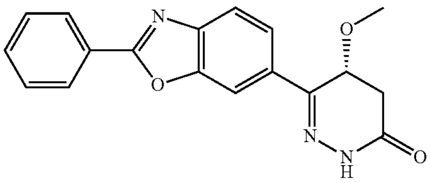 [SMILES: CO[C@@H]1CC(=O)NN=C1c1ccc2nc(-c3ccccc3)oc2c1]

(a) (R)-3-methoxy-4-oxo-4-(2-phenyl-benzoxazol-6-yl)-butyric acid

The preparation is carried out analogously to Example 1a from 6-bromo-2-phenyl-benzoxazole and (R)-3-methoxy-dihydro-furan-2,5-dione.

Yield: (19.8%)
$R_t$-time: 1.48 min (method A)
$C_{18}H_{15}NO_5$ (325.32)
Mass spectrum: $(M+H)^+=326$

(b) (R)-5-methoxy-6-(2-phenyl-benzoxazol-6-yl)-4,5-dihydro-2H-pyridazin-3-one 140 mg (430 μmol) (R)-3-methoxy-4-oxo-4-(2-phenyl-benzoxazol-6-yl)-butyric acid are combined at RT with 190 mg (500 μmol) HATU, 200 μl (1424 μmol) TEA and 2 ml DMF. The mixture is stirred for 10 min, then 431 μl (431 μmol) hydrazine 1M in THF are added. The mixture is stirred for a further 2 h at RT, then extracted with DCM and phosphate buffer (pH7). The org. phase is dried and evaporated down. The residue is purified by RP-HPLC.

Yield: 31 mg (22.4%)
$R_t$-time: 1.49 min (method A)
$C_{18}H_{15}N_3O_3$ (321.33)
Mass spectrum: $(M+H)^+=322$ The following compound may be prepared analogously:

| Ex. | Structural formula | Yield | Mass peak(s) | HPLC |
|---|---|---|---|---|
| 28 | 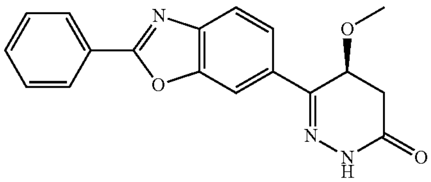 [SMILES: CO[C@H]1CC(=O)NN=C1c1ccc2nc(-c3ccccc3)oc2c1] | 9.3% | $(M+H)^+$ = 322 | 1.47 min (method A) |
| | (S)-5-methoxy-6-(2-phenyl-benzoxazol-6-yl)-4,5-dihydro-2H-pyridazin-3-one; | | | |

The following compound may be isolated as a by-product:

| Ex. | Structural formula | Yield | Mass peak(s) | HPLC |
|---|---|---|---|---|
| 204 | 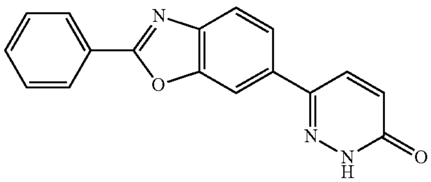 [SMILES: O=c1ccc(-c2ccc3nc(-c4ccccc4)oc3c2)n[nH]1] | 25.5% | $(M+H)^+$ = 290 | 1.47 min (method A) |
| | 6-(2-phenyl-benzoxazol-6-yl)-2H-pyridazin-3-one; | | | |

Example 29

5-ethyl-6-(2-phenyl-benzoxazol-6-yl)-4,5-dihydro-2H-pyridazin-3-one

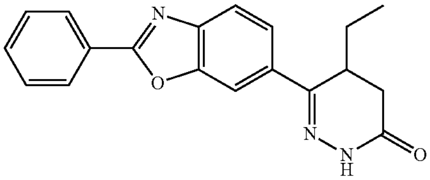

(a) 1-(2-phenyl-benzoxazol-6-yl)butan-1-one

The preparation is carried out under anhydrous conditions and under a protective gas atmosphere (argon).

10.00 g (36.48 mmol) 6-bromo-2-phenyl-benzoxazole are dissolved in 180 ml THF and cooled to −70° C., and 35.00 ml (56.00 mmol) n-butyl lithium 1.6M in hexane are added dropwise. This solution cooled to −70° C. is added dropwise after 20 min to an equally cold −70° C. solution of 2.5 g (19.1 mmol) N-methoxy-N-methyl-butyramide and 20 ml THF. After 20 min further stirring the mixture is mixed with water and allowed to come up to RT. The reaction mixture is extracted with water and DCM, the org. phase is dried on magnesium sulphate and the solv. is eliminated by rotary evaporation i.V. The residue is separated through silica gel (eluant cyclohexane/EA).

Yield: 2.6 g (51.4%)

$R_t$-time: 1.80 min (method A)

$C_{17}H_{15}NO_2$ (265.31)

Mass spectrum: $(M+H)^+$=266

(b) 3-ethyl-4-oxo-4-(2-phenyl-benzoxazol-6-yl)-butyric acid 625.00 µl (313 µmol) potassium bis(trimethylsilyl)amide 0.5M in toluene are placed in 15 ml THF and cooled to −78° C. 75.00 mg (283 µmol) 1-(2-phenyl-benzoxazol-6-yl)-butan-1-one, dissolved in 15 ml THF, are added dropwise to this solution and the mixture is stirred for 15 min at −78° C. Then 55 mg (360 µmol) methylbromoacetate, dissolved in 5 ml THF, are also added dropwise and the mixture is stirred for 30 min at −78° C., then 1N hydrochloric acid is added and the mixture is extracted with diethyl ether. The org. phase is dried on magnesium sulphate and the solv. is eliminated i.V.

Yield: 107 mg (78.5%)

$R_t$-time: 1.77 min (method A)

$C_{20}H_{19}NO_4$ (337.37)

Mass spectrum: $(M+H)^+$=338

(c) 5-ethyl-6-(2-phenyl-benzoxazol-6-yl)-4,5-dihydro-2H-pyridazin-3-one

The preparation is carried out analogously to Example 1b from methyl 3-(2-phenyl-benzoxazole-6-carbonyl)-pentanoate.

Yield: 28 mg (27.6%)

$R_t$-time: 1.58 min (method A)

$C_{19}H_{17}N_3O_2$ (319.36)

Mass spectrum: $(M+H)^+$=320

The following stereoisomers may be isolated by separation using chiral HPLC by method D:

| time in min (retention time) | flow rate in ml/min | eluted peak |
|---|---|---|
| 6.04 | 70 | 1 |
| 10.56 | 70 | 2 |

| Ex. | Structural formula | Yield | Mass peak(s) | HPLC |
|---|---|---|---|---|
| 30 | 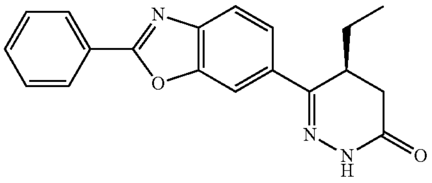 [SMILES: CC[C@H]1CC(=O)NN=C1c1ccc2nc(-c3ccccc3)oc2c1] | 11.1% | $(M + H)^+ = 322$ | 1.58 min (method A) |
| | (S)-5-ethyl-6-(2-phenyl-benzoxazol-6-yl)-4,5-dihydro-2H-pyridazin-3-one; | | | |
| 31 | 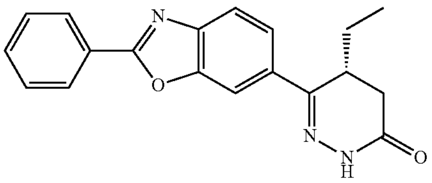 [SMILES: CC[C@@H]1CC(=O)NN=C1c1ccc2nc(-c3ccccc3)oc2c1] | 10.7% | $(M + H)^+ = 320$ | 1.58 min (method A) |
| | (R)-5-ethyl-6-(2-phenyl-benzoxazol-6-yl)-4,5-dihydro-2H-pyridazin-3-one; | | | |

Example 32

5-isopropyl-6-(2-phenyl-benzoxazol-6-yl)-4,5-dihydro-2H-pyridazin-3-one

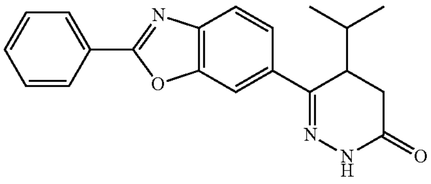 [SMILES: CC(C)C1CC(=O)NN=C1c1ccc2nc(-c3ccccc3)oc2c1]

(a) 3-methyl-1-(2-phenyl-benzoxazol-6-yl)butan-1-one

The preparation is carried out analogously to Example 29a from 6-bromo-2-phenyl-benzoxazole and N-methoxy-3,N-dimethyl-butyramide.

Yield: (35.0%)
$R_t$-time: 1.87 min (method A)
$C_{18}H_{17}NO_2$ (279.33)
Mass spectrum: $(M+H)^+=380$

(b) 3-i-propyl-4-oxo-4-(2-phenyl-benzoxazol-6-yl)-butyric acid

The preparation is carried out analogously to Example 29b from 3-methyl-1-(2-phenyl-benzoxazol-6-yl)-butan-1-one.

Yield: (95.4%)
$R_t$-time: 1.82 min (method A)
$C_{21}H_{21}NO_4$ (351.40)
Mass spectrum: $(M+H)^+=352$

(c) 4-methyl-3-(2-phenyl-benzoxazole-6-carbonyl)-pentanoic acid 100 mg (285 μmol) methyl 4-methyl-3-(2-phenyl-benzoxazole-6-carbonyl)-pentanoate, 10 mg (418 μmol) lithium hydroxide, 1 ml of water and 1 ml dioxane are stirred for 24 h at RT. The reaction mixture is acidified with conc. hydrochloric acid and extracted with diethyl ether, the org. phase is dried on magnesium sulphate and the solv. is eliminated by rotary evaporation i.V.

Yield: 96 mg (100.0%)
$R_t$-time: 1.65 min (method A)
$C_{20}H_{19}NO_4$ (337.34)
Mass spectrum: $(M+H)^+=338$

(d) 5-isopropyl-6-(2-phenyl-benzoxazol-6-yl)-4,5-dihydro-2H-pyridazin-3-one The preparation is carried out analogously to Example 27b from 4-methyl-3-(2-phenyl-benzoxazole-6-carbonyl)-pentanoic acid.

Yield: 18 mg (9.1%)
$R_t$-time: 1.57 min (method A)
$C_{20}H_{19}N_3O_2$ (333.39)
Mass spectrum: $(M+H)^+=334$

Example 33

6-[2-(4-benzyloxy-phenyl)-benzoxazol-6-yl]-5-ethyl-4,5-dihydro-2H-pyridazin-3-one

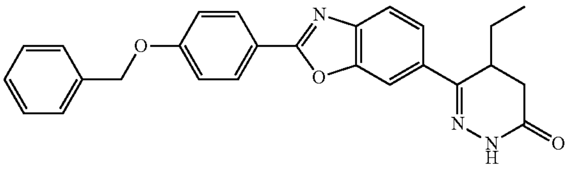 [SMILES: CCC1CC(=O)NN=C1c1ccc2nc(-c3ccc(OCc4ccccc4)cc3)oc2c1]

(a) 1-[2-(4-benzyloxy-phenyl)-benzoxazol-6-yl]-butan-1-one

The preparation is carried out analogously to Example 29a from 2-(4-benzyloxy-phenyl)-6-bromo-benzoxazole and N-methoxy-N-methyl-butyramide.

Yield: (38.9%)
$R_t$-time: 1.69 min (method C)

$C_{24}H_{21}NO_3$ (371.43)

Mass spectrum: $(M+H)^+$=372

(b) methyl 3-[2-(4-benzyloxy-phenyl)-benzoxazole-6-carbonyl]-pentanoate

The preparation is carried out analogously to Example 29b from 1-[2-(4-benzyloxy-phenyl)-benzoxazol-6-yl]-butan-1-one.

Yield: (45%)

$R_t$-time: 1.90 min (method A)

$C_{27}H_{25}NO_5$ (443.49)

Mass spectrum: $(M+H)^+$=444/5

(c) 3-[2-(4-benzyloxy-phenyl)-benzoxazole-6-carbonyl]-pentanoic acid

The preparation is carried out analogously to Example 32c from methyl 3-[2-(4-benzyloxy-phenyl)-benzoxazole-6-carbonyl]-pentanoate.

Yield: (54.4%)

$R_t$-time: 1.60 min (method C)

$C_{26}H_{23}NO_5$ (429.47)

Mass spectrum: $(M+H)^+$=430/1

(d) 6-[2-(4-benzyloxy-phenyl)-benzoxazol-6-yl]-5-ethyl-4,5-dihydro-2H-pyridazin-3-one The preparation is carried out analogously to Example 1b from 3-[2-(4-benzyloxy-phenyl)-benzoxazole-6-carbonyl]-pentanoic acid.

Yield: (22.6%)

$R_t$-time: 1.75 min (method A)

$C_{26}H_{23}N_3O_3$ (425.48)

Mass spectrum: $(M+H)^+$=426

The following compounds may be prepared analogously:

| Ex. | Structural formula | Yield | Mass peak(s) | HPLC |
|---|---|---|---|---|
| 34 | 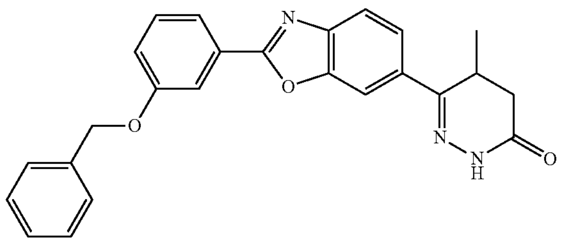 [SMILES: CC1CC(=O)NN=C1c1ccc2nc(-c3cccc(OCc4ccccc4)c3)oc2c1] 6-[2-(3-benzyloxy-phenyl)-benzoxazol-6-yl]-5-methyl-4,5-dihydro-2H-pyridazin-3-one; | 84.1% | $(M + H)^+$ = 412 | 1.57 min (method C) |
| 35 | 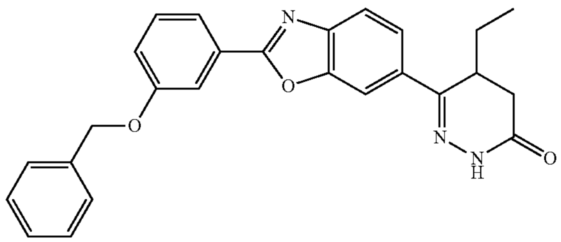 [SMILES: CCC1CC(=O)NN=C1c1ccc2nc(-c3cccc(OCc4ccccc4)c3)oc2c1] 6-[2-(3-benzyloxy-phenyl)-benzoxazol-6-yl]-5-ethyl-4,5-dihydro-2H-pyridazin-3-one; | 59.6% | $(M + H)^+$ = 426 | 1.61 min (method C) |
| 36 | 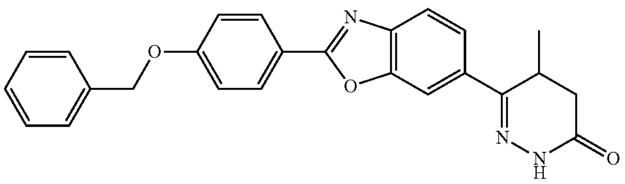 [SMILES: CC1CC(=O)NN=C1c1ccc2nc(-c3ccc(OCc4ccccc4)cc3)oc2c1] 6-[2-(4-benzyloxy-phenyl)-benzoxazol-6-yl]-5-methyl-4,5-dihydro-2H-pyridazin-3-one; | 58.1% | $(M + H)^+$ = 412 | 1.56 min (method C) |

Example 37

5-ethyl-6-[2-(4-hydroxy-phenyl)-benzoxazol-6-yl]-4,5-dihydro-2H-pyridazin-3-one

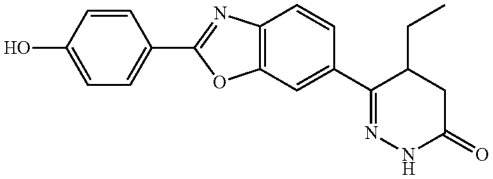 [SMILES: CCC1CC(=O)NN=C1c1ccc2nc(-c3ccc(O)cc3)oc2c1]

235 mg (552 μmol) 6-[2-(4-benzyloxy-phenyl)-benzoxazol-6-yl]-5-ethyl-4,5-dihydro-2H-pyridazin-3-one are hydrogenated together with 50 mg palladium on charcoal 10% and 50 ml of methanol at RT and 3.45 bar hydrogen pressure for 2.5 h, then the catalyst is filtered off and the filtrate is evaporated down completely i.V.

Yield: 170 mg (91.8%)

$R_t$-time: 1.39 min (method A)

$C_{19}H_{17}N_3O_3$ (335.36)

Mass spectrum: $(M+H)^+$=336/7

The following compounds may be prepared analogously:

Example 40

5-ethyl-6-{2-[4-(pyrimidin-2-ylmethoxy)-phenyl]-benzoxazol-6-yl}-4,5-dihydro-2H-pyridazin-3-one

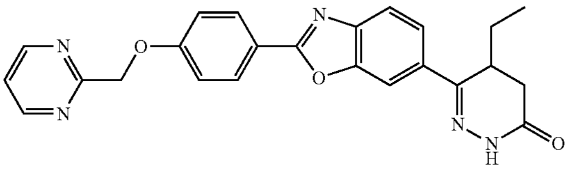

40 mg (119 μmol) 5-ethyl-6-[2-(4-hydroxy-phenyl)-benzoxazol-6-yl]-4,5-dihydro-2H-pyridazin-3-one, 23.5 mg (142 μmol) 2-(chloromethyl)-pyrimidine, 50 mg (362 μmol) potassium carbonate and 2 ml DMF are together heated to 80° C. for 2.5 h. Then the mixture is extracted with 10% sodium carbonate solution and EA. The org. phase is washed with sat. saline solution, dried on sodium sulphate and then the solv. is totally eliminated i.V. The residue is recrystallised from cyclohexane/EA.

Yield: 23.2 mg (45.5%)

$R_t$-time: 1.31 min (method C)

$C_{24}H_{21}N_5O_3$ (427.46)

Mass spectrum: $(M+H)^+$=428

The following compounds may be prepared analogously:

| Ex. | Structural formula | Yield | Mass peak(s) | HPLC |
|---|---|---|---|---|
| 38 | 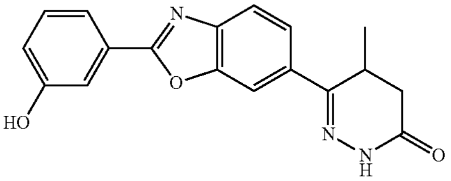 [SMILES: CC1CC(=O)NN=C1c1ccc2nc(-c3cccc(O)c3)oc2c1] 6-[2-(3-hydroxy-phenyl)-benzoxazol-6-yl]-5-methyl-4,5-dihydro-2H-pyridazin-3-one; | 55.7% | $(M + H)^+ = 322$ | 1.23 min (method C) |
| 39 | 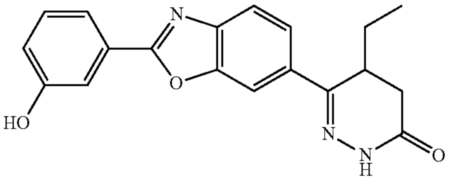 [SMILES: CCC1CC(=O)NN=C1c1ccc2nc(-c3cccc(O)c3)oc2c1] 6-[2-(3-hydroxy-phenyl)-benzoxazol-6-yl]-5-ethyl-4,5-dihydro-2H-pyridazin-3-one; | 24.7% | $(M + H)^+ = 336$ | 1.28 min (method C) |
| 203 | 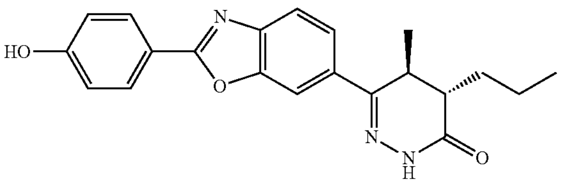 [SMILES: CCC[C@@H]1C(=O)NN=C(c2ccc3nc(-c4ccc(O)cc4)oc3c2)[C@H]1C] Trans-6-[2-(4-hydroxy-phenyl)-benzoxazol-6-yl]-5-ethyl-4-propyl-4,5-dihydro-2H-pyridazin-3-one; | 74.3% | $(M + H)^+ = 364$ | 1.37 min (method C) |

| Ex. | Structural formula | Yield | Mass peak(s) | HPLC |
|---|---|---|---|---|
| 41 | 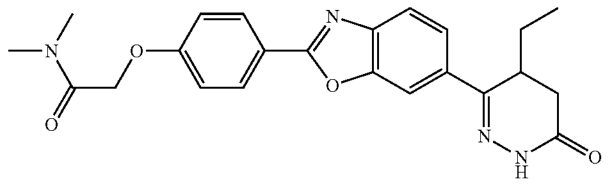 [SMILES: CCC1CC(=O)NN=C1c1ccc2nc(-c3ccc(OCC(=O)N(C)C)cc3)oc2c1] 2-{4-[6-(4-ethyl-6-oxo-1,4,5,6-tetrahydro-pyridazin-3-yl)-benzoxazol-2-yl]-phenoxy}-N,N-dimethyl-acetamide; | 47.9% | $(M + H)^+ = 421$ | 1.24 min (method C) |
| 42 | 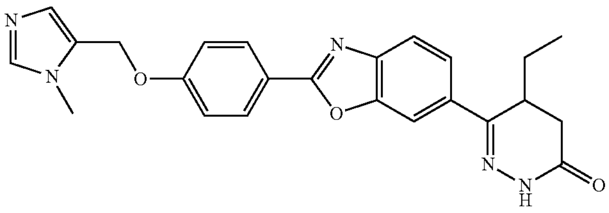 [SMILES: CCC1CC(=O)NN=C1c1ccc2nc(-c3ccc(OCc4cncn4C)cc3)oc2c1] 5-ethyl-6-{2-[4-(3-methyl-3H-imidazol-4-ylmethoxy)-phenyl]-benzoxazol-6-yl}-4,5-dihydro-2H-pyridazin-3-one; | 11.1% | $(M + H)^+ = 430$ | 1.13 min (method C) |
| 43 | 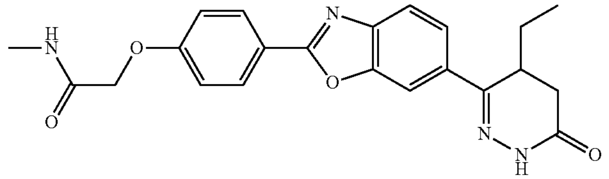 [SMILES: CCC1CC(=O)NN=C1c1ccc2nc(-c3ccc(OCC(=O)NC)cc3)oc2c1] 2-{4-[6-(4-ethyl-6-oxo-1,4,5,6-tetrahydro-pyridazin-3-yl)-benzoxazol-2-yl]-phenoxy}-N-methyl-acetamide; | 39.2% | $(M + H)^+ = 407$ | 1.24 min (method C) |
| 44 | 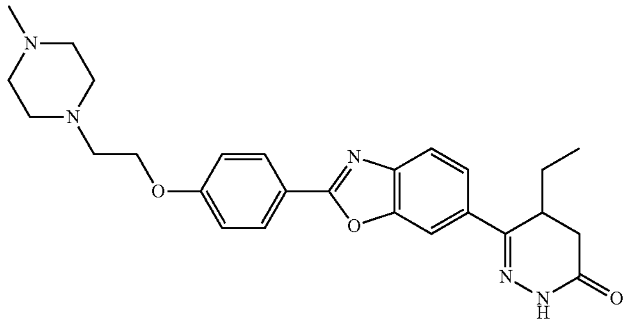 [SMILES: CCC1CC(=O)NN=C1c1ccc2nc(-c3ccc(OCCN4CCN(C)CC4)cc3)oc2c1] 5-ethyl-6-(2-{4-[2-(4-methyl-piperazin-1-yl)-ethoxy]-phenyl}-benzoxazol-6-yl)-4,5-dihydro-2H-pyridazin-3-one dihydrochloride; | 11.7% | $(M + H)^+ = 462$ | 1.10 min (method C) |
| 45 | 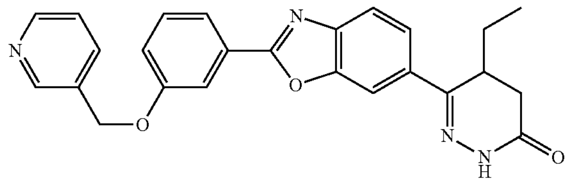 [SMILES: CCC1CC(=O)NN=C1c1ccc2nc(-c3cccc(OCc4cccnc4)c3)oc2c1] 5-ethyl-6-{2-[3-(pyridin-3-ylmethoxy)-phenyl]-benzoxazol-6-yl}-4,5-dihydro-2H-pyridazin-3-one; | 33.6% | $(M + H)^+ = 427$ | 1.22 min (method C) |

-continued

| Ex. | Structural formula | Yield | Mass peak(s) | HPLC |
|---|---|---|---|---|
| 46 | 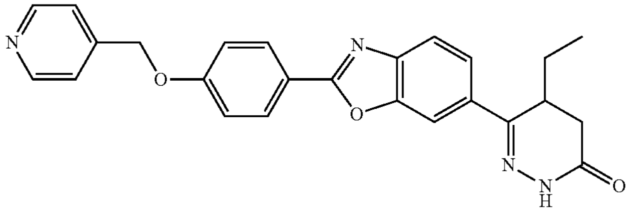 [SMILES: CCC1CC(=O)NN=C1c1ccc2nc(-c3ccc(OCc4ccncc4)cc3)oc2c1]<br>5-ethyl-6-{2-[4-(pyridin-4-ylmethoxy)-phenyl]-benzoxazol-6-yl}-4,5-dihydro-2H-pyridazin-3-one; | 20.4% | $(M + H)^+ = 427$ | 1.16 min (method C) |
| 47 | 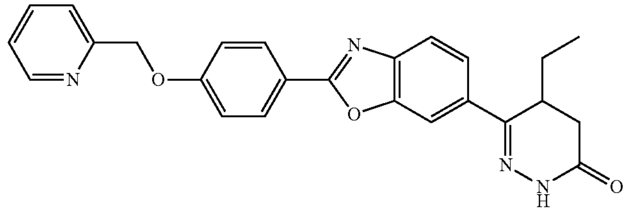 [SMILES: CCC1CC(=O)NN=C1c1ccc2nc(-c3ccc(OCc4ccccn4)cc3)oc2c1]<br>5-ethyl-6-{2-[4-(pyridin-2-ylmethoxy)-phenyl]-benzoxazol-6-yl}-4,5-dihydro-2H-pyridazin-3-one; | 37.4% | $(M + H)^+ = 427$ | 1.29 min (method C) |
| 48 | 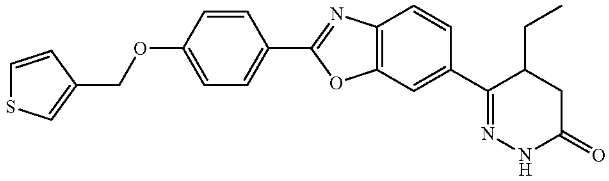 [SMILES: CCC1CC(=O)NN=C1c1ccc2nc(-c3ccc(OCc4ccsc4)cc3)oc2c1]<br>5-ethyl-6-{2-[4-(thiophen-3-ylmethoxy)-phenyl]-benzoxazol-6-yl}-4,5-dihydro-2H-pyridazin-3-one; | 61.4% | $(M + H)^+ = 432$ | 1.56 min (method C) |
| 49 | 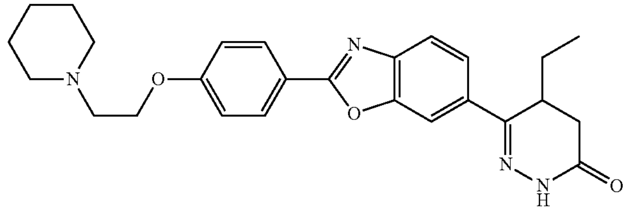 [SMILES: CCC1CC(=O)NN=C1c1ccc2nc(-c3ccc(OCCN4CCCCC4)cc3)oc2c1]<br>5-ethyl-6-{2-[4-(2-piperidin-1-yl-ethoxy)-phenyl]-benzoxazol-6-yl}-4,5-dihydro-2H-pyridazin-3-one; | 45.1% | $(M + H)^+ = 447$ | 1.13 min (method C) |
| 50 | 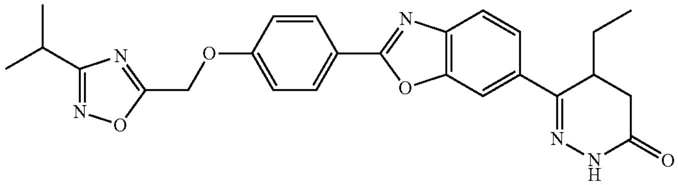 [SMILES: CCC1CC(=O)NN=C1c1ccc2nc(-c3ccc(OCc4nc(C(C)C)no4)cc3)oc2c1]<br>5-ethyl-6-{2-[4-(3-isopropyl-[1,2,4]oxadiazol-5-ylmethoxy)-phenyl]-benzoxazol-6-yl}-4,5-dihydro-2H-pyridazin-3-one; | 50.2% | $(M + H)^+ = 460$ | 1.50 min (method C) |

-continued

| Ex. | Structural formula | Yield | Mass peak(s) | HPLC |
|---|---|---|---|---|
| 51 | 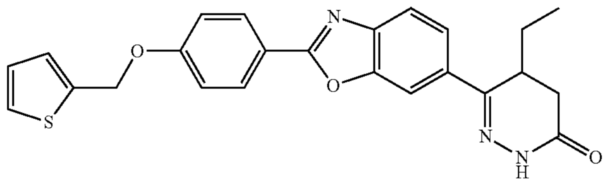 [SMILES: CCC1CC(=O)NN=C1c1ccc2nc(-c3ccc(OCc4cccs4)cc3)oc2c1] 5-ethyl-6-{2-[4-(thiophen-2-ylmethoxy)-phenyl]-benzoxazol-6-yl}-4,5-dihydro-2H-pyridazin-3-one; | 45.1% | $(M + H)^+ = 432$ | 1.55 min (method C) |
| 52 | 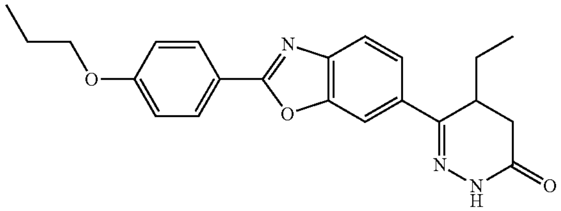 [SMILES: CCCOc1ccc(-c2nc3ccc(C4=NNC(=O)CC4CC)cc3o2)cc1] 5-ethyl-6-[2-(4-propoxy-phenyl)-benzoxazol-6-yl]-4,5-dihydro-2H-pyridazin-3-one; | 27.7% | $(M + H)^+ = 378$ | 1.56 min (method C) |
| 53 | 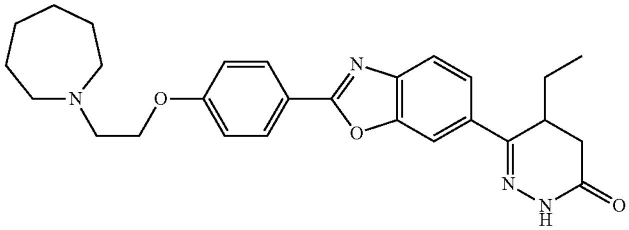 [SMILES: CCC1CC(=O)NN=C1c1ccc2nc(-c3ccc(OCCN4CCCCCC4)cc3)oc2c1] 6-{2-[4-(2-azepan-1-yl-ethoxy)-phenyl]-benzoxazol-6-yl}-5-ethyl-4,5-dihydro-2H-pyridazin-3-one; | 15.5% | $(M + H)^+ = 461$ | 1.16 min (method C) |
| 54 | 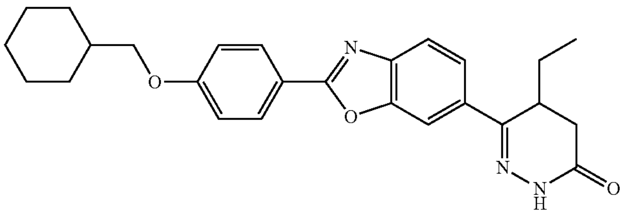 [SMILES: CCC1CC(=O)NN=C1c1ccc2nc(-c3ccc(OCC4CCCCC4)cc3)oc2c1] 6-[2-(4-cyclohexylmethoxy-phenyl)-benzoxazol-6-yl]-5-ethyl-4,5-dihydro-2H-pyridazin-3-one; | 37.7% | $(M + H)^+ = 432$ | 1.73 min (method C) |
| 55 | 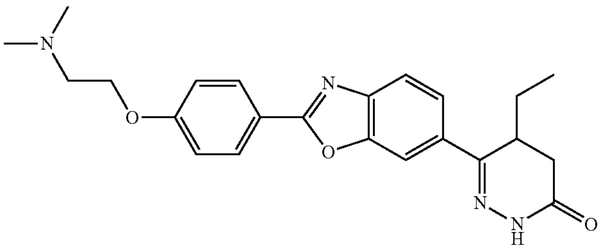 [SMILES: CCC1CC(=O)NN=C1c1ccc2nc(-c3ccc(OCCN(C)C)cc3)oc2c1] 6-{2-[4-(2-dimethylamino-ethoxy)-phenyl]-benzoxazol-6-yl}-5-ethyl-4,5-dihydro-2H-pyridazin-3-one; | 22.7% | $(M + H)^+ = 407$ | 1.09 min (method C) |

-continued

| Ex. | Structural formula | Yield | Mass peak(s) | HPLC |
|---|---|---|---|---|
| 56 | 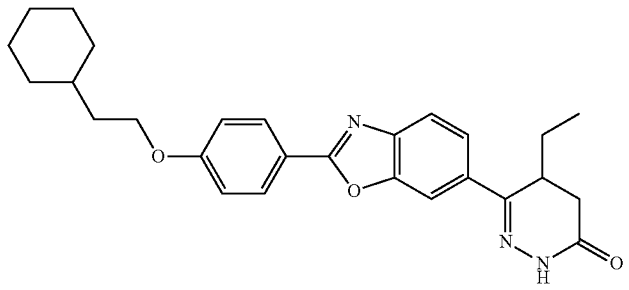 [SMILES: CCC1CC(=O)NN=C1c1ccc2nc(-c3ccc(OCCC4CCCCC4)cc3)oc2c1] 6-{2-[4-(2-cyclohexyl-ethoxy)-phenyl]-benzoxazol-6-yl}-5-ethyl-4,5-dihydro-2H-pyridazin-3-one; | 49.9% | $(M + H)^+$ = 446 | 1.75 min (method C) |
| 57 | 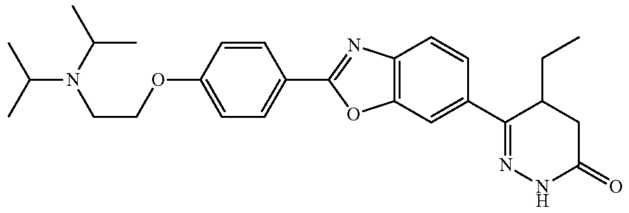 [SMILES: CCC1CC(=O)NN=C1c1ccc2nc(-c3ccc(OCCN(C(C)C)C(C)C)cc3)oc2c1] 6-{2-[4-(2-diisopropylamino-ethoxy)-phenyl]-benzoxazol-6-yl}-5-ethyl-4,5-dihydro-2H-pyridazin-3-one; | 47.1% | $(M + H)^+$ = 463 | 1.17 min (method C) |
| 58 | 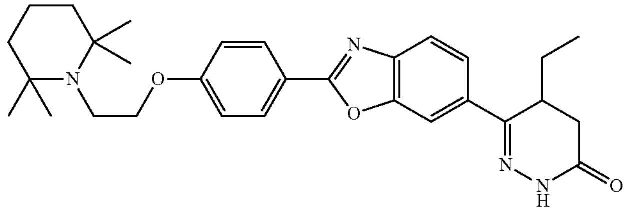 [SMILES: CCC1CC(=O)NN=C1c1ccc2nc(-c3ccc(OCCN4C(C)(C)CCCC4(C)C)cc3)oc2c1] 5-ethyl-6-(2-{4-[2-(2,2,6,6-tetramethyl-piperidin-1-yl)-ethoxy]-phenyl}-benzoxazol-6-yl)-4,5-dihydro-2H-pyridazin-3-one; | 22.5% | $(M + H)^+$ = 503 | 1.20 min (method C) |
| 59 | 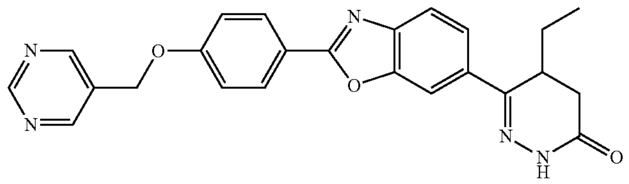 5-ethyl-6-{2-[4-(pyrimidin-5-ylmethoxy)-phenyl]-benzoxazol-6-yl}-4,5-dihydro-2H-pyridazin-3-one; | 29.8% | $(M + H)^+$ = 428 | 1.32 min (method C) |
| 60 | 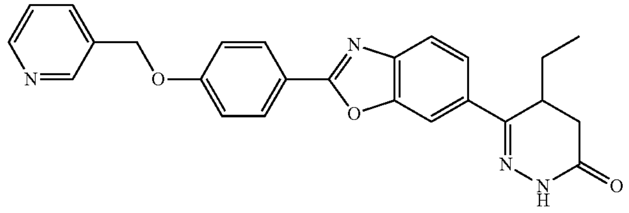 [SMILES: CCC1CC(=O)NN=C1c1ccc2nc(-c3ccc(OCc4cccnc4)cc3)oc2c1] 5-ethyl-6-{2-[4-(pyridin-3-ylmethoxy)-phenyl]-benzoxazol-6-yl}-4,5-dihydro-2H-pyridazin-3-one; | 33.8% | $(M + H)^+$ = 427 | 1.19 min (method C) |

-continued

| Ex. | Structural formula | Yield | Mass peak(s) | HPLC |
|---|---|---|---|---|
| 61 | 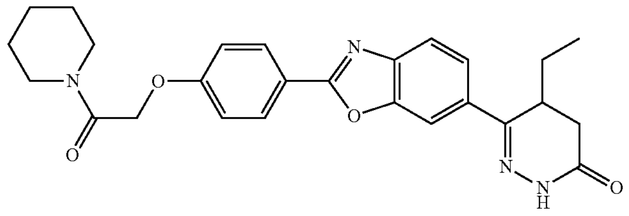 [SMILES: CCC1CC(=O)NN=C1c1ccc2nc(-c3ccc(OCC(=O)N4CCCCC4)cc3)oc2c1] 5-ethyl-6-{2-[4-(2-oxo-2-piperidin-1-yl-ethoxy)-phenyl]-benzoxazol-6-yl}-4,5-dihydro-2H-pyridazin-3-one; | 19.7% | $(M + H)^+ = 461$ | 1.37 min (method C) |
| 62 | 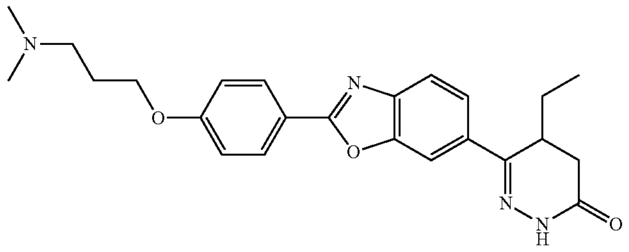 [SMILES: CCC1CC(=O)NN=C1c1ccc2nc(-c3ccc(OCCCN(C)C)cc3)oc2c1] 6-{2-[4-(3-dimethylamino-propoxy)-phenyl]-benzoxazol-6-yl}-5-ethyl-4,5-dihydro-2H-pyridazin-3-one; | 32.9% | $(M + H)^+ = 421$ | 1.15 min (method C) |
| 63 | 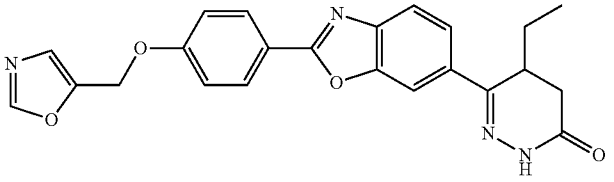 [SMILES: CCC1CC(=O)NN=C1c1ccc2nc(-c3ccc(OCc4cnco4)cc3)oc2c1] 5-ethyl-6-{2-[4-(oxazol-5-ylmethoxy)-phenyl]-benzoxazol-6-yl}-4,5-dihydro-2H-pyridazin-3-one; | 19.4% | $(M + H)^+ = 417$ | 1.34 min (method C) |
| 64 | 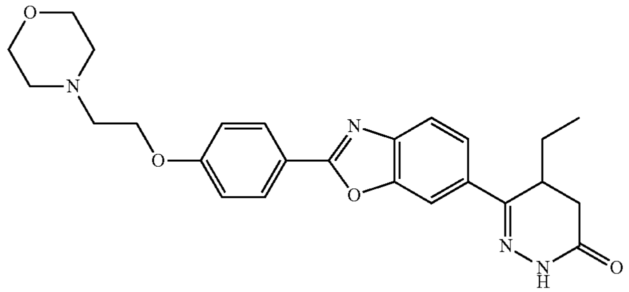 [SMILES: CCC1CC(=O)NN=C1c1ccc2nc(-c3ccc(OCCN4CCOCC4)cc3)oc2c1] 5-ethyl-6-{2-[4-(2-morpholin-4-yl-ethoxy)-phenyl]-benzoxazol-6-yl}-4,5-dihydro-2H-pyridazin-3-one; | 35.1% | $(M + H)^+ = 449$ | 1.24 min (method A) |
| 65 | 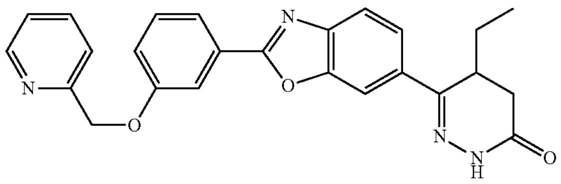 [SMILES: CCC1CC(=O)NN=C1c1ccc2nc(-c3cccc(OCc4ccccn4)c3)oc2c1] 5-ethyl-6-{2-[3-(pyridin-2-ylmethoxy)-phenyl]-benzoxazol-6-yl}-4,5-dihydro-2H-pyridazin-3-one; | 38.8% | $(M + H)^+ = 427$ | 1.30 min (method C) |

-continued

| Ex. | Structural formula | Yield | Mass peak(s) | HPLC |
|---|---|---|---|---|
| 66 | 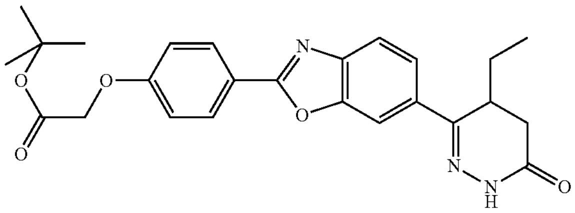 [SMILES: CCC1CC(=O)NN=C1c1ccc2nc(-c3ccc(OCC(=O)OC(C)(C)C)cc3)oc2c1] tert-butyl {4-[6-(4-ethyl-6-oxo-1,4,5,6-tetrahydro-pyridazin-3-yl)-benzoxazol-2-yl]-phenoxy}-acetate; | 36.6% | $(M+H)^+ = 450$ | 1.49 min (method C) |
| 67 | 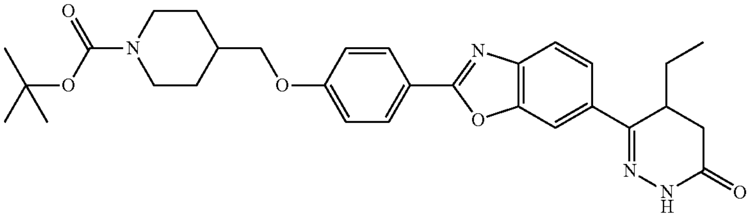 [SMILES: CCC1CC(=O)NN=C1c1ccc2nc(-c3ccc(OCC4CCN(C(=O)OC(C)(C)C)CC4)cc3)oc2c1] tert-butyl 4-{4-[6-(4-ethyl-6-oxo-1,4,5,6-tetrahydro-pyridazin-3-yl)-benzoxazol-2-yl]-phenoxymethyl}-piperidine-1-carboxylate; | 39.2% | $(M+H)^+ = 533$ | 1.61 min (method C) |
| 68 | 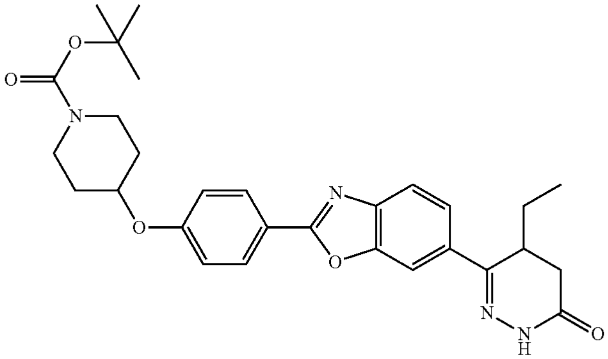 [SMILES: CCC1CC(=O)NN=C1c1ccc2nc(-c3ccc(OC4CCN(C(=O)OC(C)(C)C)CC4)cc3)oc2c1] tert-butyl 4-{4-[6-(4-ethyl-6-oxo-1,4,5,6-tetrahydro-pyridazin-3-yl)-benzoxazol-2-yl]-phenoxy}-piperidin-1-carboxylate; | 31.1% | $(M+H)^+ = 519$ | 1.58 min (method C) |
| 69 | 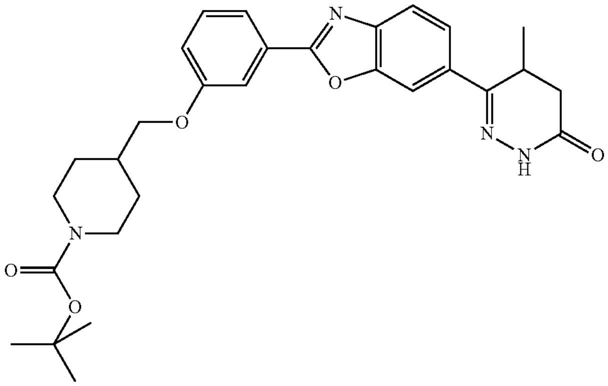 [SMILES: CC1CC(=O)NN=C1c1ccc2nc(-c3cccc(OCC4CCN(C(=O)OC(C)(C)C)CC4)c3)oc2c1] tert-butyl 4-{3-[6-(4-methyl-6-oxo-1,4,5,6-tetrahydro-pyridazin-3-yl)-benzoxazol-2-yl]-phenoxymethyl}-piperidin-1-carboxylate; | 77.5% | $(M+H)^+ = 519$ | 1.62 min (method C) |

-continued

| Ex. | Structural formula | Yield | Mass peak(s) | HPLC |
|---|---|---|---|---|
| 201 | 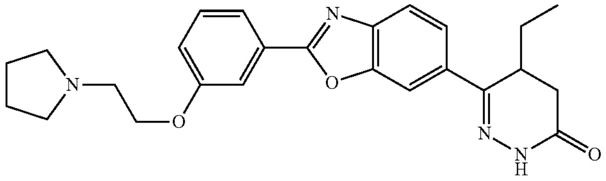 [SMILES: CCC1CC(=O)NN=C1c1ccc2nc(-c3cccc(OCCN4CCCC4)c3)oc2c1]<br>5-ethyl-6-{2-[3-(2-pyrrolidin-1-yl-ethoxy)-phenyl]-benzoxazol-6-yl}-4.5-dihydro-2H-pyridazin-3-one; | 7.2% | (M + H)+ = 433 | 1.32 min (method C) |
| 148 | 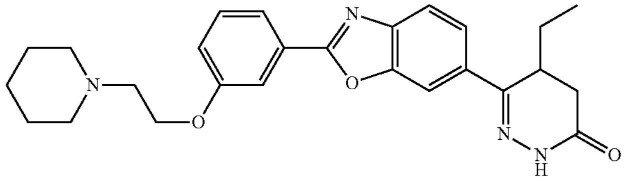 [SMILES: CCC1CC(=O)NN=C1c1ccc2nc(-c3cccc(OCCN4CCCCC4)c3)oc2c1]<br>5-ethyl-6-{2-[3-(2-piperidin-1-yl-ethoxy)-phenyl]-benzoxazol-6-yl}-4,5-dihydro-2H-pyridazin-3-one; | 12.2% | (M + H)+ = 447 | 1.16 min (method C) |
| 149 | 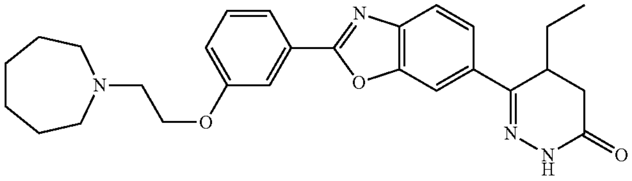 [SMILES: CCC1CC(=O)NN=C1c1ccc2nc(-c3cccc(OCCN4CCCCCC4)c3)oc2c1]<br>6-{2-[3-(2-azepan-1-yl-ethoxy)-phenyl]-benzoxazol-6-yl}-5-ethyl-4,5-dihydro-2H-pyridazin-3-one; | 21.8% | (M + H)+ = 461 | 1.20 min (method C) |
| 150 | 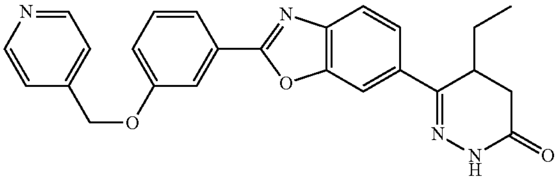 [SMILES: CCC1CC(=O)NN=C1c1ccc2nc(-c3cccc(OCc4ccncc4)c3)oc2c1]<br>5-ethyl-6-{2-[3-(pyridin-4-ylmethoxy)-phenyl]-benzoxazol-6-yl}-4,5-dihydro-2H-pyridazin-3-one; | 59.0% | (M + H)+ = 427 | 1.20 min (method C) |
| 151 | 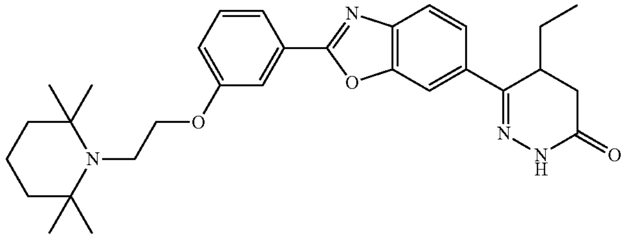 [SMILES: CCC1CC(=O)NN=C1c1ccc2nc(-c3cccc(OCCN4C(C)(C)CCCC4(C)C)c3)oc2c1]<br>5-ethyl-6-(2-{3-[2-(2,2,6,6-tetramethyl-piperidin-1-yl)-ethoxy]-phenyl}-benzoxazol-6-yl)-4,5-dihydro-2H-pyridazin-3-one; | 50.0% | (M + H)+ = 503 | 1.25 min (method C) |
| 152 | 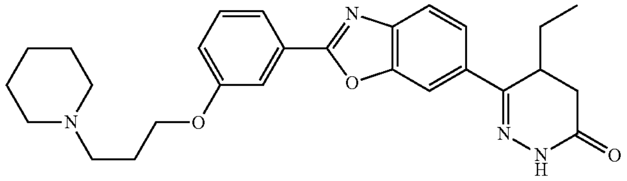 [SMILES: CCC1CC(=O)NN=C1c1ccc2nc(-c3cccc(OCCCN4CCCCC4)c3)oc2c1]<br>5-ethyl-6-{2-[3-(3-piperidin-1-yl-propoxy)-phenyl]-benzoxazol-6-yl}-4,5-dihydro-2H-pyridazin-3-one; | 32.9% | (M + H)+ = 461 | 1.23 min (method C) |

-continued

| Ex. | Structural formula | Yield | Mass peak(s) | HPLC |
|---|---|---|---|---|
| 153 | 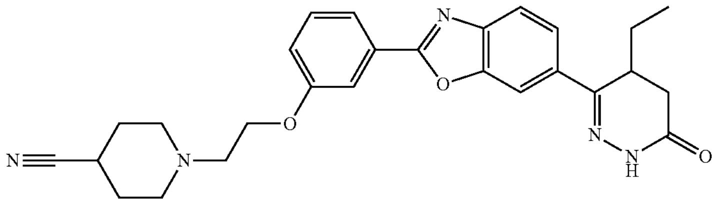 [SMILES: CCC1CC(=O)NN=C1c1ccc2nc(-c3cccc(OCCN4CCC(C#N)CC4)c3)oc2c1]<br>1-(2-{3-[6-(4-ethyl-6-oxo-1,4,5,6-tetrahydro-pyridazin-3-yl)-benzoxazol-2-yl]-phenoxy}-ethyl)-piperidine-4-carbonitrile; | 54.0% | (M + H)+ = 472 | 1.12 min (method C) |
| 154 | 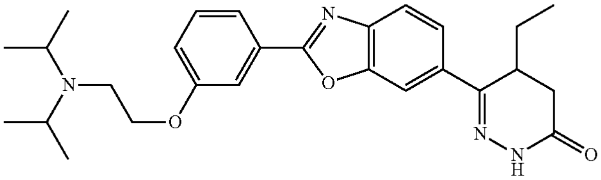 [SMILES: CCC1CC(=O)NN=C1c1ccc2nc(-c3cccc(OCCN(C(C)C)C(C)C)c3)oc2c1]<br>6-{2-[3-(2-diisopropylamino-ethoxy)-phenyl]-benzoxazol-6-yl}-5-ethyl-4,5-dihydro-2H-pyridazin-3-one; | 29.2% | (M + H)+ = 463 | 1.20 min (method C) |
| 155 | 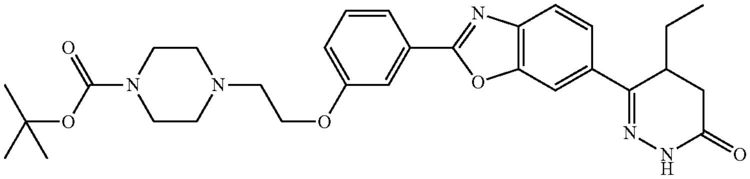 [SMILES: CCC1CC(=O)NN=C1c1ccc2nc(-c3cccc(OCCN4CCN(C(=O)OC(C)(C)C)CC4)c3)oc2c1]<br>tert-butyl 4-(2-{3-[6-(4-ethyl-6-oxo-1,4,5,6-tetrahydro-pyridazin-3-yl)-benzoxazol-2-yl]-phenoxy}-ethyl)-piperazine-1-carboxylate; | 8.9% | (M + H)+ = 548 | 1.29 min (method C) |
| 156 | 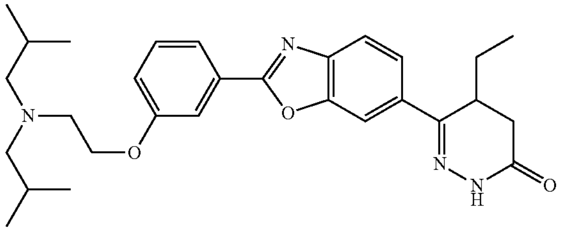 [SMILES: CCC1CC(=O)NN=C1c1ccc2nc(-c3cccc(OCCN(CC(C)C)CC(C)C)c3)oc2c1]<br>6-{2-[3-(2-diisobutylamino-ethoxy)-phenyl]-benzoxazol-6-yl}-5-ethyl-4,5-dihydro-2H-pyridazin-3-one; | 19.3% | (M + H)+ = 491 | 1.31 min (method C) |
| 157 | 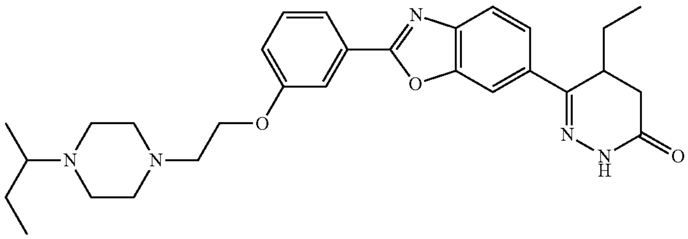 [SMILES: CCC1CC(=O)NN=C1c1ccc2nc(-c3cccc(OCCN4CCN(C(C)CC)CC4)c3)oc2c1]<br>6-(2-{3-[2-(4-sec-butyl-piperazin-1-yl)-ethoxy]-phenyl}-benzoxazol-6-yl)-5-ethyl-4,5-dihydro-2H-pyridazin-3-one; | 13.5% | (M + H)+ = 504 | 1.17 min (method C) |

-continued

| Ex. | Structural formula | Yield | Mass peak(s) | HPLC |
|---|---|---|---|---|
| 158 | 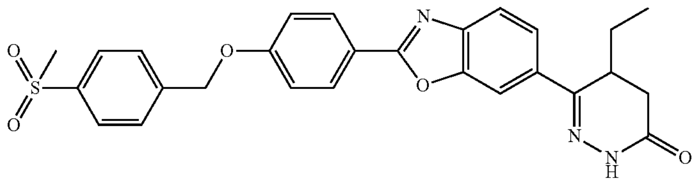 [SMILES: CCC1CC(=O)NN=C1c1ccc2nc(-c3ccc(OCc4ccc(S(C)(=O)=O)cc4)cc3)oc2c1] 5-ethyl-6-{2-[4-(4-methanesulphonyl-benzoxy)-phenyl]-benzoxazol-6-yl}-4,5-dihydro-2H-pyridazin-3-one; | 26.5% | (M + H)+ = 504 | 1.39 min (method C) |
| 159 | 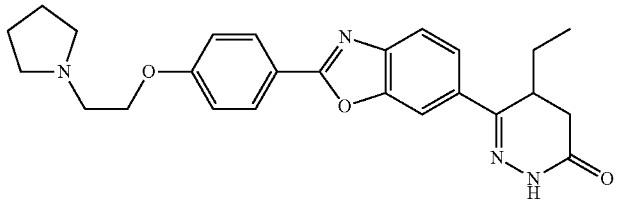 [SMILES: CCC1CC(=O)NN=C1c1ccc2nc(-c3ccc(OCCN4CCCC4)cc3)oc2c1] 5-ethyl-6-{2-[4-(2-pyrrolidin-1-yl-ethoxy)-phenyl]-benzoxazol-6-yl}-4.5-dihydro-2H-pyridazin-3-one; | 43.8% | (M + H)+ = 433 | 1.11 min (method C) |
| 160 | 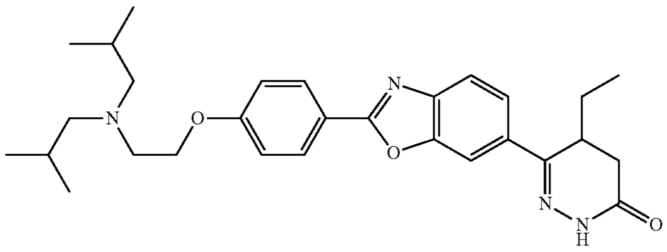 [SMILES: CCC1CC(=O)NN=C1c1ccc2nc(-c3ccc(OCCN(CC(C)C)CC(C)C)cc3)oc2c1] 6-{2-[4-(2-diisobulylamino-ethoxy)-phenyl]-benzoxazol-6-yl}-5-ethyl-4,5-dihydro-2H-pyridazin-3-one; | 1.9% | (M + H)+ = 491 | 1.27 min (method C) |
| 161 | 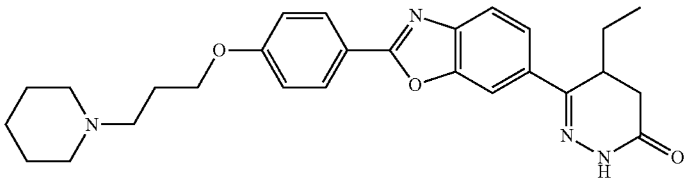 [SMILES: CCC1CC(=O)NN=C1c1ccc2nc(-c3ccc(OCCCN4CCCCC4)cc3)oc2c1] 5-ethyl-6-{2-[4-(3-piperidin-1-yl-propoxy)-phenyl]-benzoxazol-6-yl}-4,5-dihydro-2H-pyridazin-3-one x HCl; | 59.4% | (M + H)+ = 461 | 1.16 min (method C) |
| 162 | 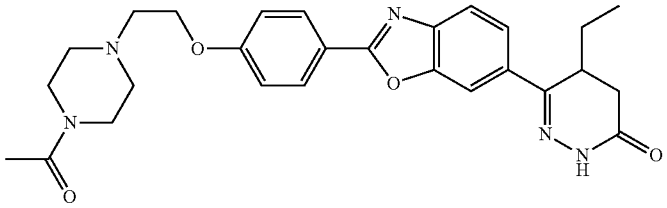 [SMILES: CCC1CC(=O)NN=C1c1ccc2nc(-c3ccc(OCCN4CCN(C(C)=O)CC4)cc3)oc2c1] 6-(2-{4-[2-(4-acetyl-piperazin-1-yl)-ethoxy]-phenyl}-benzoxazol-6-yl)-5-ethyl-4,5-dihydro-2H-pyridazin-3-one; | 64.4% | (M + H)+ = 490 | 1.07 min (method C) |

-continued

| Ex. | Structural formula | Yield | Mass peak(s) | HPLC |
|---|---|---|---|---|
| 163 | 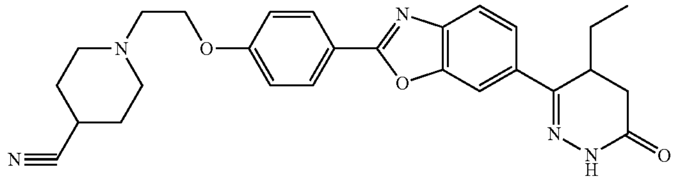 [SMILES: CCC1CC(=O)NN=C1c1ccc2nc(-c3ccc(OCCN4CCC(C#N)CC4)cc3)oc2c1] 1-(2-{4-[6-(4-ethyl-6-oxo-1,4,5,6-tetrahydro-pyridazin-3-yl)-benzoxazol-2-yl]-phenoxy}-ethyl)-piperidin-4-carbonitrile; | 52.8% | (M + H)+ = 472 | 1.09 min (method C) |
| 164 | 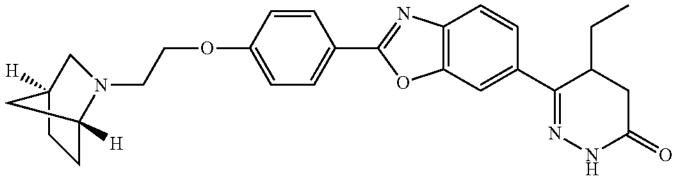 [SMILES: CCC1CC(=O)NN=C1c1ccc2nc(-c3ccc(OCCN4C[C@H]5CC[C@@H]4C5)cc3)oc2c1] 6-(2-{4-[2-(2-aza-bicyclo[2.2.1]-hept-2-yl)-ethoxy]-phenyl}-benzoxazol-6-yl)-5-ethyl-4,5-dihydro-2H-pyridazin-3-one; | 61.6% | (M + H)+ = 459 | 1.14 min (method C) |
| 165 | 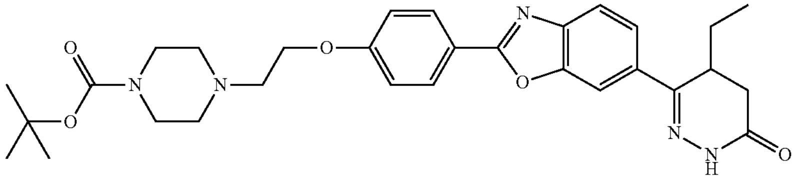 [SMILES: CCC1CC(=O)NN=C1c1ccc2nc(-c3ccc(OCCN4CCN(C(=O)OC(C)(C)C)CC4)cc3)oc2c1] terl-butyl 4-(2-{4-[6-(4-ethyl-6-oxo-1,4,5,6-tetrahydro-pyridazin-3-yl)-benzoxazol-2-yl]-phenoxy}-ethyl)-piperazine-1-carboxylate; | 45.3% | (M + H)+ = 548 | 1.26 min (method C) |
| 166 | 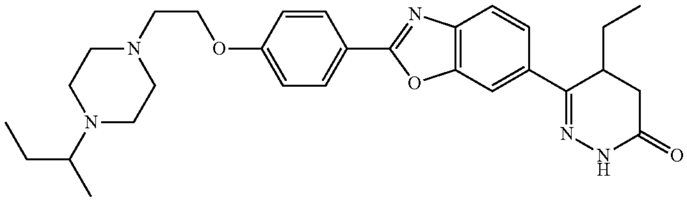 [SMILES: CCC1CC(=O)NN=C1c1ccc2nc(-c3ccc(OCCN4CCN(C(C)CC)CC4)cc3)oc2c1] 6-(2-{4-[2-(4-sec-butyl-piperazin-1-yl)-ethoxy]-phenyl}-benzoxazol-6-yl)-5-ethyl-4,5-dihydro-2H-pyridazin-3-one; | 67.8% | (M + H)+ = 504 | 1.14 min (method C) |
| 167 | 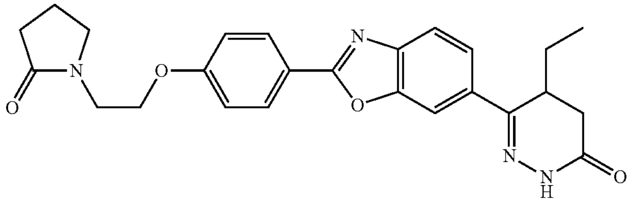 [SMILES: CCC1CC(=O)NN=C1c1ccc2nc(-c3ccc(OCCN4CCCC4=O)cc3)oc2c1] 5-ethyl-6-(2-{4-[2-(2-oxo-pyrrolidin-1-yl)-ethoxy]-phenyl}-benzoxazol-6-yl)-4,5-dihydro-2H-pyridazin-3-one; | 26.3% | (M + H)+ = 447 | 1.31 min (method C) |
| 168 | 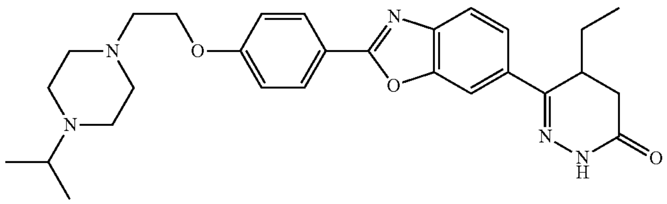 [SMILES: CCC1CC(=O)NN=C1c1ccc2nc(-c3ccc(OCCN4CCN(C(C)C)CC4)cc3)oc2c1] 5-ethyl-6-(2-{4-[2-(4-isopropyl-piperazin-1-yl)-ethoxy]-phenyl}-benzoxazol-6-yl)-4,5-dihydro-2H-pyridazin-3-one; | 38.4% | (M + H)+ = 490 | 1.11 min (method C) |

-continued

| Ex. | Structural formula | Yield | Mass peak(s) | HPLC |
|---|---|---|---|---|
| 169 | 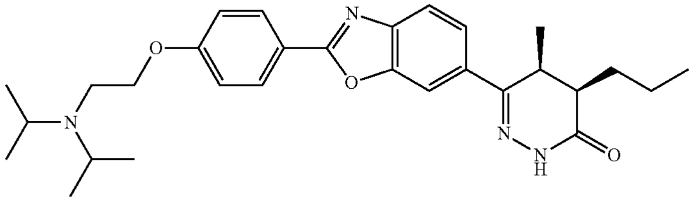 [SMILES: CCC[C@H]1C(=O)NN=C(c2ccc3nc(-c4ccc(OCCN(C(C)C)C(C)C)cc4)oc3c2)[C@H]1C]<br>cis-6-{2-[4-(2-diisopropylamino-ethoxy)-phenyl]-benzoxazol-6-yl}-5-methyl-4-propyl-4,5-dihydro-2H-pyridazin-3-one; | 63.7% | (M + H)+ = 491 | 1.29 min (method C) |
| 170 | 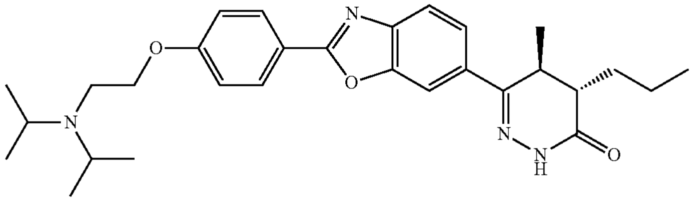 [SMILES: CCC[C@@H]1C(=O)NN=C(c2ccc3nc(-c4ccc(OCCN(C(C)C)C(C)C)cc4)oc3c2)[C@H]1C]<br>trans-6-{2-[4-(2-diisopropylamino-ethoxy)-phenyl]-benzoxazol-6-yl}-5-methyl-4-propyl-4,5-dihydro-2H-pyridazin-3-one; | 39.9% | (M + H)+ = 491 | 1.24 min (method C) |
| 171 | 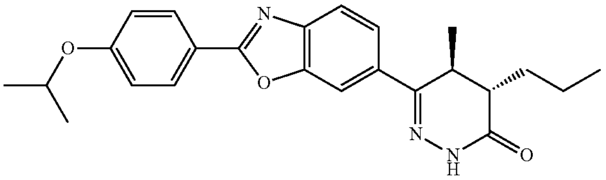 [SMILES: CCC[C@@H]1C(=O)NN=C(c2ccc3nc(-c4ccc(OC(C)C)cc4)oc3c2)[C@H]1C]<br>trans-6-[2-(4-isopropoxy-phenyl)-benzoxazol-6-yl]-5-methyl-4-propyl-4,5-dihydro-2H-pyridazin-3-one; | 87.8% | (M + H)+ = 406 | 1.60 min (method C) |
| 172 | 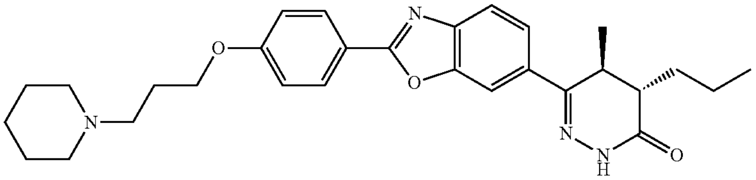 [SMILES: CCC[C@@H]1C(=O)NN=C(c2ccc3nc(-c4ccc(OCCCN5CCCCC5)cc4)oc3c2)[C@H]1C]<br>trans-5-methyl-6-{2-[4-(3-piperidin-1-yl-propoxy)-phenyl]-benzoxazol-6-yl}-4-propyl-4,5-dihydro-2H-pyridazin-3-one; | 37.9% | (M + H)+ = 489 | 1.25 min (method C) |
| 173 | 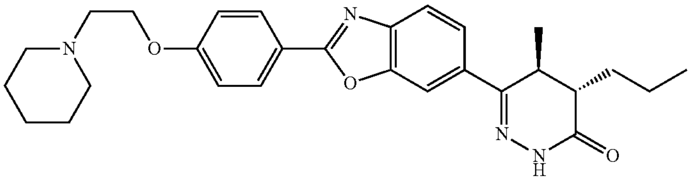 [SMILES: CCC[C@@H]1C(=O)NN=C(c2ccc3nc(-c4ccc(OCCN5CCCCC5)cc4)oc3c2)[C@H]1C]<br>trans-5-methyl-6-{2-[4-(3-piperidin-1-yl-ethoxy)-phenyl]-benzoxazol-6-yl}-4-propyl-4,5-dihydro-2H-pyridazin-3-one; | 89.5% | (M + H)+ = 475 | 1.22 min (method C) |
| 174 | 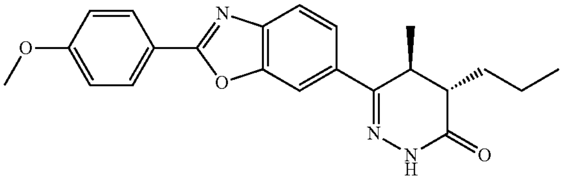 [SMILES: CCC[C@@H]1C(=O)NN=C(c2ccc3nc(-c4ccc(OC)cc4)oc3c2)[C@H]1C]<br>trans-6-[2-(4-methoxy-phenyl)-benzoxazol-6-yl]-5-methyl-4-propyl-4,5-dihydro-2H-pyridazin-3-one; | 88.1% | (M + H)+ = 378 | 1.69 min (method A) |

The following stereoisomers may be isolated by separation using chiral HPLC by method G:

Mobile phase: A: 75% CO2; B: 25% MeOH+0.2% diethylamine (DEA)

| time in min (retention time) | flow rate in ml/min | eluted peak |
|---|---|---|
| 5.70 | 4 | 1 |
| 6.80 | 4 | 2 |

| Ex. | Structural formula | Yield | Mass peak(s) | HPLC |
|---|---|---|---|---|
| 258 | Chiral 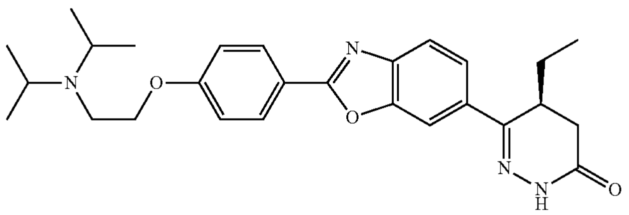 (S)-6-{2-[4-(2-diisopropylamino-ethoxy)-phenyl]-benzoxazol-6-yl}-5-ethyl-4,5-dihydro-2H-pyridazin-3-one; | 26.3% | $(M + H)^+ = 463$ | 1.17 min (method C) |
| 259 | Chiral 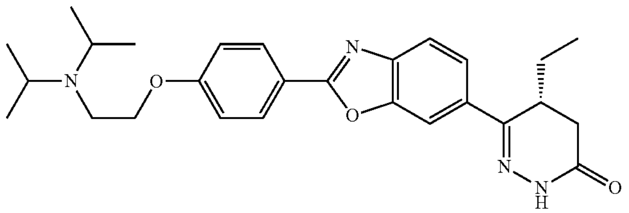 (R)-6-{2-[4-(2-diisopropylamino-ethoxy)-phenyl]-benzoxazol-6-yl}-5-ethyl-4,5-dihydro-2H-pyridazin-3-one; | 26.7% | $(M + H)^+ = 463$ | 1.16 min (method C) |

Mobile phase: A: 60% CO2; B: 40% isopropanol+0.2% diethylamine (DEA)

| time in min (retention time) | flow rate in ml/min | eluted peak |
|---|---|---|
| 4.40 | 4 | 1 |
| 5.35 | 4 | 2 |

| | | | | |
|---|---|---|---|---|
| 260 | 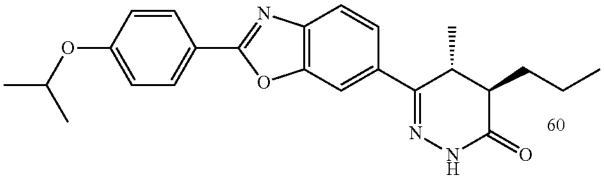 [SMILES: CCC[C@H]1C(=O)NN=C(c2ccc3nc(-c4ccc(OC(C)C)cc4)oc3c2)[C@@H]1C] (4S,5S)-6-[2-(4-isopropoxy-phenyl)-benzoxazol-6-yl]-5-methyl-4-propyl-4,5-dihydro-2H-pyridazin-3-one; | 44.5% | $(M + H)^+ = 406$ | 1.60 min (method C) |

Example 209

5-ethyl-6-{2-[4-(2-pyrrolidin-1-yl-propoxy)-phenyl]-benzoxazol-6-yl}-4,5-dihydro-2H-pyridazin-3-one

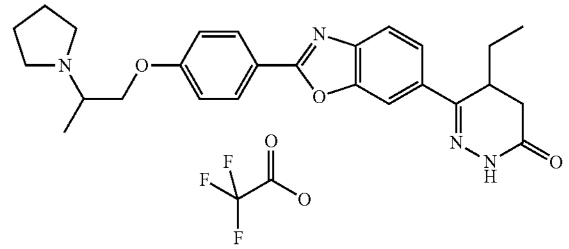

40 mg (119 μmol) 5-ethyl-6-[2-(4-hydroxy-phenyl)-benzoxazol-6-yl]-4,5-dihydro-2H-pyridazin-3-one, 23.5 mg (128 μmol) 1-(2-chloro-1-methylethyl)pyrrolidine×HCl, 50 mg (362 μmol) potassium carbonate and 2 ml DMF are heated together for 6 h to 80° C. Then the mixture is extracted with 10% sodium carbonate solution and EA. The org. phase is washed with sat. saline solution, dried on sodium sulphate and then the solv. is totally eliminated i.V. The residue is separated by semipreparative HPLC-MS. (xBridge, MeOH/H2O+TFA)

Yield: 29.8 mg (44.6%)

$R_t$-time: 1.13 min (method C)

$C_{26}H_{30}N_4O_3 \times C_2HF_3O_2$ (560.56)

Mass spectrum: $(M+H)^+$=447

The following compound may be prepared as a by-product:

(a) 5-ethyl-6-{2-[4-(2-oxo-propoxy)-phenyl]-benzoxazol-6-yl}-4,5-dihydro-2H-pyridazin-3-one 100 mg (298 μmol) 5-ethyl-6-[2-(4-hydroxy-phenyl)-benzoxazol-6-yl]-4,5-dihydro-2H-pyridazin-3-one, 24 μL (301 μmol) chloroacetone, 83 mg (601 μmol) potassium carbonate, 50 mg (301 μmol) potassium iodide and 10 ml acetone are heated together at 60° C. overnight. Then the mixture is extracted with 10% sodium carbonate solution and EA. The org. phase is washed with sat. saline solution, dried on sodium sulphate and then the solv. is totally eliminated i.V. The residue is purified through silica gel (eluant: DCM/methanol)

Yield: 75.4 mg (64.6%)

$R_t$-time: 1.28 min (method C)

$C_{22}H_{21}N_3O_4$ (391.42)

Mass spectrum: $(M+H)^+$=392

(b) 5-ethyl-6-{2-[4-(2-hydroxy-propoxy)-phenyl]-benzoxazol-6-yl}-4,5-dihydro-2H-pyridazin-3-one 27 mg (69 μmol) 5-ethyl-6-{2-[4-(2-oxo-propoxy)-phenyl]-benzoxazol-6-yl}-4,5-dihydro-2H pyridazin-3-one are placed in 5 mL EtOH, 5.5 mg (145 μmol) sodium borohydride are added with cooling and the mixture is stirred for 3 h at RT.

| Ex. | Structural formula | Yield | Mass peak(s) | HPLC |
|---|---|---|---|---|
| 210 | 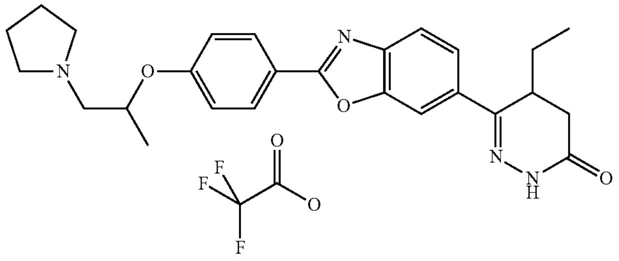 5-ethyl-6-{2-[4-(1-methyl-2-pyrrolidin-1-yl-ethoxy)-phenyl]-benzoxazol-6-yl}-4,5-dihydro-2H-pyridazin-3-one; | 9.6% | $(M+H)^+ = 447$ | 1.15 min (method C) |

Example 211

5-ethyl-6-{2-[4-(2-hydroxy-propoxy)-phenyl]-benzoxazol-6-yl}-4,5-dihydro-2H-pyridazin-3-one

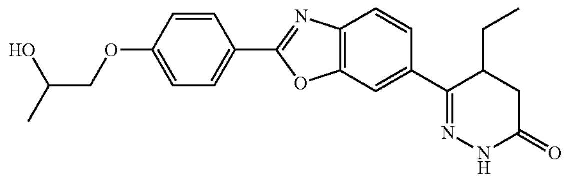 [SMILES: CCC1CC(=O)NN=C1c1ccc2nc(-c3ccc(OCC(C)O)cc3)oc2c1]

The reaction mixture is added to 50 mL ice water and extracted with DCM. The org. phase is washed with sat. saline solution and then the solv. is totally eliminated i.V. The residue is crystallised from cyclohexane/EA.

Yield: 12.0 mg (44.2%)

$R_t$-time: 1.33 min (method C)

$C_{22}H_{23}N_3O_4$ (393.44)

Mass spectrum: $(M+H)^+$=394

The following compounds may be prepared analogously:

| Ex. | Structural formula | Yield | Mass peak(s) | HPLC |
|---|---|---|---|---|
| 212 | 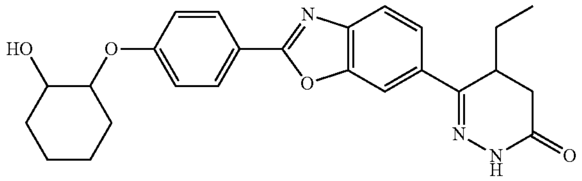 [SMILES: CCC1CC(=O)NN=C1c1ccc2nc(-c3ccc(OC4CCCCC4O)cc3)oc2c1]<br>5-ethyl-6-{2-[4-(2-hydroxy-cyclohexyloxy)-phenyl]-benzoxazol-6-yl}-4,5-dihydro-2H-pyridazin-3-one; | 6.6% | $(M + H)^+ = 434$ | 1.44 min (method C) |

Example 70

4-[6-(4-ethyl-6-oxo-1,4,5,6-tetrahydro-pyridazin-3-yl)-benzoxazol-2-yl]-phenoxy-acetic acid

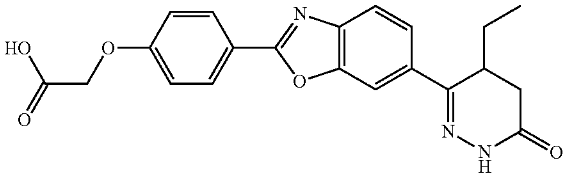 [SMILES: CCC1CC(=O)NN=C1c1ccc2nc(-c3ccc(OCC(=O)O)cc3)oc2c1]

20 mg (44 μmol) tert-butyl {4-[6-(4-ethyl-6-oxo-1,4,5,6-tetrahydro-pyridazin-3-yl)-benzoxazol-2-yl]-phenoxy}-acetate (Example 66), 500 μl TFA and 1 ml DCM are stirred together for 2 h at RT, then the solv. is totally eliminated i.V. and the residue is crystallised from cyclohexane/EA.

Yield: 14 mg (80%)

$R_t$-time: 1.27 min (method C)

$C_{21}H_{19}N_3O_5$ (393.39)

Mass spectrum: $(M+H)^+=394$

Example 71

4-{4-[6-(4-ethyl-6-oxo-1,4,5,6-tetrahydro-pyridazin-3-yl)-benzoxazol-2-yl]-phenoxymethyl}-piperidine as hydrochloride

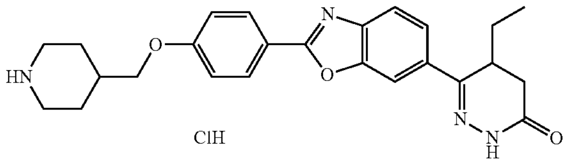 [SMILES: CCC1CC(=O)NN=C1c1ccc2nc(-c3ccc(OCC4CCNCC4)cc3)oc2c1 ; Cl]

28 mg (53 μmol) tert-butyl 4-{4-[6-(4-ethyl-6-oxo-1,4,5,6-tetrahydro-pyridazin-3-yl)-benzoxazol-2-yl]-phenoxymethyl}-piperidine-1-carboxylate (Example 67), 500 μl of 2N HCl in diethyl ether and 4 ml DCM are stirred together overnight at RT, then a further 2 ml of 2N HCl in diethyl ether are added and the mixture is again stirred overnight. The solv. is then evaporated off completely i.V. and the residue is crystallised from methanol/diethyl ether.

Yield: 20.4 mg (82.7%)

$R_t$-time: 1.18 min (method C)

$C_{25}H_{28}N_4O_3$*HCl (468.98)

Mass spectrum: $(M+H)^+=433$

The following compounds may be prepared analogously:

| Ex. | Structural formula | Yield | Mass peak(s) | HPLC |
|---|---|---|---|---|
| 72 | 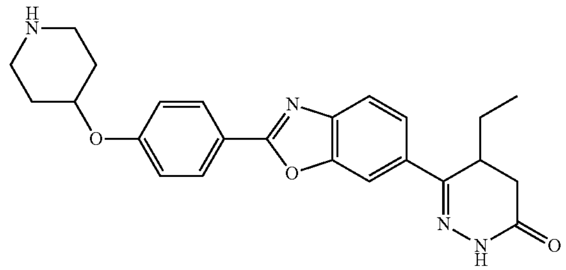 [SMILES: CCC1CC(=O)NN=C1c1ccc2nc(-c3ccc(OC4CCNCC4)cc3)oc2c1]<br>5-ethyl-6-{2-[4-(piperidin-4-yloxy)-phenyl]-benzoxazol-6-yl}-4,5-dihydro-2H-pyridazin-3-one hydrochloride; | 99% | $(M + H)^+ = 419$ | 1.15 min (method C) |

-continued

| Ex. | Structural formula | Yield | Mass peak(s) | HPLC |
|---|---|---|---|---|
| 73 | 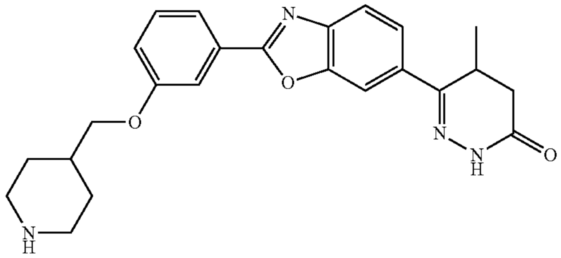 [SMILES: CC1CC(=O)NN=C1c1ccc2nc(-c3cccc(OCC4CCNCC4)c3)oc2c1] 5-methyl-6-{2-[3-(piperidin-4-ylmethoxy)-phenyl]-benzoxazol-6-yl}-4,5-dihydro-2H-pyridazin-3-one hydrochloride; | 71.2% | $(M + H)^+ = 419$ | 1.19 min (method C) |

Example 74

5-ethyl-6-{2-[4-(1-methanesulphonyl-piperidin-4-ylmethoxy)-phenyl]-benzoxazol-6-yl}-4,5-dihydro-2H-pyridazin-3-one

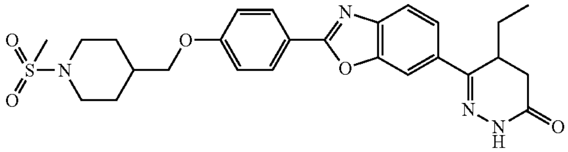 [SMILES: CCC1CC(=O)NN=C1c1ccc2nc(-c3ccc(OCC4CCN(S(C)(=O)=O)CC4)cc3)oc2c1]

15.5 mg (33 μmol) 4-{4-[6-(4-ethyl-6-oxo-1,4,5,6-tetrahydro-pyridazin-3-yl)-benzoxazol-2-yl]-phenoxymethyl}-piperidine as hydrochloride are stirred together with 2.6 μl (34 μmol) methanesulphonic acid chloride, 14 μl (100 μmol) triethylamine and 2 ml DCM at RT overnight within the next 4 days a further 14.4 μl methanesulphonic acid chloride and 24.5 μl triethylamine are added batchwise. Then the reaction mixture is combined with DCM and extracted 2× with 25 ml of water+3 drops of glacial acetic acid, 5% sodium carbonate solution and sat. saline solution. The solv. of the org. phase is evaporated off completely i.V. and the residue is stirred with cyclohexane/EA.

Yield: 7.5 mg (44.4%)

$R_t$-time: 1.37 min (method C)

$C_{26}H_{30}N_4O_5S$ (510.60)

Mass spectrum: $(M+H)^+=511$

Example 75

5-ethyl-6-{2-[4-styryl-phenyl]-benzoxazol-6-yl}-4,5-dihydro-2H-pyridazin-3-one

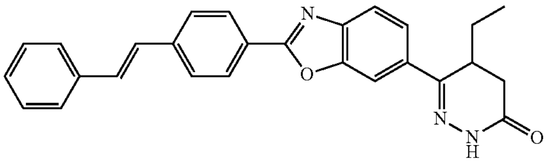 [SMILES: CCC1CC(=O)NN=C1c1ccc2nc(-c3ccc(/C=C/c4ccccc4)cc3)oc2c1]

(a) 4-[6-(4-ethyl-6-oxo-1,4,5,6-tetrahydro-pyridazin-3-yl)-benzoxazol-2-yl]-phenyl trifluoro-methane-sulphonate 100 mg (298 μmol) 5-ethyl-6-[2-(4-hydroxy-phenyl)-benzoxazol-6-yl]-4,5-dihydro-2H-pyridazin-3-one (Example 37), 140 mg (392 μmol) N-phenyl-trifluoromethanesulphonic acid imide and 10 ml DMF are combined and cooled to 0° C. At this temperature 55.34 μl (392 μmol) triethylamine are added dropwise, the mixture is stirred further overnight at RT, then it is diluted with DCM and extracted successively with 10% sodium carbonate solution, water and sat. saline solution. The org. phase is evaporated down completely i.V. and the residue is purified through silica gel (eluant: DCM/methanol)

Yield: 105 mg (75.3%)

$R_t$-time: 1.54 min (method C)

$C_{20}H_{16}F_3N_3O_5S$ (467.42)

Mass spectrum: $(M+H)^+=468$

(b) 5-ethyl-6-{2-[4-styryl-phenyl]-benzoxazol-6-yl}-4,5-dihydro-2H-pyridazin-3-one The reaction is carried out under a protective gas atmosphere (argon).

60 mg (128 μmol) 4-[6-(4-ethyl-6-oxo-1,4,5,6-tetrahydro-pyridazin-3-yl)-benzoxazol-2-yl]-phenyl trifluoro-methane-sulphonate, 14.7 μl (128 μmol) styrene, 2.9 mg (13 μmol) palladium-(II)-acetate, 4.1 mg (13 μmol) tri-o-tolylphosphine, 72 μl (513 μmol) triethylamine and 2 ml acetonitrile are combined and stirred overnight at 80° C. Then a further 7.5 μl styrene, 2.9 mg palladium-(II)-acetate and 4 mg tri-o-tolyphosphine are added and the mixture is stirred for 5 days at 80° C. Then it is diluted with DCM and extracted successively with 10% sodium carbonate solution and sat. saline solution. The org. phase is evaporated down completely i.V. and the residue is purified through silica gel (eluant: DCM/methanol). The residue obtained is crystallised from cyclohexane/EA.

Yield: 12.5 mg (23.1%)

$R_t$-time: 1.66 min (method C)

$C_{27}H_{23}N_3O_2$ (421.49)

Mass spectrum: $(M+H)^+=422$

Example 76

5-ethyl-6-[2-(4-phenethyl-phenyl)-benzoxazol-6-yl]-4,5-dihydro-2H-pyridazin-3-one

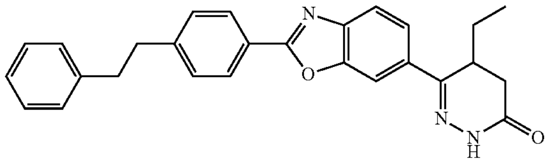 [SMILES: CCC1CC(=O)NN=C1c1ccc2nc(-c3ccc(CCc4ccccc4)cc3)oc2c1]

9 mg (21 μmol) 5-ethyl-6-{2-[4-styryl-phenyl]-benzoxazol-6-yl}-4,5-dihydro-2H-pyridazin-3-one are hydrogenated together with 2 mg palladium on charcoal 10% and 10 ml of methanol at RT and 3.45 bar hydrogen pressure for 80 min, then the catalyst is filtered off and the filtrate is evaporated down completely i.V. The residue is purified through silica gel (eluant: DCM/methanol) and then stirred with cyclohexane/EA.

Yield: 3.8 mg (42%)

$R_t$-time: 1.65 min (method C)

$C_{27}H_{25}N_3O_2$ (423.51)

Mass spectrum: $(M+H)^+$=424

Example 77

6-ethyl-5-(2-phenyl-benzoxazol-6-yl)-3,6-dihydro-[1,3,4]thiadiazin-2-one

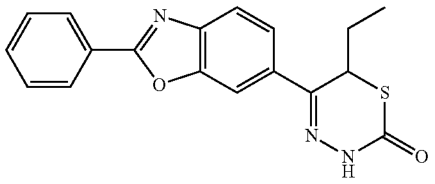

(a) 2-bromo-1-(2-phenyl-benzoxazol-6-yl)-butan-1-one 400 mg (1.51 mmol) 1-(2-phenyl-benzoxazol-6-yl)-butan-1-one and 643 mg (1.81 mmol) pyridinium tribromide are dissolved in 4 ml glacial acetic acid at RT, then 1.04 ml (5.40 mmol) hydrogen bromide, dissolved 30% in glacial acetic acid, are added and the mixture is stirred for 1 h at RT. Then the reaction mixture is mixed with water and adjusted to pH 8 with 5% potassium carbonate solution, then it is extracted with DCM, the org. phase is dried on magnesium sulphate and the solv. is eliminated completely in vacuo. The residue is separated through silica gel (eluant cyclohexane/EA).

Yield: 390 mg (75.2%)

$R_t$-time: 1.85 min (method A)

$C_{17}H_{14}BrNO_2$ (344.20)

Mass spectrum: $(M+H)^+$=344/346

6-ethyl-5-(2-phenyl-benzoxazol-6-yl)-3,6-dihydro-[1,3,4]thiadiazin-2-one 50 mg (145 μmol) 2-bromo-1-(2-phenyl-benzoxazol-6-yl)-butan-1-one, 60 mg (293 μmol) O-phenyl hydrazinethiocarbamate, 50 μl (363 μmol) TEA, 2 ml acetonitrile and 200 μl water are stirred together at 80° C. for 1 h. The reaction mixture is extracted with water and DCM. The org. phase is dried and the solv. is eliminated completely in vacuo. The residue is combined with 1 ml acetonitrile and 2 drops of water. 10 mg (53 μmol) para-toluenesulphonic acid monohydrate are added under argon and the mixture is also stirred for 1 h at RT under argon. Then it is left to react for 30 min under argon at 100° C. in the microwave. The reaction mixture is purified by RP-HPLC.

Yield: 2 mg (4.1%)

$R_t$-time: 1.66 min (method A)

$C_{18}H_{15}N_3O_2S$ (337.40)

Mass spectrum: $(M+H)^+$=338

Example 78

6-ethyl-5-(2-phenyl-benzoxazol-6-yl)-3,6-dihydro-[1,3,4]oxadiazin-2-one

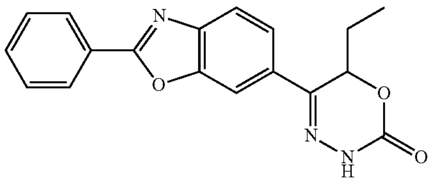

(a) 2-hydroxy-1-(2-phenyl-benzoxazol-6-yl)-butan-1-one 200 mg (581 μmol) 2-bromo-1-(2-phenyl-benzoxazol-6-yl)-butan-1-one are combined with 1.2 ml DMF and 0.8 ml of water. The mixture is stirred for 3 h at 100° C. and then separated by RP-HPLC.

Yield: 50 mg (30.6%)

$R_t$-time: 1.58 min (method A)

$C_{17}H_{15}NO_3$ (281.31)

Mass spectrum: $(M+H)^+$=282

(b) 6-ethyl-5-(2-phenyl-benzoxazol-6-yl)-3,6-dihydro-[1.3.4]oxadiazin-2-one 50 mg (178 μmol) 2-hydroxy-1-(2-phenyl-benzoxazol-6-yl)-butan-1-one are refluxed together with 20.36 mg (196 μmol) ethyl hydrazinoformate, 1 drop of 0.1N hydrochloric acid and 500 μl ethanol for 10 min, then the solvent is completely removed i. V. The residue is dissolved in 2 ml dry ethanol. 40 mg (1740 μmol) sodium are dissolved in 1.2 ml dry ethanol and added dropwise to the first solution, the mixture is stirred overnight at RT, then separated by RP-HPLC.

Yield: 16.5 mg (58%)

$R_t$-time: 1.59 min (method A)

$C_{18}H_{15}N_3O_3$ (321.33)

Mass spectrum: $(M+H)^+$=322

The following stereoisomers may be isolated by separation using chiral HPLC by the following method D:

| time in min (retention time) | flow rate in ml/min | eluted peak |
|---|---|---|
| 6.04 | 70 | 1 |
| 10.56 | 70 | 2 |

| Ex. | Structural formula | Yield | Mass peak(s) | HPLC |
|---|---|---|---|---|
| 79 | 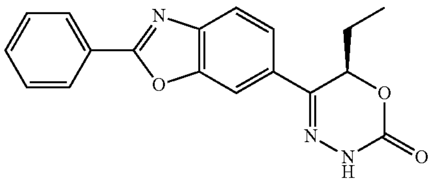 [SMILES: CC[C@H]1OC(=O)NN=C1c1ccc2nc(-c3ccccc3)oc2c1] (S)-6-ethyl-5-(2-phenyl-benzoxazol-6-yl)-3,6-dihydro-[1,3,4]oxadiazin-2-one; | 17.0% | $(M + H)^+ = 322$ | 1.42 min (method C) |
| 80 | 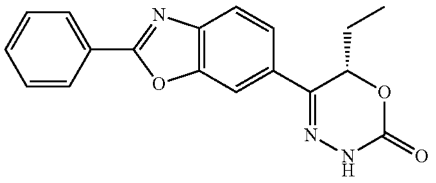 [SMILES: CC[C@@H]1OC(=O)NN=C1c1ccc2nc(-c3ccccc3)oc2c1] (R)-6-ethyl-5-(2-phenyl-benzoxazol-6-yl)-3,6-dihydro-[1,3,4]oxadiazin-2-one; | 13.2% | $(M + H)^+ = 322$ | 1.42 min (method C) |

The following compound may be prepared analogously:

| Ex. | Structural formula | Yield | Mass peak(s) | HPLC |
|---|---|---|---|---|
| 81 | 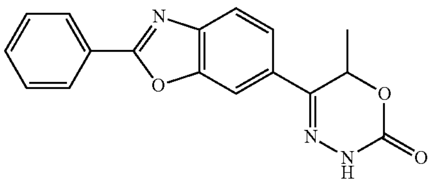 6-methyl-5-(2-phenyl-benzoxazol-6-yl)-3,6-dihydro-[1,3,4]oxadiazin-2-one; | 60.3% | $(M + H)^+ = 308$ | 1.36 min (method C) |

Example 82

5-methyl-6-(2-phenyl-benzoxazol-6-yl)-4,5-dihydro-2H-pyridazin-3-one

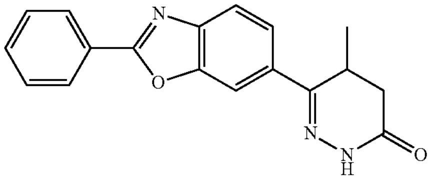

(a) 6-(2-chloro-propionyl)-3H-benzoxazol-2-one 81.1 g (600 mmol) 2-benzoxazolinone are dissolved at 80° C. in 720 g polyphosphoric acid. Then 66.1 ml (720 mmol) 2-chloropropionic acid are added dropwise and the mixture is heated for 3 h to 125° C., then the reaction mixture is poured onto ice water, the precipitated product is suction filtered, washed with water and dried at 98° C. in the circulating air dryer.

Yield: 120 g (79.8%)

$C_{10}H_8ClNO_3$ (225.63)

Mass spectrum: $(M-H)^-=224$ $(M+NH_4)^+=243$

(b) 3-benzyl-6-(2-chloro-propionyl)-3H-benzoxazol-2-one 120.5 g (401 mmol) 6-(2-chloro-propionyl)-3H-benzoxazol-2-one, 49.4 ml (416 mmol) benzylbromide and 57.5 g (416 mmol) potassium carbonate added to 700 ml acetone are stirred overnight at RT. Then the solv. is completely removed i. V. and the residue is extracted with water and DCM. The org. phase is separated off, dried on magnesium sulphate and the solv. is eliminated by rotary evaporation i.V. The residue obtained is purified through silica gel (eluant: DCM).

Yield: 77.0 g (60.9%)

$C_{17}H_{14}ClNO_3$ (315.75)

Mass spectrum: $(M+H)^+=316$

(c) diethyl 2-[2-(3-benzyl-2-oxo-2,3-dihydro-benzoxazol-6-yl)-1-methyl-2-oxo-ethyl]-malonate 30.0 g (267.6 mmol) potassium-tert.-butoxide are suspended in 192 ml DMSO and combined with 40.6 ml (267.6 mmol) malonic acid ester with stirring, then 76.8 g (243.2 mmol) 3-benzyl-6-(2-chloro-propionyl)-3H-benzoxazol-2-one are added while cooling with an ice bath in such a way that the temperature does not rise above 40° C. The mixture is stirred for another 1 h, then combined with ice water and neutralised with 15 ml glacial acetic acid. The reaction mixture is extracted with DCM, then the org. phase is again washed with water, dried and the solv. is eliminated i.V. The residue is separated on silica gel (eluant: DCM).

Yield: 105 g (98.2%)

$C_{24}H_{25}NO_7$ (439.46)

Mass spectrum: $(M+H)^+$=440

(d) 2-[2-(4-benzylamino-3-hydroxy-phenyl)-1-methyl-2-oxo-ethyl]-malonic acid 5 g (11.4 mmol) diethyl 2-[2-(3-benzyl-2-oxo-2,3-dihydro-benzoxazol-6-yl)-1-methyl-2-oxo-ethyl]-malonate are combined with 50 ml of ethanol, then 28 ml 1N sodium hydroxide solution are added and the mixture is stirred overnight at RT. The next day another 28 ml of 1N sodium hydroxide solution are added and the mixture is refluxed for 6 h. After cooling to RT 50 ml 1N hydrochloric acid are added and the mixture is extracted with DCM. The phases are separated using a phase transfer cartridge. The filtrate is evaporated down i. V.

Yield: 3.3 g (81.2%)

$C_{19}H_{19}NO_6$ (357.36)

Mass spectrum: $(M+H)^+$=358

(e) 4-(4-benzylamino-3-hydroxy-phenyl)-3-methyl-4-oxo-butyric acid 78.9 g (220.8 mmol) 2-[2-(4-benzylamino-3-hydroxy-phenyl)-1-methyl-2-oxo-ethyl]-malonic acid are combined with 200 ml diethyleneglycol-dimethylether and stirred for 3 h at 140° C. The mixture is combined with water and diisopropylether, then it is adjusted with 6N hydrochloric acid to pH=2 and extracted with DCM. The org. phase is separated off and dried on magnesium sulphate, then the solv. is eliminated by rotary evaporation i.V., the residue is stirred with diisopropylether and filtered off.

Yield: 78.9 g (79.1%)

$C_{18}H_{19}NO_4$ (313.35)

Mass spectrum: $(M+H)^+$=314

(f) 6-(4-benzylamino-3-hydroxy-phenyl)-5-methyl-4,5-dihydro-2H-pyridazin-3-one

While cooling with the ice bath 69.9 ml (1396 mmol) hydrazine hydrate are added dropwise to 220 ml glacial acetic acid, then 54.7 g (175 mmol) 4-(4-benzylamino-3-hydroxy-phenyl)-3-methyl-4-oxo-butyric acid are added and the mixture is stirred for 1.5 h at 110° C. Then the mixture is cooled somewhat and poured onto ice water, the precipitated product is suction filtered, washed first with copious amounts of water, then with a little acetone and then dried in the vacuum dryer.

Yield: 43 g (79.6%)

$C_{18}H_{19}N_3O_2$ (309.36)

Mass spectrum: $(M+H)^+$=310

(g) 6-(4-amino-3-hydroxy-phenyl)-5-methyl-4,5-dihydro-2H-pyridazin-3-one 43.0 g (139 mmol) 6-(4-benzylamino-3-hydroxy-phenyl)-5-methyl-4,5-dihydro-2H-pyridazin-3-one, 2.2 g of 10% palladium/charcoal and 400 ml of methanol are hydrogenated together for 24 h at RT and 3.45 bar of hydrogen pressure. The catalyst is filtered off and the filtrate is concentrated by rotary evaporation i. V., the residue is triturated with ethyl acetate, suction filtered and then dried at 50° C. in the vacuum dryer.

Yield: 11.5 g (37.7%)

$C_{11}H_{13}N_3O_2$ (219.24)

Mass spectrum: $(M+H)^+$=220

(h) 5-methyl-6-(2-phenyl-benzoxazol-6-yl)-4,5-dihydro-2H-pyridazin-3-one 219 mg (1 mmol) 6-(4-amino-3-hydroxy-phenyl)-5-methyl-4,5-dihydro-2H-pyridazin-3-one, 122 mg (1 mmol) benzoic acid, 1.7 g (3 mmol) polymer-bound triphenylphosphine, 289 mg (2 mmol) trichloroacetonitrile and 7.5 ml acetonitrile are placed in a microwave vial and heated to 120° C. for 15 min at 200 W. The resin is filtered off and washed with methanol as well as acetonitrile. The solv. is eliminated by rotary evaporation i.V. and the residue is purified by RP-HPLC.

Yield: 11.0 mg (3.6%)

$R_t$-time: 2.77 min (method B)

$C_{18}H_{15}N_3O_2$ (305.33)

Mass spectrum: $(M+H)^+$=306

The following compounds may be prepared analogously:

| Ex. | Structural formula | Yield | Mass peak(s) | HPLC |
|---|---|---|---|---|
| 83 | 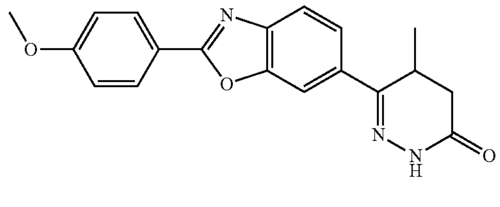 [SMILES: COc1ccc(-c2nc3ccc(C4=NNC(=O)CC4C)cc3o2)cc1] 6-[2-(4-methoxy-phenyl)-benzoxazol-6-yl]-5-methyl-4,5-dihydro-2H-pyridazin-3-one; | 40.6% | $(M + H)^+ = 336$ | 3.00 min (method B) |
| 84 | 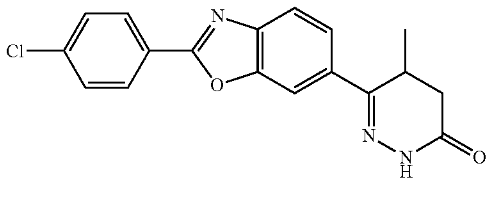 [SMILES: CC1CC(=O)NN=C1c1ccc2nc(-c3ccc(Cl)cc3)oc2c1] 6-[2-(4-chloro-phenyl)-benzoxazol-6-yl]-5-methyl-4,5-dihydro-2H-pyridazin-3-one; | 11.2% | $(M + H)^+ = 340$ | 3.22 min (method B) |

-continued

| Ex. | Structural formula | Yield | Mass peak(s) | HPLC |
|---|---|---|---|---|
| 85 | 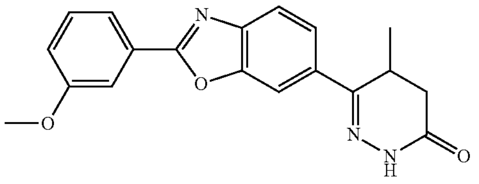 [SMILES: COc1cccc(-c2nc3ccc(C4=NNC(=O)CC4C)cc3o2)c1] 6-[2-(3-methoxy-phenyl)-benzoxazol-6-yl]-5-methyl-4,5-dihydro-2H-pyridazin-3-one; | 5.7% | $(M + H)^+ = 336$ | 3.00 min (method B) |
| 86 | 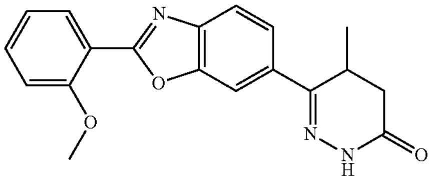 [SMILES: COc1ccccc1-c1nc2ccc(C3=NNC(=O)CC3C)cc2o1] 6-[2-(2-methoxy-phenyl)-benzoxazol-6-yl]-5-methyl-4,5-dihydro-2H-pyridazin-3-one; | 3.5% | $(M + H)^+ = 336$ | 2.76 min (method B)) |
| 87 | 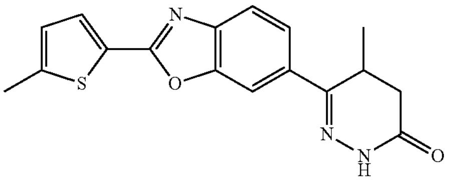 [SMILES: Cc1ccc(-c2nc3ccc(C4=NNC(=O)CC4C)cc3o2)s1] 5-methyl-6-[2-(5-methyl-thiophen-2-yl)-benzoxazol-6-yl]-4,5-dihydro-2H-pyridazin-3-one; | 2.0% | $(M + H)^+ = 326$ | 3.04 min (method B) |
| 88 | 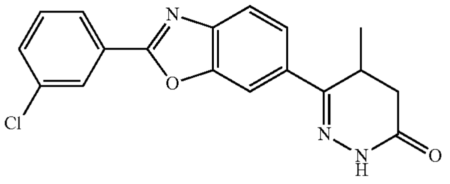 [SMILES: CC1CC(=O)NN=C1c1ccc2nc(-c3cccc(Cl)c3)oc2c1] 6-[2-(3-chloro-phenyl)-benzoxazol-6-yl]-5-methyl-4,5-dihydro-2H-pyridazin-3-one; | 29.4% | $(M + H)^+ = 340$ | 3.25 min (method B) |
| 89 | 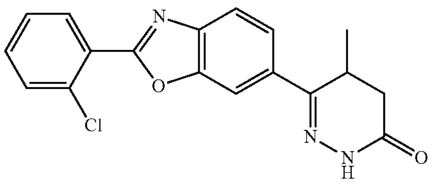 [SMILES: CC1CC(=O)NN=C1c1ccc2nc(-c3ccccc3Cl)oc2c1] 6-[2-(2-chloro-phenyl)-benzoxazol-6-yl]-5-methyl-4,5-dihydro-2H-pyridazin-3-one; | 11.8% | $(M + H)^+ = 340$ | 3.05 min (method B) |
| 90 | 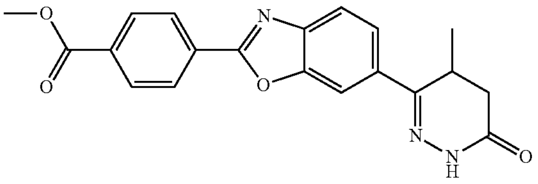 [SMILES: COC(=O)c1ccc(-c2nc3ccc(C4=NNC(=O)CC4C)cc3o2)cc1] methyl 4-[6-(4-methyl-6-oxo-1,4,5,6-tetrahydro-pyridazin-3-yl)-benzoxazol-2-yl]-benzoate; | 4.8% | $(M + H)^+ = 364$ | 3.48 min (method B) |

Example 91

5-ethyl-6-[2-(2-fluoro-4-methoxy-phenyl)-benzoxazol-6-yl]-4,5-dihydro-2H-pyridazin-3-one

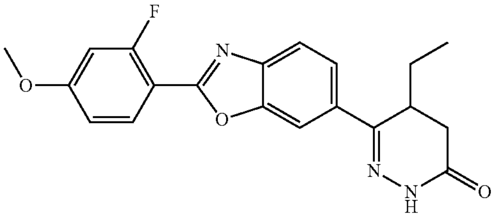 [SMILES: CCC1CC(=O)NN=C1c1ccc2nc(-c3ccc(OC)cc3F)oc2c1]

(a) 6-(4-amino-3-hydroxy-phenyl)-5-ethyl-4,5-dihydro-2H-pyridazin-3-one

The preparation up to this point is carried out analogously to Example 82 Step a-g from 2-benzoxazolinone and 2-chlorobutyric acid to obtain 6-(4-amino-3-hydroxy-phenyl)-5-ethyl-4,5-dihydro-2H-pyridazin-3-one.

(b) 5-ethyl-6-[2-(2-fluoro-4-methoxy-phenyl)-benzoxazol-6-yl]-4,5-dihydro-2H-pyridazin-3-one 200 mg (857 μmol) 6-(4-amino-3-hydroxy-phenyl)-5-ethyl-4,5-dihydro-2H-pyridazin-3-one are refluxed together with 170 mg (901 μmol) 2-fluoro-4-methoxybenzoyl chloride, 70 mg (885 μmol) pyridine, 160 mg (841 μmol) para-toluenesulphonic acid monohydrate and 5 ml xylene for 4 h. The reaction mixture is evaporated down completely i.V. and the residue is crystallised from acetonitrile.

Yield: 17.0 mg (5.4%)

$R_t$-time: 1.35 min (method C)

$C_{20}H_{18}FN_3O_3$ (367.37)

Mass spectrum: $(M+H)^+$=368

The following compounds may be prepared analogously:

| Ex. | Structural formula | Yield | Mass peak(s) | HPLC |
|---|---|---|---|---|
| 92 | 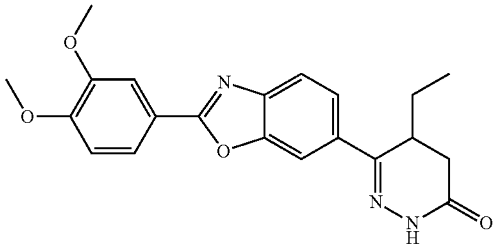 [SMILES: CCC1CC(=O)NN=C1c1ccc2nc(-c3ccc(OC)c(OC)c3)oc2c1] 6-[2-(3,4-dimethoxy-phenyl)-benzoxazol-6-yl]-5-ethyl-4,5-dihydro-2H-pyridazin-3-one; | 24.3% | $(M + H)^+$ = 380 | 1.21 min (method C) |
| 93 | 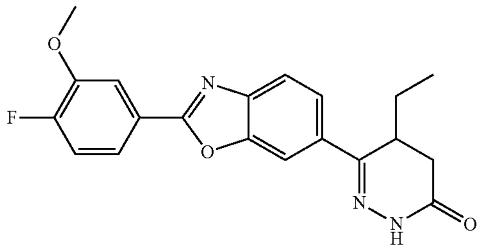 [SMILES: CCC1CC(=O)NN=C1c1ccc2nc(-c3ccc(F)c(OC)c3)oc2c1] 5-ethyl-6-[2-(4-fluoro-3-methoxy-phenyl)-benzoxazol-6-yl]-4,5-dihydro-2H-pyridazin-3-one; | 18.4% | $(M + H)^+$ = 368 | 1.45 min (method C) |
| 94 | 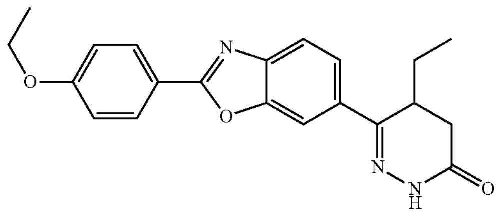 6-[2-(4-ethoxy-phenyl)-benzoxazol-6-yl]-5-ethyl-4,5-dihydro-2H-pyridazin-3-one; | 5.9% | $(M + H)^+$ = 380 | 1.48 min (method C) |

-continued

| Ex. | Structural formula | Yield | Mass peak(s) | HPLC |
|---|---|---|---|---|
| 95 | 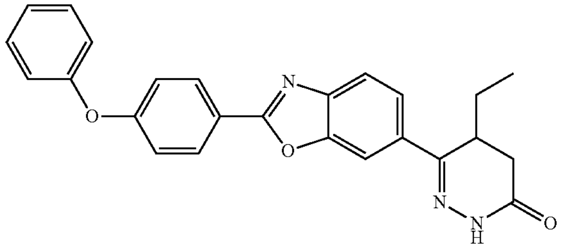 [SMILES: CCC1CC(=O)NN=C1c1ccc2nc(-c3ccc(Oc4ccccc4)cc3)oc2c1] 5-ethyl-6-[2-(4-phenoxy-phenyl)-benzoxazol-6-yl]-4,5-dihydro-2H-pyridazin-3-one; | 34.9% | $(M + H)^+ = 412$ | 1.48 min (method C) |
| 96 | 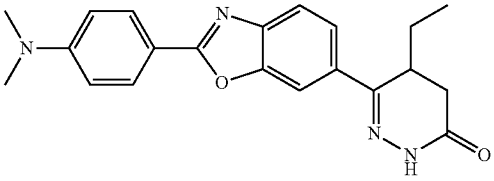 [SMILES: CCC1CC(=O)NN=C1c1ccc2nc(-c3ccc(N(C)C)cc3)oc2c1] 6-[2-(4-dimethylamino-phenyl)-benzoxazol-6-yl]-5-ethyl-4,5-dihydro-2H-pyridazin-3-one; | 14.8% | $(M + H)^+ = 363$ | 1.45 min (method C) |
| 97 | 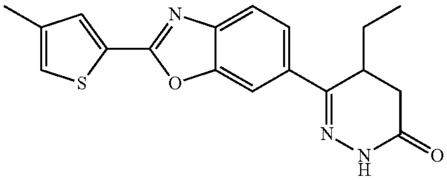 [SMILES: CCC1CC(=O)NN=C1c1ccc2nc(-c3cc(C)cs3)oc2c1] 5-ethyl-6-[2-(4-methyl-thiophen-2-yl)-benzoxazol-6-yl]-4,5-dihydro-2H-pyridazin-3-one; | 16.2% | $(M + H)^+ = 340$ | 1.43 min (method C) |
| 98 | 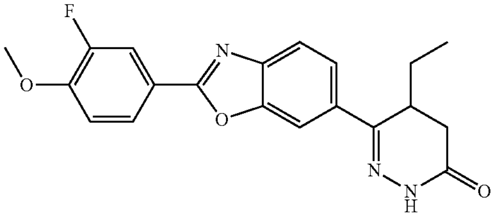 [SMILES: CCC1CC(=O)NN=C1c1ccc2nc(-c3ccc(OC)c(F)c3)oc2c1] 5-ethyl-6-[2-(3-fluoro-4-methoxy-phenyl)-benzoxazol-6-yl]-4,5-dihydro-2H-pyridazin-3-one; | 15.9% | $(M + H)^+ = 368$ | 1.44 min (method C) |
| 99 | 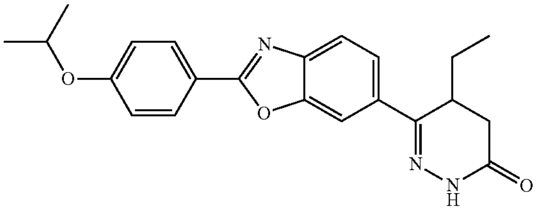 [SMILES: CCC1CC(=O)NN=C1c1ccc2nc(-c3ccc(OC(C)C)cc3)oc2c1] 5-ethyl-6-[2-(4-isopropoxy-phenyl)-benzoxazol-6-yl]-4,5-dihydro-2H-pyridazin-3-one; | 43.3% | $(M + H)^+ = 378$ | 1.53 min (method C) |

-continued

| Ex. | Structural formula | Yield | Mass peak(s) | HPLC |
|---|---|---|---|---|
| 100 | 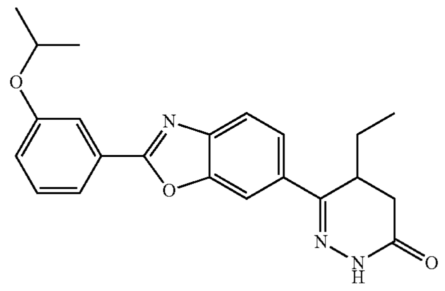 [SMILES: CCC1CC(=O)NN=C1c1ccc2nc(-c3cccc(OC(C)C)c3)oc2c1]<br>5-ethyl-6-[2-(3-isopropoxy-phenyl)-benzoxazol-6-yl]-4,5-dihydro-2H-pyridazin-3-one; | 52.2% | $(M + H)^+ = 378$ | 1.54 min (method C) |
| 101 | 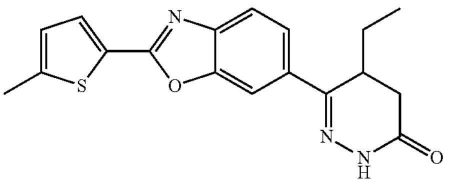 [SMILES: CCC1CC(=O)NN=C1c1ccc2nc(-c3ccc(C)s3)oc2c1]<br>5-ethyl-6-[2-(5-methyl-thiophen-2-yl)-benzoxazol-6-yl]-4,5-dihydro-2H-pyridazin-3-one; | 36.4% | $(M + H)^+ = 340$ | 1.43 min (method C) |
| 102 | 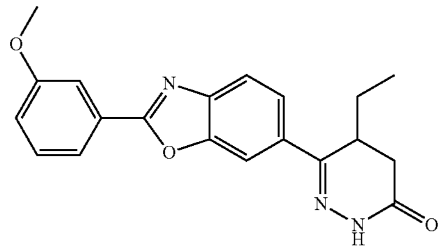 [SMILES: CCC1CC(=O)NN=C1c1ccc2nc(-c3cccc(OC)c3)oc2c1]<br>5-ethyl-6-[2-(3-methoxy-phenyl)-benzoxazol-6-yl]-4,5-dihydro-2H-pyridazin-3-one; | 48.7% | $(M + H)^+ = 350$ | 1.44 min (method C) |
| 103 | 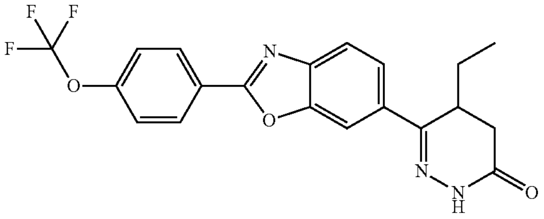 [SMILES: CCC1CC(=O)NN=C1c1ccc2nc(-c3ccc(OC(F)(F)F)cc3)oc2c1]<br>5-ethyl-6-[2-(4-trifluoromethoxy-phenyl)-benzoxazol-6-yl]-4,5-dihydro-2H-pyridazin-3-one; | 16.2% | $(M + H)^+ = 404$ | 1.55 min (method C) |
| 104 | 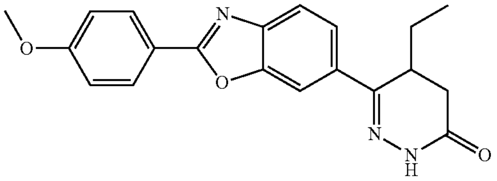 [SMILES: CCC1CC(=O)NN=C1c1ccc2nc(-c3ccc(OC)cc3)oc2c1]<br>5-ethyl-6-[2-(4-methoxy-phenyl)-benzoxazol-6-yl]-4,5-dihydro-2H-pyridazin-3-one; | 41.7% | $(M + H)^+ = 350$ | 1.43 min (method C) |

-continued

| Ex. | Structural formula | Yield | Mass peak(s) | HPLC |
|---|---|---|---|---|
| 105 | 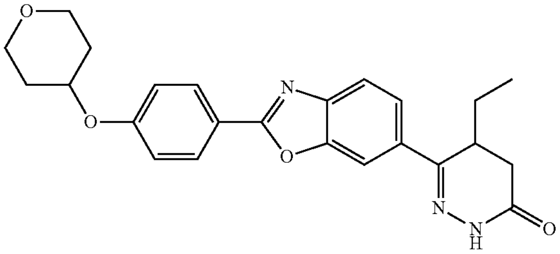 [SMILES: CCC1CC(=O)NN=C1c1ccc2nc(-c3ccc(OC4CCOCC4)cc3)oc2c1]<br>5-ethyl-6-{2-[4-(tetrahydro-pyran-4-yloxy)-phenyl]-benzoxazol-6-yl}-4,5-dihydro-2H-pyridazin-3-one; | 25.6% | $(M + H)^+ = 420$ | 1.43 min (method C) |

The following stereoisomers are isolated by separation using chiral HPLC by method G:

Mobile phase: A: 75% CO2; B: 25% MeOH+0.2% diethylamine (DEA)

| time in min (retention time) | flow rate in ml/min | eluted peak |
|---|---|---|
| 3.69 | 4 | 1 |
| 4.70 | 4 | 2 |

Mobile phase: A: 60% CO2; B: 40% EtOH+0.2% diethylamine (DEA)

| time in min (retention time) | flow rate in ml/min | eluted peak |
|---|---|---|
| 1.68 | 4 | 1 |
| 2.10 | 4 | 2 |

| Ex. | Structural formula | Yield | Mass peak(s) | HPLC |
|---|---|---|---|---|
| 190 | 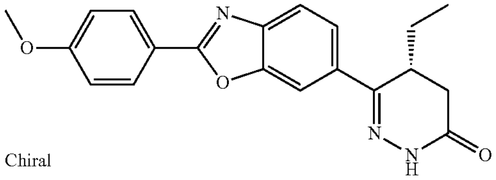 [SMILES: CC[C@@H]1CC(=O)NN=C1c1ccc2nc(-c3ccc(OC)cc3)oc2c1]<br>Chiral<br>(R)-5-ethyl-6-[2-(4-methoxy-phenyl)benzoxazol-6-yl]-4,5-dihydro-2H-pyridazin-3-one; | 29.2% | $(M + H)^+ = 350$ | 1.42 min (method C) |

Mobile phase: A: 70% CO2; B: 30% MeOH+0.2% diethylamine (DEA)

| time in min (retention time) | flow rate in ml/min | eluted peak |
|---|---|---|
| 4.05 | 4 | 1 |
| 5.16 | 4 | 2 |

| Ex. | Structural formula | Yield | Mass peak(s) | HPLC |
|---|---|---|---|---|
| 191 | 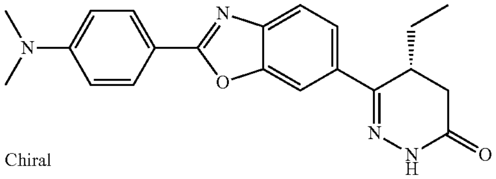 [SMILES: CC[C@@H]1CC(=O)NN=C1c1ccc2nc(-c3ccc(N(C)C)cc3)oc2c1]<br>Chiral<br>(R)-6-[2-(4-dimethylamino-phenyl)-benzoxazol-6-yl]-5-ethyl-4,5-dihydro-2H-pyridazin-3-one; | 14.6% | $(M + H)^+ = 363$ | 1.45 min (method C) |

| Ex. | Structural formula | Yield | Mass peak(s) | HPLC |
| --- | --- | --- | --- | --- |
| 192 | 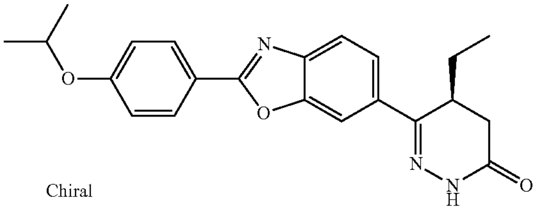 [SMILES: CC[C@H]1CC(=O)NN=C1c1ccc2nc(-c3ccc(OC(C)C)cc3)oc2c1] Chiral | 23.5% | $(M+H)^+$ = 378 | 1.53 min (method C) |
| | (S)-5-ethyl-6-[2-(4-isopropoxy-phenyl)-benzoxazol-6-yl]-4,5-dihydro-2H-pyridazin-3-one; | | | |
| 193 | 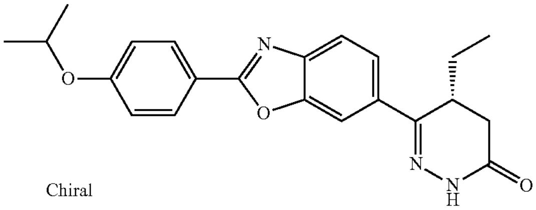 [SMILES: CC[C@@H]1CC(=O)NN=C1c1ccc2nc(-c3ccc(OC(C)C)cc3)oc2c1] Chiral | 17.6% | $(M+H)^+$ = 378 | 1.53 min (method C) |
| | (R)-5-ethyl-6-[2-(4-isopropoxy-phenyl)-benzoxazol-6-yl]-4,5-dihydro-2H-pyridazin-3-one; | | | |

The following stereoisomers may be isolated by separation using chiral HPLC according to method H:

Mobile phase: A: 60% CO2; B: 40% EtOH+0.2% diethylamine (DEA)

| time in min (retention time) | flow rate in ml/min | eluted peak |
| --- | --- | --- |
| 1.68 | 4 | 1 |
| 2.10 | 4 | 2 |

| Ex. | Structural formula | Yield | Mass peak(s) | HPLC |
| --- | --- | --- | --- | --- |
| 194 | 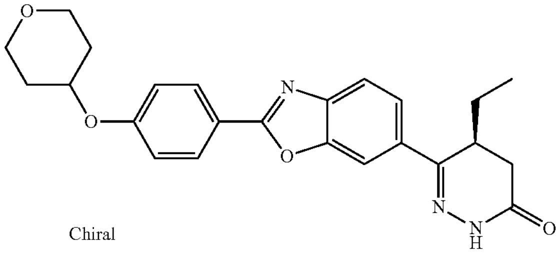 [SMILES: CC[C@H]1CC(=O)NN=C1c1ccc2nc(-c3ccc(OC4CCOCC4)cc3)oc2c1] Chiral | 13.8% | $(M+H)^+$ = 420 | 1.43 min (method C) |
| | (S)-5-ethyl-6-{2-[4-(tetrahydro-pyran-4-yloxy)-phenyl]-benzoxazol-6-yl}-4,5-dihydro-2H-pyridazin-3-one; | | | |
| 195 | 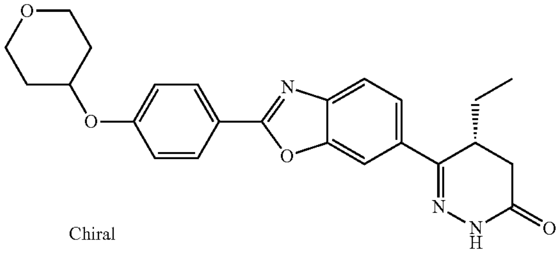 [SMILES: CC[C@@H]1CC(=O)NN=C1c1ccc2nc(-c3ccc(OC4CCOCC4)cc3)oc2c1] Chiral | 8.0% | $(M+H)^+$ = 420 | 1.43 min (method C) |
| | (R)-5-ethyl-6-{2-[4-(tetrahydro-pyran-4-yloxy)-phenyl]-benzoxazol-6-yl}-4,5-dihydro-2H-pyridazin-3-one; | | | |

Example 175

5-ethyl-6-[2-(4-isopropyl-phenyl)-benzoxazol-6-yl]-4,5-dihydro-2H-pyridazin-3-one

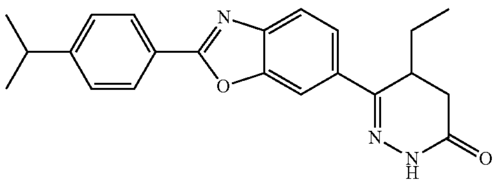

200 mg (857 μmol) 6-(4-amino-3-hydroxy-phenyl)-5-ethyl-4,5-dihydro-2H-pyridazin-3-one are placed in 5 ml dioxane. 175 mg (958 μmol) 4-isopropyl-benzoyl chloride are added and the mixture is stirred for 15 min at 200° C. in the microwave. The solvent is eliminated by rotary evaporation in vacuo and the residue is separated through silica gel (eluant cyclohexane/EA).

Yield: 145.0 mg (46.8%)

$R_t$-time: 1.58 min (method C)

$C_{22}H_{23}N_3O_2$ (361.44)

Mass spectrum: $(M+H)^+=362$

The following compounds may be prepared analogously:

| Ex. | Structural formula | Yield | Mass peak(s) | HPLC |
|---|---|---|---|---|
| 176 | 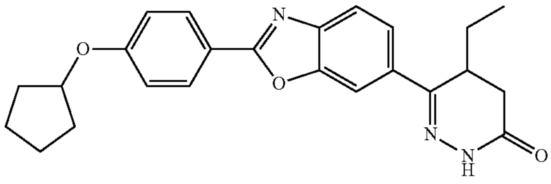 [SMILES: CCC1CC(=O)NN=C1c1ccc2nc(-c3ccc(OC4CCCC4)cc3)oc2c1] 6-[2-(4-cyclopentyloxy-phenyl)-benzoxazol-6-yl]-5-ethyl-4,5-dihydro-2H-pyridazin-3-one; | 47.2% | $(M + H)^+ = 404$ | 1.60 min (method C) |
| 177 | 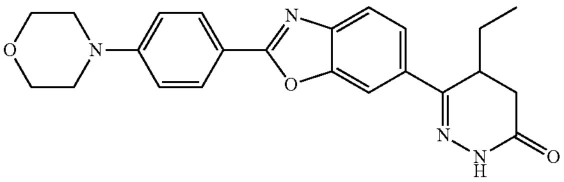 [SMILES: CCC1CC(=O)NN=C1c1ccc2nc(-c3ccc(N4CCOCC4)cc3)oc2c1] 5-ethyl-6-[2-(4-morpholin-4-yl-phenyl)-benzoxazol-6-yl]-4,5-dihydro-2H-pyridazin-3-one; | 6.7% | $(M + H)^+ = 405$ | 1.37 min (method C) |
| 178 | 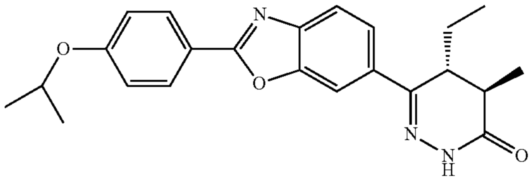 [SMILES: CC[C@H]1C(c2ccc3nc(-c4ccc(OC(C)C)cc4)oc3c2)=NNC(=O)[C@@H]1C] trans-5-ethyl-6-[2-(4-isopropoxy-phenyl)-benzoxazol-6-yl]-4-methyl-4,5-dihydro-2H-pyridazin-3-one; | 18.6% | $(M + H)^+ = 392$ | 1.55 min (method C) |
| 179 | 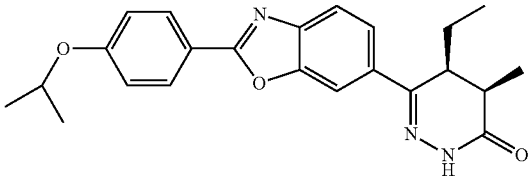 [SMILES: CC[C@@H]1C(c2ccc3nc(-c4ccc(OC(C)C)cc4)oc3c2)=NNC(=O)[C@@H]1C] cis-5-ethyl-6-[2-(4-isopropoxy-phenyl)-benzoxazol-6-yl]-4-methyl-4,5-dihydro-2H-pyridazin-3-one; | 4.0% | $(M + H)^+ = 392$ | 1.57 min (method C) |
| 180 | 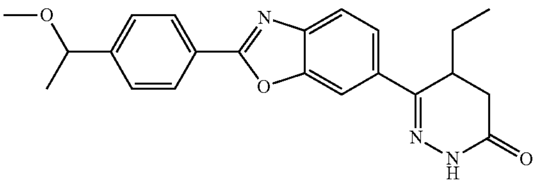 [SMILES: CCC1CC(=O)NN=C1c1ccc2nc(-c3ccc(C(C)OC)cc3)oc2c1] 5-ethyl-6-{2-[4-(1-methoxy-ethyl)-phenyl]-benzoxazol-6-yl}-4,5-dihydro-2H-pyridazin-3-one; | 63.5% | $(M + H)^+ = 378$ | 1.43 min (method C) |

-continued

| Ex. | Structural formula | Yield | Mass peak(s) | HPLC |
|---|---|---|---|---|
| 181 | 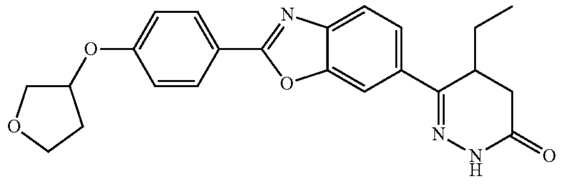 [SMILES: CCC1CC(=O)NN=C1c1ccc2nc(-c3ccc(OC4CCOC4)cc3)oc2c1] 5-ethyl-6-{2-[4-(tetrahydro-furan-3-yloxy)-phenyl]-benzoxazol-6-yl}-4,5-dihydro-2H-pyridazin-3-one; | 43.7% | $(M + H)^+ = 406$ | 1.38 min (method C) |
| 182 | 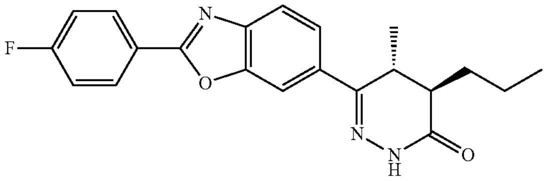 [SMILES: CCC[C@H]1C(=O)NN=C(c2ccc3nc(-c4ccc(F)cc4)oc3c2)[C@@H]1C] trans-6-[2-(4-fluoro-phenyl)-benzoxazol-6-yl]-5-methyl-4-propyl-4,5-dihydro-2H-pyridazin-3-one; | 13.0% | $(M + H)^+ = 366$ | 1.53 min (method C) |
| 183 | 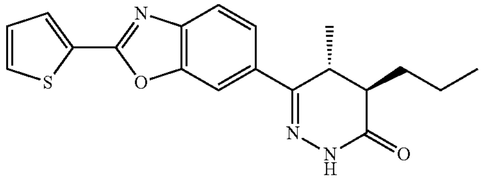 [SMILES: CCC[C@H]1C(=O)NN=C(c2ccc3nc(-c4cccs4)oc3c2)[C@@H]1C] trans-5-methyl-4-propyl-6-(2-thiophen-2-yl-benzoxazol-6-yl)-4,5-dihydro-2H-pyridazin-3-one; | 9.2% | $(M + H)^+ = 354$ | 1.46 min (method C) |
| 184 | 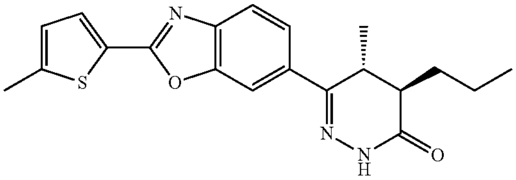 [SMILES: CCC[C@H]1C(=O)NN=C(c2ccc3nc(-c4ccc(C)s4)oc3c2)[C@@H]1C] trans-5-methyl-6-[2-(5-methyl-thiophen-2-yl)-benzoxazol-6-yl]-4-propyl-4,5-dihydro-2H-pyridazin-3-one; | 8.9% | $(M + H)^+ = 368$ | 1.52 min (method C) |
| 185 | 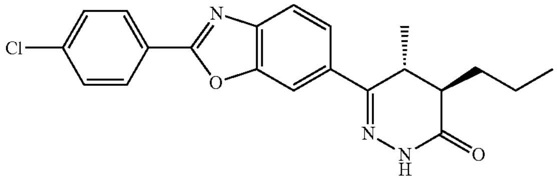 [SMILES: CCC[C@H]1C(=O)NN=C(c2ccc3nc(-c4ccc(Cl)cc4)oc3c2)[C@@H]1C] trans-6-[2-(4-chloro-phenyl)-benzoxazol-6-yl]-5-methyl-4-propyl-4,5-dihydro-2H-pyridazin-3-one; | 20.5% | $(M + H)^+ = 382$ | 1.62 min (method C) |
| 186 | 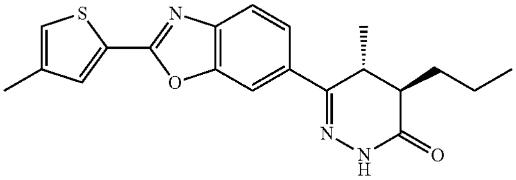 [SMILES: CCC[C@H]1C(=O)NN=C(c2ccc3nc(-c4cc(C)cs4)oc3c2)[C@@H]1C] trans-5-methyl-6-[2-(4-methyl-thiophen-2-yl)-benzoxazol-6-yl]-4-propyl-4,5-dihydro-2H-pyridazin-3-one; | 10.0% | $(M + H)^+ = 368$ | 1.55 min (method C) |

-continued

| Ex. | Structural formula | Yield | Mass peak(s) | HPLC |
|---|---|---|---|---|
| 187 | 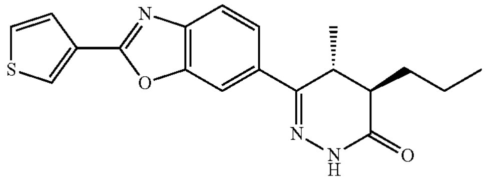 [SMILES: CCC[C@H]1C(=O)NN=C(c2ccc3nc(-c4ccsc4)oc3c2)[C@@H]1C]<br>trans-5-methyl-4-propyl-6-(2-thiophen-3-yl-benzoxazol-6-yl)-4,5-dihydro-2H-pyridazin-3-one; | 23.7% | $(M + H)^+ = 354$ | 1.47 min (method C) |
| 188 | 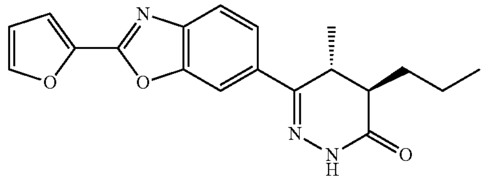<br>trans-6-(2-uran-2-yl-benzoxazol-6-yl)-5-methyl-4-propyl-4,5-dihydro-2H-pyridazin-3-one; | 18.6% | $(M + H)^+ = 338$ | 1.37 min (method C) |
| 189 | 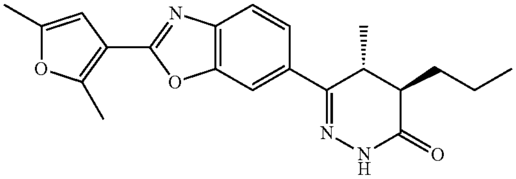 [SMILES: CCC[C@H]1C(=O)NN=C(c2ccc3nc(-c4cc(C)oc4C)oc3c2)[C@@H]1C]<br>trans-6-[2-(2,5-dimethyl-furan-3-yl)-benzoxazol-6-yl]-5-methyl-4-propyl-4,5-dihydro-2H-pyridazin-3-one; | 14.3% | $(M + H)^+ = 366$ | 1.57 min (method C) |

The following stereoisomers may be isolated by separation using chiral HPLC according to method J:

Mobile phase: A: 75% CO2; B: 25% isopropanol+0.2% diethylamine (DEA)

| time in min (retention time) | flow rate in ml/min | eluted peak |
|---|---|---|
| 20.44 | 10 | 1 |
| 24.23 | 10 | 2 |

| Ex. | Structural formula | Yield | Mass peak(s) | HPLC |
|---|---|---|---|---|
| 208 | Chiral<br>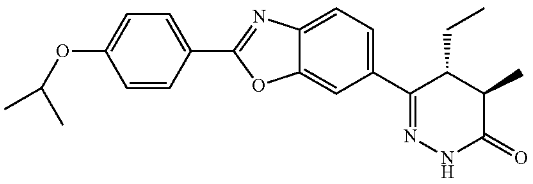<br>(4S,5S)-5-ethyl-6-[2-(4-isopropoxy-phenyl)-benzoxazol-6-yl]-4-methyl-4,5-dihydro 2H-pyridazin-3-one; | 37.9% | $(M + H)^+ = 392$ | 1.54 min (method C) |

Example 252

Trans-5-methyl-6-[2-(1-methyl-1H-pyrrol-2-yl)-benzoxazol-6-yl]-4-propyl-4,5-dihydro-2H-pyridazin-3-one

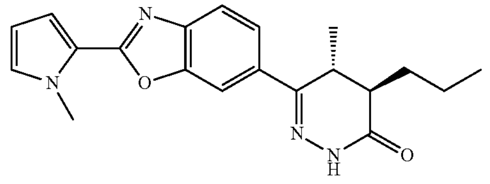 [SMILES: CCC[C@H]1C(=O)NN=C(c2ccc3nc(-c4cccn4C)oc3c2)[C@@H]1C]

(a) 1-methyl-1H-pyrrole-2-carboxylic acid[2-hydroxy-4-(4-methyl-6-oxo-5-propyl-1,4,5,6-tetrahydro-pyridazin-3-yl)phenyl]-amide 240 mg (1.92 mmol) 1-methyl-1H-pyrrol-2-carboxylic acid is placed in 20 mL DCM. 760 mg (2.00 mmol) HATU, 1.50 mL (8.76 mmol) DIPEA and 600 mg (2.30 mmol) 6-(4-amino-3-hydroxy-phenyl)-5-methyl-4-propyl-4,5-dihydro-2H-pyridazin-3-one are added and the mixture is stirred for 3 h at RT. The reaction mixture is extracted successively with 0.5% acetic acid, 10% sodium carbonate solution and saline solution. Then the organic phase is dried and the solv. is eliminated i.V.

Yield: 800.00 mg (94.6%)
$R_t$-time: 1.27/1.34 min (method C)
$C_{20}H_{24}N_4O_3$ (368.43)
Mass spectrum: $(M+H)^+$=

(b) Trans-5-methyl-6-[2-(1-methyl-1H-pyrrol-2-yl)-benzoxazol-6-yl]-4-propyl-4,5-dihydro-2H-pyridazin-3-one 150 mg (407 mmol) 1-methyl-1H-pyrrole-2-carboxylic acid[2-hydroxy-4-(4-methyl-6-oxo-5-propyl-1,4,5,6-tetrahydro-pyridazin-3-yl)-phenyl]-amide are placed in 5 mL dioxane. 300 μL (5.19 mmol) acetic acid and 140 mg (814 μmol) p-toluenesulphonic acid monohydrate are added and the mixture is stirred for 60 min in the microwave at 200° C. The reaction mixture is extracted successively with 10% sodium carbonate solution, 1% acetic acid, 10% sodium carbonate solution and saline solution. Then the solv. of the organic phase is eliminated i.V. and the residue is purified through silica gel. (Cyclohexane/EA) The solv. of the corresponding fractions is eliminated i.V. and the residue is crystallised with diethyl ether/petroleum ether.

Yield: 15.00 mg (10.5%)
$R_t$-time: 1.48 min (method C)
$C_{20}H_{22}N_4O_2$ (350.41)
Mass spectrum: $(M+H)^+$=351

The following compounds may be prepared analogously:

| Ex. | Structural formula | Yield | Mass peak(s) | HPLC |
|---|---|---|---|---|
| 253 | 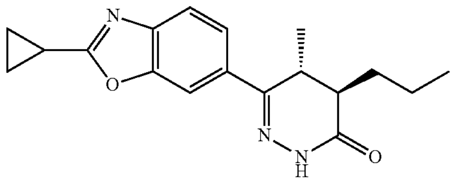 [SMILES: CCC[C@H]1C(=O)NN=C(c2ccc3nc(C4CC4)oc3c2)[C@@H]1C] 6-(2-cyclopropyl-benzoxazol-6-yl)-5-methyl-4-propyl-4,5-dihydro-2H-pyridazin-3-one; | 15.9% | $(M + H)^+ = 312$ | 1.36 min (method C) |
| 254 | 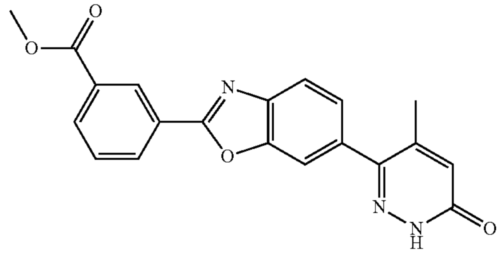 [SMILES: COC(=O)c1cccc(-c2nc3ccc(-c4n[nH]c(=O)cc4C)cc3o2)c1] methyl 3-[6-(4-methyl-6-oxo-1,6-dihydro-pyridazin-3-yl)-benzoxazol-2-yl]-benzoate; | 85.1% | $(M + H)^+ = 362$ | 2.69 min (method B) |

Example 255

4-[6-(4-methyl-6-oxo-1,6-dihydro-pyridazin-3-yl)-benzoxazol-2-yl]-benzoic acid

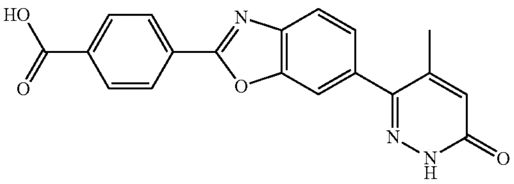 [SMILES: Cc1cc(=O)[nH]nc1-c1ccc2nc(-c3ccc(C(=O)O)cc3)oc2c1]

25 mg (69 μmol) methyl 4-[6-(4-methyl-6-oxo-1,6-dihydro-pyridazin-3-yl)-benzoxazol-2-yl]-benzoate is placed in 4 mL DMSO, 350 μL (1 mmol/mL; 346 μmol) sodium hydroxide solution are added and the mixture is stirred overnight at RT. The reaction mixture is adjusted to pH 4 with 10% citric acid and extracted with H2O and DCM. Then the solv. of the organic phase is eliminated i.V. and the residue is separated by HPLC-MS. (xTerra, ACN/H2O+TFA)

Yield: 10.00 mg (49.9%)

$R_t$-time: 2.32 min (method B)

$C_{19}H_{13}N_3O_4$ (347.32)

Mass spectrum: $(M+H)^+$=348

Example 106

5-methyl-6-(2-thiophen-2-yl-benzoxazol-6-yl)-4,5-dihydro-2H-pyridazin-3-one

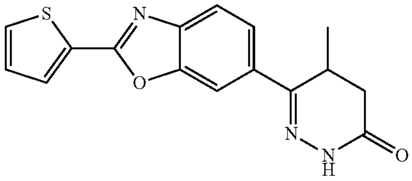

(a) 5-methyl-6-(2-thiophen-2-yl-benzoxazol-6-yl)-4,5-dihydro-2H-pyridazin-3-one 2.6 g (0.02 mol) thiophene-2-carboxylic acid, 3.3 g (0.02 mol) 1,1'carbonyldiimidazole and 50 ml DMF are combined and the mixture is stirred for 30 min at RT, then 4.4 g (0.02 mol) 6-(4-amino-3-hydroxy-phenyl)-5-methyl-4,5-dihydro-2H-pyridazin-3-one are added and the mixture is stirred for 4 h at 60° C. The reaction mixture is diluted with water and acidified with glacial acetic acid, the precipitated solid is filtered off, washed with water and isopropanol and then dried. The solid obtained is heated to 130° C. with 60 g polyphosphoric acid for 30 min, then poured onto ice water and then extracted with chloroform. The org. phase is washed with water, dried on magnesium sulphate and the solv. is eliminated by rotary evaporation i.V. The residue is stirred with acetone/diethyl ether, filtered off and then recrystallised from isopropanol/dioxane.

Yield: 1.0 g (16.1%)

$C_{16}H_{13}N_3O_2S$ (311.37)

melting point: 222° C.

The following compounds may be prepared analogously:

| Ex. | Structural formula | Yield | melting point |
|---|---|---|---|
| 107 | 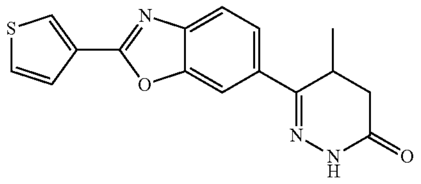 5-methyl-6-(3-thiophen-2-yl-benzoxazol-6-yl)-4,5-dihydro-2H-pyridazin-3-one; | 53.5% | 234° C. |
| 108 | 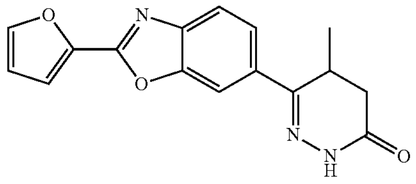 [SMILES: CC1CC(=O)NN=C1c1ccc2nc(-c3cccs3)oc2c1] 5-methyl-6-(2-furan-2-yl-benzoxazol-6-yl)-4,5-dihydro-2H-pyridazin-3-one; | 40.6% | 209° C. |
| 109 | 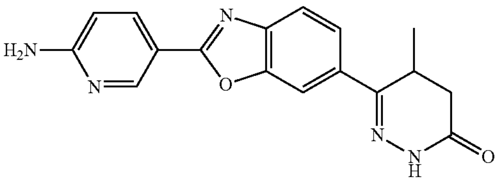 [SMILES: CC1CC(=O)NN=C1c1ccc2nc(-c3ccc(N)nc3)oc2c1] 6-[2-(6-amino-pyridin-3-yl)-benzoxazol-6-yl]-5-methyl-4,5-dihydro-2H- | 8.2% | 293° C. |

-continued

| Ex. | Structural formula | Yield | melting point |
|---|---|---|---|
| | pyridazin-3-one; | | |
| 110 | 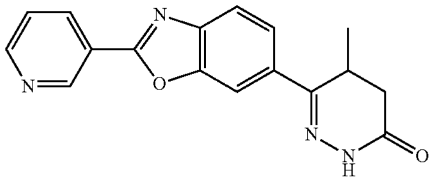 [SMILES: CC1CC(=O)NN=C1c1ccc2nc(-c3cccnc3)oc2c1] 5-methyl-6-(2-pyridin-3-yl-benzoxazol-6-yl)-4,5-dihydro-2H-pyridazin-3-one; | 29.4% | 218° C. |
| 111 | 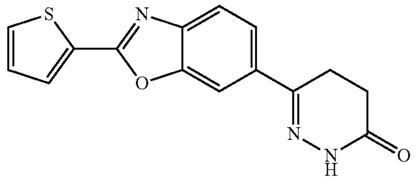 [SMILES: O=C1CCC(c2ccc3nc(-c4cccs4)oc3c2)=NN1] 6-(2-thiophen-2-yl-benzoxazol-6-yl)-4,5-dihydro-2H-pyridazin-3-one; | $(M + H)^+ = 298$ | 1.25 min (method A) |
| 112 | 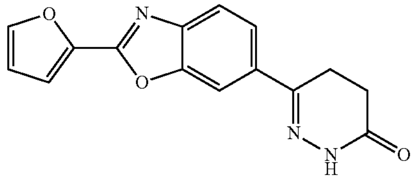 6-(2-furan-2-yl-benzoxazol-6-yl)-4,5-dihydro-2H-pyridazin-3-one; | $(M + H)^+ = 282$ | 1.12 min (method A) |

Example 113

5-methyl-6-(2-thiomorpholin-4-yl-benzoxazol-6-yl)-4,5-dihydro-2H-pyridazin-3-one

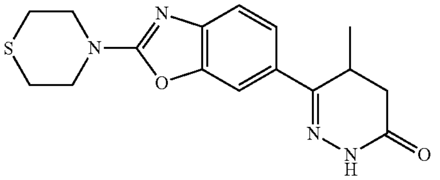 [SMILES: CC1CC(=O)NN=C1c1ccc2nc(N3CCSCC3)oc2c1]

(a) 6-(4-methyl-6-oxo-1,4,5,6-tetrahydro-pyridazin-3-yl)-benzoxazole-2-thiolate as Potassium Salt 22 g (0.1 mol) of 6-(4-amino-3-hydroxy-phenyl)-5-methyl-4,5-dihydro-2H-pyridazin-3-one, 25 g (0.15 mol) potassium-ethylxanthogenate and 300 ml of ethanol are combined and the mixture is refluxed for 4 h. Then the reaction mixture is cooled to 0° C. and the precipitated solid is suction filtered, then it is washed with ethanol and diethyl ether.

Yield: 25.0 g (83.5%)

(b) 5-methyl-6-(2-methylsulphanyl-benzoxazol-6-yl)-4,5-dihydro-2H-pyridazin-3-one 85 g (0.284 mol) 6-(4-methyl-6-oxo-1,4,5,6-tetrahydro-pyridazin-3-yl)-benzoxazol-2-thiolate as potassium salt, 34.3 ml (0.55 mol) methyl iodide and 200 ml DMF are combined and the mixture is stirred for 1 h at 50° C., then the reaction mixture is poured onto ice water. The precipitated solid is suction filtered and washed with water, isopropanol and diethyl ether.

Yield: 65.0 g (83.4%)

melting point: 188° C.

(c) 5-methyl-6-(2-thiomorpholin-4-yl-benzoxazol-6-yl)-4,5-dihydro-2H-pyridazin-3-one A mixture of 4.1 g (0.015 mol) 5-methyl-6-(2-methylsulphanyl-benzoxazol-6-yl)-4,5-dihydro-2H-pyridazin-3-one and 10.3 g (0.1 mol) thiomorpholine is stirred for 6 h at 130° C. Then the excess thiomorpholine is eliminated by rotary evaporation in vacuo, the residue is stirred with water and diisopropylether, the crystals obtained are suction filtered. The crude product is washed with water and isopropanol and then recrystallised from aqueous isopropanol.

Yield: 2.8 g (56.5%)

$C_{16}H_{18}N_4O_2S$ (330.42)

melting point: 218° C.

The following compounds may be prepared analogously:

| Ex. | Structural formula | Yield | melting point |
|---|---|---|---|
| 114 | 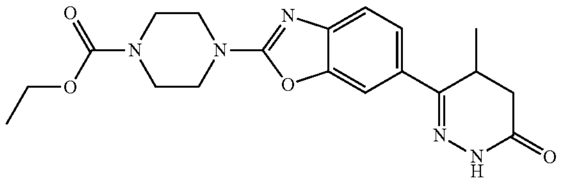 [SMILES: CCOC(=O)N1CCN(c2nc3ccc(C4=NNC(=O)CC4C)cc3o2)CC1] ethyl 4-[6-(4-methyl-6-oxo-1,4,5,6-tetrahydro-pyridazin-3-yl)-benzoxazol-2-yl]-piperazine-1-carboxylate; | 72.7% | 239° C. |
| 115 | 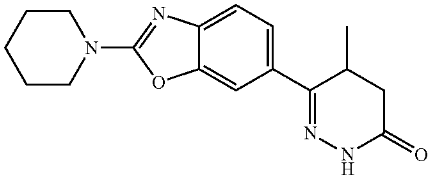 [SMILES: CC1CC(=O)NN=C1c1ccc2nc(N3CCCCC3)oc2c1] 5-methyl-6-(2-piperidin-1-yl-benzoxazol-6-yl)-4,5-dihydro-2H-pyridazin-3-one; | 85.4% | 235° C. |
| 116 | 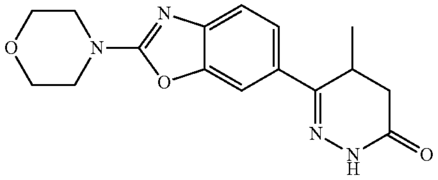 5-methyl-6-(2-morpholine-1-yl-benzoxazol-6-yl)-4,5-dihydro-2H-pyridazin-3-one; | 81.2% | 209° C. |
| 117 | 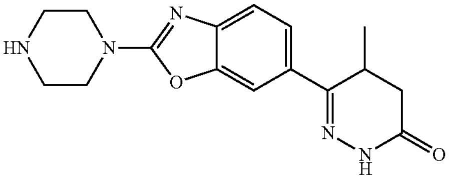 [SMILES: CC1CC(=O)NN=C1c1ccc2nc(N3CCNCC3)oc2c1] 5-methyl-6-(2-piperazin-1-yl-benzoxazol-6-yl)-4,5-dihydro-2H-pyridazin-3-one; | 70.0% | 213° C. |
| 118 | 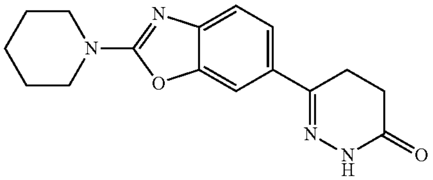 [SMILES: O=C1CCC(c2ccc3nc(N4CCCCC4)oc3c2)=NN1] 6-(2-piperidin-1-yl-benzoxazol-6-yl)-4,5-dihydro-2H-pyridazin-3-one; | $(M + H)^+ = 299$ | 1.10 min (method A) |
| 119 | 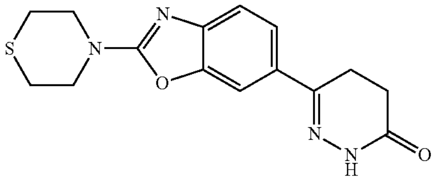 [SMILES: O=C1CCC(c2ccc3nc(N4CCSCC4)oc3c2)=NN1] 6-(2-thiomorpholin-1-yl-benzoxazol-6-yl)-4,5-dihydro-2H-pyridazin-3-one; | $(M + H)^+ = 317$ | 1.11 min (method A) |

Example 120

6-[2-(2,6-dichloro-pyridin-3-yl)-benzoxazol-6-yl]-5-methyl-4,5-dihydro-2H-pyridazin-3-one

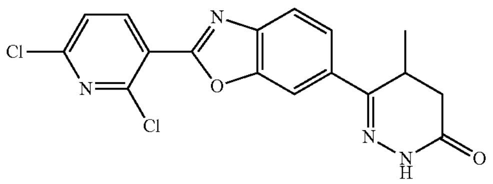 [SMILES: CC1CC(=O)NN=C1c1ccc2nc(-c3ccc(Cl)nc3Cl)oc2c1]

(a) 2,6-dichloro-N-[2-hydroxy-4-(4-methyl-6-oxo-1,4,5,6-tetrahydro-pyridazin-3-yl)-phenyl]-nicotinamide A solution of 8.5 g (0.0405 mol) 2,6-dichloronicotinoyl chloride in 20 ml DMF is slowly added dropwise to a suspension of 8.8 g (0.04 mol) 6-(4-amino-3-hydroxy-phenyl)-5-methyl-4,5-dihydro-2H-pyridazin-3-one, 6.9 g (0.05 mol) potassium carbonate and 50 ml DMF and it is then stirred overnight. The reaction mixture is mixed with water, then the aqueous supernatant is decanted off, the residue is washed with water again, filtered off and then purified through silica gel (eluant: ethylene chloride/ethanol).

Yield: 5.85 g (37.2%)

(b) 6-[2-(2,6-dichloro-pyridin-3-yl)-benzoxazol-6-yl]-5-methyl-4,5-dihydro-2H-pyridazin-3-one 5.8 g (0.015 mol) 2,6-dichloro-N-[2-hydroxy-4-(4-methyl-6-oxo-1,4,5,6-tetrahydro-pyridazin-3-yl)-phenyl]-nicotinamide, 0.6 g para-toluenesulphonic acid and 60 ml glacial acetic acid are refluxed together for 15 h, then 40 ml glacial acetic acid are eliminated in vacuo and the residue is mixed with water. The precipitate formed is filtered off, washed with ethanol and then recrystallised from dioxane/DMF.

Yield: 2.2 g (40%)

$C_{17}H_{12}Cl_2N_4O_2$ (375.23)

melting point: 268° C.

Example 121

6-[2-(2-chloro-6-morpholin-4-yl-pyridin-3-yl)-benzoxazol-6-yl]-5-methyl-4,5-dihydro-2H-pyridazin-3-one

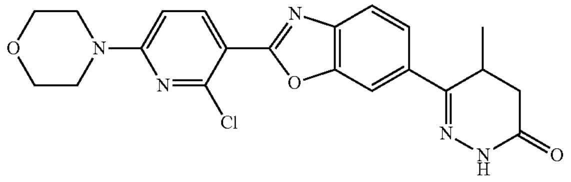 [SMILES: CC1CC(=O)NN=C1c1ccc2nc(-c3ccc(N4CCOCC4)nc3Cl)oc2c1]

(a) 6-[2-(2-chloro-6-morpholin-4-yl-pyridin-3-yl)-benzoxazol-6-yl]-5-methyl-4,5-dihydro-2H-pyridazin-3-one 1.1 g (2.9 mmol) 6-[2-(2,6-dichloro-pyridin-3-yl)-benzoxazol-6-yl]-5-methyl-4,5-dihydro-2H-pyridazin-3-one, 1 ml morpholine and 50 ml of ethanol are refluxed together for 3 h, then the solv. is eliminated by rotary evaporation i.V., the residue is stirred with water and filtered off. The crude product is recrystallised from aqueous isopropanol.

Yield: 0.25 g (20.2%)

$C_{21}H_{20}ClN_5O_3$ (425.89)

melting point: 236° C.

Example 122

4-[6-(4-methyl-6-oxo-1,4,5,6-tetrahydro-pyridazin-3-yl)-benzoxazol-2-yl]-benzonitrile

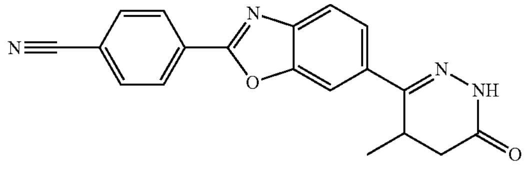 [SMILES: CC1CC(=O)NN=C1c1ccc2nc(-c3ccc(C#N)cc3)oc2c1]

(a) 4-cyano-N-[2-hydroxy-4-(4-methyl-6-oxo-1,4,5,6-tetrahydro-pyridazin-3-yl)-phenyl]-benzamide 403 mg (2.74 mmol) 4-cyano-benzoic acid and 967 mg (3.01 mmol) TBTU are added to 40 ml DMF and the mixture is stirred for 30 min at RT, then 791 μl (5.47 mmol) diisopropylamine and 600 mg (2.74 mmol) 6-(4-amino-3-hydroxy-phenyl)-5-methyl-4,5-dihydro-2H-pyridazin-3-one are added and the mixture is stirred overnight. The reaction mixture is mixed with water and extracted with DCM. The org. phase is again washed with water, dried on sodium sulphate and concentrated by rotary evaporation i. V. The residue is extracted with methanol, filtered off, washed with methanol and then dried in the vacuum dryer at 50° C.

Yield: 0.256 g (24.8%)

$C_{19}H_{16}N_4O_3$ (348.34)

Mass spectrum: $(M+H)^+=349$ (b) 4-[6-(4-methyl-6-oxo-1,4,5,6-tetrahydro-pyridazin-3-yl)-benzoxazol-2-yl]-benzonitrile 250 mg (718 μmol) 4-cyano-N-[2-hydroxy-4-(4-methyl-6-oxo-1,4,5,6-tetrahydro-pyridazin-3-yl)-phenyl]-benzamide and 126 mg (718 μmol) para-toluenesulphonic acid monohydrate are refluxed with 10 ml glacial acetic acid for 3 h. Then the solv. is eliminated by rotary evaporation i.V., water is added to the residue and the product is filtered off.

Yield: 0.2 g (75.9%)

$R_t$-time: 2.72 min (method B)

$C_{19}H_{14}N_4O_2$ (330.34)

Mass spectrum: $(M+H)^+=331$

The following compound may be prepared analogously:

| Ex. | Structural formula | Yield | Mass peak(s) | HPLC |
|---|---|---|---|---|
| 123 | 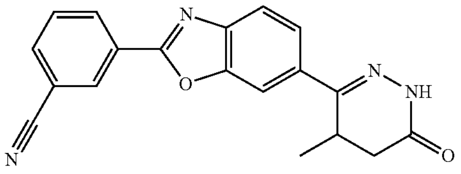 [SMILES: CC1CC(=O)NN=C1c1ccc2nc(-c3cccc(C#N)c3)oc2c1]<br>3-[6-(4-methyl-6-oxo-1,4,5,6-tetrahydro-pyridazin-3-yl)-benzoxazol-2-yl]-benzonitrile; | 44.6% | $(M+H)^+ = 331$ | 3.00 min (method B) |

Example 124

6-[2-(4-aminomethyl-phenyl)-benzoxazol-6-yl]-5-methyl-4,5-dihydro-2H-pyridazin-3-one

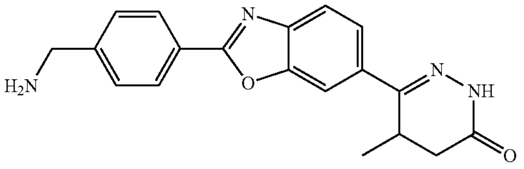 [SMILES: CC1CC(=O)NN=C1c1ccc2nc(-c3ccc(CN)cc3)oc2c1]

100 mg (303 μmol) 4-[6-(4-methyl-6-oxo-1,4,5,6-tetrahydro-pyridazin-3-yl)-benzoxazol-2-yl]-benzonitrile, 10 mg Raney nickel and 20 ml of methanolic ammonia are hydrogenated at RT and 3.45 bar hydrogen pressure for 4 h. Then the mixture is neutralised with conc. hydrochloric acid and the solv. is eliminated from the reaction mixture by rotary evaporation in vacuo. The residue is purified by RP-HPLC.

Yield: 6 mg (5.5%)

$R_t$-time: 1.82 min (method B)

$C_{19}H_{18}N_4O_2$ (334.37)

Mass spectrum: $(M+H)^+=335$

The following compound may be prepared analogously:

(a) 1-(2-phenyl-benzoxazol-6-yl)-propan-1-one

The preparation is carried out analogously to Example 29a from 6-bromo-2-phenyl-benzoxazole and N-methoxy-N-methyl-propionamide.

Yield: (50.2%)

$R_t$-time: 1.48 min (method C)

$C_{16}H_{13}NO_2$ (251.28)

Mass spectrum: $(M+H)^+=252$ (b) 2-bromo-1-(2-phenyl-benzoxazol-6-yl)-propan-1-one The preparation is carried out analogously to Example 77a from 1-(2-phenyl-benzoxazol-6-yl)-propan-1-one.

Yield: (89.3%)

$R_t$-time: 1.56 min (method C)

$C_{16}H_{12}BrNO_2$ (330.18)

Mass spectrum: $(M+H)^+=330$

| Ex. | Structural formula | Yield | Mass peak(s) | HPLC |
|---|---|---|---|---|
| 125 | 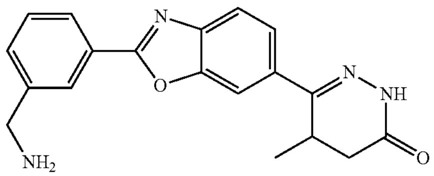 [SMILES: CC1CC(=O)NN=C1c1ccc2nc(-c3cccc(CN)c3)oc2c1]<br>6-[2-(3-aminomethyl-phenyl)-benzoxazol-6-yl]-5-methyl-4,5-dihydro-2H-pyridazin-3-one; | 25.7% | $(M+H)^+ = 335$ | 1.78 min (method B) |

Example 126 trans-4-ethyl-5-methyl-6-(2-phenyl-benzoxazol-6-yl)-4,5-dihydro-2H-pyridazin-3-one

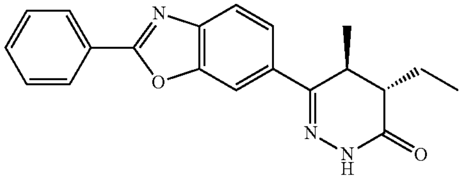 [SMILES: CC[C@@H]1C(=O)NN=C(c2ccc3nc(-c4ccccc4)oc3c2)[C@H]1C]

(c) dimethyl 2-ethyl-2-[1-methyl-2-oxo-2-(2-phenyl-benzoxazol-6-yl)-ethyl]-malonate The reaction is carried out under protective gas (argon).

22.8 μl (151 μmol) dimethyl-ethyl malonate are placed in 1 ml THF and cooled to 0° C., then 302.9 μl (151 μmol) potassium bis(trimethylsilyl)amide 0.5M in toluene are added dropwise. After 10 min, 50 mg (151 μmol) 2-bromo-1-(2-phenyl-benzoxazol-6-yl)-propan-1-one are added, then the mixture is allowed to come up to RT, after 1 h water is added and the mixture is extracted with diethyl ether. The org. phase is dried and the solv. is eliminated by rotary evaporation i.V.

Yield: 25 mg (40.3%)

$R_t$-time: 1.55 min (method C)

$C_{23}H_{23}NO_6$ (409.43)

Mass spectrum: $(M+H)^+=410$ (d) 2-ethyl-2-[1-methyl-2-oxo-2-(2-phenyl-benzoxazol-6-yl)-ethyl]-malonic acid 660 mg (1.13 mmol) dimethyl 2-ethyl-2-[1-methyl-2-oxo-2-(2-phenyl-benzoxazol-6-yl)-ethyl]-malonate are dissolved in 20 ml dioxane. Then 170 mg (7.10 mmol) lithium hydroxide, dissolved in 5 ml of water, are added and the mixture is stirred overnight at RT. The reaction mixture is extracted with DCM, the aqueous phase is acidified and extracted again with DCM. Then the org. phase is dried and the solv. is completely eliminated by rotary evaporation i.V. The residue is separated by RP-HPLC (basic).

Yield: 200 mg (46.5%)

$R_t$-time: 1.42 min (method C)

$C_{21}H_{19}N^{O}_{6}$ (381.38)

Mass spectrum: $(M+H)^+$=382

(e) 2-ethyl-3-methyl-4-oxo-4-(2-phenyl-benzoxazol-6-yl)-butyric acid 200 mg (524 μmol) 2-ethyl-2-[1-methyl-2-oxo-2-(2-phenyl-benzoxazol-6-yl)-ethyl]-malonic acid are heated together with 5 ml diethyleneglycol-dimethylether for 1 h at 140° C. in the microwave. The solv. is largely removed i.V., the residue is mixed with a little water and freeze-dried.

Yield: 150 mg (84.8%)

$R_t$-time: 1.50 min (method C)

$C_{20}H_{19}NO_4$ (337.37)

Mass spectrum: $(M+H)^+$=338

(f) trans-4-ethyl-5-methyl-6-(2-phenyl-benzoxazol-6-yl)-4,5-dihydro-2H-pyridazin-3-one The preparation is carried out analogously to Example 1b from 2-ethyl-3-methyl-4-oxo-4-(2-phenyl-benzoxazol-6-yl)-butyric acid. By separation through silica gel (eluant: cyclohexane/EA) both the trans and the cis compound were able to be isolated.

Yield: 23 mg (17.9%)

$R_t$-time: 1.48 min (method C)

$C_{20}H_{19}N_3O_2$ (333.38)

Mass spectrum: $(M+H)^+$=334

The other diastereomer was obtained as a further fraction:

| Ex. | Structural formula | Yield | Mass peak(s) | HPLC |
|---|---|---|---|---|
| 127 | 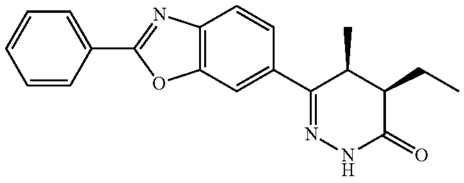 [SMILES: CC[C@H]1C(=O)NN=C(c2ccc3nc(-c4ccccc4)oc3c2)[C@H]1C] | 24.9% | $(M + H)^+$ = 334 | 1.51 min (method C) |
| | cis-4-ethyl-5-methyl-6-(2-phenyl-benzoxazol-6-yl)-4,5-dihydro-2H-pyridazin-3-one; | | | |

The following diastereomers may be prepared analogously:

| Ex. | Structural formula | Yield | Mass peak(s) | HPLC |
|---|---|---|---|---|
| 128 | 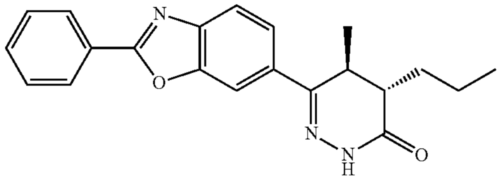 [SMILES: CCC[C@@H]1C(=O)NN=C(c2ccc3nc(-c4ccccc4)oc3c2)[C@H]1C] | 12.2% | $(M + H)^+$ = 348 | 1.56 min (method C) |
| | trans-5-methyl-6-(2-phenyl-benzoxazol-6-yl)-4-propyl-4,5-dihydro-2H-pyridazin-3-one; | | | |
| 129 | 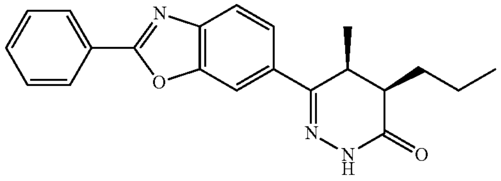 [SMILES: CCC[C@H]1C(=O)NN=C(c2ccc3nc(-c4ccccc4)oc3c2)[C@H]1C] | 28.1% | $(M + H)^+$ = 348 | 1.60 min (method C) |
| | cis-5-methyl-6-(2-phenyl-benzoxazol-6-yl)-4-propyl-4,5-dihydro-2H-pyridazin-3-one; | | | |

-continued

| Ex. | Structural formula | Yield | Mass peak(s) | HPLC |
|---|---|---|---|---|
| 197 | 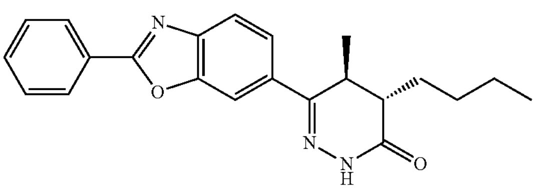 [SMILES: CCCC[C@@H]1C(=O)NN=C(c2ccc3nc(-c4ccccc4)oc3c2)[C@H]1C] trans-4-butyl-5-methyl-6-(2-phenyl-benzoxazol-6-yl)-4,5-dihydro-2H-pyridazin-3-one; | 19.0% | $(M + H)^+ = 362$ | 1.57 min (method C) |

The following stereoisomers may be isolated by separation by chiral HPLC using method I:

Mobile phase: A: 70% CO2; B: 30% MeOH+0.2% diethylamine (DEA)

| time in min (retention time) | flow rate in ml/min | eluted peak |
|---|---|---|
| 5.23 | 4 | 1 |
| 7.21 | 4 | 2 |

| Ex. | Structural formula | Yield | Mass peak(s) | HPLC |
|---|---|---|---|---|
| 196 | Chiral 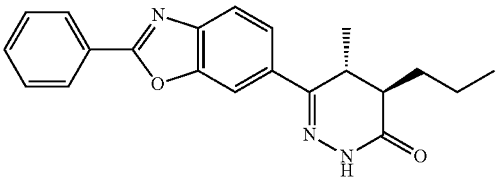 (4R,5R)-5-methyl-6-(2-phenyl-benzoxazol-6-yl)-4-propyl-4,5-dihydro-2H-pyridazin-3-one; | 74.0% | $(M + H)^+ = 348$ | 1.52 min (method C) |

Example 130

5-(2-phenyl-4,5,6,7-tetrahydro-benzoxazol-6-yl)-3,4-diaza-bicyclo[4.1.0]hept-4-en-2-one

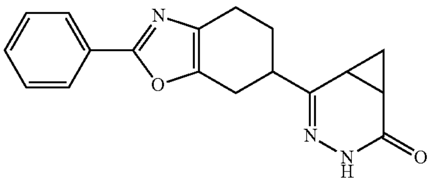 [SMILES: O=C1NN=C(C2CCc3nc(-c4ccccc4)oc3C2)C2CC12]

(a) ethyl 3-bromo-4-oxo-cyclohexanecarboxylate 11.65 g (68.45 mmol) ethyl-4-oxo-cyclohexanecarboxylate are dissolved in 200 ml diethyl ether and cooled to −13° C., at this temperature 3.5 ml (68.45 mmol) bromine are slowly added dropwise. The reaction mixture is extracted with water, with 10% sodium hydrogen carbonate solution and then again with water, then it is dried on magnesium sulphate and the solv. is eliminated completely i. V.

Yield: 16.37 g (96.0%)

$C_9H_{13}BrO_3$ (249.10)

Mass spectrum: $(M+H)^+=249$

(b) ethyl 2-phenyl-4,5,6,7-tetrahydro-benzoxazole-6-carboxylate 16.0 g (64.23 mmol) ethyl 3-bromo-4-oxo-cyclohexanecarboxylate are combined with 7.8 g (64.39 mmol) benzamide and 50 ml of dichloroethane in a pressure vessel and stirred overnight at 120° C. The reaction mixture is diluted with DCM and washed 2× with 5% potassium carbonate solution as well as 1× with sat. saline solution. The org. phase is dried on magnesium sulphate and the solv. is eliminated completely in vacuo, the residue is purified through silica gel (eluant cyclohexane/EA).

Yield: 5.66 g (31.5%)

$R_t$-time: 1.66 min (method A)

$C_{16}H_{17}NO_3$ (271.31)

Mass spectrum: $(M+H)^+=272$

(c) ethyl 6-(2-carbohydroxy-cyclopropanecarbonyl)-2-phenyl-4,5,6,7-tetrahydro-benzoxazole-6-carboxylate The preparation is carried out under a protective gas atmosphere (argon).

At −70° C., a solution of 2.9 ml (4.64 mmol) butyl lithium (1.6 molar in THF) and 650 µl (4.60 mmol) diisopropylamine in 25 ml THF is added dropwise to a solution of 500 mg (1.84 mmol) ethyl 2-phenyl-4,5,6,7-tetrahydro-benzoxazole-6-carboxylate in 25 ml THF, and the mixture is stirred for 30 min. The mixture, still at −70° C., is then added dropwise to a −70° C. solution of 420 mg (3.75 mmol) 1,2-cyclopropanedicarboxylic acid anhydride and 25 ml THF and stirred for 15 min. The mixture is then added to semisaturated hydrochloric saline solution and extracted with diethyl ether, the org. phase is extracted with sodium carbonate solution. The carbonate phase is acidified with conc. hydrochloric acid and then extracted with diethyl ether, the phases are separated, the org. phase is dried on magnesium sulphate and the solv. is eliminated by rotary evaporation i.V.

Yield: 800 mg (96.2%)

$R_t$-time: 1.49 min (method A)

$C_{21}H_{21}NO_6$ (383.34)

Mass spectrum: $(M+H)^+=384$ (d) 2-(2-phenyl-4,5,6,7-tetrahydro-benzoxazole-6-carbonyl)-cyclopropanecarboxylic acid 790 mg (2.06 mmol) ethyl 6-(2-carboxy-cyclopropanecarbonyl)-2-phenyl-4,5,6,7-tetrahydro-benzoxazole-6-carboxylate, 5 ml of 32% hydrochloric acid and 5 ml of water are refluxed together for 6 h. The reaction mixture is extracted with DCM, the org. phase is dried on magnesium sulphate and then the solv. is eliminated by rotary evaporation i.V.

Yield: 450 mg (70.1%)

$R_t$-time: 1.38/1.39 min (method A)

$C_{18}H_{17}NO_4$ (311.33)

Mass spectrum: $(M+H)^+=312$ (e) 5-(2-phenyl-4,5,6,7-tetrahydro-benzoxazol-6-yl)-3,4-diaza-bicyclo[4.1.0]hept-4-en-2-one The preparation is carried out analogously to Example 1b from 2-(2-phenyl-4,5,6,7-tetrahydro-benzoxazole-6-carbonyl)-cyclopropanecarboxylic acid.

Yield: 162 mg (36.5%)

$R_t$-time: 1.40 min (method A)

$C_{18}H_{17}N_3O_2$ (307.35)

Mass spectrum: $(M+H)^+=308$

The following compounds were isolated by chiral separation of the compound described in Example 130 by the following method E:

| time in min (retention time) | flow rate in ml/min | eluted peak |
|---|---|---|
| 3.78 | 9.5 | 1 |
| 4.32 | 9.5 | 2 |
| 4.73 | 9.5 | 3 |
| 5.46 | 9.5 | 4 |

| Ex. | Structural formula | Mass peak(s) | DC/HPLC |
|---|---|---|---|
| 131 | 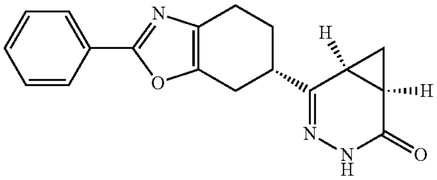 [SMILES: O=C1NN=C([C@H]2CCc3nc(-c4ccccc4)oc3C2)[C@H]2C[C@@H]12] (1R,6S)-5-((S)-2-phenyl-4,5,6,7-tetrahydro-benzoxazol-6-yl)-3,4-diaza-bicyclo[4.1.0]hept-4-en-2-one; | $(M + H)^+ = 308$ | 1.40 min (method A) |
| 132 | 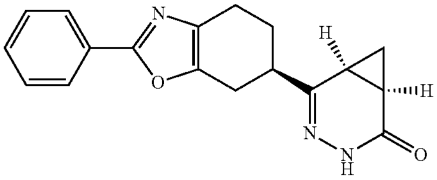 [SMILES: O=C1NN=C([C@@H]2CCc3nc(-c4ccccc4)oc3C2)[C@H]2C[C@@H]12] (1R,6S)-5-((R)-2-phenyl-4,5,6,7-tetrahydro-benzoxazol-6-yl)-3,4-diaza-bicyclo[4.1.0]hept-4-en-2-one; | $(M + H)^+ = 308$ | 1.40 min (method A) |
| 133 | 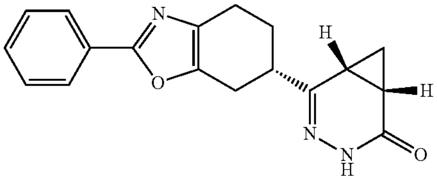 [SMILES: O=C1NN=C([C@H]2CCc3nc(-c4ccccc4)oc3C2)[C@@H]2C[C@H]12] (1S,6R)-5-((S)-2-phenyl-4,5,6,7-tetrahydro-benzoxazol-6-yl)-3,4-diaza-bicyclo[4.1.0]hept-4-en-2-one; | $(M + H)^+ = 308$ | 1.40 min (method A) |
| 134 | 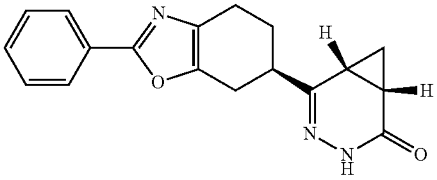 [SMILES: O=C1NN=C([C@@H]2CCc3nc(-c4ccccc4)oc3C2)[C@@H]2C[C@H]12] (1S,6R)-5-((R)-2-phenyl-4,5,6,7-tetrahydro-benzoxazol-6-yl)-3,4-diaza-bicyclo[4.1.0]hept-4-en-2-one; | $(M + H)^+ = 308$ | 1.40 min (method A) |

Example 135

5-(2-phenyl-4,5,6,7-tetrahydro-4H-oxazolo[5,4-c]pyridin-5-yl)-3,4-diaza-bicyclo[4.1.0]hept-4-en-2-one

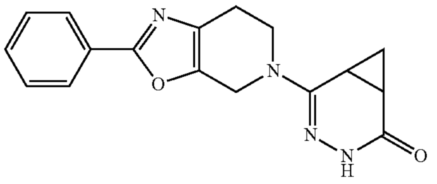 [SMILES: O=C1NN=C(N2CCc3nc(-c4ccccc4)oc3C2)C2CC12]

(a) 3-(4-methoxy-benzyl)-3,4-diaza-bicyclo[4.1.0]heptan-2,5-dione 1.0 g (8.92 mmol) 1,2-cyclopropanedicarboxylic acid anhydride is dissolved in 5 ml acetonitrile, 1.5 g (9.86 mmol) 4-methoxy-benzyl-hydrazine dissolved in 5 ml acetonitrile are added dropwise and the mixture is refluxed overnight. During cooling to RT a precipitate is formed, which is filtered off, washed with acetonitrile and dried in the vacuum dryer at 50° C.

Yield: 561 mg (25.5%)

$R_t$-time: 1.12 min (method A)

$C_{13}H_{14}N_2O_3$ (246.26)

Mass spectrum: $(M+H)^+$=247

(b) 4-(4-methoxy-benzyl)-5-oxo-3,4-diaza-bicyclo[4.1.0]hept-2-en-2-yltrifluoro-methanesulphonate 210 mg (0.85 mmol) 3-(4-methoxy-benzyl)-3,4-diaza-bicyclo[4.1.0]heptan-2,5-dione are dissolved in 20 ml DCM, 190 µl (1.37 mmol) triethylamine are added and the mixture is cooled to −30° C., at this temperature 170 µl (1.01 mmol) trifluoromethanesulphonic acid anhydride are added dropwise. After 15 min stirring at −30° C. it is extracted first with sat. sodium hydrogen carbonate solution, then with water and then extracted with 1N hydrochloric acid. The org. phase is dried on magnesium sulphate and the solv. is eliminated by rotary evaporation i.V.

Yield: 322 mg (99.8%)

$R_t$-time: 1.66 min (method A)

$C_{14}H_{13}F_3N_2O_5S$ (378.33)

Mass spectrum: $(M+H)^+$=379

(c) 3-(4-methoxy-benzyl)-5-(2-phenyl-6,7-dihydro-4H-oxazolo[5,4-c]pyridin-5-yl)-3,4-diaza-bicyclo[4.1.0]hept-4-en-2-one 322 mg (0.85 mmol) 4-(4-methoxy-benzyl)-5-oxo-3,4-diaza-bicyclo[4.1.0]hept-2-en-2-yl trifluoro-methanesulphonate dissolved in 4 ml DMSO and some molecular sieve are added to 400 mg (1.69 mmol) 2-phenyl-4,5,6,7-tetrahydro-oxazolo[5,4-C]pyridine. The mixture is stirred for 5 h at 40° C. and then combined with DCM. It is extracted 1× each with sat. sodium carbonate solution and sat. saline solution, the org. phase is dried on magnesium sulphate and the solv. is eliminated by rotary evaporation i.V., the residue is purified through silica gel (eluant: DCM/methanol).

Yield: 323 mg (88.6%)

$R_t$-time: 1.66 min (method A)

$C_{25}H_{24}N_4O_3$ (428.48)

Mass spectrum: $(M+H)^+$=429

(d) 5-(2-phenyl-6,7-dihydro-4H-oxazolo[5,4-c]pyridin-5-yl)-3,4-diaza-bicyclo[4.1.0]hept-4-en-2-one 320 mg (0.75 mmol) 3-(4-methoxy-benzyl)-5-(2-phenyl-6,7-dihydro-4H-oxazolo[5,4-c]pyridin-5-yl)-3,4-diaza-bicyclo[4.1.0]hept-4-en-2-one, 1 ml (7.84 mmol) Veratrol and 6 ml TFA are heated to 100° C. in a pressure vessel for 24 h. The cooled mixture is combined with sat. sodium carbonate solution and extracted with DCM, the org. phase is concentrated by rotary evaporation i. V. and the residue is purified by silica gel (eluant: DCM/methanol).

Yield: 170 mg (73.8%)

$R_t$-time: 1.35 min (method A)

$C_{17}H_{16}N_4O_2$ (308.34)

Mass spectrum: $(M+H)^+$=309

Example 136

5-(2-benzyl-benzoxazol-6-yl)-3,4-diaza-bicyclo[4.1.0]hept-4-en-2-one

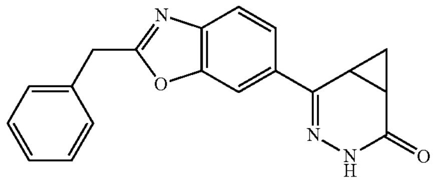 [SMILES: O=C1NN=C(c2ccc3nc(Cc4ccccc4)oc3c2)C2CC12]

(a) 2-benzyl-6-bromo-benzoxazole

Preparation is carried out analogously to 4.1.a from phenylacetic acid.

Yield: (39.7%)

$R_t$-time: 1.78 min (method A)

$C_{14}H_{10}BrNO$ (288.14)

Mass spectrum: $(M+H)^+$=288/290

(b) 2-benzyl-6-(4,4,5,5-tetramethyl-[1,3,2]dioxaborolan-2-yl)-benzoxazole

The preparation is carried out under protective gas (argon).

300 mg (1.04 mmol) 2-benzyl-6-bromo-benzoxazole, 370 mg (1.46 mmol) bis-(pinacolato)-diboron and 320 mg (3.26 mmol) potassium acetate are combined with 5 ml dioxane and stirred for 15 min at RT, then 75 mg (0.11 mmol) bis-(triphenylphosphine)-palladium(II)-chloride are added and the mixture is stirred overnight at 60° C. Then DCM is added and the mixture is extracted with sat. saline solution, the phases are separated through a phase separation cartridge and the solv. of the org. phase is eliminated by rotary evaporation i. V. The residue is purified on silica gel (eluant: cyclohexane/EA).

Yield: 273 mg (78.2%)

$R_t$-time: 1.85 min (method A)

$C_{20}H_{22}BNO_3$ (335.21)

Mass spectrum: $(M+H)^+$=336

(c) 5-(2-benzyl-benzoxazol-6-yl)-3-(4-methoxy-benzyl)-3,4-diaza-bicyclo[4.1.0]hept-4-en-2-one The preparation is carried out under protective gas (argon). 210 mg (0.63 mmol) 2-benzyl-6-(4,4,5,5-tetramethyl-[1,3,2]dioxaborolan-2-yl)-benzoxazole and 150 mg (1.42 mmol) sodium carbonate are combined with 0.5 ml of water, 10 ml dioxane and 240 mg (0.63 mmol) of 4-(4-methoxy-benzyl)-5-oxo-3,4-diaza-bicyclo[4.1.0]hept-2-en-2-yltrifluoro-methanesulphonate. 45 mg (0.04 mmol) of tetrakis-(triphenylphosphine)-palladium(0) are added to this mixture and it is reacted for 60 min at 80° C. in the microwave. Then DCM is added and the suspension is filtered through kieselguhr. The filtrate is concentrated by rotary evaporation i. V. and the residue is purified through silica gel (eluant cyclohexane/EA).

Yield: 235 mg (85.7%)

$R_t$-time: 1.73 min (method A)

$C_{27}H_{23}N_3O_3$ (437.49)

Mass spectrum: $(M+H)^+$=438

(d) 5-(2-benzyl-benzoxazol-6-yl)-3,4-diaza-bicyclo[4.1.0]hept-4-en-2-one

The preparation is carried out analogously to Example 135d from 5-(2-benzyl-benzoxazol-6-yl)-3-(4-methoxy-benzyl)-3,4-diaza-bicyclo[4.1.0]hept-4-en-2-one.

Yield: 104 mg (75.5%)

$R_t$-time: 1.44 min (method A)

$C_{19}H_{15}N_3O_2$ (317.34)

Mass spectrum: $(M+H)^+$=318

Example 137

5-{2-[4-(2-morpholin-4-yl-ethoxy)-phenyl]-benzoxazol-6-yl}-3,4-diaza-bicyclo[4.1.0]hept-4-en-2-one

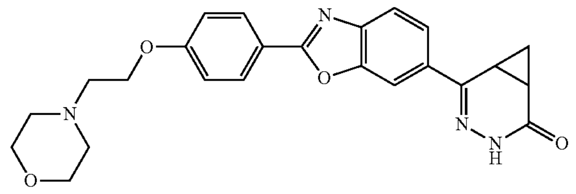 [SMILES: O=C1NN=C(c2ccc3nc(-c4ccc(OCCN5CCOCC5)cc4)oc3c2)C2CC12]

(a) 6-bromo-2-[4-(2-morpholin-4-yl-ethoxy)-phenyl]-benzoxazole

The preparation is carried out analogously to Example 40 from 4-(6-bromo-benzoxazol-2-yl)-phenol and N-(2-chloro-ethyl)morpholine hydrochloride with ACN as solv.

Yield: (46.3%)

$R_t$-time: 1.42 min (method A)

$C_{19}H_{19}BrN_2O_3$ (403.27)

Mass spectrum: $(M+H)^+$=403/5

(b) 2-[4-(2-morpholin-4-yl-ethoxy)-phenyl]-6-(4,4,5,5-tetramethyl-[1,3,2]dioxaborolan-2-yl)-benzoxazole The preparation is carried out analogously to Example 136b from 6-bromo-2-[4-(2-morpholin-4-yl-ethoxy)-phenyl]-benzoxazole.

$R_t$-time: 1.50 min (method A)

$C_{25}H_{31}BN_2O_5$ (450.34)

Mass spectrum: $(M+H)^+$=451/2

(c) 3-(4-methoxy-benzyl)-5-{2-[4-(2-morpholin-4-yl-ethoxy)-phenyl]-benzoxazol-6-yl}-3,4-diaza-bicyclo[4.1.0]hept-4-en-2-one The preparation is carried out analogously to Example 136c from 2-[4-(2-morpholin-4-yl-ethoxy)-phenyl]-6-(4,4,5,5-tetramethyl-[1,3,2]dioxaborolan-2-yl)-benzoxazole and 4-(4-methoxy-benzyl)-5-oxo-3,4-diaza-bicyclo[4.1.0]hept-2-en-2-yl trifluoromethanesulphonate.

Yield: (62% over two steps)

$R_t$-time: 1.42 min (method A)

$C_{32}H_{32}N_4O_5$ (552.62)

Mass spectrum: $(M+H)^+$=553/4

(d) 5-{2-[4-(2-morpholin-4-yl-ethoxy)-phenyl]-benzoxazol-6-yl}-3,4-diaza-bicyclo[4.1.0]hept-4-en-2-one 107 mg (194 μmol) 3-(4-methoxy-benzyl)-5-{2-[4-(2-morpholin-4-yl-ethoxy)-phenyl]-benzoxazol-6-yl}-3,4-diaza-bicyclo[4.1.0]hept-4-en-2-one and 2 ml TFA are stirred in the microwave for 30 min at 150° C. The reaction mixture is made basic with 10% sodium carbonate solution, the precipitate formed is filtered off and the residue is purified on silica gel (eluant: DCM/methanol/ammonia).

Yield: 52 mg (62.1%)

$R_t$-time: 1.20 min (method A)

$C_{24}H_{24}N_4O_4$ (432.47)

Mass spectrum: $(M+H)^+$=433/4

Example 138

5-cyclopropyl-6-(2-phenyl-6,7-dihydro-4H-oxazolo[5,4-c]pyridin-5-yl)-4,5-dihydro-2H-pyridazin-3-one

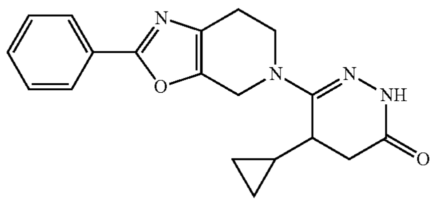 [SMILES: O=C1CC(C2CC2)C(N2CCc3nc(-c4ccccc4)oc3C2)=NN1]

(a) tert-butyl 3-cyclopropyl-4-(2-phenyl-6,7-dihydro-4H-oxazolo[5,4-c]pyridin-5-yl)-4-oxobutanoate 1 g (4.2 mmol) 1-(2-phenyl-6,7-dihydro-4H-oxazolo[5,4-c]pyridine-hydrochloride and 0.9 g (4.2 mmol) R-4-tert-butoxy-2-cyclopropyl-4-oxobutanoic acid is taken up in 10 ml DMF and combined successively with 2.4 ml TEA and 1.9 g HATU. It is stirred for 30 min. at RT. The solvent is eliminated, the residue is taken up in dichloromethane and shaken 1× with water and 1× with 5% $K_2CO_3$ solution. Org. phase separated off and evaporated down. The residue is purified on silica gel (eluant: cyclohexane/EA).

Yield: 1.46 g (88%)

$R_t$-time: 1.5 min (method C)

$C_{23}H_{28}N_2O_4$ (396.48)
Mass spectrum: $(M+H)^+$=397

(b) methyl 3-cyclopropyl-4-(2-phenyl-6,7-dihydro-4H-oxazolo[5,4-c]pyridin-5-yl)-4-oxobutanoate 1.4 g (3.6 mmol) tert-butyl 3-cyclopropyl-4-(2-phenyl-6,7-dihydro-4H-oxazolo[5,4-c]pyridin-5-yl)-4-oxobutanoate are mixed with 150 ml of 1.25 M HCl and stirred for 8 h at 60° C. The mixture is evaporated down and the residue is taken up in dichloromethane. It is filtered to remove the precipitate and the filtrate is evaporated down. This yields 650 mg of colourless resin which is dissolved in 10 ml MeOH and combined with 1 ml 2M trimethylsilyl-diazomethane solution in hexane while being cooled to −5° C. The yellow solution is left overnight with stirring while the ice bath is heated. The solvent is eliminated and the residue is reacted in the following step without any further purification.

(c) methyl 3-cyclopropyl-4-(2-phenyl-6,7-dihydro-4H-oxazolo[5,4-c]pyridin-5-yl)-4-thiobutanoate 0.6 g (0.7 mmol) methyl 3-cyclopropyl-4-(2-phenyl-6,7-dihydro-4H-oxazolo[5,4-c]pyridin-5-yl)-4-oxobutanoate are dissolved in 35 ml of toluene, mixed with 1.2 g Lawesson's reagent and stirred overnight at 90° C. The mixture is evaporated down and the residue is triturated with diethyl ether and insoluble ingredients are filtered off. The ether phase is evaporated down and the solid is combined with methanol and suction filtered to remove the precipitate. The filtrate is evaporated down and the residue is purified on silica gel (eluant: cyclohexane/EA).

Yield: 132 mg (46%)
$R_t$-time: 1.5 min (method C)
$C_{20}H_{22}N_2O_3S$ (370.47)
Mass spectrum: $(M+H)^+$=371

(d) 5-cyclopropyl-6-(2-phenyl-6,7-dihydro-4H-oxazolo[5,4-c]pyridin-5-yl)-4,5-dihydro-2H-pyridazin-3-one 120 mg (0.3 mmol) methyl 3-cyclopropyl-4-(2-phenyl-6,7-dihydro-4H-oxazolo[5,4-c]pyridin-5-yl)-4-thiobutanoate are placed in 5 ml of ethanol, 100 μl hydrazine are added and the mixture is stirred for 3 days at 80° C. It is stirred for another 2 days at 80° C. and in each case 50 μl hydrazine are added until no more starting product can be detected. The mixture is evaporated down and the residue is purified on silica gel (eluant: cyclohexane/EA).

Yield: 30 mg (28%)
$R_t$-time: 1.3 min (method C)
$C_{19}H_{20}N_4O_2$ (336.39)
Mass spectrum: $(M+H)^+$=337

The following compounds may be prepared analogously:

Example 139

4-methyl-6-(2-thiophen-2-yl-benzoxazol-6-yl)-4,5-dihydro-2H-pyridazin-3-one

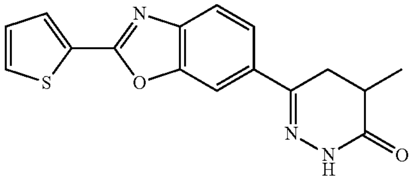

(a) (2-thiophen-2-yl-benzoxazol-6-yl)methanol 6.1 g (23.53 mmol) methyl 2-thiophen-2-yl-benzoxazole-6-carboxylate are dissolved in 300 ml THF and cooled with dry ice/acetone, then 40 ml (40.00 mmol) of 1M lithium aluminium hydride dissolved in THF are slowly added dropwise. The mixture is stirred for 30 min at 0° C., then 4 ml of water dissolved in 20 ml THF are added dropwise, followed by 4 ml of 4N sodium hydroxide solution and another 4 ml of water. The resulting suspension is mixed with magnesium sulphate and filtered through kieselguhr, the filtrate is concentrated by rotary evaporation i. V. and the residue is purified on silica gel (eluant: cyclohexane/EA).

Yield: 3.7 g (68%)
$R_t$-time: 1.39 min (method A)
$C_{12}H_9NO_2S$ (231.27)
Mass spectrum: $(M+H)^+$=232

(b) 2-thiophen-2-yl-benzoxazole-6-carbaldehyde 3.7 g (16.0 mmol) (2-thiophen-2-yl-benzoxazol-6-yl)-methanol are dissolved in 200 ml DCM, 15.0 g (10.78 mmol) manganese dioxide are added and the suspension is stirred overnight at RT. The next day the suspension is filtered through kieselguhr and the filtrate is concentrated completely by rotary evaporation i. V.

Yield: 3.53 g (96.2%)
$R_t$-time: 1.58 min (method A)
$C_{12}H_7NO_2S$ (229.26)
Mass spectrum: $(M+H)^+$=230

(c) ethyl (E)-4-hydroxy-4-(2-thiophen-2-yl-benzoxazol-6-yl)but-2-enoate

The reaction is carried out under absolutely anhydrous conditions and under a protective gas atmosphere (Argon).

| Ex. | Structural formula | Yield | Mass peak(s) | HPLC |
|---|---|---|---|---|
| 202 | 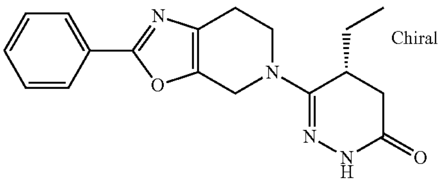 [SMILES: CC[C@@H]1CC(=O)NN=C1N1CCc2nc(-c3ccccc3)oc2C1] Chiral<br>(R)-5-ethyl-6-(2-phenyl-6,7-dihydro-4H-oxazolo[5,4-c]pyridin-5-yl)-4,5-dihydro-2H-pyridazin-3-one; | 9.5% | $(M + H)^+$ = 325 | 1.27 min (method C) |

A solution of 1.2 g (5.23 mmol) 2-thiophen-2-yl-benzoxazole-6-carbaldehyde and 2.5 g (11.06 mmol) ethyl (E)-3-iodoacrylate in DMSO is added dropwise at RT to 4.0 g (32.55 mmol) chromium-(II)-chloride and 10 mg (0.08 mmol) nickel-(II)-chloride. The reaction mixture is stirred overnight at RT, then combined with sat. ammonium chloride solution and extracted 3× with DCM. The combined org. phases are concentrated by rotary evaporation i. V. and the residue is purified on silica gel (eluant: cyclohexane/EA).

Yield: 1.09 g (63.2%)

$R_t$-time: 1.54 min (method A)

$C_{17}H_{15}NO_4S$ (329.37)

Mass spectrum: $(M+H)^+$=330

(d) ethyl (E)-4-oxo-4-(2-thiophen-2-yl-benzoxazol-6-yl)-but-2-enoate

The preparation is carried out analogously to Example 139b from ethyl (E)-4-hydroxy-4-(2-thiophen-2-yl-benzoxazol-6-yl)-but-2-enoate.

Yield: (86.6%)

$R_t$-time: 1.79 min (method A)

$C_{17}H_{13}NO_4S$ (327.36)

Mass spectrum: $(M+H)^+$=328

(e) ethyl 2-methyl-4-oxo-4-(2-thiophen-2-yl-benzoxazol-6-yl)-butyrate 5 ml THF are added to 110 mg (1.23 mmol) copper-(I)-cyanide, the suspension is cooled to −5° C., then 770 µl (1.23 mmol) 1.6M methyl lithium dissolved in THF are added dropwise at a maximum temperature of 0° C., the mixture is stirred for 45 min, then cooled to −70° C. 1.23 ml (1.23 mmol) 1M diethyl aluminium chloride dissolved in hexane are then added dropwise to the reaction mixture, it is stirred for 25 min at −70° C., then are 100 mg (0.31 mmol) ethyl (E)-4-oxo-4-(2-thiophen-2-yl-benzoxazol-6-yl)-but-2-enoate dissolved in 5 ml THF are added dropwise. The reaction solution is then added to sat. ammonium chloride solution and extracted with diethyl ether. The org. phase is concentrated by rotary evaporation i. V. and the residue is purified by RP-HPLC.

Yield: 30 mg (28.6%)

$R_t$-time: 1.75 min (method A)

$C_{18}H_{17}NO_4S$ (343.40)

Mass spectrum: $(M+H)^+$=344

(f) 4-methyl-6-(2-thiophen-2-yl-benzoxazol-6-yl)-4,5-dihydro-2H-pyridazin-3-one

The preparation is carried out analogously to Example 82f from ethyl 2-methyl-4-oxo-4-(2-thiophen-2-yl-benzoxazol-6-yl)-butyrate.

Yield: 46 mg (56.4%)

$R_t$-time: 1.50 min (method A)

$C_{16}H_{13}N_3O_2S$ (311.36)

Mass spectrum: $(M+H)^+$=312

The following compounds may be prepared analogously:

| Ex. | Structural formula | Yield | Mass peak(s) | HPLC |
|---|---|---|---|---|
| 140 | 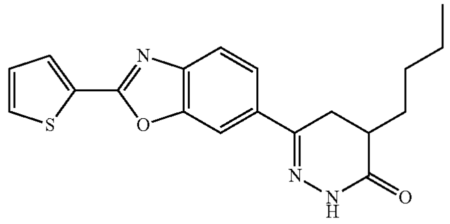 [SMILES: CCCCC1CC(c2ccc3nc(-c4cccs4)oc3c2)=NNC1=O]<br>4-butyl-6-(2-thiophen-2-yl-benzoxazol-6-yl)-4,5-dihydro-2H-pyridazin-3-one; | 57.9% | $(M + H)^+ = 354$ | 1.71 min (method A) |
| 141 | 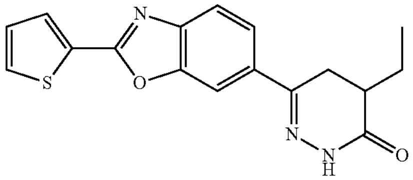 [SMILES: CCC1CC(c2ccc3nc(-c4cccs4)oc3c2)=NNC1=O]<br>4-ethyl-6-(2-thiophen-2-yl-benzoxazol-6-yl)-4,5-dihydro-2H-pyridazin-3-one; | 21.0% | $(M + H)^+ = 326$ | 1.55 min (method A) |

Example 142

5-methyl-6-(2-phenyl-benzoxazol-6-yl)-4,5-dihydro-2H-[1,2,4]triazin-3-one

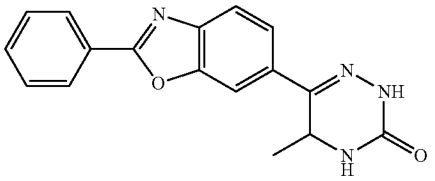 [SMILES: CC1NC(=O)NN=C1c1ccc2nc(-c3ccccc3)oc2c1]

(a) tert-butyl 1-methyl-2-oxo-2-(2-phenyl-benzoxazol-6-yl)ethyl]-carbamate

The preparation is carried out under absolutely anhydrous conditions and under a protective gas atmosphere (argon).

2.0 g (7.30 mmol) 6-bromo-2-phenyl-benzoxazole are dissolved in 40 ml THF and cooled to −70° C., then 4.7 ml (7.52 mmol) 1.6M butyl lithium dissolved in hexane are added dropwise. The mixture is stirred for 20 min at −70° C. Then at −50° C. a solution of 0.7 g (3.01 mmol) tert-butyl [1-(methoxy-methyl-carbamoyl)-ethyl]-carbamate in 10 ml THF is added dropwise to the reaction solution. Within 45 min the reaction mixture is allowed to come up to −35° C. and then combined with water, then it is extracted with DCM, the org. phase is dried on magnesium sulphate and the solv. is eliminated by rotary evaporation i.V. The residue is purified on silica gel (eluant: cyclohexane/EA).

Yield: 1.8 g (81.5%)
$R_t$-time: 1.77 min (method A)
$C_{21}H_{22}N_2O_4$ (366.41)
Mass spectrum: $(M+H)^+$=367

(b) 2-amino-1-(2-phenyl-benzoxazol-6-yl)-propan-1-one as the hydrochloride 1.8 g (2.46 mmol) tert-butyl [1-methyl-2-oxo-2-(2-phenyl-benzoxazol-6-yl)-ethyl]carbamate, 10 ml of 4 N hydrochloric acid dissolved in dioxane and 10 ml DCM are stirred together for 4 h at RT. The mixture is diluted with diethyl ether and the precipitated solid is filtered off.

Yield: 630 mg (84.7%)
$R_t$-time: 1.27 min (method A)
$C_{16}H_{14}N_2O_2$*HCl (302.76)
Mass spectrum: $(M+H)^+$=267

(c) S-ethyl [1-methyl-2-oxo-2-(2-phenyl-benzoxazol-6-yl)-ethyl]-thiocarbamate 100.0 mg (330 μmol) 2-amino-1-(2-phenyl-benzoxazol-6-yl)-propan-1-one as the hydrochloride are cooled to 0° C. together with 183.1 μl (1321 μmol) triethylamine and 3 ml THF, then 34.7 μl (333 μmol) ethyl chlorothiolformate are added dropwise. The mixture is stirred for 2 h at 0° C., then the reaction mixture is combined with DCM and extracted with water, the org. phase is dried on magnesium sulphate and the solv. is eliminated by rotary evaporation i. V.

Yield: 80 mg (68.3%)
$R_t$-time: 1.71 min (method A)
$C_{19}H_{18}N_2O_3S$ (354.42)
Mass spectrum: $(M+H)^+$=355

(d) 5-methyl-6-(2-phenyl-benzoxazol-6-yl)-4,5-dihydro-2H-[1,2,4]triazin-3-one The preparation is carried out analogously to Example 1b from S-ethyl [1-methyl-2-oxo-2-(2-phenyl-benzoxazol-6-yl) ethyl]-thiocarbamate.

Yield: 1 mg (1.4%)
$R_t$-time: 1.44 min (method A)
$C_{17}H_{14}N_4O_2$ (306.32)
Mass spectrum: $(M+H)^+$=307

The following compounds may be prepared analogously:

| Ex. | Structural formula | Yield | Mass peak(s) | HPLC |
|---|---|---|---|---|
| 143 | 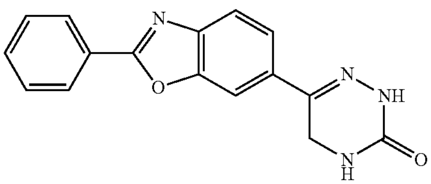 [SMILES: O=C1NCC(c2ccc3nc(-c4ccccc4)oc3c2)=NN1] 6-(2-phenyl-benzoxazol-6-yl)-4,5-dihydro-2H-[1,2,4]triazin-3-one; | 11.6% | $(M + H)^+$ = 293 | 1.42 min (method A) |
| 144 | 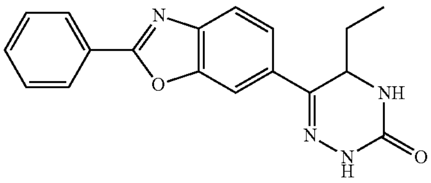 [SMILES: CCC1NC(=O)NN=C1c1ccc2nc(-c3ccccc3)oc2c1] 5-ethyl-6-(2-phenyl-benzoxazol-6-yl)-4,5-dihydro-2H-[1,2,4]triazin-3-one; | 1.7% | $(M + H)^+$ = 321 | 1.38 min (method C) |

Example 145 trans-5-ethyl-4-methyl-6-(2-phenyl-benzoxazol-6-yl)-4,5-dihydro-2H-pyridazin-3-one

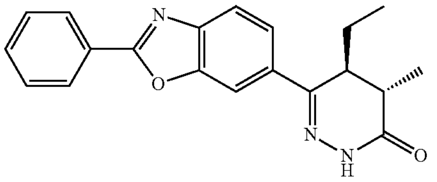 [SMILES: CC[C@@H]1C(c2ccc3nc(-c4ccccc4)oc3c2)=NNC(=O)[C@H]1C]

(a) diethyl 2-methyl-2-[1-(2-phenyl-benzoxazole-6-carbonyl)-propyl]-malonate

The preparation is carried out under a protective gas atmosphere (argon).

75.91 mg (436 μmol) diethyl methylmalonate are placed in THF at 0° C., then 871.58 μl (436 μmol) 0.5M potassium bis(trimethylsilyl)amide dissolved in toluene are added dropwise, after 10 min 150.00 mg (436 μmol) 2-bromo-1-(2-phenyl-benzoxazol-6-yl)-butan-1-one are added, then the reaction mixture is allowed to come up to RT. After 1 h the mixture is combined with DCM and extracted with water, the org. phase is dried on magnesium sulphate and the solv. is removed i. V., the residue is purified on silica gel. (Eluant: cyclohexane/EA).

Yield: 160 mg (83.9%)

$R_t$-time: 1.90 min (method A)

$C_{25}H_{27}NO_6$ (437.49)

Mass spectrum: $(M+H)^+$=438

(b) 2-methyl-3-(2-phenyl-benzoxazole-6-carbonyl)-pentanoic acid 850 mg (1.94 mmol) diethyl 2-methyl-2-[1-(2-phenyl-benzoxazole-6-carbonyl)-propyl]-malonate are mixed with 10 ml dioxane, then a solution of 300 mg (12.53 mmol) lithium hydroxide in 10 ml of water is added and the mixture is left overnight at RT with stirring. The next day the reaction mixture is acidified with 4N hydrochloric acid and extracted with DCM. The org. phase is dried on magnesium sulphate and concentrated by rotary evaporation i. V., the residue is stirred with 5 ml DMSO and 500 mg lithium chloride for 1.5 h at 150° C., the reaction mixture is purified by RP-HPLC.

Yield: 200 mg (30.5%)

$R_t$-time: 1.65 min (method A)

$C_{20}H_{19}NO_4$ (337.37)

Mass spectrum: $(M+H)^+$=338

(c) trans-5-ethyl-4-methyl-6-(2-phenyl-benzoxazol-6-yl)-4,5-dihydro-2H-pyridazin-3-one The preparation is carried out analogously to Example 1b from 2-methyl-3-(2-phenyl-benzoxazole-6-carbonyl)-pentanoic acid. The diastereomers are separated by preparative DC.

Yield: 9 mg (4%)

$R_t$-time: 1.57 min (method A)

$C_{20}H_{19}N_3O_2$ (333.38)

Mass spectrum: $(M+H)^+$=334

The other diastereomer was obtained as a further fraction:

| Ex. | Structural formula | Yield | Mass peak(s) | HPLC |
|---|---|---|---|---|
| 146 | 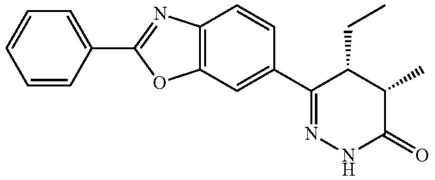 [SMILES: CC[C@H]1C(c2ccc3nc(-c4ccccc4)oc3c2)=NNC(=O)[C@H]1C] cis-5-ethyl-4-methyl-6-(2-phenyl-benzoxazol-6-yl)-4,5-dihydro-2H-pyridazin-3-one; | 3.5% | $(M + H)^+ = 334$ | 1.65 min (method A) |

The following compounds may be prepared analogously:

| Ex. | Structural formula | Yield | Mass peak(s) | HPLC |
|---|---|---|---|---|
| 198 | 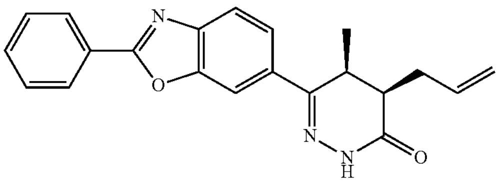 [SMILES: C=CC[C@H]1C(=O)NN=C(c2ccc3nc(-c4ccccc4)oc3c2)[C@H]1C] cis-4-allyl-5-methyl-6-(2-phenyl-benzoxazol-6-yl)-4,5-dihydro-2H-pyridazin-3-one; | 7.1% | $(M + H)^+ = 346$ | 1.54 min (method C) |

-continued

| Ex. | Structural formula | Yield | Mass peak(s) | HPLC |
|---|---|---|---|---|
| 199 | 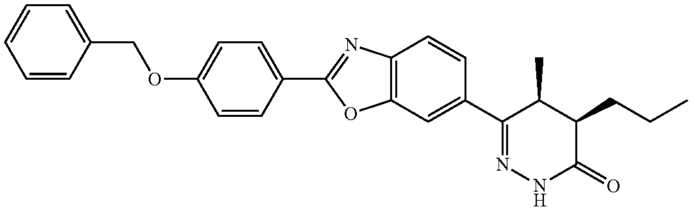 [SMILES: CCC[C@H]1C(=O)NN=C(c2ccc3nc(-c4ccc(OCc5ccccc5)cc4)oc3c2)[C@H]1C] | 22.7% | $(M + H)^+ = 454$ | 1.67 min (method C) |
| | cis-6-[2-(4-benzoxy-phenyl)-benzoxazol-6-yl]-5-methyl-4-propyl-4,5-dihydro-2H-pyridazin-3-one; | | | |
| 200 | 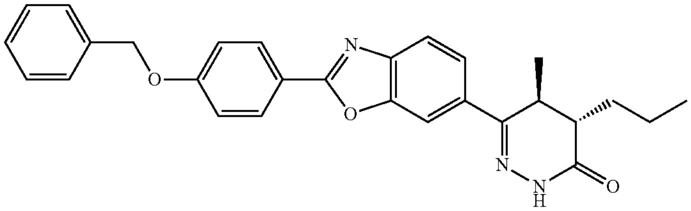 [SMILES: CCC[C@@H]1C(=O)NN=C(c2ccc3nc(-c4ccc(OCc5ccccc5)cc4)oc3c2)[C@H]1C] | 12.1% | $(M + H)^+ = 454$ | 1.63 min (method C) |
| | trans-6-[2-(4-benzoxy-phenyl)-benzoxazol-6-yl]-5-methyl-4-propyl-4,5-dihydro-2H-pyridazin-3-one; | | | |

The following stereoisomers may be isolated by separation by chiral HPLC using method F:

| time in min (retention time) | flow rate in ml/min | eluted peak |
|---|---|---|
| 3.78 | 9.5 | 1 |
| 4.32 | 9.5 | 2 |
| 4.73 | 9.5 | 3 |
| 5.46 | 9.5 | 4 |

| Ex. | Structural formula | Yield | Mass peak(s) | HPLC |
|---|---|---|---|---|
| 147 | 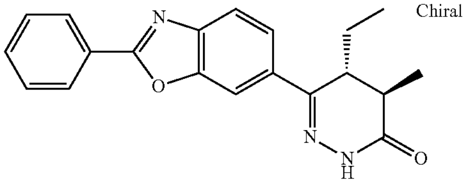 [SMILES: CC[C@H]1C(c2ccc3nc(-c4ccccc4)oc3c2)=NNC(=O)[C@@H]1C] Chiral | 30% | $(M + H)^+ = 334$ | 1.57 min (method A) |
| | (4R,5R)-5-ethyl-4-methyl-6-(2-phenyl-benzoxazol-6-yl)-4,5-dihydro-2H-pyridazin-3-one; | | | |

Example 205

6-ethyl-5-(2-phenyl-6,7-dihydro-4H-oxazolo[5,4-c]pyridin-5-yl)-3,6-dihydro-[1,3,4]oxadiazin-2-one

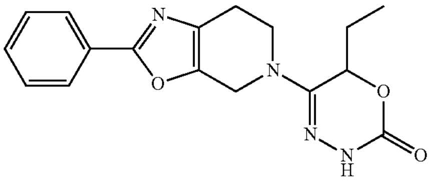 [SMILES: CCC1OC(=O)NN=C1N1CCc2nc(-c3ccccc3)oc2C1]

(a) 2-hydroxy-1-(2-phenyl-6,7-dihydro-4H-oxazolo[5,4-c]pyridin-5-yl)butan-1-one 1.14 g (4.80 mmol) 2-phenyl-4,5,6,7-tetrahydro-oxazolo[5,4-c]pyridine×HCl, 500.00 g (4.80 mmol) 2-hydroxybutanoic acid are placed in 10 mL DMF. Then 2.60 mL (18.51 mmol) triethylamine and 2.10 g (5.52 mmol) HATU are added and the mixture is stirred for 30 min at RT. The DMF is eliminated i.V., the residue is added to DCM and extracted 1 time each with 5% potassium hydrogen carbonate solution and 1N HCl. The solvent of the org. phase is eliminated in vacuo and the residue is purified on silica gel. (Eluant: cyclohexane/EA).

Yield: 720 mg (52.4%)

$R_t$-time: 1.23 min (method C)

$C_{16}H_{18}N_2O_3$ (286.33)

Mass spectrum: $(M+H)^+=287$

(b) 2-(tert-butyl-dimethyl-silanyloxy)-1-(2-phenyl-6,7-dihydro-4H-oxazolo[5,4-c]pyridin-5-yl)-butan-1-one 710.00 mg (2.48 mmol) 2-hydroxy-1-(2-phenyl-6,7-dihydro-4H-oxazolo[5,4-c]pyridin-5-yl)-butan-1-one are placed in 10 mL DMF and combined with 340.00 mg (4.99 mmol) imidazole. Then 600.00 mg (3.98 mmol) tert.-butyl-chlorodimethyl-silane and 30.00 mg (0.25 mmol) DMAP are added and the mixture is stirred overnight at RT. The DMF is eliminated i.V., the residue is added to DCM and extracted 1 time each with H2O, 1N HCl and saturated sodium chloride solution. The solvent of the org. phase is eliminated in vacuo and the residue is purified on silica gel. (Eluant: cyclohexane/EA).

Yield: 684 mg (68.9%)

$R_t$-time: 1.66 min (method C)

$C_{22}H_{32}N_2O_3Si$ (400.59)

Mass spectrum: $(M+H)^+=401$ (c) 2-(tert-butyl-dimethyl-silanyloxy)-1-(2-phenyl-6,7-dihydro-4H-oxazolo[5,4-c]pyridin-5-yl)-butan-1-thione 680.00 mg (1.70 mmol) 2-(tert-butyl-dimethyl-silanyloxy)-1-(2-phenyl-6,7-dihydro-4H-oxazolo[5,4-c]pyridin-5-yl)-butan-1-one and 1.40 g (3.46 mmol) Lawesson's reagent are placed in 35 mL toluene and stirred overnight at 90° C. The solvent of the reaction mixture is eliminated in vacuo and the residue is purified on silica gel. (Eluant: cyclohexane/EA).

Yield: 315 mg (44.5%)

$R_t$-time: 1.74 min (method C)

$C_{22}H_{32}N_2O_2SSi$ (416.65)

Mass spectrum: $(M+H)^+=417$ (d) 2-hydroxy-1-(2-phenyl-6,7-dihydro-4H-oxazolo[5,4-c]pyridin-5-yl)-butan-1-thione 310.00 mg (744 μmol) 2-(tert-butyl-dimethyl-silanyloxy)-1-(2-phenyl-6,7-dihydro-4H-oxazolo[5,4-c]pyridin-5-yl)-butan-1-thione are placed in 10 mL DCM, 2.50 mL TFA are added and the mixture is stirred for 4 h at RT. The solvent of the reaction mixture is eliminated in vacuo and the residue is purified on silica gel. (Eluant: cyclohexane/EA).

Yield: 192 mg (85.3%)

$R_t$-time: 1.41 min (method C)

$C_{16}H_{18}N_2O_2S$ (302.39)

Mass spectrum: $(M+H)^+=303$ (e) Ethyl N'-[2-hydroxy-1-(2-phenyl-6,7-dihydro-4H-oxazolo[5,4-c]pyridin-5-yl)-butylidene]-hydrazinecarboxylate 185.00 mg (612 μmol) 2-hydroxy-1-(2-phenyl-6,7-dihydro-4H-oxazolo[5,4-c]pyridin-5-yl)-butan-1-thione, 70.00 mg (672 μmol) ethylhydrazinecarboxylate and 200.00 mg (628 μmol) mercury acetate are placed in 10 mL THF and the mixture is stirred for 2 h at RT. The reaction mixture is filtered through silica gel suction and the solvent is eliminated in vacuo.

Yield: 330 mg (94.1%)

$R_t$-time: 1.15 min (method C)

$C_{19}H_{24}N_4O_4$ (372.42)

Mass spectrum: $(M+H)^+=373$ (f) 6-ethyl-5-(2-phenyl-6,7-dihydro-4H-oxazolo[5,4-c]pyridin-5-yl)-3,6-dihydro-[1.3.4]oxadiazin-2-one 330.00 mg (576 μmol) ethyl N'-[2-hydroxy-1-(2-phenyl-6,7-dihydro-4H-oxazolo[5,4-c]pyridin-5-yl) butylidene]-hydrazinecarboxylate are placed in 10 mL EtOH, a solution of 280.00 mg (12.17 mmol) sodium in 10 mL EtOH is added and the mixture is stirred overnight at RT. The reaction mixture is adjusted to pH 5-6 with ethanolic HCl and the solvent is eliminated in vacuo. The residue is extracted with EA and H2O, the organic phase is dried and the solvent is eliminated in vacuo. The residue is purified on silica gel. (Eluant: cyclohexane/EA).

Yield: 107 mg (56.9%)

$R_t$-time: 1.25 min (method C)

$C_{17}H_{18}N_4O_3$ (326.35)

Mass spectrum: $(M+H)^+=327$

The following stereoisomers may be isolated by separation by chiral HPLC using method J:

Mobile phase: A: 70% CO2; B: 30% isopropanol+0.2% diethylamine (DEA)

| time in min (retention time) | flow rate in ml/min | eluted peak |
|---|---|---|
| 7.66 | 4 | 1 |
| 8.88 | 4 | 2 |

| Ex. | Structural formula | | Yield | Mass peak(s) | HPLC |
|---|---|---|---|---|---|
| 206 | 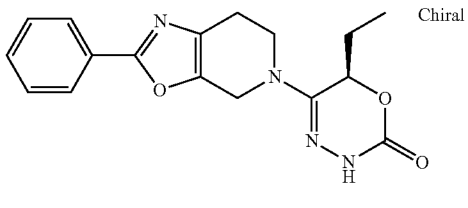 [SMILES: CC[C@H]1OC(=O)NN=C1N1CCc2nc(-c3ccccc3)oc2C1] (R)-6-ethyl-5-(2-phenyl-6,7-dihydro-4H-oxazolo[5,4-c]pyridin-5-yl)-3,6-dihydro-[1.3.4]oxadiazin-2-one; | Chiral | 28.6% | $(M + H)^+ = 327$ | 1.25 min (method C) |
| 207 | 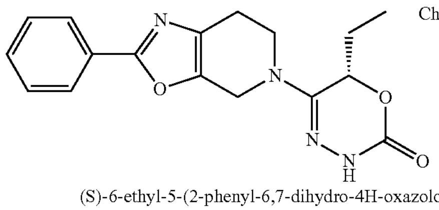 (S)-6-ethyl-5-(2-phenyl-6,7-dihydro-4H-oxazolo[5,4-c]pyridin-5-yl)-3,6-dihydro-[1.3.4]oxadiazin-2-one; | Chiral | 28.6% | $(M + H)^+ = 327$ | 1.25 min (method C) |

Example 213

6-[2-(4-allyloxy-phenyl)-benzoxazol-6-yl]-5-ethyl-4,5-dihydro-2H-pyridazin-3-one

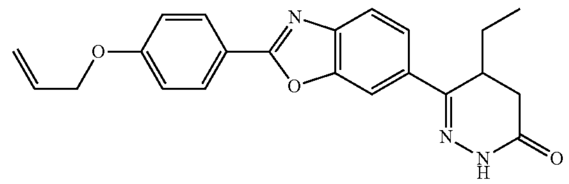 [SMILES: C=CCOc1ccc(-c2nc3ccc(C4=NNC(=O)CC4CC)cc3o2)cc1]

(a) 4-[6-(4-ethyl-6-oxo-1,4,5,6-tetrahydropyridazin-3-yl)-benzoxazol-2-yl]-phenyl trifluoro-methanoate 100 mg (298 μmol) 5-ethyl-6-[2-(4-hydroxy-phenyl)-benzoxazol-6-yl]-4,5-dihydro-2H-pyridazin-3-one, 140 mg (392 μmol) N-phenyltrifluoromethanesulphonamide and 10 ml DMF are taken. At 0° C. 55.04 μL triethylamine are added and then the mixture is stirred overnight at RT. Then it is diluted with DCM, and extracted with 10% sodium carbonate solution, H2O and sat. saline solution. The solv. of the org. phase is eliminated i.V. The residue is purified on silica gel (eluant: DCM/methanol)

Yield: 105.0 mg (75.3%)

$R_t$-time: 1.54 min (method C)

$C_{20}H_{16}F_3N_3O_5S$ (467.42)

Mass spectrum: $(M+H)^+$=468

(b) 6-[2-(4-allyloxy-phenyl)-benzoxazol-6-yl]-5-ethyl-4,5-dihydro-2H-pyridazin-3-one 105 mg (225 μmol) 4-[6-(4-ethyl-6-oxo-1,4,5,6-tetrahydropyridazin-3-yl)-benzoxazol-2-yl]-phenyl trifluoro-methanoate in 5 mL DMF are placed under argon, 15.37 μL (225 μmol) ally alcohol, 62 mg (449 μmol) potassium carbonate and 7 mg (6 μmol) tetrakis-(triphenylphosphine)-palladium(0) are added and the mixture is stirred at 80° C. The reaction mixture is diluted with DCM and extracted successively with 10% sodium carbonate solution and sat. saline solution. The solv. of the organic phase is eliminated i.V. The residue is purified with semipreparative HPLC-MS. (xBridge, MeOH/H2O+TFA)

Yield: 7.0 mg (8.3%)

$R_t$-time: 1.51 min (method C)

$C_{22}H_{21}N_3O_3$ (375.42)

Mass spectrum: $(M+H)^+$=376

Example 214

5-ethyl-6-{2-[4-(2-methoxy-ethoxy)-phenyl]-benzoxazol-6-yl}-4,5-dihydro-2H-pyridazin-3-one

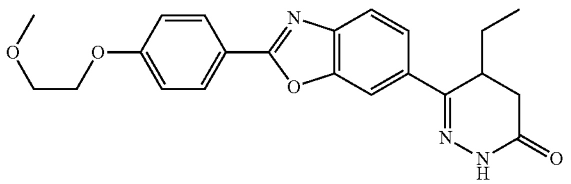 [SMILES: CCC1CC(=O)NN=C1c1ccc2nc(-c3ccc(OCCOC)cc3)oc2c1]

40 mg (119 μmol) 5-ethyl-6-[2-(4-hydroxy-phenyl)-benzoxazol-6-yl]-4,5-dihydro-2H-pyridazin-3-one, 19 μL (241 μmol) 2-methoxyethanol, 66 mg (251 μmol) diphenyl-2-pyridylphosphine and 10 ml THF are placed under protective gas. At 0° C. 58 mg (252 μmol) DBAD are added and then the mixture is stirred overnight at RT. Then it is diluted with EA and extracted with 10% sodium carbonate solution. The organic phase is stirred with 20 mL of 4N HCl for 5 min and then extracted. The organic phase is washed with saturated saline solution and then the solv. is eliminated i.V. The residue is purified on silica gel. (Eluant: DCM/MeOH/ammonia) The solv. of the corresponding fractions is eliminated i.V. and the residue is crystallised with cyclohexane/EA.

Yield: 24.0 mg (51.1%)

$R_t$-time: 1.38 min (method C)

$C_{22}H_{23}N_3O_4$ (393.44)

Mass spectrum: $(M+H)^+$=394

Example 215

5-ethyl-6-(2-{4-[2-(ethyl-isopropyl-amino)-ethoxy]-phenyl}-benzoxazol-6-yl)-4,5-dihydro-2H-pyridazin-3-one

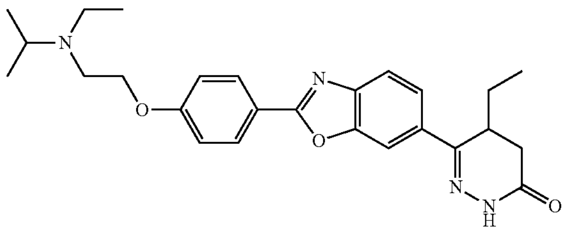 [SMILES: CCC1CC(=O)NN=C1c1ccc2nc(-c3ccc(OCCN(CC)C(C)C)cc3)oc2c1]

40 mg (119 μmol) 5-ethyl-6-[2-(4-hydroxy-phenyl)-benzoxazol-6-yl]-4,5-dihydro-2H-pyridazin-3-one, 31 mg (238 μmol) 2-(ethyl-isopropyl-amino)-ethanol, 66 mg (251 μmol) triphenylphosphine and 5 ml THF are placed under protective gas. At 0° C., 58 mg (251 μmol) of DBAD are added and then the mixture is stirred overnight at RT. Then it is diluted with EA and extracted with 10% sodium carbonate solution. The organic phase is stirred with 15 mL of 4N HCl for 5 min and then extracted twice with diethyl ether. The acid H2O phase is made basic with sodium carbonate solution and extracted 3 times with DCM. The organic phase is washed with saturated saline solution and then the solv. is eliminated i.V. The residue is recrystallised with cyclohexane/EA.

Yield: 22.7 mg (42.4%)

$R_t$-time: 1.14 min (method C)
$C_{26}H_{32}N_4O_3$ (448.56)
Mass spectrum: $(M+H)^+$=449
The following compounds may be prepared analogously:

| Ex. | Structural formula | Yield | Mass peak(s) | HPLC |
|---|---|---|---|---|
| 216 | 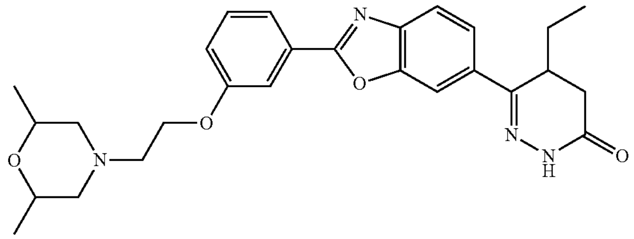 [SMILES: CCC1CC(=O)NN=C1c1ccc2nc(-c3cccc(OCCN4CC(C)OC(C)C4)c3)oc2c1]<br>6-(2-{3-[2-(2,6-dimethyl-morpholin-4-yl)-ethoxy]-phenyl}-benzoxazol-6-yl)-5-ethyl-4,5-dihydro-2H-pyridazin-3-one; | 25.6% | $(M + H)^+$ = 477 | 1.19 min (method C) |
| 217 | 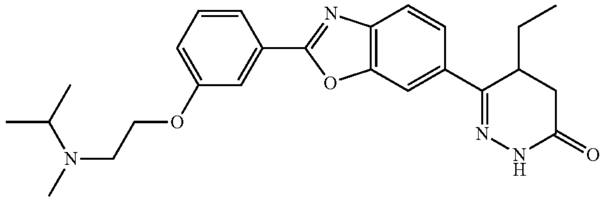 [SMILES: CCC1CC(=O)NN=C1c1ccc2nc(-c3cccc(OCCN(C)C(C)C)c3)oc2c1]<br>5-ethyl-6-(2-{3-[2-(2-(isopropyl-methyl-amino)-ethoxy]-phenyl}-benzoxazol-6-yl)-4,5-dihydro-2H-pyridazin-3-one; | 31.7% | $(M + H)^+$ = 435 | 1.16 min (method C) |
| 218 | 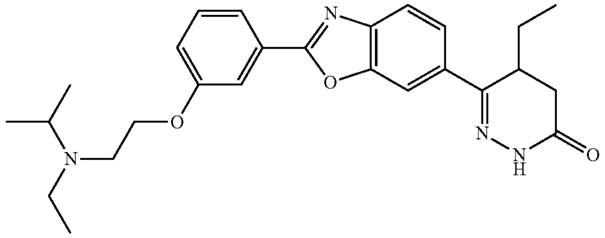 [SMILES: CCC1CC(=O)NN=C1c1ccc2nc(-c3cccc(OCCN(CC)C(C)C)c3)oc2c1]<br>5-ethyl-6-(2-{3-[2-(2-(ethyl-isopropyl-amino)-ethoxy]-phenyl}-benzoxazol-6-yl)-4,5-dihydro-2H-pyridazin-3-one; | 55.6% | $(M + H)^+$ = 449 | 1.16 min (method C) |
| 219 | 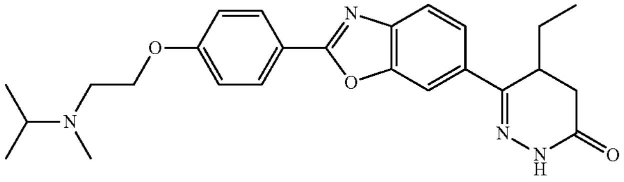 [SMILES: CCC1CC(=O)NN=C1c1ccc2nc(-c3ccc(OCCN(C)C(C)C)cc3)oc2c1]<br>5-ethyl-6-(2-{4-[2-(isopropyl-methyl-amino)-ethoxy]-phenyl}-benzoxazol-6-yl)-4,5-dihydro-2H-pyridazin-3-one; | 58.8% | $(M + H)^+$ = 435 | 1.13 min (method C) |
| 220 | 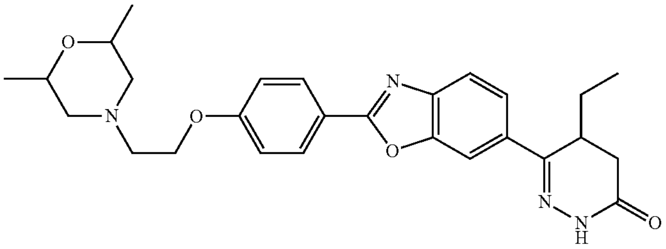 [SMILES: CCC1CC(=O)NN=C1c1ccc2nc(-c3ccc(OCCN4CC(C)OC(C)C4)cc3)oc2c1]<br>6-(2-{4-[2-(2,6-dimethyl-morpholin-4-yl)-ethoxy]-phenyl}-benzoxazol-6-yl)-5-ethyl-4,5-dihydro-2H-pyridazin-3-one; | 12.8% | $(M + H)^+$ = 477 | 1.16 min (method C) |

-continued

| Ex. | Structural formula | Yield | Mass peak(s) | HPLC |
|---|---|---|---|---|
| 221 | 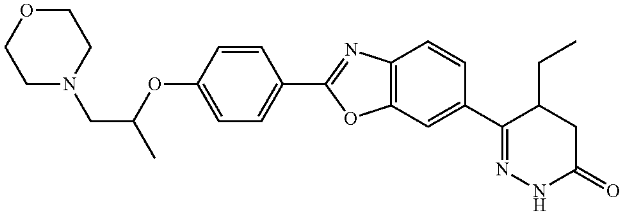 [SMILES: CCC1CC(=O)NN=C1c1ccc2nc(-c3ccc(OC(C)CN4CCOCC4)cc3)oc2c1] | 77.6% | $(M + H)^+ = 463$ | 1.13 min (method C) |
| | 5-ethyl-6-{2-[4-(1-methyl-2-morpholin-4-yl-ethoxy)-phenyl]-benzoxazol-6-yl}-4,5-dihydro-2H-pyridazin-3-one; | | | |
| 222 | 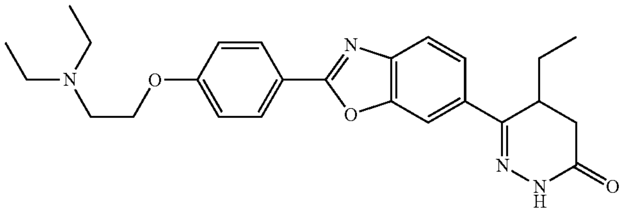 [SMILES: CCC1CC(=O)NN=C1c1ccc2nc(-c3ccc(OCCN(CC)CC)cc3)oc2c1] | 74.9% | $(M + H)^+ = 435$ | 1.13 min (method C) |
| | 6-{2-[4-(2-diethylamino-ethoxy)-phenyl]-benzoxazol-6-yl}-5-ethyl-4,5-dihydro-2H-pyridazin-3-one; | | | |
| 223 | 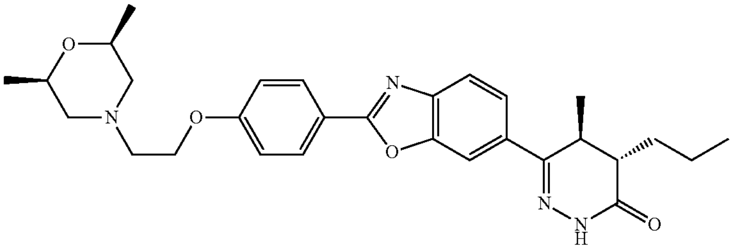 [SMILES: CCC[C@@H]1C(=O)NN=C(c2ccc3nc(-c4ccc(OCCN5C[C@@H](C)O[C@@H](C)C5)cc4)oc3c2)[C@H]1C] | 21.2% | $(M + H)^+ = 505$ | 1.23 min (method C) |
| | Trans-6-(2-{4-[2-(2S,6R-dimethyl-morphoin-4-yl)-ethoxy]-phenyl}-benzoxazol-6-yl)-5-methyl-4-propyl-4,5-dihydro-2H-pyridazin-3-one; | | | |
| 224 | 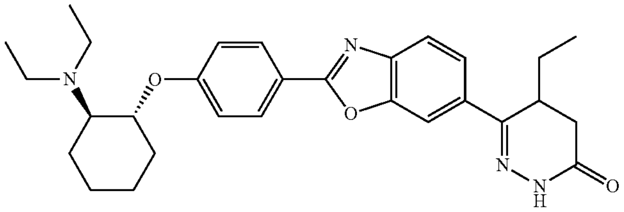 [SMILES: CCC1CC(=O)NN=C1c1ccc2nc(-c3ccc(O[C@@H]4CCCC[C@H]4N(CC)CC)cc3)oc2c1] | 17.2% | $(M + H)^+ = 489$ | 1.23 min (method C) |
| | 6-{2-[4-(trans-2-diethylamino-cyclohexyloxy)-phenyl]-benzoxazol-6-yl}-5-ethyl-4,5-dihydro-2H-pyridazin-3-one; | | | |
| 225 | 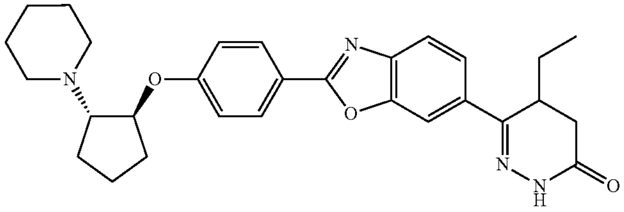 [SMILES: CCC1CC(=O)NN=C1c1ccc2nc(-c3ccc(O[C@H]4CCC[C@@H]4N4CCCCC4)cc3)oc2c1] | 55.8% | $(M + H)^+ = 487$ | 1.24 min (method C) |
| | 5-ethyl-6-{2-[4-(trans-2-piperidin-1-yl-cyclopentyloxy)-phenyl]-benzoxazol-6-yl}-4,5-dihydro-2H-pyridazin-3-one; | | | |

-continued

| Ex. | Structural formula | Yield | Mass peak(s) | HPLC |
|---|---|---|---|---|
| 226 | 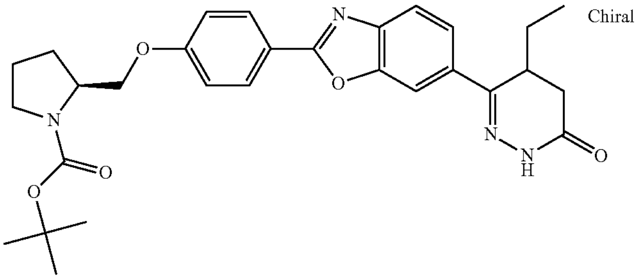 [SMILES: CCC1CC(=O)NN=C1c1ccc2nc(-c3ccc(OC[C@@H]4CCCN4C(=O)OC(C)(C)C)cc3)oc2c1] | 59.1% | $(M + H)^+ = 519$ | 1.60 min (method C) |
| | tert-butyl 2-{4-[6-(4-ethyl-6-oxo-1,4,5,6-tetrahydro-pyridazin-3-yl)]-benzoxazol-2-yl]-phenoxymethyl}-S-pyrrolidine-1-carboxylate; | | | |
| 227 | 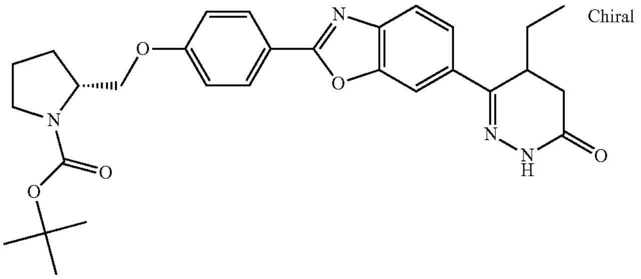 [SMILES: CCC1CC(=O)NN=C1c1ccc2nc(-c3ccc(OC[C@H]4CCCN4C(=O)OC(C)(C)C)cc3)oc2c1] | 55.4% | $(M + H)^+ = 519$ | 1.59 min (method C) |
| | tert-butyl 2-{4-[6-(4-ethyl-6-oxo-1,4,5,6-tetrahydro-pyridazin-3-yl)]-benzoxazol-2-yl]-phenoxymethyl}-R-pyrrolidin-1-carboxylate; | | | |

Example 228

6-{2-[4-(1,1-dimethyl-2-pyrrolidin-1-yl-ethoxy)-phenyl]-benzoxazol-6-yl}-5-ethyl-4,5-dihydro-2H-pyridazin-3-one

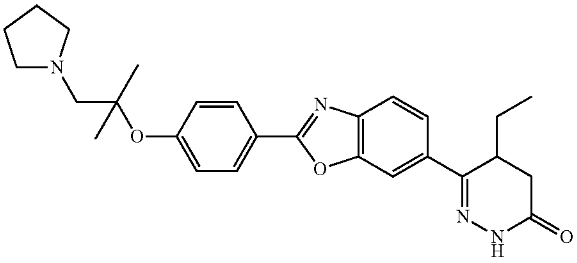 [SMILES: CCC1CC(=O)NN=C1c1ccc2nc(-c3ccc(OC(C)(C)CN4CCCC4)cc3)oc2c1]

40 mg (119 μmol) 5-ethyl-6-[2-(4-hydroxy-phenyl)-benzoxazol-6-yl]-4,5-dihydro-2H-pyridazin-3-one, 88 mg (616 μmol) 2-methyl-2-(1-pyrrolidinyl)-1-propanol, 97 mg (371 μmol) triphenylphosphine and 5 ml THF are placed under protective gas. At 0° C., 85 mg (371 μmol) DBAD are added and then the mixture is stirred overnight at RT. Then it is diluted with EA and extracted with 10% sodium carbonate solution. The organic phase is stirred with 15 mL of 4N HCl for 5 min and then extracted twice with diethyl ether. The acid H2O phase is made basic with sodium carbonate solution and extracted 3 times with DCM. The organic phase is washed with saturated saline solution and then the solv. is eliminated i.V. The residue is separated on silica gel. (Eluant: DCM/MeOH+ammonia)

Yield: 7.7 mg (14.0%)

$R_t$-time: 1.18 min (method C)

$C_{27}H_{32}N_4O_3$ (460.57)

Mass spectrum: $(M+H)^+$=461

The following may be isolated as secondary compounds:

| Ex. | Structural formula | Yield | Mass peak(s) | HPLC |
|---|---|---|---|---|
| 229 | 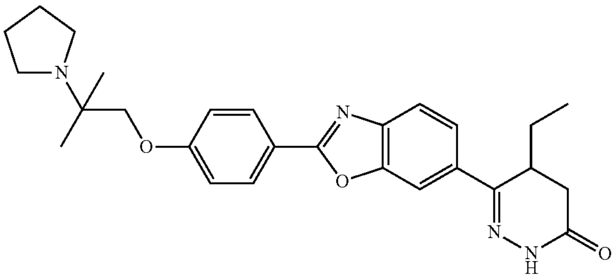 [SMILES: CCC1CC(=O)NN=C1c1ccc2nc(-c3ccc(OCC(C)(C)N4CCCC4)cc3)oc2c1] | 5.8% | $(M + H)^+ = 461$ | 1.16 min (method C) |
| | 5-ethyl-6-{2-[3-(2-methyl-2-piperidin-1-yl-propoxy)-phenyl]-benzoxazol-6-yl}-4,5-dihydro-2H-pyridazin-3-one; | | | |

The following compounds may be prepared analogously:

| Ex. | Structural formula | Yield | Mass peak(s) | HPLC |
|---|---|---|---|---|
| 230 | 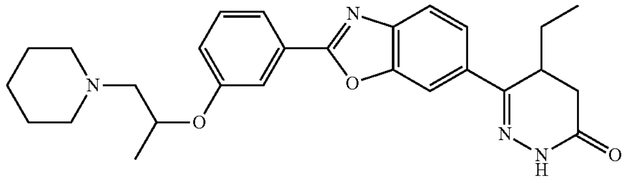 [SMILES: CCC1CC(=O)NN=C1c1ccc2nc(-c3cccc(OC(C)CN4CCCCC4)c3)oc2c1]<br>5-ethyl-6-{2-[3-(1-methyl-2-piperidin-1-yl-ethoxy)-phenyl]-benzoxazol-6-yl}-4,5-dihydro-2H-pyridazin-3-one; | 29.1% | $(M + H)^+ = 461$ | 1.21 min (method C) |
| 231 | 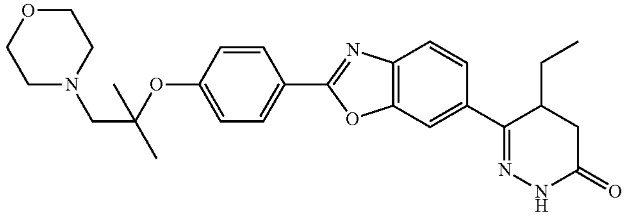 [SMILES: CCC1CC(=O)NN=C1c1ccc2nc(-c3ccc(OC(C)(C)CN4CCOCC4)cc3)oc2c1]<br>6-{2-[4-(1,1-dimethyl-2-morpholin-4-yl-ethoxy)-phenyl]-benzoxazol-6-yl}-5-ethyl-4,5-dihydro-2H-pyridazin-3-one; | 32.5% | $(M + H)^+ = 477$ | 1.15 min (method C) |
| 232 | 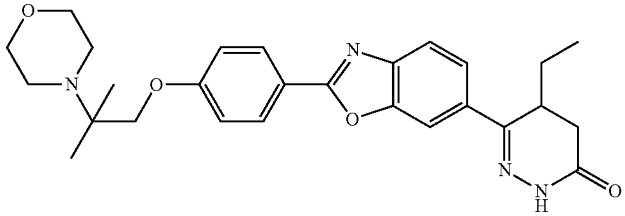 [SMILES: CCC1CC(=O)NN=C1c1ccc2nc(-c3ccc(OCC(C)(C)N4CCOCC4)cc3)oc2c1]<br>5-ethyl-6-{2-[4-(2-methyl-2-morpholin-4-yl-propoxy)-phenyl]-benzoxazol-6-yl}-4,5-dihydro-2H-pyridazin-3-one; | 10.6% | $(M + H)^+ = 477$ | 1.12 min (method C) |
| 233 | 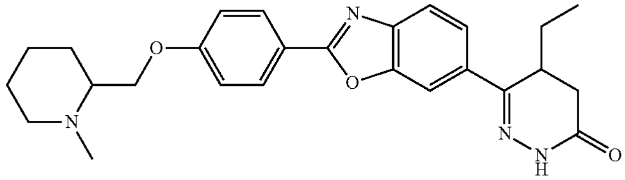 [SMILES: CCC1CC(=O)NN=C1c1ccc2nc(-c3ccc(OCC4CCCCN4C)cc3)oc2c1]<br>5-ethyl-6-{2-[4-(1-methyl-2-piperidin-2-yl-methoxy)-phenyl]-benzoxazol-6-yl}-4,5-dihydro-2H-pyridazin-3-one; | 21.7% | $(M + H)^+ = 447$ | 1.15 min (method C) |
| 234 | 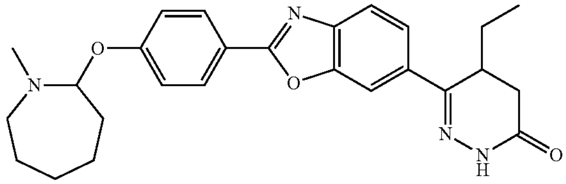 [SMILES: CCC1CC(=O)NN=C1c1ccc2nc(-c3ccc(OC4CCCCCN4C)cc3)oc2c1]<br>5-ethyl-6-{2-[4-(1-methyl-2-azepan-2-yloxy)-phenyl]-benzoxazol-6-yl}-4,5-dihydro-2H-pyridazin-3-one; | 33.5% | $(M + H)^+ = 447$ | 1.16 min (method C) |

The following stereoisomers may be isolated by separation by chiral HPLC using method G:

Mobile phase: A: 65% CO2; B: 35% MeOH+0.2% diethylamine (DEA)

| time in min (retention time) | flow rate in ml/min | eluted peak |
|---|---|---|
| 2.62 | 4 | 1 |
| 3.20 | 4 | 2 |
| 3.73 | 4 | 3 |
| 4.73 | 4 | 4 |

| Ex. | Structural formula | Yield | Mass peak(s) | HPLC |
|---|---|---|---|---|
| 235 | 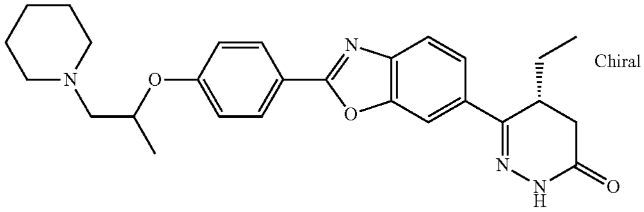 [SMILES: CC[C@@H]1CC(=O)NN=C1c1ccc2nc(-c3ccc(OC(C)CN4CCCCC4)cc3)oc2c1] | 11.5% | $(M + H)^+ = 461$ | 1.16 min (method C) |
| | 5(R)-ethyl-6-{2-[3-(1-methyl-2-piperidin-1-yl-ethoxy)-phenyl]-benzoxazol-6-yl}-4,5-dihydro-2H-pyridazin-3-one; | | | |
| 236 | 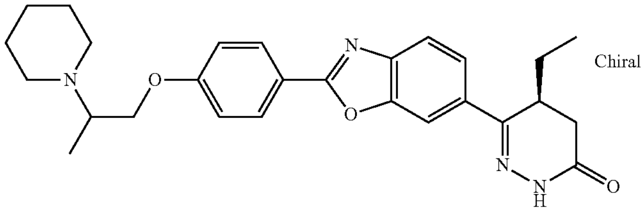 [SMILES: CC[C@H]1CC(=O)NN=C1c1ccc2nc(-c3ccc(OCC(C)N4CCCCC4)cc3)oc2c1] | 9.9% | $(M + H)^+ = 461$ | 1.17 min (method C) |
| | 5(S)-ethyl-6-{2-[4-(2-piperidin-1-yl-propoxy)-phenyl]-benzoxazol-6-yl}-4,5-dihydro-2H-pyridazin-3-one; | | | |
| 237 | 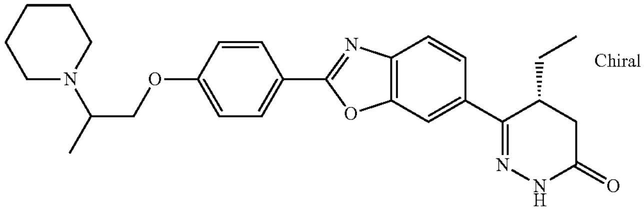 [SMILES: CC[C@@H]1CC(=O)NN=C1c1ccc2nc(-c3ccc(OCC(C)N4CCCCC4)cc3)oc2c1] | 5.6% | $(M + H)^+ = 461$ | 1.15 min (method C) |
| | 5(R)-ethyl-6-{2-[4-(2-piperidin-1-yl-propoxy)-phenyl]-benzoxazol-6-yl}-4,5-dihydro-2H-pyridazin-3-one; | | | |

Example 238

5-ethyl-6-{2-[4-(S-pyrrolidin-2-yl-methoxy)-phenyl]-benzoxazol-6-yl}-4,5-dihydro-2H-pyridazin-3-one×HCl

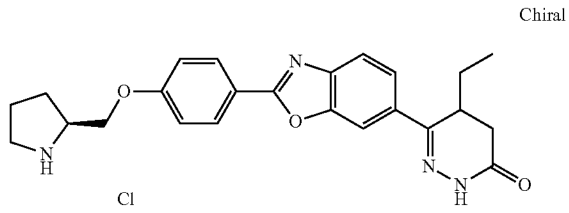 [SMILES: CCC1CC(=O)NN=C1c1ccc2nc(-c3ccc(OC[C@@H]4CCCN4)cc3)oc2c1 ; Cl]

57 mg (110 μmol) tert-butyl 2-{4-[6-(4-ethyl-6-oxo-1,4,5,6-tetrahydro-pyridazin-3-yl)]-benzoxazol-2-yl]-phenoxymethyl}-S-pyrrolidine-1-carboxylate and 1 mL (2 mmol/mL in diethyl ether, 2 mmol) hydrochloric acid in 10 ml DCM and stirred overnight at RT. Then the solv. is eliminated i.V. and the residue is crystallised with MeOH.

Yield: 47.2 mg (94.4%)

$R_t$-time: 1.13 min (method C)

$C_{24}H_{26}N_4O_3 \times HCl$ (454.95)

Mass spectrum: $(M+H)^+=419$

The following compounds may be prepared analogously:

| Ex. | Structural formula | Yield | Mass peak(s) | HPLC |
|---|---|---|---|---|
| 239 | 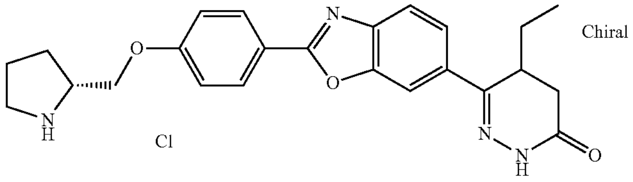 [SMILES: CCC1CC(=O)NN=C1c1ccc2nc(-c3ccc(OC[C@H]4CCCN4)cc3)oc2c1 ; Cl] | 52.5% | $(M + H)^+ = 419$ | 1.13 min (method C) |
| | 5-ethyl-6-{2-[4-(R-pyrrolidin-2-yl-methoxy)-phenyl]-benzoxazol-6-yl}-4,5-dihydro-2H-pyridazin-3-one × HCl | | | |

Example 240

5-ethyl-6-{2-[4-(1-isopropyl-5-pyrrolidin-2-yl-methoxy)-phenyl]-benzoxazol-6-yl}-4,5-dihydro-2H-pyridazin-3-one Chiral

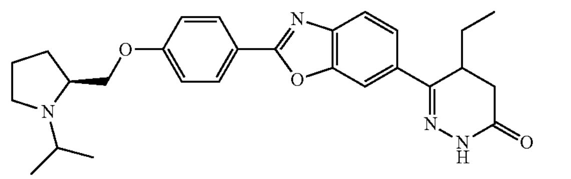

21 mg (46 μmol) 5-ethyl-6-{2-[4-(S-pyrrolidin-2-yl-methoxy)-phenyl]-benzoxazol-6-yl}-4,5-dihydro-2H-pyridazin-3-onexHCl, 6 mg (73 μmol) sodium acetate, 250 μL DMF and 2 mL dichloroethane are taken, 12 μL (165 μmol) acetone are added dropwise and the mixture is stirred for 20 min at RT. 37 mg (166 μmol) sodium triacetoxyborohydride are added stirred overnight at RT. The reaction mixture is diluted with DCM and extracted successively with 10% sodium carbonate solution and sat. saline solution. The solv. of the organic phase is eliminated i.V. and the residue is purified through KG. (DCM/MeOH+ammonia)

The solv. of the corresponding fractions is eliminated i.V. and the residue is suspended in ACN and H2O and freeze-dried.

Yield: 11.0 mg (51.7%)

$R_t$-time: 1.17 min (method C)

$C_{27}H_{32}N_4O_3$ (460.57)

Mass spectrum: $(M+H)^+$=461

The following compounds may be prepared analogously:

Example 243

5-ethyl-6-(2-{4-[2-(4-methyl-piperidin-1-yl)-ethoxy]-phenyl}-benzoxazol-6-yl)-4,5-dihydro-2H-pyridazin-3-one

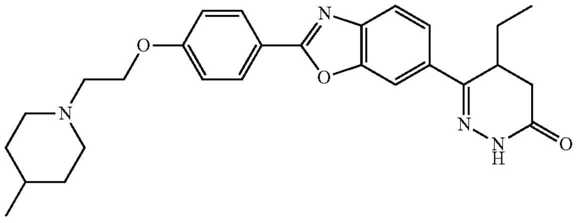

(a) 6-{2-[4-(2,2-dimethoxy-ethoxy)-phenyl]-benzoxazol-6-yl}-5-ethyl-4,5-dihydro-2H-pyridazin-3-one 100 mg (298 μmol) 5-ethyl-6-[2-(4-hydroxy-phenyl)-benzoxazol-6-yl]-4,5-dihydro-2H-pyridazin-3-one, 38.5 μL (316 μmol) 2-bromo-1,1-dimethoxy-ethane, 125 mg (904 μmol) potassium carbonate and 3 ml DMF are stirred for 6 h at 150° C. and then at RT over the weekend. Then the mixture is diluted with EA, and extracted with 10% sodium carbonate solution and then with sat. saline solution. The solv. of the org. phase is eliminated i.V. The residue is purified on silica gel (eluant: DCM/methanol) the solv. of the corresponding fractions is eliminated i.V. and the residue is recrystallised with EA/cyclohexane.

Yield: 36.0 mg (28.5%)

$R_t$-time: 1.39 min (method C)

$C_{23}H_{25}N_3O_5$ (423.46)

Mass spectrum: $(M+H)^+$=424

| Ex. | Structural formula | Yield | Mass peak(s) | HPLC |
|---|---|---|---|---|
| 241 | 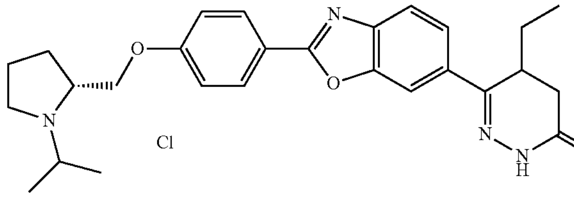 Chiral | 73.6% | $(M + H)^+ = 461$ | 1.16 min (method C) |
| | 5-ethyl-6-{2-[4-(1-isopropyl-R-pyrrolidin-2-yl-methoxy)-phenyl]-benzoxazol-6-yl}-4,5-dihydro-2H-pyridazin-3-one; | | | |
| 242 | 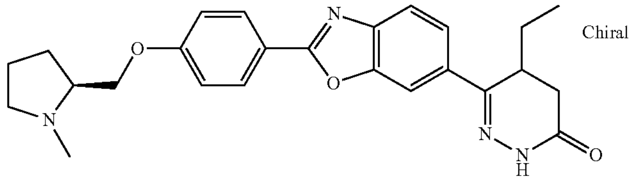 [SMILES: CCC1CC(=O)NN=C1c1ccc2nc(-c3ccc(OC[C@@H]4CCCN4C)cc3)oc2c1] Chiral | 50.1% | $(M + H)^+ = 433$ | 1.12 min (method C) |
| | 5-ethyl-6-{2-[4-(1-methyl-S-pyrrolidin-2-yl-methoxy)-phenyl]-benzoxazol-6-yl}-4,5-dihydro-2H-pyridazin-3-one; | | | |

(b) {4-[6-(4-ethyl-6-oxo-1,4,5,6-tetrahydro-pyridazin-3-yl)-benzoxazol-2-yl]-phenoxy}-acetaldehyde 22.2 mg (52 μmol) 6-{2-[4-(2,2-dimethoxy-ethoxy)-phenyl]-benzoxazol-6-yl}-5-ethyl-4,5-dihydro-2H-pyridazin-3-one, 130 μL (4 mmol/mL; 520 μmol) HCl and 2 ml dioxane are stirred for 3 h at 50° C. Then the mixture is diluted with EA, extracted with H2O and then with 10% sodium carbonate solution. The solv. of the org. phase is eliminated i.V.

Yield: 11.0 mg (55.6%)

$R_t$-time: 1.28 min (method C)

$C_{21}H_{19}N_3O_4$ (377.39)

Mass spectrum: $(M+H)^+$=376

(c) 5-ethyl-6-(2-{4-[2-(4-methyl-piperidin-1-yl)-ethoxy]-phenyl}-benzoxazol-6-yl)-4,5-dihydro-2H-pyridazin-3-one 11 mg (29 μmol) {4-[6-(4-ethyl-6-oxo-1,4,5,6-tetrahydro-pyridazin-3-yl)-benzoxazol-2-yl]-phenoxy}-acetaldehyde are placed in 2 mL DCM and 250 μL DMF. 1.70 μL (29 mmol) acetic acid and 3 μL (42 μmol) 4-methylpiperidine are added and the mixture is stirred for 20 min at RT. Then 9 mg (42 μmol) sodium triacetoxyborohydride are added and the mixture is stirred overnight at RT. The reaction mixture is diluted with DCM and extracted successively with 10% sodium carbonate solution and sat. saline solution. The solv. of the organic phase is eliminated i.V. and the residue is purified through KG. (DCM/MeOH+ammonia) the solv. of the corresponding fractions is eliminated i.V. and the residue is crystallised from EN petroleum ether.

Yield: 3.0 mg (22.3%)

$R_t$-time: 1.18 min (method C)

$C_{27}H_{32}N_4O_3$ (460.57)

Mass spectrum: $(M+H)^+$=461

The following compounds may be prepared analogously:

| Ex. | Structural formula | Yield | Mass peak(s) | HPLC |
|---|---|---|---|---|
| 244 | 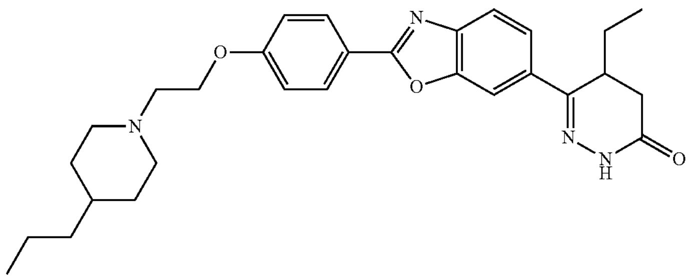 [SMILES: CCCC1CCN(CCOc2ccc(-c3nc4ccc(C5=NNC(=O)CC5CC)cc4o3)cc2)CC1]<br>5-ethyl-6-(2-{4-[2-(4-propyl-piperidin-1-yl)-ethoxy]-phenyl}-benzoxazol-6-yl)-4,5-dihydro-2H-pyridazin-3-one; | 32.2% | $(M + H)^+ = 489$ | 1.29 min (method C) |
| 245 | 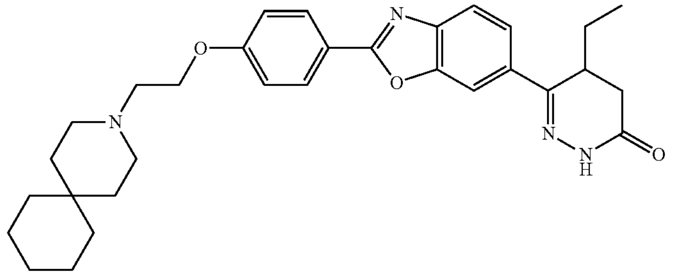 [SMILES: CCC1CC(=O)NN=C1c1ccc2nc(-c3ccc(OCCN4CCC5(CCCCC5)CC4)cc3)oc2c1]<br>6-(2-{4-[2-(3-aza-spiro[5.5]undec-3-yl)-ethoxy]-phenyl}-benzoxazol-6-yl)-5-ethyl-4,5-dihydro-2H-pyridazin-3-one; | 49.1% | $(M + H)^+ = 515$ | 1.34 min (method C) |
| 246 | 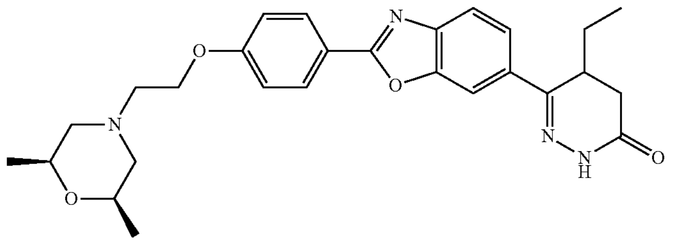 [SMILES: CCC1CC(=O)NN=C1c1ccc2nc(-c3ccc(OCCN4C[C@@H](C)O[C@@H](C)C4)cc3)oc2c1]<br>6-(2-{4-[2-(cis-2,6-dimethyl-morpholin-4-yl)-ethoxy]-phenyl}-benzoxazol-6-yl)-5-ethyl-4,5-dihydro-2H-pyridazin-3-one; | 26.7% | $(M + H)^+ = 477$ | 1.16 min (method C) |

-continued

| Ex. | Structural formula | Yield | Mass peak(s) | HPLC |
|---|---|---|---|---|
| 247 | 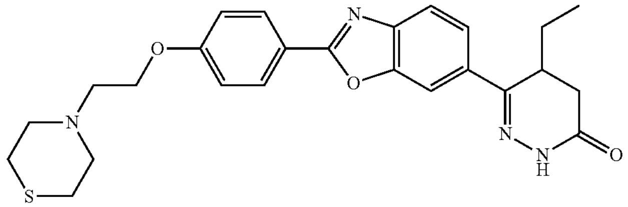 [SMILES: CCC1CC(=O)NN=C1c1ccc2nc(-c3ccc(OCCN4CCSCC4)cc3)oc2c1] | 19.7% | $(M + H)^+ = 465$ | 1.13 min (method C) |
| | 5-ethyl-6-{2-[4-(2-thiomorpholin-4-yl-ethoxy)-phenyl]-benzoxazol-6-yl}-4,5-dihydro-2H-pyridazin-3-one; | | | |
| 248 | 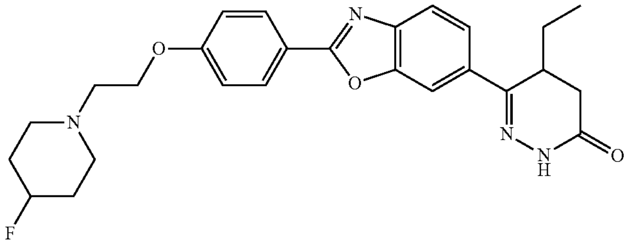 [SMILES: CCC1CC(=O)NN=C1c1ccc2nc(-c3ccc(OCCN4CCC(F)CC4)cc3)oc2c1] | 35.9% | $(M + H)^+ = 465$ | 1.12 min (method C) |
| | 5-ethyl-6-(2-{4-[2-(4-fluoro-piperidin-1-yl)-ethoxy]-phenyl}-benzoxazol-6-yl)-4,5-dihydro-2H-pyridazin-3-one; | | | |
| 249 | 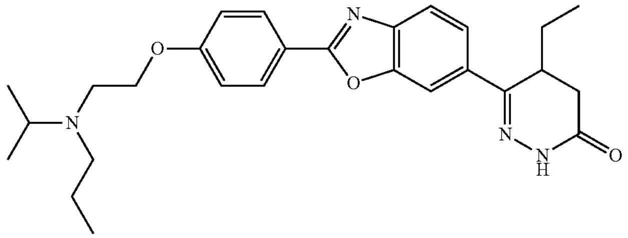 [SMILES: CCCN(CCOc1ccc(-c2nc3ccc(C4=NNC(=O)CC4CC)cc3o2)cc1)C(C)C] | 10.3% | $(M + H)^+ = 463$ | 1.16 min (method C) |
| | 5-ethyl-6-(2-{4-[2-(isopropyl-propyl-amino)-ethoxy]-phenyl}-benzoxazol-6-yl)-4,5-dihydro-2H-pyridazin-3-one; | | | |
| 250 | 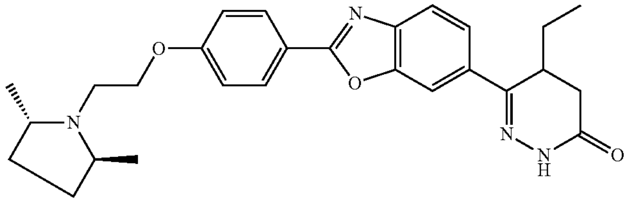 [SMILES: CCC1CC(=O)NN=C1c1ccc2nc(-c3ccc(OCCN4[C@@H](C)CC[C@@H]4C)cc3)oc2c1] | 10.3% | $(M + H)^+ = 461$ | 1.16 min (method C) |
| | 6-(2-{4-[2-((2R,5R)-trans-2,5-dimethylpyrrolidin-1-yl)-ethoxy]-phenyl}-benzoxazol-6-yl)-5-ethyl-4,5-dihydro-2H-pyridazin-3-one; | | | |

Example 251

5-ethyl-6-{2-[4-(2-hydroxy-1-methyl-ethoxy)-phenyl]-benzoxazol-6-yl}-4,5-dihydro-2H-pyridazin-3-one

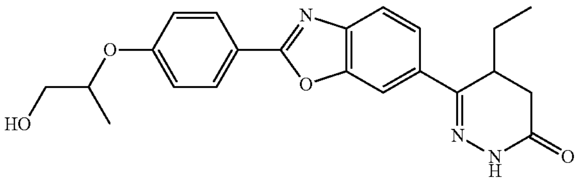 [SMILES: CCC1CC(=O)NN=C1c1ccc2nc(-c3ccc(OC(C)CO)cc3)oc2c1]

(a) 6-{2-[4-(2,2-dimethoxy-1-methyl-ethoxy)-phenyl]-benzoxazol-6-yl}-5-ethyl-4,5-dihydro-2H-pyridazin-3-one 146 mg (435 μmol) 5-ethyl-6-[2-(4-hydroxy-phenyl)-benzoxazol-6-yl]-4,5-dihydro-2H-pyridazin-3-one, 910 mg (4.89 mmol) 2-bromo-1,1-dimethoxy-propane, 720 mg (5.21 mmol) potassium carbonate and 5 ml DMF are stirred overnight at 150° C. under protective gas. Then the mixture is diluted with EA, and extracted with 10% sodium carbonate solution and then with sat. saline solution. The solv. of the org. phase is eliminated i.V. The residue is purified on silica gel (eluant: DCM/methanol)

Yield: 54.0 mg (17.0%)

$R_t$-time: 1.42/1.45 min (method C)

$C_{24}H_{27}N_3O_5$ (423.46)

Mass spectrum: $(M+H)^+$=438

(b) 2-{4-[6-(4-ethyl-6-oxo-1,4,5,6-tetrahydro-pyridazin-3-yl)-benzoxazol-2-yl]-phenoxy}-propionaldehyde 54 mg (74 μmol) 6-{2-[4-(2,2-dimethoxy-1-methyl-ethoxy)-phenyl]-benzoxazol-6-yl}-5-ethyl-4,5-dihydro-2H-pyridazin-3-one, 200 μL (4 mmol/mL; 800 μmol) HCl and 5 ml dioxane are stirred for 40 min at 80° C. Then the mixture is extracted with EA, extracted twice with H2O and then with sat. saline solution. The solv. of the org. phase is eliminated i.V.

Yield: 40.0 mg (138.0%)

$R_t$-time: min (method C)

$C_{22}H_{21}N_3O_4$ (377.39)

Mass spectrum: $(M+H_2O)^+$=410

(c) 5-ethyl-6-{2-[4-(2-hydroxy-1-methyl-ethoxy)-phenyl]-benzoxazol-6-yl}-4,5-dihydro-2H-pyridazin-3-one 40 mg (102 μmol) 2-{4-[6-(4-ethyl-6-oxo-1,4,5,6-tetrahydro-pyridazin-3-yl)-benzoxazol-2-yl]-phenoxy}-propionaldehyde are placed in 2 mL DCM and 250 μL DMF. 6 μL (104 mmol) acetic acid and 22 μL (156 μmol) diisopropylamine are added and the mixture is stirred for 40 min at RT. Then 33 mg (156 μmol) sodium triacetoxyborohydride are added and the mixture is stirred for 3.5 h at RT. The reaction mixture is diluted with DCM and extracted successively with 10% sodium carbonate solution and sat. saline solution. The solv. of the organic phase is eliminated i.V. and the residue is purified through HPLC. (xBridge, MeOH/H2O+TFA) The corresponding fractions are freeze-dried.

Yield: 6.0 mg (14.9%)

$R_t$-time: 1.33 min (method C)

$C_{22}H_{23}N_3O_4$ (393.44)

Mass spectrum: $(M+H)^+$=394

Example 256

5-methyl-6-(2-thiophen-2-yl-benzoxazol-6-yl)-2H-pyridazin-3-one

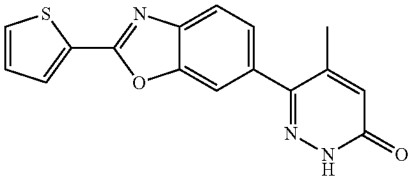 [SMILES: Cc1cc(=O)[nH]nc1-c1ccc2nc(-c3cccs3)oc2c1]

100 mg (321 μmol) 5-methyl-6-(2-thiophen-2-yl-benzoxazol-6-yl)-4,5-dihydro-2H-pyridazin-3-one, 0.08 mg (964 μmol) activated manganese(IV)oxide and 10 ml dioxane are combined and stirred overnight at 120° C. The reaction mixture is filtered through Celite, washed with DCM and EA and the solv. of the filtrate is eliminated i.V. The residue is recrystallised with DMF.

Yield: 22.0 mg (21.0%)

$R_t$-time: 2.49 min (method B)

$C_{16}H_{11}N_3O_2S$ (309.34)

Mass spectrum: $(M+H)^+$=310

Example 257

6-(2-thiophen-2-yl-benzoxazol-6-yl)-2H-pyridazin-3-one

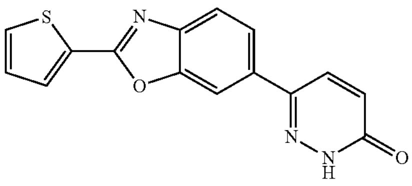 [SMILES: O=c1ccc(-c2ccc3nc(-c4cccs4)oc3c2)n[nH]1]

(a) 6-(6-chloro-pyridazin-3-yl)-2-thiophen-2-yl-benzoxazole 250 mg (1.63 mmol) 3,6-dichloropyridazine and 13.29 mg (16 μmol) dichloro[1,1'-bis(diphenylphosphino)ferrocene] palladium dichloromethane complex and 5 ml DMF are placed under protective gas, 431 mg (4.07 mmol) sodium carbonate dissolved in 2 mL H2O are added and the reaction mixture is heated to 90° C. 533 mg (1.63 mmol) 6-(4,4,5,5-tetramethyl-[1,3,2]dioxaborlan-2-yl)-2-thiophen-2-yl-benzoxazole dissolved in 5 mL dioxane are combined and stirred for 1 h at 110° C. The reaction mixture is combined with H2O and extracted with EA. The solv. of the org. phase is eliminated i.V.

Yield: 550.0 mg (107.7%)

$R_t$-time: 1.61 min (method A)

$C_{15}H_8ClN_3OS$ (313.76)

Mass spectrum: $(M+H)^+$=314

(b) 6-(2-thiophen-2-yl-benzoxazol-6-yl)-2H-pyridazin-3-one 550 mg (1.75 mmol) 6-(6-chloro-pyridazin-3-yl)-2-thiophen-2-yl-benzoxazole in 15 mL glacial acetic acid are placed under protective gas in a pressurised vessel, 173 mg (2.11 mmol) sodium acetate are added and the mixture is stirred for 4 days at 120° C. The reaction mixture is combined with H2O and extracted with DCM. The solv. of the org. phase is eliminated i.V. The residue is suspended in ACN and a solid is suction filtered. The solid is suspended in DCM, stirred for 2 h at RT and suction filtered again.

Yield: 18.0 mg (3.5%)

$R_t$-time: 1.40 min (method A)

$C_{15}H_9N_3O_2S$ (295.32)

Mass spectrum: $(M+H)^+$=296

The invention claimed is:

1. A compound of formula I

I

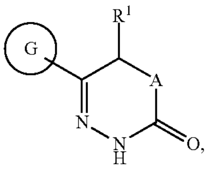

wherein:

$R^1$ is hydrogen, 1-4C-alkyl, 3-7C-cycloalkyl, 3-7C-cycloalkyl-1-4C-alkyl, 2-4C-alkenyl,2-4C-alkynyl, 1-4C-alkoxy, 1-4C-alkoxy-1-4C-alkyl, wholly or partially fluorine substituted 1-4C-alkyl, or wholly or partially fluorine substituted 1-4C-alkoxy, A is $CR^2R^3$, O, S, or $NR^2$, wherein $R^2$ is a group selected from hydrogen,1-4C-alkyl, 3-7C-cycloalkyl, 3-7C-cycloalkyl-1-4C-alkyl, 2-4C-alkenyl, 2-4C-alkynyl, 1-4C-alkoxy, 1-4C-alkoxy-1-4C-alkyl, wholly or partially fluorine substituted 1-4C-alkyl, or wholly or partially fluorine substituted 1-4C-alkoxy, or $R^1$ and $R^2$ together represent a bond, or a 1-7C-alkanediyl group wherein one or two —$CH_2$— groups are optionally replaced by —O—, and $R^3$ is hydrogen or 1-4C-alkyl, and G is a bicyclic system G1or G2:

G1

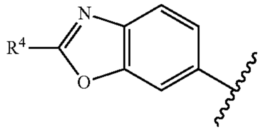

or

G2

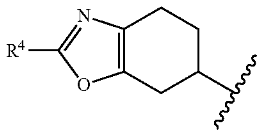

, wherein:

$R^4$ is a group optionally substituted by one to four $R^5$ and/or $R^6$,each independently selected from 1-4C-alkyl, 3-7C-cycloalkyl, 3-7C-cycloalkyl-1-4C-alkyl, 2-4C-alkenyl, 2-4C-alkynyl, aryl, heteroaryl, aryl-1-4C-alkyl, heteroaryl-1-4C-alkyl, heterocyclyl, and heterocyclyl-1-4C-alkyl, wherein:

each $R^5$ independently is hydrogen or a group optionally substituted by one to four $R^{10}$ and/or $R^{11}$ and/or $R^{12}$, each independently selected from 1-4C-alkyl, 3-7C-cycloalkyl, 3-7C-cycloalkyl-1-4C-alkyl, 2-4C-alkenyl, 2-4C-alkynyl, aryl, heteroaryl, heterocyclyl, aryl-1-4C-alkyl, heteroaryl-1-4C-alkyl, and heterocyclyl-1-4C-alkyl, and each $R^6$ independently is hydrogen or a group selected from: halogen,trifluoromethyl, cyano, oxo, —$OR^7$, —$N(R^7)R^8$, —$SR^7$, —$C(O)OR^7$, —$C(O)N(R^7)R^8$, —$S(O)_2N(R^7)R^8$, —$C(O)R^9$, —$S(O)_2R^9$, —$S(O)R^9$, —$N(R^{81})C(O)OR^7$, —$N(R^{81})C(O)N(R^7)R^8$, —$N(R^{81})S(O)_2N(R^7)R^8$, —$N(R^{81})C(O)R^9$, —$N(R^{81})S(O)_2R^9$, and —$N(R^{81})S(O)R^9$, wherein:

each $R^7$ independently is hydrogen or a group optionally substituted by one to four $R^{10}$ and/or $R^{11}$ and/or $R^{12}$, each independently selected from 1-4C-alkyl, 3-7C-cycloalkyl, 3-7C-cycloalkyl-1-4C-alkyl, 2-4C-alkenyl, 2-4C-alkynyl, aryl, heteroaryl, heterocyclyl, aryl-1-4C-alkyl, heteroaryl-1-4C-alkyl, and heterocyclyl-1-4C-alkyl, each $R^8$ independently is hydrogen or a group selected from 1-4C-alkyl and 3-7C-cycloalkyl, or $R^7$ and $R^8$ together represent a 1-9C-alkanediyl group wherein optionally one or two —$CH_2$— groups may each be replaced by —O, —$NR^{81}$, —S, —SO or —$SO_2$—, wherein each $R^{81}$ independently is hydrogen or 1-4C-alkyl, each $R^9$ independently is a group optionally substituted by one to four $R^{10}$ and/or $R^{11}$ and/or $R^{12}$, each independently selected from 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, each $R^{10}$ independently is a group selected from hydrogen, 1-4C-alkyl, 3-7C-cycloalkyl, 3-7C-cycloalkyl-1-4C-alkyl, aryl, heteroaryl, heterocyclyl, aryl-14C-alkyl, heteroaryl-1-4C-alkyl, and heterocyclyl-1-4C-alkyl, each $R^{11}$ independently is hydrogen or a group selected from halogen, trifluoromethyl, cyano, oxo, —$OR^{13}$, —$N(R^{13})R^{14}$, and —$SR^{13}$, each $R^{12}$ independently is hydrogen or a group selected from —$C(O)OR^{13}$, —$C(O)N(R^{13})R^{14}$, —$S(O)_2N(R^{13})R^{14}$, —$C(O)R^{15}$, —$S(O)_2R^{15}$—$S(O)R^{15}$, —$N(R^{141})C(O)OR^{13}$, —$N(R^{141})C(O)N(R^{13})R^{14}$, —$N(R^{141})S(O)_2N(R^{13})R^{14}$, —$N(R^{141})C(O)R^{15}$, —$N(R^{141})S(O)_2R^{15}$, and —$N(R^{141})S(O)R^{15}$, each $R^{13}$ independently is a group selected from hydrogen, 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, each $R^{14}$ independently is a group selected from hydrogen, 1-4C-alkyl, and 3-7C-cycloalkyl, or $R^{13}$ and $R^{14}$ together represent a 1-9C-alkanediyl group wherein optionally one or two —$CH_2$— groups are each replaced by —O, —$NR^{141}$, —S, —SO, or —$SO_2$—, wherein each $R^{141}$ independently is hydrogen or 1-4C-alkyl, and each $R^{15}$ independently is a group selected from 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, wherein:

aryl, on its own or as part of another group, is a carbocyclic aromatic monocyclic ring system containing 6 carbon atoms, which is optionally annelated to a second 5- or 6-membered carbocyclic aromatic, saturated or unsaturated ring system, heteroaryl, on its own or as part of another group, is a 5-to 12-membered, aromatic, monocyclic or condensed-polycyclic ring system containing 1 to 4 heteroatoms independently selected from N, O, and $S(O)_r$, with r=0, 1, or 2, wherein at least one of the heteroatoms is part of the aromatic ring, and heterocyclyl, on its own or as part of another group, a 3- to 12-membered, saturated, unsaturated or aromatic, monocyclic or condensed, bridged or spiro-polycyclic ring system containing 1 to 4 heteroatoms independently selected from N, O, and $S(O)_r$, with r=0, 1, or 2, wherein none of the heteroatoms is part of the aromatic ring, or a tautomer, enantiomer, or a salt thereof.

2. The compound of formula I according to claim 1, wherein:

$R^1$ is hydrogen, 1-4C-alkyl, or 1-4C-alkoxy,

A is $CR^2R^3$, O, S, or $NR^2$, wherein $R^2$ is a group selected from hydrogen, 1-4C-alkyl and 2-4C-alkenyl, or $R^1$ and $R^2$ together represent a bond or a 1-4C-alkanediyl group, and $R^3$ is hydrogen, and $R^4$ is a phenyl group optionally independently substituted by one or two $R^5$ and/or $R^6$, wherein:

each $R^5$ independently is hydrogen or a group optionally substituted by one to four, preferably one or two, $R^{10}$ and/or $R^{11}$ and/or $R^{12}$, each independently selected from 1-4C-alkyl, 2-4C-alkenyl, heterocyclyl, phenyl-1-4C-alkyl, and heterocyclyl-1-4C-alkyl, each $R^6$ independently is hydrogen or a group selected from: halogen, cyano, —$OR^7$, and —$N(R^7)R^8$ each $R^7$ independently is hydrogen or a group optionally substituted by one to four $R^{10}$ and/or $R^{11}$ and/or $R^{12}$, each independently selected from 1-4C-alkyl, 2-4C-alkenyl, 2-4C-alkenyl, 3-7C-cycloalkyl, 3-7C-cycloalkyl-1-4C-alkyl, phenyl, heterocyclyl, phenyl-1-4C-alkyl, heteroaryl-1-4C-alkyl, and heterocyclyl-1-4C-alkyl, each $R^8$ independently is hydrogen or 1-4C-alkyl, or $R^7$ and $R^8$ together represent a 1-7C-alkanediyl group wherein one or two —$CH_2$— groups each are optionally replaced by —O, —$NR^{81}$, —S, —SO, or —$SO_2$—, wherein each $R^{81}$ independently is hydrogen or 1-4C-alkyl, wherein each $R^{10}$ independently is a group selected from hydrogen, 1-4C-alkyl, and heterocyclyl, each $R^{11}$ independently is hydrogen or a group selected from halogen, cyano, oxo, —$OR^{13}$, and —$N(R^{13})R^{14}$, each $R^{12}$ independently is hydrogen or a group selected from $C(O)OR^{13}$, —$C(O)N(R^{13})R^{14}$—$C(O)R^{15}$, and —$S(O)_2R^{15}$, wherein each $R^{13}$ independently is a group selected from hydrogen and 1-4C-alkyl, each $R^{14}$ independently is a group selected from hydrogen and 1-4C-alkyl, or $R^{13}$ and $R^{14}$ together represent a 1-7C-alkanediyl group wherein one or two —$CH_2$— groups each are optionally replaced by —O, —$NR^{141}$, —S, —SO, or —$SO_2$—, wherein each $R^{141}$ independently is hydrogen or 1-4C-alkyl, each $R^{15}$ independently is a group selected from 1-4C-alkyl, wherein heteroaryl, on its own or as part of another group, is a 5- or 6-membered aromatic, monocyclic ring system containing 1 to 3 heteroatoms independently selected from N, O, and S, and heterocyclyl, on its own or as part of another group, is a 3- to 12-membered, saturated, monocyclic or bridged or spiro-bicyclic ring system containing 1 or 2 heteroatoms independently selected from N, O, and $S(O)_r$, with r=0, 1, or 2;

or a tautomer, enantiomer, or a salt thereof.

3. The compound of formula I according to claim 1, wherein:

$R^1$ is 1-4C-alkyl,

A is $CR^2R^3$, O, S, or NH, wherein $R^2$ is a group selected from hydrogen and 1-4C-alkyl, or $R^1$ and $R^2$ together represent a 1-2C-alkanediyl group, and $R^3$ is hydrogen, and $R^4$ is a phenyl group optionally independently substituted by one or two $R^5$ and/or $R^6$, wherein each $R^5$ independently is hydrogen, 1-4C-alkyl, or heterocyclyl, wherein each $R^6$ independently is hydrogen or a group selected from: halogen, cyano,—$OR^7$, and —$N(R^7)R^8$, wherein each $R^7$ independently is a group selected from hydrogen, 1-4C-alkyl, 3-7C-cycloalkyl, 3-7C-cycloalkyl-1-4C-alkyl, $H_2N$-2-4C-alkyl, mono-or di-(1-4C-alkylamino)-2-4C-alkyl, 1-4C-alkoxy-2-4C-alkyl, hydroxy-2-4C-alkyl, 1-4C-alkoxycarbonyl-1-4C-alkyl, phenyl, heterocyclyl, benzyl, 2-phenylethyl, heteroaryl-1-4C-alkyl, and heterocyclyl-1-4C-alkyl, wherein 3-7C-cycloalkyl, on its own or as part of another group, is optionally substituted by a hydroxy, mono- or di-1-4C-alkylamino, or heterocyclyl, each $R^8$ independently is hydrogen or 1-4C-alkyl, or $R^7$ and $R^8$ together represent a 1-7C-alkanediyl group wherein one or two —$CH_2$— groups each are optionally replaced by —O, —$NR^{81}$, —S, —SO, or —$SO_2$—, wherein each $R^{81}$ independently is hydrogen or 1-4C-alkyl, wherein heteroaryl, on its own or as part of another group, is a 5- or 6-membered aromatic, monocyclic ring system containing 1 to 3 heteroatoms independently selected from N, O, and S, each optionally independently substituted by one or two halogen and/or 1-4C-alkyl, and heterocyclyl, on its own or as part of another group, is a 3- to 12-membered, saturated, monocyclic or bridged or spiro-bicyclic ring system containing 1 or 2 heteroatoms independently selected from N, O, and $S(O)_r$, with r=0, 1, or 2, which are each optionally independently substituted by one to four, halogen, cyano, 1-4C-alkoxycarbonyl, and/or 1-4C-alkyl, or a tautomer, enantiomer, or a salt thereof.

4. The compound of formula I according to claim 1, wherein:

$R^1$ is 1-4C-alkyl,

A is $CR^2R^3$, O, S, or NH, wherein $R^2$ is a group selected from 1-4C-alkyl, or $R^1$ and $R^2$ together represent a 1-2C-alkanediyl group, and $R^3$ is hydrogen, and $R^4$ is a group optionally independently substituted by one or two $R^5$ and/or $R^6$ selected from phenyl and heteroaryl, wherein each $R^5$ independently is hydrogen, 1-4C-alkyl, or heterocyclyl, wherein each $R^6$ independently is hydrogen or a group selected from halogen, cyano, —$OR^7$, and —$N(R^7)R^8$, wherein each $R^7$ independently is a group selected from hydrogen, 1-4C-alkyl, 3-7C-cycloalkyl, 3-7C-cycloalkyl-1-4C-alkyl, $H_2N$-2-4C-alkyl, mono- or di-(1-4C-alkylamino)-2-4C-alkyl, 1-4C-alkoxy-2-4C-alkyl, hydroxy-2-4C-alkyl, 1-4C-alkoxycarbonyl-1-4C-alkyl, phenyl, heterocyclyl, benzyl, 2-phenylethyl, heteroaryl-1-4C-alkyl and heterocyclyl-1-4C-alkyl, wherein 3-7C-cycloalkyl, on its own or as part of another group, is optionally substituted by a hydroxy, mono- or di-1-4C-alkylamino, or heterocyclyl, each $R^8$ independently is hydrogen or 1-4C-alkyl, or $R^7$ and $R^8$ together represent a 1-7C-alkanediyl group wherein one or two —$CH_2$— groups each are optionally replaced by —O, —$NR^{81}$, —S, —SO, or —$SO_2$—, wherein each $R^{81}$ independently is hydrogen or 1-4C-alkyl, wherein heteroaryl, on its own or as part of another group, is a 5- or 6-membered aromatic, monocyclic ring system containing 1 to 3 heteroatoms independently selected from N, O, and S, each optionally independently substituted by one or two halogen and/or 1-4C-alkyl, and heterocyclyl, on its own or as part of another group, is a 3- to 12-membered, saturated, monocyclic or bridged or spiro-bicyclic ring system containing 1 or 2 heteroatoms independently selected from N, O, and $S(O)_r$, with r=0, 1, or 2, each optionally independently substituted by one to four halogen, cyano, 1-4C-alkoxycarbonyl, and/or 1-4C-alkyl, or a tautomer, enantiomer, or a salt thereof.

5. The compounds of formula I according to claim 1, wherein:

$R^1$ is 1-4C-alkyl,

A is $CR^2R^3$, O, S, or NH, wherein $R^2$ is a group selected from hydrogen and 1-4C-alkyl, or $R^1$ and $R^2$ together represent a 1-2C-alkanediyl group, and $R^3$ is hydrogen, and G is G1

G1

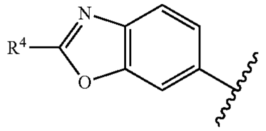

G2

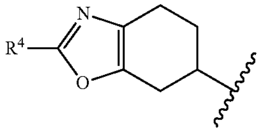

and

G3

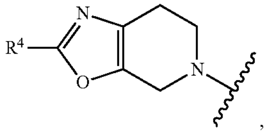

, wherein:

$R^4$ is a phenyl group optionally independently substituted by $R^6$ and/or one or two halogen or 1-2C-alkyl, $R^6$ is —$OR^7$, wherein the phenyl group carries the substituent $R^6$ in the meta or para position, relative to the point of attachment of the phenyl group to the system G1, wherein each $R^7$ independently is a group selected from hydrogen, 1-4C-alkyl, 3-7C-cycloalkyl, 3-7C-cycloalkyl-1-4C-alkyl, di-(1-4C-alkylamino)-2-4C-alkyl, 1-4C-alkoxy-2-4C-alkyl, hydroxy-2-4C-alkyl, 1-4C-alkoxycarbonyl-1-4C-alkyl, phenyl, heterocyclyl, benzyl, 2-phenylethyl, heteroaryl-1-4C-alkyl, and heterocyclyl-1-4C-alkyl, wherein 3-7C-cycloalkyl, on its own or as part of another group is optionally substituted by a hydroxy, di-1-4C-alkylamino, piperidin-1-yl, pyrrolidin-1-yl, or morpholin-1-yl, wherein heteroaryl, on its own or as part of another group, is a 5- or 6-membered aromatic, monocyclic ring system containing 1 to 3 heteroatoms independently selected from N, O, and S, each optionally independently substituted by one or two halogen and/or 1-4C-alkyl, and heterocyclyl, on its own or as part of another group, is a 3- to 12-membered, saturated, monocyclic or bridged or spiro-bicyclic ring system containing 1 or 2 heteroatoms independently selected from N, O, and $S(O)_r$, with r=0, 1, or 2,each optionally independently substituted by one to four, halogen, cyano, 1-4C-alkoxycarbonyl, and/or 1-4C-alkyl, or a tautomer, enantiomer, or a salt thereof.

6. A physiologically acceptable salt of a compound of formula I according to claim 1.

7. The compound according to claim 1, excluding each of the compounds:

5-methyl-6-[2-(3-thienyl)-benzoxazol-6-yl]-4,5-dihydro-3(2H)-pyridazinone, 5-methyl-6-[2-(2-pyridyl)-benzoxazol-6-yl]-4,5-dihydro-3(2H)-pyridazinone, 5-methyl-6-[2-(2-furyl)-benzoxazol-6-yl]-4,5-dihydro-3(2H)-pyridazinone, 5-methyl-6-[2-(2-thienyl)-benzoxazol-6-yl]-4,5-dihydro-3(2H)-pyridazinone, 5-methyl-6-[2-(3-pyridyl)-benzoxazol-6-yl]-4,5-dihydro-3(2H)-pyridazinone, 5-methyl-6-[2-(2-pyrazinyl)-benzoxazol-6-yl]-4,5-dihydro-3(2H)-pyridazinone, 5-methyl-6-[2-(4-pyridyl)-benzoxazol-6-yl]-4,5-dihydro-3(2H)-pyridazinone, 5-methyl-6-[2-(1-acetyl-piperidino)-benzoxazol-6-yl]-4,5-dihydro-3(2H)-pyridazinone, 5-methyl-6-[2-(4-methyl-5-oxazolyl)-benzoxazol-6-yl]-4,5-dihydro-3(2H)-pyridazinone, 5-methyl-6-[2-(5-pyrimidinyl)-benzoxazol-6-yl]-4,5-dihydro-3(2H)-pyridazinone, 5-methyl-6-[2-(2-amino-5-pyridyl)-benzoxazol-6-yl]-4,5-dihydro-3(2H)-pyridazinone, 6-[2-(2-pyridyl)-benzoxazol-6-yl]-4,5-dihydro-3(2H)-pyridazinone, 6-[2-(2-furyl)-benzoxazol-6-yl]-4,5-dihydro-3(2H)-pyridazinone, 5-methyl-6-[2-(4-thiomorpholino)-benzoxazol-6-yl]-4,5-dihydro-3(2H)-pyridazinone, 5-methyl-6-[2-(1-piperidino)-benzoxazol-6-yl]-4,5-dihydro-3(2H)-pyridazinone, 5-methyl-6-[2-(1-oxido-4-thiomorpholino)-benzoxazol-6-yl]-4,5-dihydro-3(2H)-pyridazinone, 5-methyl-6-[2-(1,1-dioxido-4-thiomorpholino)-benzoxazol-6-yl]-4,5-dihydro-3(2H)-pyridazinone, 5-methyl-6-[2-(4-methyl-1-piperazinyl)-benzoxazol-6-yl]-4,5-dihydro-3(2H)-pyridazinone, 5-methyl-6-[2-(4-carbethoxy-1-piperazinyl)-benzoxazol-6-yl]-4,5-dihydro-3(2H)-pyridazinone, 5-methyl-6-[2-(1-pyrrolidinyl)-benzoxazol-6-yl]-4,5-dihydro-3(2H)-pyridazinone, 5-methyl-6-[2-(1-piperazinyl)-benzoxazol-6-yl]-4,5-dihydro-3(2H)-pyridazinone, 5-methyl-6-[2-(4-methyl-1-imidazolyl)-benzoxazol-6-yl]-4,5-dihydro-3(2H)-pyridazinone, 6-[2-(1-piperidino)-benzoxazol-6-yl]-4,5-dihydro-3(2H)-pyridazinone, 6-[2-(4-morpholino)-benzoxazol-6-yl]-4,5-dihydro-3(2H)-pyridazinone, 6-[2-(1-pyrrolidinyl)-benzoxazol-6-yl]-4,5-dihydro-3(2H)-pyridazinone, 6-[2-(4-methyl-1-imidazolyl)-benzoxazol-6-yl]-4,5-dihydro-3(2H)-pyridazinone, 6-[2-(4-carbethoxy-1-piperazinyl)-benzoxazol-6-yl]-4,5-dihydro-3(2H)-pyridazinone, 6-[2-(1-piperazinyl)-benzoxazol-6-yl]-4,5-dihydro-3(2H)-pyridazinone, 6-[2-(1-oxido-4-thiomorpholino)-benzoxazol-6-yl]-4,5-dihydro-3(2H)-pyridazinone, 6-[2-(1,1-dioxido-4-thiomorpholino)-benzoxazol-6-yl]-4,5-dihydro-3(2H)-pyridazinone, 6-[2-(4-methyl-1-piperazinyl)-benzoxazol-6-yl]-4,5-dihydro-3(2H)-pyridazinone, 6-[2-(4-thiomorpholino)-benzoxazol-6-yl]-4,5-dihydro-3(2H)-pyridazinone, 5-methyl-6-[2-(1-imidazolyl)-benzoxazol-6-yl]-4,5-dihydro-3(2H)-pyridazinone, 5-methyl-6-[2-(4-morpholino)-benzoxazol-6-yl]-4,5-dihydro-3(2H)-pyridazinone, 6-[2-(3-thienyl)-benzoxazol-6-yl]-4,5-dihydro-3(2H)-pyridazinone, 5-methyl-6-[2-(2-acetamido-5-pyridyl)-benzoxazol-6-yl]-4,5-dihydro-3(2H)-pyridazinone, 5-methyl-6-[2-(2,6-dichloro-3-pyridyl)-benzoxazol-6-yl]-4,5-dihydro-3(2H)-pyridazinone and 5-methyl-6-[2-(2-chloro-6-morpholino-3-pyridyl) benzoxazol-6-yl]-4,5-dihydro-3(2H)-pyridazinone.

8. A compound according to claim 1 selected from the following:

(5S)-5-methyl-6-(2-phenyl-1,3-benzoxazol-6-yl)-2,3,4,5-tetrahydropyridazin-3-one, (4S)-4-methyl-6-(2-phenyl-1,3-benzoxazol-6-yl)-2,3,4,5-tetrahydropyridazin-3-one, (5R)-5-methyl-6-(2-phenyl-1,3-benzoxazol-6-yl)-2,3,4,5-tetrahydropyridazin-3-one, (4R)-4-methyl-6-(2-phenyl-1,3-benzoxazol-6-yl)-2,3,4,5-tetrahydropyridazin-3-one, 5-(2-phenyl-1,3-benzoxazol-6-yl)-3,4-diazabicyclo [4.1.0]hept-4-en-2-one, 5-(7-methyl-2-phenyl-1,3-benzoxazol-6-yl)-3,4-diazabicyclol[4.1.0]hept-4-en-2-one, 6-(2-phenyl-1,3-benzoxazol-6-yl)-4-(prop-2-en-1-yl)-2,3,4,5-tetrahydropyridazin-3-one, 6-(2-phenyl-1,3-benzoxazol-6-yl)-5-propyl-2,3,4,5-tetrahydropyridazin-3-one, 6-(2-phenyl-1,3-benzoxazol-6-yl)-4-propyl-2,3,4,5-tetrahydropyridazin-3-one, 5-(2-phenyl-1,3-benzoxazol-6-yl)-3,4-diazabicyclol [4.2.0]oct-4-en-2-one, 5-(4-methyl-2-phenyl-1,3-benzoxazol-6-yl)-3,4-diazabicyclol[4.1.0]hept-4-en-2-one, 5-[2-(3-methylphenyl)-1,3-benzoxazol-6-yl]-3,4-diazabicyclol[4.1.01]hept-4-en-2-one, 5-[2-(4-methylphenyl)-1,3-benzoxazol-6-yl]3,4-diazabicyclo [4.1.0]hept-4-en-2-one, 5-[2-(3,4-dimethylphenyl)-1,3-benzoxazol-6-yl]-3,4-diazabicyclo[4.1.0]hept-4-en-2-one, 5-{2-[4-(piperidin-1-ylmethyl)phenyl]-1,3-benzoxazol-6-yl}-3,4-diazabicyclo[4.1.0]hept-4-en-2-one, 6-(2-phenyl-1,3-benzoxazol-6-yl)-2,3,4,5-tetrahydropyridazin-3-one, 5-[2-(3-fluorophenyl)-1,3-benzoxazol-6-yl]-3,4-diazabicyclo[4.1.0]hept-4-en-2-one, 5-[2-(4-fluorophenyl)-1,3-benzoxazol-6-yl]-3,4-diazabicyclo[4.1.0]hept-4-en-2-one, 5-[2-(4-fluorophenyl)-1,3-benzoxazol-6-yl]-3,4-diazabicyclo[4.2.0]oct-4-en-2-one, 5-[2-(2-fluorophenyl)-1,3-benzoxazol-6-yl]-3,4-diazabicyclo[4.1.0]hept-4-en-2-one, 4.4-dimethyl-6-(2-phenyl-1,3-benzoxazol-6-yl)-2,3,4,5-tetrahydropyridazin-3-one, 5-{2-[4-(morpholin-4-ylmethyl)phenyl]-1,3-benzoxazol-6-yl}-3,4-diazabicyclo[4.1.0]hept-4-en-2-one, tert-butyl 4-{[4-(6-{5-oxo-3,4-diazabicyclo[4.1.0]hept-2-en-2-yl}-1,3-benzoxazol-2-yl)phenyl] methyl}piperazine-1-carboxylate, (4S,5R)-4,5-dimethyl-6-[2-(5-methylthiophen-2-yl)-1,3-benzoxazol-6-yl]-2,3,4,5-tetrahydropyridazin-3-one, (4R,5S)-4,5-dimethyl-6-(2-phenyl-1,3-benzoxazol-6-yl)-2,3,4,5-tetrahydropyridazin-3-one, (4S,5S)-4,5-dimethyl-6-(2-phenyl-1,3-benzoxazol-6-yl)-2,3,4,5-tetrahydropyridazin-3-one, (5R)-5-methoxy-6-(2-phenyl-1,3-benzoxazol-6-yl)-2,3,4,5-tetrahydropyridazin-3-one, (5S)-5-methoxy-6-(2-phenyl-1,3-benzoxazol-6-yl)-2,3,4,5-tetrahydropyridazin-3-one, 5-ethyl-6-(2-phenyl-1,3-benzoxazol-6-yl)-2,3,4,5-tetrahydropyridazin-3-one, (5S)-5-ethyl-6-(2-phenyl-1,3-benzoxazol-6-yl)-2,3,4,5-tetrahydropyridazin-3-one, (5R)-5-ethyl-6-(2-phenyl-1,3-benzoxazol-6-yl)-2,3,4,5-tetrahydropyridazin-3-one, 6-(2-phenyl-1,3-benzoxazol-6-yl)-5-(propan-2-yl)-2,3,4,5-tetrahydropyridazin-3-one, 6-{2-[4-(benzyloxy)phenyl]-1,3-benzoxazol-6-yl}-5-ethyl-2,3,4,5-tetrahydropyridazin-3-one, 6-{2-[3-(benzyloxy)phenyl]-1,3-benzoxazol-6-yl}-5-methyl-2,3,4,5-tetrahydropyridazin-3-one, 6{2-[3-(benzyloxy)phenyl]-1,3-benzoxazol-6-yl}-5-ethyl-2,3,4,5-tetrahydropyridazin-3-one, 6{2-[4-(benzyloxy)phenyl]-1,3-benzoxazol-6-yl}-5-methyl-2,3,4,5-tetrahydropyridazin-3-one, 5-ethyl-6-[2-(4-hydroxyphenyl)-1,3-benzoxazol-6-yl]-2,3,4,5-tetrahydropyridazin-3-one, 6-[2-(3-hydroxyphenyl)-1,3-benzoxazol-6-yl]-5-methyl-2,3,4,5-tetrahydropyridazin-3-one, 5-ethyl-6-[2-(3-hydroxyphenyl)-1,3-benzoxazol-6-yl]-2,3,4,5-tetrahydropyridazin-3-one, 5-ethyl-6-{2-[4-(pyrimidin-2-ylmethoxy)phenyl]-1,3-benzoxazol-6-yl}-2,3,4,5-tetrahydropyridazin-3-one, 2-{4-[6-(4-ethyl-6-oxo-1,4,5,6-tetrahydropyridazin-3-yl)-1,3-benzoxazol-2-yl]phenoxy}-N,N-dimethylacetamide, 5-ethyl-6-(2-{4-[(1-methyl-1H-imidazol-5-yl)methoxy] phenyl}-1,3-benzoxazol-6-yl)-2,3,4,5-tetrahydropyridazin-3-one, 2-{4-[6-(4-ethyl-6-oxo-1,4,5,6-tetrahydropyridazin-3-yl)-1,3-benzoxazol-2-yl]phenoxyl}-N-methylacetamide, 5-ethyl-6-(2-{4-[2-(4-methylpiperazin-1-yl)ethoxy]phenyl}-1,3-benzoxazol-6-yl)-2,3,4,5-tetrahydropyridazin-3-one, 5-ethyl-6-{2-[3-(pyridin-3-ylmethoxy)phenyl]-1,3-benzoxazol-6-yl}-2,3,4,5-tetrahydropyridazin-3-one, 5-ethyl-6-{2-[4-(pyridin-4-ylmethoxy)phenyl]-1,3-benzoxazol-6-yl}-2,3,4,5-tetrahydropyridazin-3-one, 5-ethyl-6-{2-[4-(pyridin-2-ylmethoxy)phenyl]-1,3-benzoxazol-6-yl}-2,3,4,5-tetrahydropyridazin-3-one, 5-ethyl-6-{2-[4-(thiophen-3-ylmethoxy)phenyl]-1,3-benzoxazol-6-yl}-2,3,4,5-tetrahydropyridazin-3-one, 5-ethyl-6-(2-{4-[2-(piperidin-1-yl)ethoxy]phenyl}1,3-benzoxazol-6-yl)-2,3,4,5-tetrahydropyridazin-3-one, 5-ethyl-6-[2-(4-{[3-(propan-2-yl)-1,2,4-oxadiazol-5-yl] methoxy}phenyl)-1,3-benzoxazol-6-yl]-2,3,4,5-tetrahydropyridazin-3-one, 5-ethyl-6-{2-[4-(thiophen-2-ylmethoxy)phenyl]-1,3-benzoxazol-6-yl}-2,3,4,5-tetrahydropyridazin-3-one, 5-ethyl-6-[2-(4-propoxyphenyl)-1,3-benzoxazol-6-yl]-2,3,4,5-tetrahydropyridazin-3-one, 6-(2-{4-[2-(azepan-1-yl)ethoxy]phenyl}-1,3-benzoxazol-6-yl)-5-ethyl-2,3,4,5-tetrahydropyridazin-3-one, 6-{2-[4-(cyclohexylmethoxy)phenyl]-1,3-benzoxazol-6-yl}-5-ethyl-2,3,4,5-tetrahydropyridazin-3-one, 6-(2-{4-[2-(dimethylamino)ethoxy]phenyl}-1,3-benzoxazol-6-yl)-5-ethyl-2,3,4,5-tetrahydropyridazin-3-one, 6-{2-[4-(2-cyclohexylethoxy)phenyl]-1,3-benzoxazol-6-yl}-5-ethyl-2,3,4,5-tetrahydropyridazin-3-one, 6-[2-(4-{2-[bis(propan-2-yl)amino]ethoxy}phenyl)-1,3-benzoxazol-6-yl]-5-ethyl-2,3,4,5-tetrahydropyridazin-3-one, 5-ethyl-6-(2-{4-[2-(2,2,6,6tetramethylpiperidin-1-yl)ethoxy]phenyl}-1,3-benzoxazol-6-yl)-2,3,4,5-tetrahydropyridazin-3-one, 5-ethyl-6-{2-[4-(pyrimidin-5-ylmethoxy)phenyl]-1,3-benzoxazol-6-yl}-2,3,4,5-tetrahydropyridazin-3-one, 5-ethyl-6-{2-[4-(pyridin-3-ylmethoxy)phenyl]-1,3-benzoxazol-6-yl}-2,3,4,5-tetrahydropyridazin-3-one, 5-ethyl-6-(2-{4-[2-oxo-2-(piperidin-1-yl)ethoxy]phenyl}-1,3-benzoxazol-6-yl)-2,3,4,5-tetrahydropyridazin-3-one, 6-(2-{4-[3-(dimethylamino)propoxy]phenyl}-1,3-benzoxazol-6-yl)-5-ethyl-2,3,4,5-tetrahydropyridazin-3-one, 5-ethyl-6{-2-[4-(1,3-oxazol-5-ylmethoxy)phenyl]-1,3-benzoxazol-6-yl}-2,3,4,5-tetrahydropyridazin-3-one, 5-ethyl-6-(2-{4-[2-(morpholin-4-yl)ethoxy]phenyl}-1,3-benzoxazol-6-yl)-2,3,4,5-tetrahydropyridazin-3-one, 5-ethyl-6{-2-[3-(pyridin-2-ylmethoxy)phenyl]-1,3-benzoxazol-6-yl}-2,3,4,5-tetrahydropyridazin-3-one, tert-butyl 2-{4-[6-(4-ethyl-6-oxo-1,4,5,6-tetrahydropyridazin-3-yl)-1,3-benzoxazol-2-yl]phenoxy}acetate, tert-butyl 4-{4-[6-(4-ethyl-6-oxo-1,4,5,6tetrahydropyridazin-3-yl)-1,3-benzoxazol-2-yl]phenoxymethyl}piperidine-1-carboxylate, tert-butyl 4-{4-[6-(4-ethyl-6-oxo-1,4,5,6-tetrahydropyridazin-3-yl)-1,3-benzoxazol-2-yl]phenoxyl}piperidine-1-carboxylate, tert-butyl 4-{3-[6-(4-methyl-6-oxo-1,4,5,6-tetrahydropyridazin-3-yl)-1,3-benzoxazol-2-yl]phenoxymethyl}piperidine-1-carboxylate, 2-{4-[6-(4-ethyl-6-oxo-1,4,5,6-tetrahydropyridazin-3-yl)-1,3-benzoxazol-2-yl]phenoxy}acetic acid, 5-ethyl-6-{2-[4-(piperidin-4-ylmethoxy)phenyl]-1,3-benzoxazol-6-yl}-2,3,4,5-tetrahydropyridazin-3-one, 5-ethyl-6-{2-[4-(piperidin-4-yloxy)phenyl]-1,3-benzoxazol-6-yl}-2,3,4,5-tetrahydropyridazin-3-one, 5-methyl-6-{2-[3-(piperidin-4-ylmethoxy)phenyl]-1,3-benzoxazol-6-yl}-2,3,4,5-tetrahydropyridazin-3-one, 5-ethyl-6-(2-{4-[(1-methanesulphonylpiperidin-4-yl)methoxy]phenyl}-1,3-benzoxazol-6-yl)-2,3,4,5-tetrahydropyridazin-3-one, 5-ethyl-6-(2-{4-[(E)-2-phenylethenyl]phenyl}-1,3-benzoxazol-6-yl)-2,3,4,5-tetrahydropyridazin-3-one, 5-ethyl-6-{2-[4-(2-phenylethyl)phenyl]-1,3-benzoxazol-6-yl}-2,3,4,5-tetrahydropyridazin-3-one, 6-ethyl-5-(2-phenyl-1,3-benzoxazol-6-yl)-3,6-dihydro-2H-1,3,4-thiadiazin-2-one, 6-ethyl-5-(2-phenyl-1,3-benzoxazol-6-yl)-3,6-dihydro-2H-1,3,4-oxadiazin-2-one, (6R)-6-ethyl-5-(2-phenyl-1,3-benzoxazol-6-yl)-3,6-dihydro-2H-1,3,4-oxadiazin-2-one, (6S)-6-ethyl-5-(2-phenyl-1,3-benzoxazol-6-yl)-3,6-dihydro-2H-1,3,4-oxadiazin-2-one, 6-methyl-5-(2-phenyl-1,3-benzoxazol-6-yl)-3,6-dihydro-2H-1,3,4-oxadiazin-2-one, 5-methyl-6-(2-phenyl-1,3-benzoxazol-6-yl)-2,3,4,5-tetrahydropyridazin-3-one, 6-[2-(4-methoxyphenyl)-1,3-benzoxazol-6-yl]-5-methyl-2,3,4,5-tetrahydropyridazin-3-one, 6-[2-(4-chlorophenyl)-1,3-benzoxazol-6-yl]-5-methyl-2,3,4,5-tetrahydropyridazin-3-one, 6-[2-(3-methoxyphenyl)-1,3-benzoxazol-6-yl]-5-methyl-2,3,4,5-tetrahydropyridazin-3-one, 6-[2-(2-methoxyphenyl)-1,3-benzoxazol-6-yl]-5-methyl-2,3,4,5-tetrahydropyridazin-3-one, 5-methyl-6-[2-(5-methylthiophen-2-yl)-1,3-benzoxazol-6-yl]-2,3,4,5-tetrahydropyridazin-3-one, 6-[2-(3-chlorophenyl)-1,3-benzoxazol-6-yl]-5-methyl-2,3,4,5-tetrahydropyridazin-3-one, 6-[2-(2-chlorophenyl)-1,3-benzoxazol-6-yl]-5-methyl-2,3,4,5-tetrahydropyridazin-3-one, methyl 4-[6-(4-methyl-6-oxo-1,4,5,6-tetrahydropyridazin-3-yl)-1,3-benzoxazol-2-yl]benzoate, 5-ethyl-6-[2-(2-fluoro-4-methoxyphenyl)-1,3-benzoxazol-6-yl]-2,3,4,5-tetrahydropyridazin-3-one, 6-[2-(3 ,4-dimethoxyphenyl)-1,3-benzoxazol-6-yl]-5-ethyl-2,3,4,5-tetrahydropyridazin-3-one, 5-ethyl-6-[2-(4-fluoro-3-methoxyphenyl)-1,3-benzoxazol-6-yl]-2,3,4,5-tetrahydropyridazin-3-one, 6-[2-(4-ethoxyphenyl)-1,3-benzoxazol-6-yl]-5-ethyl-2,3,4,5-tetrahydropyridazin-3-one, 5-ethyl-6-[2-(4-phenoxyphenyl)-1,3-benzoxazol-6-yl]-2,3,4,5-tetrahydropyridazin-3-one, 6-{2-[4-(dimethylamino)phenyl]-1,3-benzoxazol-6-yl}-5-ethyl-2,3,4,5-tetrahydropyridazin-3-one 5-ethyl-6-[2-(4-methylthiophen-2-yl)-1,3-benzoxazol-6-yl]-2,3,4,5-tetrahydropyridazin-3-one, 5-ethyl-6-[2-(3-fluoro-4-methoxyphenyl)-1,3-benzoxazol-6-yl]-2,3,4,5-tetrahydropyridazin-3-one, 5-ethyl-6-{2-[4-(propan-2-yloxy)phenyl]-1,3-benzoxazol-6-yl}-2,3,4,5-tetrahydropyridazin-3-one, 5-ethyl-6-{2-[3-(propan-2-yloxy)phenyl]-1,3-benzoxazol-6-yl}-2,3,4,5-tetrahydropyridazin-3-one, 5-ethyl-6-[2-(5-methylthiophen-2-yl)-1,3-benzoxazol-6-yl]-2,3,4,5-tetrahydropyridazin-3-one, 5-ethyl-6-[2-(3-methoxyphenyl)-1,3-benzoxazol-6-yl]-2,3,4,5-tetrahydropyridazin-3-one, 5-ethyl-6-{2-[4-(trifluoromethoxy)phenyl]-1,3-benzoxazol-6-yl}-2,3,4,5-tetrahydropyridazin-3-one, 5-ethyl-6-[2-(4-methoxyphenyl)-1,3-benzoxazol-6-yl]-2,3,4,5-tetrahydropyridazin-3-one, 5-ethyl-6-{2-[4-(oxan-4-yloxy)phenyl]-1,3-benzoxazol-6-yl}-2,3,4,5-tetrahydropyridazin-3-one, 5-methyl-6-[2-(thiophen-2-yl)-1,3-benzoxazol-6-yl]-2,3,4,5-tetrahydropyridazin-3-one, 5-methyl-6-[2-(thiophen-3-yl)-1,3-benzoxazol-6-yl]-2,3,4,5-tetrahydropyridazin-3-one, 6-[2-(furan-2-yl)-1,3-benzoxazol-6-yl]-5-methyl-2,3,4,5-tetrahydropyridazin-3-one, 6-[2-(6-aminopyridin-3-yl)-1,3-benzoxazol-6-yl]-5-methyl-2,3,4,5-tetrahydropyridazin-3-one, 5-methyl-6-[2-(pyridin-3-yl)-1,3-benzoxazol-6-yl]-2,3,4,5-tetrahydropyridazin-3-one, 6-[2-(thiophen-2-yl)-1,3-benzoxazol-6-yl]-2,3,4,5-tetrahydropyridazin-3-one, 6-[2-(furan-2-yl)-1,3-benzoxazol-6-yl]-2,3,4,5-tetrahydropyridazin-3-one, 5-methyl-6-[2-(thiomorpholin-4-yl)-1,3-benzoxazol-6-yl]-2,3,4,5-tetrahydropyridazin-3-one, ethyl 4-[6-(4-methyl-6-oxo-1,4,5,6-tetrahydropyridazin-3-yl)-1,3-benzoxazol-2-yl]piperazine-1-carboxylate, 5-methyl-6[2-(piperidin-1-yl)-1,3-benzoxazol-6-yl]-2,3,4,5-tetrahydropyridazin-3-one, 5-methyl-6-[2-(morpholin-4-yl)-1,3-benzoxazol-6-yl]-2,3,4,5-tetrahydropyridazin-3-one, 5-methyl-6[2-(piperazin-1-yl)-1,3-benzoxazol-6-yl]-2,3,4,5-tetrahydropyridazin-3-one, 6-[2-(piperidin-1-yl)-1,3-benzoxazol-6-yl]-2,3,4,5-tetrahydropyridazin-3-one, 6-[2-(thiomorpholin-4-yl)-1,3-benzoxazol-6-yl]-2,3,4,5-tetrahydropyridazin-3-one, 6-[2-(2,6-dichloropyridin-3-yl)-1,3-benzoxazol-6-yl]-5-methyl-2,3,4,5-tetrahydropyridazin-3-one, 6-{2-[2-chloro-6-(morpholin-4-yl)pyridin-3-yl]-1,3-benzoxazol-6-yl}-5-methyl-2,3,4,5-tetrahydropyridazin-3-one, 4-[6-(4-methyl-6-oxo-1,4,5,6-tetrahydropyridazin-3-yl)-1,3-benzoxazol-2-yl]benzonitrile, 3-[6-(4-methyl-6-oxo-1,4,5,6-tetrahydropyridazin-3-yl)-1,3-benzoxazol-2-yl]benzonitrile, 6-{2-[4-(aminomethyl)phenyl]-1,3-benzoxazol-6-yl}-5-methyl-2,3,4,5-tetrahydropyridazin-3-one, 6-{2-[3-(aminomethyl)phenyl]-1,3-benzoxazol-6-}-5-methyl-2,3,4,5-tetrahydropyridazin-3-one, (4S,5S)-4-ethyl-5-methyl-6-(2-phenyl-1,3-benzoxazol-6-yl)-2,3,4,5-tetrahydropyridazin-3-one, (4R,5S)-4-ethyl-5-methyl-6-(2-phenyl-1,3-benzoxazol-6-yl)-2,3,4,5-tetrahydropyridazin-3-one, (4S,5S)-5-methyl-6-(2-phenyl-1,3-benzoxazol-6-yl)-4-propyl-2,3,4,5-tetrahydropyridazin-3-one, (4R,5S)-5-methyl-6-(2-phenyl-1,3-benzoxazol-6-yl)-4-propyl-2,3,4,5-tetrahydropyridazin-3-one, 5(2-phenyl-4,5,6,7-tetrahydro-1,3-benzoxazol-6-yl)-3,4-diazabicyclo[4.1.0]hept-4-en-2-one, (1R,6S)-5-[(6S)-2-phenyl-4,5,6,7-tetrahydro-1,3-benzoxazol-6-yl]-3,4-diazabicyclo[4.1.0]hept-4-en-2-one, (1R,6S)-5-[(6R)-2-phenyl-4,5,6,7-tetrahydro-1,3-benzoxazol-6-yl]-3,4-diazabicyclo[4.1.0]hept-4-en-2-one, (1S,6R)-5-[(6S)-2-phenyl-4,5,6,7-tetrahydro-1,3-benzoxazol-6-yl]-3,4-diazabicyclo[4.1.0]hept-4-en-2-one, (1S,6R)-5-[(6R)-2-phenyl-4,5,6,7-tetrahydro-1,3-benzoxazol-6-yl]-3,4-diazabicyclo[4.1.0]hept-4-en-2-one, 5-(2-benzyl-1,3-benzoxazol-6-yl)-3,4-diazabicyclo[4.1.0]hept-4-en-2-one, 5-(2-{4-[2-(morpholin-4-yl)ethoxy]phenyl}-1,3-benzoxazol-6-yl)-3,4-diazabicyclo[4.1.0]hept-4-en-2-one, 4-methyl-6-[2-(thiophen-2-yl)-1,3-benzoxazol-6-yl]-2,3,4,5-tetrahydropyridazin-3-one, 4-butyl-6-[2-(thiophen-2-yl)-1,3-benzoxazol-6-yl]-2,3,4,5-tetrahydropyridazin-3-one, 4-ethyl-6-[2-(thiophen-2-yl)-1,3-benzoxazol-6-yl]-2,3,4,5-tetrahydropyridazin-3-one, 5-methyl-6-(2-phenyl-1,3-benzoxazol-6-yl)-2,3,4,5-tetrahydro-1,2,4-triazin-3-one, 6-(2-phenyl-1,3-benzoxazol-6-yl)-2,3,4,5-tetrahydro-1,2,4-triazin-3-one, 5-ethyl-6-(2-phenyl-1,3-benzoxazol-6-yl)-2,3,4,5-tetrahydro-1,2,4-triazin-3-one, (4S ,5S)-5-ethyl-4-methyl-6-(2-phenyl-1,3-benzoxazol-6-yl)-2,3,4,5-tetrahydropyridazin-3-one, 4S ,5R)-5-ethyl-4-methyl-6-(2-phenyl-1,3-benzoxazol-6-yl)-2,3,4,5-tetrahydropyridazin-3-one, (4R,5R)-5-ethyl-4-methyl-6-(2-phenyl-1,3-benzoxazol-6-yl)-2,3,4,5-tetrahydropyridazin-3-one, 5-ethyl-6-(2-{3-[2-(piperidin-1-yl)ethoxy]phenyl }-1,3-benzoxazol-6-yl)-2,3,4,5-tetrahydropyridazin-3-one, 6-(2-{3-[2-(azepan-1-yl)ethoxy]phenyl }-1,3-benzoxazol-6-yl)-5-ethyl-2,3,4,5-tetrahydropyridazin-3-one, 5-ethyl-6-{2-[3-(pyridin-4-ylmethoxy)phenyl]-1,3-benzoxazol-6-yl}-2,3,4,5-tetrahydropyridazin-3-one, 5-ethyl-6-(2-{3-[2-(2,2,6,6-tetramethylpiperidin-1-yl)ethoxy]phenyl}-1,3-benzoxazol-6-yl)-2,3,4,5-tetrahydropyridazin-3-one, 5-ethyl-6-(2-{3-[3-(piperidin-1-yl)propoxy]phenyl }-1,3-benzoxazol-6-yl)-2,3,4,5-tetrahydropyridazin-3-one, 1-(2-{3-[6-(4-ethyl-6-oxo-1,4,5,6-tetrahydropyridazin-3-yl)-1,3-benzoxazol-2-yl]phenoxy}ethyl)piperidine-4-carbonitrile, 6-[2-(3-{2-[bis(propan-2-yl)amino]ethoxy}phenyl)-1,3-benzoxazol-6-yl]-5-ethyl-2,3,4,5-tetrahydropyridazin-3-one, tert-butyl 4-(2-{3-[6-(4-ethyl-6-oxo-1,4,5,6-tetrahydropyridazin-3-yl)-1,3-benzoxazol-2-yl]phenoxy }ethyl)piperazine-1-carboxylate, 6-[2-(3-{2-[bis(2-methylpropyl)amino]ethoxy}phenyl)-1,3-benzoxazol-6-yl]-5-ethyl-2,3,4,5-tetrahydropyridazin-3-one, 6-[2-3-{2-[4-(butan-2-yl)piperazin-1-yl]ethoxy}phenyl)-1,3-benzoxazol-6-yl]-5-ethyl-2,3,4,5-tetrahydropyridazin-3-one, 5-ethyl-6-(2-{4-[(4-methanesulphonylphenyl)methoxyl]phenyl}-1,3-benzoxazol-6-yl)-2,3,4,5-tetrahydropyridazin-3-one, 5-ethyl-6-(2-{4-[2-(pyrrolidin-1-yl)ethoxy]phenyl}-1,3-benzoxazol-6-yl)-2,3,4,5-tetrahydropyridazin-3-one, 6-[2-(4-{2-[bis(2-methylpropyl)amino]ethoxy}phenyl)-1,3-benzoxazol-6-yl]-5-ethyl-2,3,4,5-tetrahydropyridazin-3-one, 5-ethyl-6-(2-{4-[3-(piperidin-1-yl)propoxy]phenyl}-1,3-benzoxazol-6-yl)-2,3,4,5-tetrahydropyridazin-3-one, 6-(2-{4-[2-(4-acetylpiperazin-1-yl)ethoxy]phenyl}-1,3-benzoxazol-6-yl)-5-ethyl-2,3,4,5-tetrahydropyridazin-3-one, 1-(2-{4-[6-(4-ethyl-6-oxo-1,4,5,6-tetrahydropyridazin-3-yl)-1,3-benzoxazol-2-yl]phenoxy}ethyl)piperidine-4-carbonitrile, 6-[2-(4-{2-[(1R,4S)-2-azabicyclo[2.2.1]heptan-2-yl]ethoxy}phenyl)-1,3-benzoxazol-6-yl]-5-ethyl-2,3,4,5-tetrahydropyridazin-3-one, tert-butyl 4-(2-{4-[6-(4-ethyl-6-oxo-1,4,5,6-tetrahydropyridazin-3-yl)-1,3-benzoxazol-2-yl]phenoxy}ethyl)piperazine-1-carboxylate, 6-[2-(4-{2-[4-(butan-2-yl)piperazin-1-yl]ethoxy}phenyl)-1,3-benzoxazol-6-yl]-5-ethyl-2,3,4,5-tetrahydropyridazin-3-one, 5-ethyl-6-(2-{4-[2-(2-oxopyrrolidin-1-yl)ethoxyl]phenyl}-1,3-benzoxazol-6-yl)-2,3,4,5-tetrahydropyridazin-3-one, 5-ethyl-6-[2-(4-{2-[4-(propan-2-yl)piperazin-1-yl]ethoxy}phenyl)-1,3-benzoxazol-6-yl]-2,3,4,5-tetrahydropyridazin-3-one, (4R,5S)-6-[2-(4-{2-[bis(propan-2-yl)aminolethoxy]phenyl})-1,3-benzoxazol-6-yl]-5-methyl-4-propyl-2,3,4,5-tetrahydropyridazin-3-one, (4S ,5S)-6-[2-(4-{2-[bis(propan-2-yl)amino]ethoxy}phenyl)-1,3-benzoxazol-6-yl]-5-methyl-4-propyl-2,3,4,5-tetrahydropyridazin-3-one, (4S ,5S)-5-methyl-6-{2-[4-(propan-2-yloxy)phenyl]-1,3-benzoxazol-6-yl}-4-propyl2,3,4,5-tetrahydropyridazin-3-one, (4S ,5S)-5-methyl-6-(2-{4-[3-(piperidin-1-yl)propoxy]phenyl}-1,3-benzoxazol-6-yl)-4-propyl-2,3,4,5-tetrahydropyridazin-3-one, (4R,5R)-5-methyl-6-(2-{4-[2-(piperidin-1-yl)ethoxy]phenyl}-1,3-benzoxazol-6-yl)-4-propyl-2,3,4,5-tetrahydropyridazin-3-one, (4R,5R)-6-[2-(4-methoxyphenyl)-1,3-benzoxazol-6-yl]-5-methyl-4-propyl-2,3,4,5-tetrahydropyridazin-3-one, 5-ethyl-6-{2-[4-(propan-2-yl)phenyl]-1,3-benzoxazol-6-yl}-2,3,4,5-tetrahydropyridazin-3-one, 6-{2-[4-(cyclopentyloxy)phenyl]-1,3-benzoxazol-6-yl}-5-ethyl-2,3,4,5-tetrahydropyridazin-3-one, 5-ethyl-6-{2-[4-(morpholin-4-yl)phenyl]-1,3-benzoxazol-6-yl}-2,3,4,5-tetrahydropyridazin-3-one, (4R,5R)-5-ethyl-4-methyl-6-{2-[4-(propan-2-yloxy)phenyl]-1,3-benzoxazol-6-yl}-2,3,4,5-tetrahydropyridazin-3-one, (4R,5S)-5-ethyl-4-methyl-6-{2-[4-(propan-2-yloxy)phenyl]-1,3-benzoxazol-6-yl}-2,3,4,5-tetrahydropyridazin-3-one, 5-ethyl-6-{2-[4-(1-methoxyethyl)phenyl]-1,3-benzoxazol-6-yl}-2,3,4,5-tetrahydropyridazin-3-one, 5-ethyl-6-{2-[4-(oxolan-3-yloxy)phenyl]-1,3-benzoxazol-6-yl}-2,3,4,5-tetrahydropyridazin-3-one, (4R,5R)-6-[2-(4-fluorophenyl)-1,3-benzoxazol-6-yl]-5-methyl-4-propyl-2,3,4,5-tetrahydropyridazin-3-one, (4R,5R)-5-methyl-4-propyl-6-[2-(thiophen-2-yl)-1,3-benzoxazol-6-yl]-2,3,4,5-tetrahydropyridazin-3-one, (4R,5R)-5-methyl-6-[2-(5-methylthiophen-2-yl)-1,3-benzoxazol-6-yl]-4-propyl-2,3,4,5-tetrahydropyridazin-3-one, (4R,5R)-6-[2-(4-chlorophenyl)-1,3-benzoxazol-6-yl]-5-methyl-4-propyl-2,3,4,5-tetrahydropyridazin-3-one, (4R,5R)-5-methyl-6-[2-(4-methylthiophen-2-yl)-1,3-benzoxazol-6-yl]-4-propyl-2,3,4,5-tetrahydropyridazin-3-one, (4R,5R)-5-methyl-4-propyl-6-[2-(thiophen-3-yl)-1,3-benzoxazol-6-yl]-2,3,4,5-tetrahydropyridazin-3-one, -

(4R,5R)-6-[2-(furan-2-yl)-1,3-benzoxazol-6-yl]-5-methyl-4-propyl-2,3,4,5-tetrahydropyridazin-3-one, (4R,5R)-6-[(2-(2,5-dimethylfuran-3-yl)-1,3-benzoxazol-6-yl]-5-methyl-4-propyl-2,3,4,5-tetrahydropyridazin-3-one, (5R)-5-ethyl-6-[(2-(4-methoxyphenyl)-1,3-benzoxazol-6-yl]-2,3,4,5-tetrahydropyridazin-3-one, (5R)-6-{2-[4-(dimethylamino)phenyl]-1,3-benzoxazol-6-yl}-5-ethyl-2,3,4,5-tetrahydropyridazin-3-one, (5S)-5-ethyl-6-{2-[4-(propan-2-yloxy)phenyl]-1,3-benzoxazol-6-yl}-2,3,4,5-tetrahydropyridazin-3-one, (5R)-5-ethyl-6-{2-[4-(propan-2-yloxy)phenyl]-1,3-benzoxazol-6-yl}-2,3,4,5-tetrahydropyridazin-3-one, (5S)-5-ethyl-6-{2-[4-(oxan-4-yloxy)phenyl]-1,3-benzoxazol-6-yl}-2,3,4,5-tetrahydropyridazin-3-one, (5R)-5-ethyl-6-{2-[4-(oxan-4-yloxy)phenyl]-1,3-benzoxazol-6-yl}-2,3,4,5-tetrahydropyridazin-3-one, (4R,5R)-5-methyl-6-(2-phenyl-1,3-benzoxazol-6-yl)-4-propyl-2,3,4,5-tetrahydropyridazin-3-one, (4S ,5S)-4-butyl-5-methyl-6-(2-phenyl-1,3-benzoxazol-6-yl)-2,3,4,5-tetrahydropyridazin-3-one, (4R,5S)-5-methyl-6-(2-phenyl-1,3-benzoxazol-6-yl)-4-(prop-2-en-1-yl)-2,3,4,5-tetrahydropyridazin-3-one, (4R,5S)-6-{2-[4-(benzyloxy)phenyl]-1,3-benzoxazol-6-yl}-5-methyl-4-propyl-2,3,4,5-tetrahydropyridazin-3-one, (4S ,5S)-6-{2-[4-(benzyloxy)phenyl]-1,3-benzoxazol-6-yl}-5-methyl-4-propyl-2,3,4,5-tetrahydropyridazin-3-one, 5-ethyl-6-(2-{3-[2-(pyrrolidin-1-yl)ethoxy]phenyl}-1,3-benzoxazol-6-yl)-2,3,4,5-tetrahydropyridazin-3-one, (4S ,5 S)-6-[2-(4-hydroxyphenyl)-1,3-benzoxazol-6-yl]-5-methyl-4-propyl-2,3,4,5-tetrahydropyridazin-3-one, 6-(2-phenyl-1,3-benzoxazol-6-yl)-2,3-dihydropyridazin-3-one, (4R,5R)-5-ethyl-4-methyl-6-{2-[4-(propan-2-yloxy)phenyl]-1,3-benzoxazol-6-yl}-2,3,4,5-tetrahydropyridazin-3-one, 5-ethyl-6-(2-{4-[2-(pyrrolidin-1-yl)propoxy]phenyl}-1,3-benzoxazol-6-yl)-2,3,4,5-tetrahydropyridazin-3-one, 5-ethyl-6-[2(4-{[1-(pyrrolidin-1-yl)propan-2-yl]oxy}phenyl)-1,3-benzoxazol-6-yl]-2,3,4,5-tetrahydropyridazin-3-one, 5-ethyl-6-{2-[4-(2-hydroxypropoxy)phenyl]-1,3-benzoxazol-6-yl}-2,3,4,5-tetrahydropyridazin-3-one, 5-ethyl-6-(2-{4-[(2-hydroxycyclohexyl)oxy]phenyl}-1,3-benzoxazol-6-yl)-2,3,4,5-tetrahydropyridazin-3-one, 5-ethyl-6-{2-[4-(prop-2-en-1-yloxy)phenyl]-1,3-benzoxazol-6-yl}-2,3,4,5-tetrahydropyridazin-3-one, 5-ethyl-6-{2-[4-(2-methoxyethoxy)phenyl]-1,3-benzoxazol-6-yl}-2,3,4,5-tetrahydropyridazin-3-one, 5-ethyl-6-[2-(4-{2-[ethyl(propan-2-yl)aminolethoxy]phenyl})-1,3-benzoxazol-6-yl]-2,3,4,5-tetrahydropyridazin-3-one, 6-(2-{3-[2-(2,6-dimethylmorpholin-4-yl)ethoxy]phenyl}-1,3-benzoxazol-6-yl)-5-ethyl-2,3,4,5-tetrahydropyridazin-3-one, 5-ethyl-6-[2(3-{2-[methyl(propan-2-yl)amino]ethoxy}phenyl)-1,3-benzoxazol-6-yl]-2,3,4,5-tetrahydropyridazin-3-one, 5-ethyl-6-[2(3-{2-[ethyl(propan-2-yl)amino]ethoxy}phenyl)-1,3-benzoxazol-6-yl]-2,3,4,5-tetrahydropyridazin-3-one, 5-ethyl-6-[2(4-{2-[methyl(propan-2-yl)amino]ethoxy}phenyl)-1,3-benzoxazol-6-yl]-2,3,4,5-tetrahydropyridazin-3-one, 6-(2-{4-[2-(2,6-dimethylmorpholin-4-yl)ethoxy]phenyl}-1,3-benzoxazol-6-yl)-5-ethyl-2,3,4,5-tetrahydropyridazin-3-one, 5-ethyl-6-[2-(4-{[1-(morpholin-4-yl)propan-2-yl]oxy}phenyl)-1,3-benzoxazol-6-yl]-2,3,4,5-tetrahydropyridazin-3-one, 6-(2-{4-[2-(diethylamino)ethoxy]phenyl }-1,3-benzoxazol-6-yl)-5-ethyl-2,3,4,5-tetrahydropyridazin-3-one, (4S ,5 S)-6-[2-(4-{2-[(R2R,6S)-2,6-dimethylmorpholin-4-yl]ethoxy }phenyl)-1,3-benzoxazol-6-yl]-5-methyl-4-propyl-2,3,4,5-tetrahydropyridazin-3-one, 6-[2-(4-{[(R1R,2R)-2(diethylamino)cyclohexyl]oxy}phenyl)-1,3-benzoxazol-6-yl]-5-ethyl-2,3,4,5-tetrahydropyridazin-3-one, 5-ethyl-6-[2-(4-{[(1R,2R)-2-(piperidin-1-yl)cyclopentyl]oxy }phenyl)-1,3-benzoxazol-6-yl]-2,3,4,5-tetrahydropyridazin-3-one, tert-butyl (2S)-2-{4-[6-(4-ethyl-6-oxo-1,4,5,6-tetrahydropyridazin-3-yl)-1,3-benzoxazol-2-yl]phenoxymethyl}pyrrolidine-1-carboxylate, tert-butyl (2R)-2-{4-[6-(4-ethyl-6-oxo-1,4,5,6-tetrahydropyridazin-3-yl)-1,3-benzoxazol-2-yl]phenoxymethyl }pyrrolidine-1-carboxylate, 5-ethyl-6-[2-(4-{[2-methyl-1-(pyrrolidin-1-yl)propan-2-yl]oxy}phenyl)-1,3-benzoxazol-6-yl]-2,3,4,5-tetrahydropyridazin-3-one, 5-ethyl-6-[2-{4-[2-methyl-2-(pyrrolidin-1-yl)propoxy]phenyl}-1,3-benzoxazol-6-yl]-2,3,4,5-tetrahydropyridazin-3-one, 5-ethyl-6-[2-(3-{[1-(piperidin-1-yl)propan-2-yl]oxy }phenyl)-1,3-benzoxazol-6-yl]-2,3,4,5-tetrahydropyridazin-3-one, 5-ethyl-6-[2-(4-{[2-methyl-1-(morpholin-4-yl)propan-2-yl]oxy }phenyl)-1,3-benzoxazol-6-yl]-2,3,4,5-tetrahydropyridazin-3-one, 5-ethyl-6-(2-{4-[2-methyl-2-(morpholin-4-yl)propoxy]phenyl}-1,3-benzoxazol-6-yl)-2,3,4,5-tetrahydropyridazin-3-one, 5-ethyl-6-(2-{4-[(1-methylpiperidin-2-yl)methoxy]phenyl}-1,3-benzoxazol-6-yl)-2,3,4,5-tetrahydropyridazin-3-one, 5-ethyl-6-(2-{4-[(1-methylazepan-2-yl)oxy]phenyl }-1,3-benzoxazol-6-yl)-2,3,4,5-tetrahydropyridazin-3-one, (5R)-5-ethyl-6-[2-(4-{[1-(piperidin-1-yl)propan-2-yl]oxy}phenyl)-1,3-benzoxazol-6-yl]-2,3,4,5-tetrahydropyridazin-3-one, (5S)-5-ethyl-6-(2-{4-[2-(piperidin-1-yl)propoxy]phenyl}-1,3-benzoxazol-6-yl)-2,3,4,5-tetrahydropyridazin-3-one, (5R)-5-ethyl-6-(2-{4-[2-(piperidin-1-yl)propoxy]phenyl}-1,3-benzoxazol-6-yl)-2,3,4,5-tetrahydropyridazin-3-one, 5-ethyl-6-(2-{4-[(2S)-pyrrolidin-2-ylmethoxy]phenyl}-1,3-benzoxazol-6-yl)-2,3,4,5-tetrahydropyridazin-3-one, 5-ethyl-6-(2-{4-[(2R)-pyrrolidin-2-ylmethoxy]phenyl}-1,3-benzoxazol-6-yl)-2,3,4,5-tetrahydropyridazin-3-one, 5-ethyl-6-[2-(4-{[(2S)-1-(propan-2-yl)pyrrolidin-2-yl]methoxy}phenyl)-1,3-benzoxazol-6-yl]-2,3,4,5-tetrahydropyridazin-3-one, 5-ethyl-6-[2-(4-{[(2R)-1-(propan-2-yl)pyrrolidin-2-yl]methoxy}phenyl)-1,3-benzoxazol-6-yl]-2,3,4,5-tetrahydropyridazin-3-one, 5-ethyl-6-[2-(4-{[(2S)-1-methylpyrrolidin-2-yl]methoxy}phenyl)-1,3-benzoxazol-6-yl]-2,3,4,5-tetrahydropyridazin-3-one, 5-ethyl-6-(2-{4-[2-(4-methylpiperidin-1-yl)ethoxy]phenyl}-1,3-benzoxazol-6-yl)-2,3,4,5-tetrahydropyridazin-3-one, 5-ethyl-6-(2-{4-[2-(4-propylpiperidin-1-yl)ethoxy]phenyl}-1,3-benzoxazol-6-yl)-2,3,4,5-tetrahydropyridazin-3-one, 6-{2-[4-(2-{3-azaspiro[5.5]undecan-3-yl}ethoxy)phenyl]-1,3-benzoxazol-6-yl}-5-ethyl-2,3,4,5-tetrahydropyridazin-3-one, 6-[2(4-{2-[(2R,6S)-2,6-dimethylmorpholin-4-yl]ethoxy}phenyl)-1,3-benzoxazol-6-yl]-5-ethyl-2,3,4,5-tetrahydropyridazin-3-one, 5-ethyl-6-(2-{4-[2-(thiomorpholin-4-yl)ethoxy]phenyl}-1,3-benzoxazol-6-yl)-2,3,4,5-tetrahydropyridazin-3-one, 5-ethyl-6-(2-{4-[2-(4-fluoropiperidin-1-yl)ethoxy]phenyl}-1,3-benzoxazol-6-yl)-2,3,4,5-tetrahydropyridazin-3-one, 5-ethyl-6-[2-(4-{2-[propan-2-yl(propyl)amino]ethoxy}phenyl)-1,3-benzoxazol-6-yl]-2,3,4,5-tetrahydropyridazin-3-one, 6-[2(4-{2-[(2R,5R)-2,5-dimethylpyrrolidin-1-yl]ethoxy}phenyl)-1,3-benzoxazol-6-yl]-5-ethyl-2,3,4,5-tetrahydropyridazin-3-one, 5-ethyl-6-(2-{4-[(1-hydroxypropan-2-yl)oxy]phenyl}-1,3-benzoxazol-6-yl)-2,3,4,5-tetrahydropyridazin-3-one, (4R,5R)-5-methyl-6-[2-(1-methyl-1H-pyrrol-2-yl)-1,3-benzoxazol-6-yl]-4-propyl-2,3,4,5-tetrahydropyridazin-3-one, (4R,5R)-6-(2-cyclopropyl-1,3-benzoxazol-6-yl)-5-methyl-4-propyl-2,3,4,5-tetrahydropyridazin-3-one, methyl 3-[6-(4-methyl-6-oxo-1,6-dihydropyridazin-3-yl)-1,3-benzoxazol-2-yl]benzoate, 4-[6-(4-methyl-6-oxo-1,6-dihydropyridazin-3-yl)-1,3-benzoxazol-2-yl]benzoic acid, 5-methyl-6-[2-(thiophen-2-yl)-1,3-benzoxazol-6-yl]-2,3-dihydropyridazin-3-one, 6-[2-(thiophen-2-yl)-1,3-benzoxazol-6-yl]-2,3-dihydropyridazin-3-one, (5S)-6-[2-(4-{2-[bis(propan-2-yl)amino]ethoxy}phenyl)-1,3-benzoxazol-6-yl]-5-ethyl-2,3,4,5-tetrahydropyridazin-3-one, (5R)-6-[2-(4-{2-[bis(propan-2-yl)amino]ethoxy}phenyl)-1,3-benzoxazol-6-yl]-5-ethyl-2,3,4,5-tetrahydropyridazin-3-one, and (4R,5R)-5-methyl-6-{2-[4-(propan-2-yloxy)phenyl]-1,3-benzoxazol-6-yl}-4-propyl-2,3,4,5-tetrahydropyridazin-3-one, or a tautomer, enantiomer, or a physiologically acceptable salt thereof.

9. A medicament comprising a compound of formula I according to claim 1 or a physiologically acceptable salt thereof and an inert carrier or diluent.

10. A method of modulating G protein-coupled receptor 119 activity in a patient in need thereof comprising administering to the patient a compound according to claim 1.

11. The compound of formula I

I

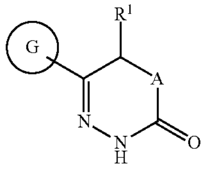

wherein:

$R^1$ is hydrogen, 1-4C-alkyl, 3-7C-cycloalkyl, 3-7C-cycloalkyl-1-4C-alkyl, 2-4C-alkenyl, 2-4C-alkynyl, 1-4C-alkoxy, 1-4C-alkoxy-1-4C-alkyl, wholly or partially fluorine-substituted 1-4C-alkyl, or wholly or partially fluorine-substituted 1-4C-alkoxy, A is $CR^2R^3$, O, S, or $NR^2$, wherein $R^2$ is a group selected from hydrogen, 1-4C-alkyl, 3-7C-cycloalkyl, 3-7C-cycloalkyl-1-4C-alkyl, 2-4C-alkenyl, 2-4C-alkynyl, 1-4C-alkoxy, 1-4C-alkoxy-1-4C-alkyl, wholly or partially fluorine-substituted 1-4C-alkyl, or wholly or partially fluorine-substituted 1-4C-alkoxy, or $R^1$ and $R^2$ together represent a bond, or a 1-7C-alkanediyl group wherein one or two —$CH_2$— groups each are optionally replaced by —O—, and $R^3$ is hydrogen or 1-4C-alkyl, and G is a bicyclic system G1or G2:

G1

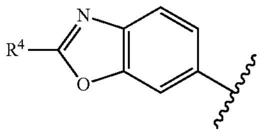

or

G2

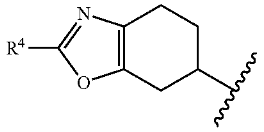

, wherein:

$R^4$ is a group optionally substituted by one to four $R^5$ and/or $R^6$ independently selected from 1-4C-alkyl, 3-7C-cycloalkyl, 3-7C-cycloalkyl-1-4C-alkyl, 2-4C-alkenyl, 2-4C-alkynyl, aryl, heteroaryl, aryl-1-4C-alkyl, heteroaryl-1-4C-alkyl, heterocyclyl, and heterocyclyl-1-4C-alkyl, wherein:

each $R^5$ independently is hydrogen or a group optionally substituted by one to four $R^{10}$ and/or $R^{11}$ and/or $R^{12}$ independently selected from 1-4C-alkyl, 3-7C- cycloalkyl, 3-7C-cycloalkyl-1-4C-alkyl, 2-4C-alkenyl, 2-4C-alkynyl, aryl, heteroaryl, heterocyclyl, aryl-1-4C-alkyl, heteroaryl-1-4C-alkyl, and heterocyclyl-1-4C-alkyl, each $R^6$ independently is hydrogen or a group selected from: halogen, trifluoromethyl, cyano, oxo, —$OR^7$, —$N(R^7)R^8$, —$SR^7$, —$C(O)OR^7$, —$C(O)N(R^7)R^8$, —$S(O)_2N(R^7)R^8$, —$C(O)R^9$, —$S(O)_2R^9$, —$S(O)R^9$, —$N(R^{81})C(O)OR^7$, —$N(R^{81})C(O)N(R^7)R^8$, —$N(R^{81})S(O)_2N(R^7)R^8$, —$N(R^{81})C(O)R^9$, —$N(R^{81})S(O)_2R^9$, and —$N(R^{81})S(O)R^9$, wherein:

each $R^7$ independently is hydrogen or a group optionally substituted by one to four $R^{10}$ and/or $R^{11}$ and/or $R^{12}$ selected from 1-4C-alkyl, 3-7C cycloalkyl, 3-7C-cycloalkyl-1-4C-alkyl, 2-4C-alkenyl, 2-4C-alkynyl, aryl, heteroaryl, heterocyclyl, aryl-1-4C-alkyl, heteroaryl-1-4C-alkyl, and heterocyclyl-1-4C-alkyl, each $R^8$ independently is hydrogen or a group selected from 1-4C-alkyl and 3-7C-cycloalkyl, or $R^7$ and $R^8$ together represent a 1-9C-alkanediyl group wherein one or two —$CH_2$— groups each are optionally replaced by —O, —$NR^{81}$, —S, —SO, or —$SO_2$—, wherein each $R^{81}$ independently is hydrogen or 1-4C-alkyl, each $R^9$ independently is a group optionally substituted by one to four $R^{10}$ and/or $R^{11}$ and/or $R^{12}$, each independently selected from 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, wherein each $R^{10}$ independently is a group selected from hydrogen, 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, each $R^{11}$ independently is hydrogen or a group selected from halogen, trifluoromethyl, cyano, oxo, —$OR^{13}$, —$N(R^{13})R_{14}$, and —$SR^{13}$, each $R^{12}$ independently is hydrogen or a group selected from $C(O)OR^{13}$, —$C(O)N(R^{13})R^{14}$, —$S(O)_2N(R^{13})R^{14}$, —$C(O)R^{15}$, —$S(O)_2R^{15}$—$S(O)R^{15}$, —$N(R^{141})C(O)OR^{13}$, —$N(R^{141})C(O)N(R^{13})R^{14}$, —$N(R^{141})S(O)_2N(R^{13})R^{14}$, —$N(R^{141})C(O)R_{15}$, —$N(R^{141})S(O)_2R^{15}$, and —$N(R^{141})S(O)R^{15}$, each $R^{13}$ independently is a group selected from hydrogen, 1-4C-alkyl, 3-7C-cycloalkyl, 3-7C-cycloalkyl-1-4C-alkyl, aryl, heteroaryl, heterocyclyl, aryl-1-4C-alkyl, heteroaryl-1-4C-alkyl, and heterocyclyl-1-4C-alkyl, each $R^{14}$ independently is a group selected from hydrogen, 1-4C-alkyl and 3-7C-cycloalkyl, or $R^{13}$ and $R^{14}$ together represent a 1-9C-alkanediyl group wherein one or two —$CH_2$— groups each are optionally replaced by —O, —$NR^{141}$, —S, —SO, or —$SO_2$—, wherein each $R^{141}$ independently is hydrogen or 1-4C-alkyl, each $R^{15}$ independently is a group selected from 1-4C-alkyl, 3-7C-cycloalkyl, 3-7C-cycloalkyl-1-4C-alkyl, aryl, heteroaryl, heterocyclyl, aryl-1-4C-alkyl,heteroaryl-1-4C-alkyl, and heterocyclyl-1-4C-alkyl, wherein:

aryl, on its own or as part of another group, is a carbocyclic aromatic monocyclic ring system containing 6 carbon atoms, which is optionally annelated to a second 5- or 6-membered carbocyclic aromatic, saturated or unsaturated ring system, heteroaryl, on its own or as part of another group, is a 5- to 12-membered, aromatic, monocyclic or condensed-polycyclic ring system containing 1 to 4 heteroatoms independently selected from N, O, and $S(O)_r$, with r=0, 1, or 2, wherein at least one of the heteroatoms is part of the aromatic ring, and heterocyclyl, on its own or as part of another group, is a 3- to 12-membered, saturated, unsaturated or aromatic, monocyclic or condensed, bridged or spiro-polycyclic ring system containing 1 to 4 heteroatoms independently selected from N, O, and $S(O)_r$, with r=0, 1, or 2, wherein none of the heteroatoms is part of the aromatic ring;

or a tautomer, enantiomer, or a salt thereof.

* * * * *